United States Patent
Percier et al.

(10) Patent No.: US 11,713,354 B2
(45) Date of Patent: Aug. 1, 2023

(54) GALECTIN-10 ANTIBODIES

(71) Applicants: argenx IIP BV, Ghent (BE); VIB VZW, Ghent (BE); Universiteit Gent, Ghent (BE)

(72) Inventors: Jean-Michel Percier, Ghent (BE); Christophe Blanchetot, Ghent (BE); Michael Saunders, Ghent (BE); Hans De Haard, Ghent (BE); Sebastian Van Der Woning, Ghent (BE); Emma Persson, Ghent (BE); Bart Lambrecht, Ghent (BE); Savvas Savvides, Ghent (BE); Hamida Hammad, Ghent (BE); Kenneth Verstraete, Ghent (BE)

(73) Assignees: ARGENX BV, Ghent (BE); VIB VZW, Ghent (BE); Universiteit Gent, Ghent (BE)

( * ) Notice: Subject to any disclaimer, the term of this patent is extended or adjusted under 35 U.S.C. 154(b) by 111 days.

(21) Appl. No.: 17/194,950

(22) Filed: Mar. 8, 2021

(65) Prior Publication Data

US 2021/0332140 A1 Oct. 28, 2021

Related U.S. Application Data

(62) Division of application No. 16/382,997, filed on Apr. 12, 2019, now Pat. No. 11,066,473.

(30) Foreign Application Priority Data

Apr. 13, 2018 (GB) ..................................... 1806099
Feb. 6, 2019 (GB) ..................................... 1901648

(51) Int. Cl.
*A61K 39/00* (2006.01)
*A61K 39/395* (2006.01)
*C07K 16/28* (2006.01)
*G01N 33/68* (2006.01)

(52) U.S. Cl.
CPC ......... *C07K 16/2851* (2013.01); *G01N 33/68* (2013.01); *A61K 2039/505* (2013.01); *C07K 2317/55* (2013.01); *C07K 2317/622* (2013.01); *G01N 2333/4724* (2013.01)

(58) Field of Classification Search
None
See application file for complete search history.

(56) References Cited

U.S. PATENT DOCUMENTS 11,066,473 B2   7/2021  Percier et al.
2008/0118515 A1  5/2008  Lutter et al.

FOREIGN PATENT DOCUMENTS

CN        106645752 A     5/2017
WO   WO-2010001251 A2    1/2010
WO   WO-2016172722 A1 * 10/2016 ............. A61K 35/17

OTHER PUBLICATIONS

Stoops, S., Scientists (dis)solve a century-long mystery to treat asthma and airway inflammation. News Release May 23, 2019, pp. 1-4. (Year: 2019).*
Edwards et al., The remarkable flexibility of the human antibody repertoire; isolation of over one thousand different antibodies to a single protein, BLyS. J Mol Biol. Nov. 14, 2003;334(1): 103-18. (Year: 2003).*
Lloyd et al., Modelling the human immune response: performance of a 1011 human antibody repertoire against a broad panel of therapeutically relevant antigens. Protein Eng Des Sel. Mar. 2009;22(3):159-68. (Year: 2009).*
Goel et al., Plasticity within the antigen-combining site may manifest as molecular mimicry in the humoral immune response. J Immunol. Dec. 15, 2004; 173(12):7358-67. (Year: 2004).*
Kanyavuz et al., Breaking the law: unconventional strategies for antibody diversification. Nat Rev Immunol. Jun. 2019; 19(6):355-368. (Year: 2019).*
Brown et al. Tolerance of single, but not multiple, amino acid replacements in antibody VH CDR 2: a means of minimizing B cell wastage from somatic hypermutation? J. Immuno. May 1996, 3285-91. (Year: 1996).*
Vajdos et al. Comprehensive functional maps of the antigen-binding site of an anti-ErbB2 antibody obtained with shotgun scanning mutagenesis. J. Mol. Biol. Jul. 5, 2002, 320(2):415-28. (Year: 2002).*
Persson et al. Protein crystallization promotes type 2 immunity and is reversible by antibody treatment. Science 364, 751, 2019. (Year: 2019).*
Ackerman et al., "Charcot-Leyden crystal protein (galectin-10) is not a dual function galectin with lysophospholipase activity but binds a lysophospholipase inhibitor in a novel structural fashion," J Biol Chem. Apr. 26, 2002;277(17):14859-68.
Chan and Carter, "Therapeutic antibodies for autoimmunity and inflammation," Nat Rev Immunol. May 2010;10(5):301-16.
Chua et al., "Galectin-10, a potential biomarker of eosinophilic airway inflammation," PLoS One. 2012;7(8):e42549.
Gevaert et al., "Charcot-Leyden crystals promote neutrophilic inflammation in patients with nasal polyposis," J Allergy Clin Immunol. Jan. 2020;145(1):427-430.e4.
Kool et al., "An unexpected role for uric acid as an inducer of T helper 2 cell immunity to inhaled antigens and inflammatory mediator of allergic asthma," Immunity. Apr. 22, 2011;34(4):527-40.

(Continued)

*Primary Examiner* — Maher M Haddad
(74) *Attorney, Agent, or Firm* — Dechert LLP; Andrew T. Wilkins; Kayla L. Metzger

(57) ABSTRACT

The present invention relates to antagonists, particularly antibodies and antigen binding fragments thereof, that bind to the protein galectin-10, particularly human galectin-10. The galectin-10 antagonists disrupt the crystallization of galectin-10 and are therefore useful in methods of preventing and treating diseases and conditions wherein the pathology is linked to the formation/presence of Charcot-Leyden crystals (CLCs).

15 Claims, 32 Drawing Sheets

Specification includes a Sequence Listing.

(56) References Cited

OTHER PUBLICATIONS

Kubach et al., "Human CD4+CD25+ regulatory T cells: proteome analysis identifies galectin-10 as a novel marker essential for their anergy and suppressive function," Blood. Sep. 1, 2007;110(5):1550-8.
Natsume et al., "Improving effector functions of antibodies for cancer treatment: Enhancing ADCC and CDC," Drug Des Devel Ther. Sep. 21, 2009;3:7-16.
Negrete-Garcie et al., "Galectin-10 is released in the nasal lavage fluid of patients with aspirin-sensitive respiratory disease," ScientificWorldJournal. 2012;2012:474020.
PCT International Search Report and Written Opinion from PCT/EP2019/059570, dated Jun. 17, 2019.
Perros et al., "Blockade of CCR4 in a humanized model of asthma reveals a critical role for DC-derived CCL17 and CCL22 in attracting Th2 cells and inducing airway inflammation," Allergy. Jul. 2009;64(7):995-1002.
Persson et al., "Protein crystallization promotes type 2 immunity and is reversible by antibody treatment," Science. May 24, 2019;364(6442):eaaw4295.
Rodriguez-Alcázar et al., "Charcot-Leyden Crystals Activate the NLRP3 Inflammasome and Cause IL-1ß Inflammation in Human Macrophages," J Immunol. Jan. 15, 2019;202(2):550-558.

\* cited by examiner

Galectin-10-Y69E dimer

Crystallographic galectin-10 dimer
(pdb 1LCL)
Galectin-10-Y69E dimer
RMSD < 0.3 Å

HDM + isotype

HDM + Gal10$^{crystals}$ + isotype

HDM + Gal10$^{crystals}$ + 1D11

```
                      SEQUENCE LISTING

<160> NUMBER OF SEQ ID NOS: 272

<210> SEQ ID NO 1
<211> LENGTH: 5
<212> TYPE: PRT
<213> ORGANISM: Artificial sequence
<220> FEATURE:
<223> OTHER INFORMATION: Synthetic peptide

<400> SEQUENCE: 1

Asp Tyr Ala Met Ser
1               5

<210> SEQ ID NO 2
<211> LENGTH: 17
```

```
<212> TYPE: PRT
<213> ORGANISM: Artificial sequence
<220> FEATURE:
<223> OTHER INFORMATION: Synthetic peptide

<400> SEQUENCE: 2

Gly Ile Ser Trp Asn Gly Gly Ser Thr Tyr Tyr Ala Glu Ser Met Lys
1               5                   10                  15

Gly

<210> SEQ ID NO 3
<211> LENGTH: 14
<212> TYPE: PRT
<213> ORGANISM: Artificial sequence
<220> FEATURE:
<223> OTHER INFORMATION: Synthetic peptide

<400> SEQUENCE: 3

Asp Arg Asn Leu Gly Tyr Arg Leu Gly Tyr Pro Tyr Asp Tyr
1               5                   10

<210> SEQ ID NO 4
<211> LENGTH: 5
<212> TYPE: PRT
<213> ORGANISM: Artificial sequence
<220> FEATURE:
<223> OTHER INFORMATION: Synthetic peptide

<400> SEQUENCE: 4

Ser Tyr Ala Met Ser
1               5

<210> SEQ ID NO 5
<211> LENGTH: 17
<212> TYPE: PRT
<213> ORGANISM: Artificial sequence
<220> FEATURE:
<223> OTHER INFORMATION: Synthetic peptide

<400> SEQUENCE: 5

Ala Ile Asn Ser Gly Gly Gly Ser Thr Ser Tyr Ala Asp Ser Val Lys
1               5                   10                  15

Gly

<210> SEQ ID NO 6
<211> LENGTH: 12
<212> TYPE: PRT
<213> ORGANISM: Artificial sequence
<220> FEATURE:
<223> OTHER INFORMATION: Synthetic peptide

<400> SEQUENCE: 6

Pro Gly Asp Arg Leu Trp Tyr Tyr Arg Tyr Asp Tyr
1               5                   10

<210> SEQ ID NO 7
<211> LENGTH: 7
<212> TYPE: PRT
<213> ORGANISM: Artificial sequence
<220> FEATURE:
<223> OTHER INFORMATION: Synthetic peptide

<400> SEQUENCE: 7

Thr Ser Tyr Tyr Ala Trp Ser
1               5
```

<210> SEQ ID NO 8
<211> LENGTH: 16
<212> TYPE: PRT
<213> ORGANISM: Artificial sequence
<220> FEATURE:
<223> OTHER INFORMATION: Synthetic peptide

<400> SEQUENCE: 8

Val Ile Ala Ser Asp Gly Ser Thr Tyr Tyr Ser Pro Ser Leu Lys Ser
1               5                   10                  15

<210> SEQ ID NO 9
<211> LENGTH: 15
<212> TYPE: PRT
<213> ORGANISM: Artificial sequence
<220> FEATURE:
<223> OTHER INFORMATION: Synthetic peptide

<400> SEQUENCE: 9

Tyr Ile Arg Gly Ser Ser Trp Ser Gly Trp Ser Ala Tyr Asp Tyr
1               5                   10                  15

<210> SEQ ID NO 10
<211> LENGTH: 7
<212> TYPE: PRT
<213> ORGANISM: Artificial sequence
<220> FEATURE:
<223> OTHER INFORMATION: Synthetic peptide

<400> SEQUENCE: 10

Thr Asn Ser Tyr Tyr Trp Ser
1               5

<210> SEQ ID NO 11
<211> LENGTH: 16
<212> TYPE: PRT
<213> ORGANISM: Artificial sequence
<220> FEATURE:
<223> OTHER INFORMATION: Synthetic peptide

<400> SEQUENCE: 11

Ala Ile Ala Tyr Ser Gly Ser Thr Tyr Tyr Ser Pro Ser Leu Lys Ser
1               5                   10                  15

<210> SEQ ID NO 12
<211> LENGTH: 10
<212> TYPE: PRT
<213> ORGANISM: Artificial sequence
<220> FEATURE:
<223> OTHER INFORMATION: Synthetic peptide

<400> SEQUENCE: 12

Arg Pro Asn Trp Tyr Arg Ala Leu Asp Ala
1               5                   10

<210> SEQ ID NO 13
<211> LENGTH: 5
<212> TYPE: PRT
<213> ORGANISM: Artificial sequence
<220> FEATURE:
<223> OTHER INFORMATION: Synthetic peptide

<400> SEQUENCE: 13

Val Tyr Ala Met Ser
1               5

```
<210> SEQ ID NO 14
<211> LENGTH: 17
<212> TYPE: PRT
<213> ORGANISM: Artificial sequence
<220> FEATURE:
<223> OTHER INFORMATION: Synthetic peptide

<400> SEQUENCE: 14

Asp Ile Asn Thr Ser Gly Asp Ser Thr Thr Tyr Ala Asp Ser Val Lys
1               5                   10                  15

Gly

<210> SEQ ID NO 15
<211> LENGTH: 5
<212> TYPE: PRT
<213> ORGANISM: Artificial sequence
<220> FEATURE:
<223> OTHER INFORMATION: Synthetic peptide

<400> SEQUENCE: 15

Arg Tyr Thr Gln Glu
1               5

<210> SEQ ID NO 16
<211> LENGTH: 5
<212> TYPE: PRT
<213> ORGANISM: Artificial sequence
<220> FEATURE:
<223> OTHER INFORMATION: Synthetic peptide

<400> SEQUENCE: 16

Ser Tyr Tyr Met Ser
1               5

<210> SEQ ID NO 17
<211> LENGTH: 17
<212> TYPE: PRT
<213> ORGANISM: Artificial sequence
<220> FEATURE:
<223> OTHER INFORMATION: Synthetic peptide

<400> SEQUENCE: 17

Ala Ile Asn Ser Gly Gly Gly Ser Thr Tyr Tyr Ala Asp Ser Val Lys
1               5                   10                  15

Gly

<210> SEQ ID NO 18
<211> LENGTH: 9
<212> TYPE: PRT
<213> ORGANISM: Artificial sequence
<220> FEATURE:
<223> OTHER INFORMATION: Synthetic peptidee

<400> SEQUENCE: 18

Asn Gly Gly Ile Trp Ser Phe Gly Ser
1               5

<210> SEQ ID NO 19
<211> LENGTH: 17
<212> TYPE: PRT
<213> ORGANISM: Artificial sequence
<220> FEATURE:
<223> OTHER INFORMATION: Synthetic peptide

<400> SEQUENCE: 19

Pro Ile Asn Ser Gly Ser Asp Ser Ala Ser Tyr Val Asp Ser Val Lys
```

```
1               5                   10                  15

Gly

<210> SEQ ID NO 20
<211> LENGTH: 12
<212> TYPE: PRT
<213> ORGANISM: Artificial sequence
<220> FEATURE:
<223> OTHER INFORMATION: Synthetic peptidee

<400> SEQUENCE: 20

Ala Arg Thr Ser Val Val Ala Gly Gly Met Asp Tyr
1               5                   10

<210> SEQ ID NO 21
<211> LENGTH: 5
<212> TYPE: PRT
<213> ORGANISM: Artificial sequence
<220> FEATURE:
<223> OTHER INFORMATION: Synthetic peptide

<400> SEQUENCE: 21

Arg Tyr Trp Met Ile
1               5

<210> SEQ ID NO 22
<211> LENGTH: 17
<212> TYPE: PRT
<213> ORGANISM: Artificial sequence
<220> FEATURE:
<223> OTHER INFORMATION: Synthetic peptide

<400> SEQUENCE: 22

Ser Ile Tyr Asn Asp Gly Gly Asn Thr Tyr Tyr Ala Asp Ser Val Lys
1               5                   10                  15

Gly

<210> SEQ ID NO 23
<211> LENGTH: 10
<212> TYPE: PRT
<213> ORGANISM: Artificial sequence
<220> FEATURE:
<223> OTHER INFORMATION: Synthetic peptide

<400> SEQUENCE: 23

Leu Lys Ala Ala Tyr Tyr Gly Met Asp Tyr
1               5                   10

<210> SEQ ID NO 24
<211> LENGTH: 17
<212> TYPE: PRT
<213> ORGANISM: Artificial sequence
<220> FEATURE:
<223> OTHER INFORMATION: Synthetic peptide

<400> SEQUENCE: 24

Asn Ile Asn Ser Gly Gly Gly Ser Thr Gly Tyr Ala Asp Ser Val Lys
1               5                   10                  15

Gly

<210> SEQ ID NO 25
<211> LENGTH: 15
<212> TYPE: PRT
<213> ORGANISM: Artificial sequence
<220> FEATURE:
```

<223> OTHER INFORMATION: Synthetic peptidee

<400> SEQUENCE: 25

Tyr Leu Arg Thr Tyr Tyr Pro Asn Ala Ala Phe Gly Met Asp Tyr
1               5                   10                  15

<210> SEQ ID NO 26
<211> LENGTH: 5
<212> TYPE: PRT
<213> ORGANISM: Artificial sequence
<220> FEATURE:
<223> OTHER INFORMATION: Synthetic peptide

<400> SEQUENCE: 26

Asn Tyr Trp Met Tyr
1               5

<210> SEQ ID NO 27
<211> LENGTH: 17
<212> TYPE: PRT
<213> ORGANISM: Artificial sequence
<220> FEATURE:
<223> OTHER INFORMATION: Synthetic peptide

<400> SEQUENCE: 27

Ala Ile Asp Val Gly Gly Gly Thr Thr Asp Tyr Ala Gly Ser Val Lys
1               5                   10                  15

Gly

<210> SEQ ID NO 28
<211> LENGTH: 10
<212> TYPE: PRT
<213> ORGANISM: Artificial sequence
<220> FEATURE:
<223> OTHER INFORMATION: Synthetic peptide

<400> SEQUENCE: 28

Gly Gly Ser Tyr Tyr Gly Gly Met Asp Tyr
1               5                   10

<210> SEQ ID NO 29
<211> LENGTH: 5
<212> TYPE: PRT
<213> ORGANISM: Artificial sequence
<220> FEATURE:
<223> OTHER INFORMATION: Synthetic peptidee

<400> SEQUENCE: 29

Ala Tyr Ala Met Asn
1               5

<210> SEQ ID NO 30
<211> LENGTH: 17
<212> TYPE: PRT
<213> ORGANISM: Artificial sequence
<220> FEATURE:
<223> OTHER INFORMATION: Synthetic peptide

<400> SEQUENCE: 30

Gly Val Asn Ser Gly Gly Gly Leu Thr Ser Tyr Gly Glu Ser Val Lys
1               5                   10                  15

Gly

<210> SEQ ID NO 31
<211> LENGTH: 14

```
<212> TYPE: PRT
<213> ORGANISM: Artificial sequence
<220> FEATURE:
<223> OTHER INFORMATION: Synthetic peptide

<400> SEQUENCE: 31

Ser Lys Arg Gly Ala Val Val Ala Gly Thr Gly Asp Asp Tyr
1               5                   10

<210> SEQ ID NO 32
<211> LENGTH: 17
<212> TYPE: PRT
<213> ORGANISM: Artificial sequence
<220> FEATURE:
<223> OTHER INFORMATION: Synthetic peptide

<400> SEQUENCE: 32

Ala Ile Ser Trp Asn Gly Gly Ser Thr Tyr Tyr Ala Glu Ser Met Lys
1               5                   10                  15
Gly

<210> SEQ ID NO 33
<211> LENGTH: 14
<212> TYPE: PRT
<213> ORGANISM: Artificial sequence
<220> FEATURE:
<223> OTHER INFORMATION: Synthetic peptide

<400> SEQUENCE: 33

Asp Leu Ser Ala Ser Gly Ser Tyr Tyr His Thr Phe Gly Ser
1               5                   10

<210> SEQ ID NO 34
<211> LENGTH: 7
<212> TYPE: PRT
<213> ORGANISM: Artificial sequence
<220> FEATURE:
<223> OTHER INFORMATION: Synthetic peptide

<400> SEQUENCE: 34

Thr Gly Pro Tyr Ser Trp Ser
1               5

<210> SEQ ID NO 35
<211> LENGTH: 16
<212> TYPE: PRT
<213> ORGANISM: Artificial sequence
<220> FEATURE:
<223> OTHER INFORMATION: Synthetic peptide

<400> SEQUENCE: 35

Tyr Ile Gly Tyr Ser Gly Ser Thr Tyr Tyr Ser Pro Ser Leu Lys Ser
1               5                   10                  15

<210> SEQ ID NO 36
<211> LENGTH: 12
<212> TYPE: PRT
<213> ORGANISM: Artificial sequence
<220> FEATURE:
<223> OTHER INFORMATION: Synthetic peptide

<400> SEQUENCE: 36

Ser Arg Ser Ser Pro Thr Thr Phe Gly Met Asp Tyr
1               5                   10

<210> SEQ ID NO 37
```

```
<211> LENGTH: 7
<212> TYPE: PRT
<213> ORGANISM: Artificial sequence
<220> FEATURE:
<223> OTHER INFORMATION: Synthetic peptide

<400> SEQUENCE: 37

Thr Asn Tyr Tyr Tyr Trp Ser
1               5

<210> SEQ ID NO 38
<211> LENGTH: 11
<212> TYPE: PRT
<213> ORGANISM: Artificial sequence
<220> FEATURE:
<223> OTHER INFORMATION: Synthetic peptide

<400> SEQUENCE: 38

Ala Pro Tyr Gly Ile Ser Arg Glu Tyr Asp Tyr
1               5                   10

<210> SEQ ID NO 39
<211> LENGTH: 5
<212> TYPE: PRT
<213> ORGANISM: Artificial sequence
<220> FEATURE:
<223> OTHER INFORMATION: Synthetic peptide

<400> SEQUENCE: 39

Asn Tyr Pro Met Thr
1               5

<210> SEQ ID NO 40
<211> LENGTH: 17
<212> TYPE: PRT
<213> ORGANISM: Artificial sequence
<220> FEATURE:
<223> OTHER INFORMATION: Synthetic peptide

<400> SEQUENCE: 40

Ala Ile Asn Gly Gly Gly Asp Ile Pro Tyr Tyr Ala Asp Ser Val Lys
1               5                   10                  15

Gly

<210> SEQ ID NO 41
<211> LENGTH: 14
<212> TYPE: PRT
<213> ORGANISM: Artificial sequence
<220> FEATURE:
<223> OTHER INFORMATION: Synthetic peptide

<400> SEQUENCE: 41

Gln Lys Trp Gly Tyr Asp Pro Arg Arg Thr Asp Phe Glu Phe
1               5                   10

<210> SEQ ID NO 42
<211> LENGTH: 17
<212> TYPE: PRT
<213> ORGANISM: Artificial sequence
<220> FEATURE:
<223> OTHER INFORMATION: Synthetic peptide

<400> SEQUENCE: 42

Ala Ile Asn Ser Gly Gly Gly Trp Thr Ser Tyr Val Asp Ser Val Lys
1               5                   10                  15

Gly
```

<210> SEQ ID NO 43
<211> LENGTH: 14
<212> TYPE: PRT
<213> ORGANISM: Artificial sequence
<220> FEATURE:
<223> OTHER INFORMATION: Synthetic peptide

<400> SEQUENCE: 43

Tyr Ser Gly Pro Glu Leu Asn Thr Gln Tyr Gly Met Asp Tyr
1               5                   10

<210> SEQ ID NO 44
<211> LENGTH: 17
<212> TYPE: PRT
<213> ORGANISM: Artificial sequence
<220> FEATURE:
<223> OTHER INFORMATION: Synthetic peptide

<400> SEQUENCE: 44

Ala Ile Asn Arg Gly Gly Gly Ser Thr Tyr Tyr Ala Asp Ser Val Lys
1               5                   10                  15

Gly

<210> SEQ ID NO 45
<211> LENGTH: 7
<212> TYPE: PRT
<213> ORGANISM: Artificial sequence
<220> FEATURE:
<223> OTHER INFORMATION: Synthetic peptide

<400> SEQUENCE: 45

Thr Asn Tyr Phe Tyr Trp Ser
1               5

<210> SEQ ID NO 46
<211> LENGTH: 16
<212> TYPE: PRT
<213> ORGANISM: Artificial sequence
<220> FEATURE:
<223> OTHER INFORMATION: Synthetic peptide

<400> SEQUENCE: 46

Ala Ile Ala Tyr Ser Gly Arg Thr Tyr Tyr Ser Pro Ser Leu Lys Ser
1               5                   10                  15

<210> SEQ ID NO 47
<211> LENGTH: 11
<212> TYPE: PRT
<213> ORGANISM: Artificial sequence
<220> FEATURE:
<223> OTHER INFORMATION: Synthetic peptide

<400> SEQUENCE: 47

Gly Pro Lys Gly Leu Ala Ser Tyr Tyr Asp Tyr
1               5                   10

<210> SEQ ID NO 48
<211> LENGTH: 5
<212> TYPE: PRT
<213> ORGANISM: Artificial sequence
<220> FEATURE:
<223> OTHER INFORMATION: Synthetic peptide

<400> SEQUENCE: 48

Arg Tyr Ser Met Ser

```
<210> SEQ ID NO 49
<211> LENGTH: 17
<212> TYPE: PRT
<213> ORGANISM: Artificial sequence
<220> FEATURE:
<223> OTHER INFORMATION: Synthetic peptide

<400> SEQUENCE: 49

Thr Ile Asn Ser Gly Gly Gly Ser Thr Ser Tyr Val Asp Ser Val Lys
1               5                   10                  15

Gly

<210> SEQ ID NO 50
<211> LENGTH: 15
<212> TYPE: PRT
<213> ORGANISM: Artificial sequence
<220> FEATURE:
<223> OTHER INFORMATION: Synthetic peptide

<400> SEQUENCE: 50

Ser Gln Gly Gly Ile Ser Phe Ser Thr Gln Tyr Gly Met Asp Tyr
1               5                   10                  15

<210> SEQ ID NO 51
<211> LENGTH: 7
<212> TYPE: PRT
<213> ORGANISM: Artificial sequence
<220> FEATURE:
<223> OTHER INFORMATION: Synthetic peptide

<400> SEQUENCE: 51

Thr Asn Tyr Tyr Ser Trp Ser
1               5

<210> SEQ ID NO 52
<211> LENGTH: 16
<212> TYPE: PRT
<213> ORGANISM: Artificial sequence
<220> FEATURE:
<223> OTHER INFORMATION: Synthetic peptide

<400> SEQUENCE: 52

Tyr Ile Ala Tyr Ser Gly Ser Thr Ser Tyr Ser Pro Ser Leu Lys Ser
1               5                   10                  15

<210> SEQ ID NO 53
<211> LENGTH: 5
<212> TYPE: PRT
<213> ORGANISM: Artificial sequence
<220> FEATURE:
<223> OTHER INFORMATION: Synthetic peptide

<400> SEQUENCE: 53

Ser Tyr Trp Met Tyr
1               5

<210> SEQ ID NO 54
<211> LENGTH: 17
<212> TYPE: PRT
<213> ORGANISM: Artificial sequence
<220> FEATURE:
<223> OTHER INFORMATION: Synthetic peptide

<400> SEQUENCE: 54
```

```
Ala Ile Asn Thr Gly Gly Gly Ser Thr Tyr Tyr Ala Asp Ser Val Lys
1               5                   10                  15

Gly

<210> SEQ ID NO 55
<211> LENGTH: 12
<212> TYPE: PRT
<213> ORGANISM: Artificial sequence
<220> FEATURE:
<223> OTHER INFORMATION: Synthetic peptide

<400> SEQUENCE: 55

Ala Gly Ser Gly Val Ala Gly Thr Gly Tyr Asp Tyr
1               5                   10

<210> SEQ ID NO 56
<211> LENGTH: 14
<212> TYPE: PRT
<213> ORGANISM: Artificial sequence
<220> FEATURE:
<223> OTHER INFORMATION: Synthetic peptide

<400> SEQUENCE: 56

Ala Gly Thr Ser Ser Asp Val Gly Tyr Gly Asn Tyr Val Ser
1               5                   10

<210> SEQ ID NO 57
<211> LENGTH: 7
<212> TYPE: PRT
<213> ORGANISM: Artificial sequence
<220> FEATURE:
<223> OTHER INFORMATION: Synthetic peptide

<400> SEQUENCE: 57

Glu Val Asn Lys Arg Ala Ser
1               5

<210> SEQ ID NO 58
<211> LENGTH: 10
<212> TYPE: PRT
<213> ORGANISM: Artificial sequence
<220> FEATURE:
<223> OTHER INFORMATION: Synthetic peptide

<400> SEQUENCE: 58

Ala Ser Tyr Arg Ser Ser Asn Asn Ala Val
1               5                   10

<210> SEQ ID NO 59
<211> LENGTH: 14
<212> TYPE: PRT
<213> ORGANISM: Artificial sequence
<220> FEATURE:
<223> OTHER INFORMATION: Synthetic peptide

<400> SEQUENCE: 59

Ala Gly Thr Ser Ser Asp Ile Gly Tyr Gly Asn Tyr Val Ser
1               5                   10

<210> SEQ ID NO 60
<211> LENGTH: 7
<212> TYPE: PRT
<213> ORGANISM: Artificial sequence
<220> FEATURE:
<223> OTHER INFORMATION: Synthetic peptide

<400> SEQUENCE: 60
```

```
Lys Val Ser Arg Arg Ala Ser
1               5

<210> SEQ ID NO 61
<211> LENGTH: 10
<212> TYPE: PRT
<213> ORGANISM: Artificial sequence
<220> FEATURE:
<223> OTHER INFORMATION: Synthetic peptide

<400> SEQUENCE: 61

Ala Ser Tyr Arg Tyr Arg Asn Asn Val Val
1               5                   10

<210> SEQ ID NO 62
<211> LENGTH: 11
<212> TYPE: PRT
<213> ORGANISM: Artificial sequence
<220> FEATURE:
<223> OTHER INFORMATION: Synthetic peptide

<400> SEQUENCE: 62

Gln Gly Gly Asn Phe Gly Tyr Tyr Tyr Gly Ser
1               5                   10

<210> SEQ ID NO 63
<211> LENGTH: 7
<212> TYPE: PRT
<213> ORGANISM: Artificial sequence
<220> FEATURE:
<223> OTHER INFORMATION: Synthetic peptide

<400> SEQUENCE: 63

Lys Asp Ser Glu Arg Pro Ser
1               5

<210> SEQ ID NO 64
<211> LENGTH: 10
<212> TYPE: PRT
<213> ORGANISM: Artificial sequence
<220> FEATURE:
<223> OTHER INFORMATION: Synthetic peptide

<400> SEQUENCE: 64

Gln Ser Ala Asp Ser Ser Asp Asn Pro Val
1               5                   10

<210> SEQ ID NO 65
<211> LENGTH: 11
<212> TYPE: PRT
<213> ORGANISM: Artificial sequence
<220> FEATURE:
<223> OTHER INFORMATION: Synthetic peptide

<400> SEQUENCE: 65

Gln Gly Ala Asn Leu Gly Arg Tyr Tyr Gly Ile
1               5                   10

<210> SEQ ID NO 66
<211> LENGTH: 7
<212> TYPE: PRT
<213> ORGANISM: Artificial sequence
<220> FEATURE:
<223> OTHER INFORMATION: Synthetic peptide

<400> SEQUENCE: 66
```

```
Gly Asp Ser Asn Arg Pro Ser
1               5

<210> SEQ ID NO 67
<211> LENGTH: 10
<212> TYPE: PRT
<213> ORGANISM: Artificial sequence
<220> FEATURE:
<223> OTHER INFORMATION: Synthetic peptide

<400> SEQUENCE: 67

Gln Ser Tyr Glu Ser Ser Thr Ser Pro Val
1               5                   10

<210> SEQ ID NO 68
<211> LENGTH: 16
<212> TYPE: PRT
<213> ORGANISM: Artificial sequence
<220> FEATURE:
<223> OTHER INFORMATION: Synthetic peptide

<400> SEQUENCE: 68

Lys Pro Gly Arg Thr Leu Val His Thr Asp Gly Arg Thr Tyr Leu Tyr
1               5                   10                  15

<210> SEQ ID NO 69
<211> LENGTH: 7
<212> TYPE: PRT
<213> ORGANISM: Artificial sequence
<220> FEATURE:
<223> OTHER INFORMATION: Synthetic peptide

<400> SEQUENCE: 69

Gln Val Ser Asn Arg Gly Ser
1               5

<210> SEQ ID NO 70
<211> LENGTH: 9
<212> TYPE: PRT
<213> ORGANISM: Artificial sequence
<220> FEATURE:
<223> OTHER INFORMATION: Synthetic peptide

<400> SEQUENCE: 70

Ala Gln Ala Thr Tyr Tyr Pro Leu Thr
1               5

<210> SEQ ID NO 71
<211> LENGTH: 11
<212> TYPE: PRT
<213> ORGANISM: Artificial sequence
<220> FEATURE:
<223> OTHER INFORMATION: Synthetic peptide

<400> SEQUENCE: 71

Gln Gly Gly Asn Phe Gly Tyr Tyr Tyr Val Ser
1               5                   10

<210> SEQ ID NO 72
<211> LENGTH: 10
<212> TYPE: PRT
<213> ORGANISM: Artificial sequence
<220> FEATURE:
<223> OTHER INFORMATION: Synthetic peptide

<400> SEQUENCE: 72

Leu Ser Tyr Glu Ser Ser Asp Tyr Pro Val
```

```
1               5                   10
```

<210> SEQ ID NO 73
<211> LENGTH: 11
<212> TYPE: PRT
<213> ORGANISM: Artificial sequence
<220> FEATURE:
<223> OTHER INFORMATION: Synthetic peptide

<400> SEQUENCE: 73

```
Gln Gly Gly Lys Phe Gly Ser Tyr Tyr Val Ser
1               5                   10
```

<210> SEQ ID NO 74
<211> LENGTH: 7
<212> TYPE: PRT
<213> ORGANISM: Artificial sequence
<220> FEATURE:
<223> OTHER INFORMATION: Synthetic peptide

<400> SEQUENCE: 74

```
Lys Asp Asn Glu Arg Pro Ser
1               5
```

<210> SEQ ID NO 75
<211> LENGTH: 10
<212> TYPE: PRT
<213> ORGANISM: Artificial sequence
<220> FEATURE:
<223> OTHER INFORMATION: Synthetic peptide

<400> SEQUENCE: 75

```
Gln Ser Gly Ser Ser Ser Asp Asn Ile Val
1               5                   10
```

<210> SEQ ID NO 76
<211> LENGTH: 11
<212> TYPE: PRT
<213> ORGANISM: Artificial sequence
<220> FEATURE:
<223> OTHER INFORMATION: Synthetic peptide

<400> SEQUENCE: 76

```
Gln Gly Gly Asn Phe Gly Arg Tyr Tyr Ala Ser
1               5                   10
```

<210> SEQ ID NO 77
<211> LENGTH: 7
<212> TYPE: PRT
<213> ORGANISM: Artificial sequence
<220> FEATURE:
<223> OTHER INFORMATION: Synthetic peptide

<400> SEQUENCE: 77

```
Arg Asp Ser Glu Arg Pro Ser
1               5
```

<210> SEQ ID NO 78
<211> LENGTH: 10
<212> TYPE: PRT
<213> ORGANISM: Artificial sequence
<220> FEATURE:
<223> OTHER INFORMATION: Synthetic peptide

<400> SEQUENCE: 78

```
Gln Ser Gly Arg Ser Ser Asp Asn Ala Val
1               5                   10
```

```
<210> SEQ ID NO 79
<211> LENGTH: 11
<212> TYPE: PRT
<213> ORGANISM: Artificial sequence
<220> FEATURE:
<223> OTHER INFORMATION: Synthetic peptide

<400> SEQUENCE: 79

Gln Gly Ala Lys Leu Gly Arg Tyr Tyr Gly Ile
1               5                   10

<210> SEQ ID NO 80
<211> LENGTH: 11
<212> TYPE: PRT
<213> ORGANISM: Artificial sequence
<220> FEATURE:
<223> OTHER INFORMATION: Synthetic peptide

<400> SEQUENCE: 80

Gln Gly Gly Asn Phe Gly Arg Tyr Tyr Val Ser
1               5                   10

<210> SEQ ID NO 81
<211> LENGTH: 10
<212> TYPE: PRT
<213> ORGANISM: Artificial sequence
<220> FEATURE:
<223> OTHER INFORMATION: Synthetic peptide

<400> SEQUENCE: 81

Gln Ser Gly Ser Ser Ser Asp Asn Ala Val
1               5                   10

<210> SEQ ID NO 82
<211> LENGTH: 14
<212> TYPE: PRT
<213> ORGANISM: Artificial sequence
<220> FEATURE:
<223> OTHER INFORMATION: Synthetic peptide

<400> SEQUENCE: 82

Ala Gly Thr Ser Ser Asp Val Gly Tyr Gly Asp Tyr Val Ser
1               5                   10

<210> SEQ ID NO 83
<211> LENGTH: 7
<212> TYPE: PRT
<213> ORGANISM: Artificial sequence
<220> FEATURE:
<223> OTHER INFORMATION: Synthetic peptide

<400> SEQUENCE: 83

Lys Val Lys Thr Arg Ala Ser
1               5

<210> SEQ ID NO 84
<211> LENGTH: 10
<212> TYPE: PRT
<213> ORGANISM: Artificial sequence
<220> FEATURE:
<223> OTHER INFORMATION: Synthetic peptide

<400> SEQUENCE: 84

Ala Ser Tyr Lys Asn Gly Gly Thr Ala Val
1               5                   10
```

<210> SEQ ID NO 85
<211> LENGTH: 11
<212> TYPE: PRT
<213> ORGANISM: Artificial sequence
<220> FEATURE:
<223> OTHER INFORMATION: Synthetic peptide

<400> SEQUENCE: 85

Gln Gly Gly Asp Phe Gly Arg Tyr Tyr Val Ala
1               5                   10

<210> SEQ ID NO 86
<211> LENGTH: 7
<212> TYPE: PRT
<213> ORGANISM: Artificial sequence
<220> FEATURE:
<223> OTHER INFORMATION: Synthetic peptide

<400> SEQUENCE: 86

Gln Asp Ser Glu Arg Pro Ser
1               5

<210> SEQ ID NO 87
<211> LENGTH: 10
<212> TYPE: PRT
<213> ORGANISM: Artificial sequence
<220> FEATURE:
<223> OTHER INFORMATION: Synthetic peptide

<400> SEQUENCE: 87

Gln Ser Gly Ile Ser Ser Asp Asn Ile Val
1               5                   10

<210> SEQ ID NO 88
<211> LENGTH: 11
<212> TYPE: PRT
<213> ORGANISM: Artificial sequence
<220> FEATURE:
<223> OTHER INFORMATION: Synthetic peptide

<400> SEQUENCE: 88

Gln Gly Gly Lys Phe Gly Arg Tyr Tyr Ala Ser
1               5                   10

<210> SEQ ID NO 89
<211> LENGTH: 17
<212> TYPE: PRT
<213> ORGANISM: Artificial sequence
<220> FEATURE:
<223> OTHER INFORMATION: Synthetic peptide

<400> SEQUENCE: 89

Lys Ser Ser Gln Ser Val Arg Ile Glu Ser Asn His Lys Thr Tyr Leu
1               5                   10                  15

Asn

<210> SEQ ID NO 90
<211> LENGTH: 7
<212> TYPE: PRT
<213> ORGANISM: Artificial sequence
<220> FEATURE:
<223> OTHER INFORMATION: Synthetic peptide

<400> SEQUENCE: 90

Asp Ala Ser Ser Arg Glu Ser
1               5

```
<210> SEQ ID NO 91
<211> LENGTH: 8
<212> TYPE: PRT
<213> ORGANISM: Artificial sequence
<220> FEATURE:
<223> OTHER INFORMATION: Synthetic peptide

<400> SEQUENCE: 91

Gln Gln Ala Tyr Ala Ala Pro Thr
1               5

<210> SEQ ID NO 92
<211> LENGTH: 11
<212> TYPE: PRT
<213> ORGANISM: Artificial sequence
<220> FEATURE:
<223> OTHER INFORMATION: Synthetic peptide

<400> SEQUENCE: 92

Gln Gly Gly Asn Phe Gly Ser Tyr Tyr Ala Ser
1               5                   10

<210> SEQ ID NO 93
<211> LENGTH: 7
<212> TYPE: PRT
<213> ORGANISM: Artificial sequence
<220> FEATURE:
<223> OTHER INFORMATION: Synthetic peptide

<400> SEQUENCE: 93

Arg Asp Ser Gly Arg Pro Ser
1               5

<210> SEQ ID NO 94
<211> LENGTH: 10
<212> TYPE: PRT
<213> ORGANISM: Artificial sequence
<220> FEATURE:
<223> OTHER INFORMATION: Synthetic peptide

<400> SEQUENCE: 94

Gln Ser Gly Ser Ser Ser Asp Asn Thr Val
1               5                   10

<210> SEQ ID NO 95
<211> LENGTH: 14
<212> TYPE: PRT
<213> ORGANISM: Artificial sequence
<220> FEATURE:
<223> OTHER INFORMATION: Synthetic peptide

<400> SEQUENCE: 95

Gly Leu Ser Ser Gly Ser Val Thr Ser Ser Asn Tyr Pro Gly
1               5                   10

<210> SEQ ID NO 96
<211> LENGTH: 7
<212> TYPE: PRT
<213> ORGANISM: Artificial sequence
<220> FEATURE:
<223> OTHER INFORMATION: Synthetic peptide

<400> SEQUENCE: 96

Asn Thr Asn Ser Arg Tyr Ser
1               5
```

<210> SEQ ID NO 97
<211> LENGTH: 11
<212> TYPE: PRT
<213> ORGANISM: Artificial sequence
<220> FEATURE:
<223> OTHER INFORMATION: Synthetic peptide

<400> SEQUENCE: 97

Ala Leu Asn Arg Val Arg Gly Thr Tyr Arg Val
1               5                   10

<210> SEQ ID NO 98
<211> LENGTH: 10
<212> TYPE: PRT
<213> ORGANISM: Artificial sequence
<220> FEATURE:
<223> OTHER INFORMATION: Synthetic peptide

<400> SEQUENCE: 98

Gln Ser Gly Thr Ser Ser Asp Asn Ile Val
1               5                   10

<210> SEQ ID NO 99
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 99

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Ser Trp Asn Gly Ser Thr Tyr Tyr Ala Glu Ser Met
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Asp Arg Asn Leu Gly Tyr Arg Leu Gly Tyr Pro Tyr Asp Tyr
            100                 105                 110

Trp Gly Gln Gly Thr Gln Val Thr Val Ser Ser
        115                 120

<210> SEQ ID NO 100
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 100

Gln Ser Val Leu Thr Gln Pro Pro Ser Val Ser Gly Ser Pro Gly Glu
1               5                   10                  15

Thr Val Thr Ile Ser Cys Ala Gly Thr Ser Ser Asp Val Gly Tyr Gly
            20                  25                  30

Asn Tyr Val Ser Trp Tyr Gln Gln Leu Pro Gly Met Ala Pro Arg Leu
        35                  40                  45

```
Leu Ile Tyr Glu Val Asn Lys Arg Ala Ser Gly Ile Thr Asp Arg Phe
 50                  55                  60

Ser Gly Ser Lys Ser Gly Asn Thr Ala Ser Leu Thr Ile Ser Gly Leu
 65                  70                  75                  80

Gln Ser Glu Asp Glu Gly Asp Tyr Tyr Cys Ala Ser Tyr Arg Ser Ser
                 85                  90                  95

Asn Asn Ala Val Phe Gly Gly Gly Thr His Leu Thr Val Leu
            100                 105                 110

<210> SEQ ID NO 101
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 101

Gln Leu Gln Leu Val Glu Ser Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ala Ile Asn Ser Gly Gly Gly Ser Thr Ser Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                 85                  90                  95

Ala Thr Pro Gly Asp Arg Leu Trp Tyr Tyr Arg Tyr Asp Tyr Trp Gly
            100                 105                 110

Gln Gly Thr Gln Val Thr Val Ser Ser
        115                 120

<210> SEQ ID NO 102
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 102

Gln Ala Gly Leu Thr Gln Pro Pro Ser Val Ser Gly Thr Leu Gly Lys
 1               5                  10                  15

Ala Val Thr Ile Ser Cys Ala Gly Thr Ser Ser Asp Ile Gly Tyr Gly
             20                  25                  30

Asn Tyr Val Ser Trp Tyr Gln Gln Leu Pro Gly Thr Ala Pro Lys Leu
             35                  40                  45

Leu Ile Tyr Lys Val Ser Arg Arg Ala Ser Gly Val Pro Asp Arg Phe
 50                  55                  60

Ser Gly Ser Lys Ser Gly Asn Thr Ala Ser Leu Ser Ile Ser Gly Leu
 65                  70                  75                  80

Gln Ser Glu Asp Glu Ala Asp Tyr Tyr Cys Ala Ser Tyr Arg Tyr Arg
                 85                  90                  95

Asn Asn Val Val Phe Gly Gly Gly Thr His Leu Thr Val Leu
            100                 105                 110

<210> SEQ ID NO 103
```

<211> LENGTH: 125
<212> TYPE: PRT
<213> ORGANISM: Artificial sequence
<220> FEATURE:
<223> OTHER INFORMATION: Synthetic polypeptide

<400> SEQUENCE: 103

Gln Val Gln Arg Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Ser
            20                  25                  30

Tyr Tyr Ala Trp Ser Trp Ile Arg Gln Pro Pro Gly Lys Gly Leu Glu
        35                  40                  45

Trp Met Gly Val Ile Ala Ser Asp Gly Ser Thr Tyr Tyr Ser Pro Ser
    50                  55                  60

Leu Lys Ser Arg Thr Ser Ile Ser Arg Asp Thr Ser Lys Asn Gln Phe
65                  70                  75                  80

Ser Leu Gln Leu Ser Ser Val Thr Pro Glu Asp Thr Ala Val Tyr Tyr
                85                  90                  95

Cys Ala Leu Tyr Ile Arg Gly Ser Ser Trp Ser Gly Trp Ser Ala Tyr
            100                 105                 110

Asp Tyr Trp Gly Gln Gly Thr Gln Val Thr Val Ser Ser
        115                 120                 125

<210> SEQ ID NO 104
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 104

Gln Pro Val Leu Asn Gln Pro Ser Ala Val Ser Val Ser Leu Gly Gln
1               5                   10                  15

Thr Ala Arg Ile Thr Cys Gln Gly Gly Asn Phe Gly Tyr Tyr Tyr Gly
            20                  25                  30

Ser Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Gly Thr Ala Thr Leu Thr Ile Ser Arg Ala Gln Ala Glu
65                  70                  75                  80

Asp Glu Ala Asp Tyr Tyr Cys Gln Ser Ala Asp Ser Ser Asp Asn Pro
                85                  90                  95

Val Phe Gly Gly Gly Thr His Leu Thr Val Leu
            100                 105

<210> SEQ ID NO 105
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 105

Gln Val Gln Leu Val Glu Ser Gly Pro Gly Leu Val Lys Pro Ser Gln
1               5                   10                  15

Thr Leu Ser Leu Thr Cys Thr Val Ser Gly Gly Ser Ile Thr Thr Asn
            20                  25                  30

```
Ser Tyr Tyr Trp Ser Trp Ile Arg Gln Pro Pro Gly Lys Gly Leu Glu
        35                  40                  45

Trp Met Gly Ala Ile Ala Tyr Ser Gly Ser Thr Tyr Tyr Ser Pro Ser
 50                  55                  60

Leu Lys Ser Arg Thr Ser Ile Ser Arg Asp Thr Ser Lys Asn Gln Phe
65                  70                  75                  80

Thr Leu His Leu Ser Ser Val Thr Pro Glu Asp Thr Ala Val Tyr Tyr
                85                  90                  95

Cys Ala Arg Arg Pro Asn Trp Tyr Arg Ala Leu Asp Ala Trp Gly Gln
            100                 105                 110

Gly Thr Leu Val Thr Val Ser Ser
        115                 120

<210> SEQ ID NO 106
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 106

Asn Phe Met Leu Thr Gln Pro Ser Ala Val Ser Val Ser Leu Gly Gln
1               5                   10                  15

Thr Ala Arg Ile Thr Cys Gln Gly Ala Asn Leu Gly Arg Tyr Tyr Gly
            20                  25                  30

Ile Trp Tyr Gln Gln Lys Pro Gly Gln Ala Pro Val Gln Val Ile Tyr
        35                  40                  45

Gly Asp Ser Asn Arg Pro Ser Gly Ile Pro Glu Arg Phe Ser Gly Ser
 50                  55                  60

Ser Ser Gly Gly Thr Ala Thr Leu Thr Ile Ser Gly Ala Gln Ala Glu
65                  70                  75                  80

Asp Glu Ala Asp Tyr Tyr Cys Gln Ser Tyr Glu Ser Ser Thr Ser Pro
                85                  90                  95

Val Phe Gly Gly Gly Thr His Leu Thr Val Leu
            100                 105

<210> SEQ ID NO 107
<211> LENGTH: 114
<212> TYPE: PRT
<213> ORGANISM: Artificial sequence
<220> FEATURE:
<223> OTHER INFORMATION: Synthetic polypeptide

<400> SEQUENCE: 107

Gln Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Val Tyr
            20                  25                  30

Ala Met Ser Trp Val Arg Gln Ala Pro Gly Lys Gly Leu Glu Trp Val
        35                  40                  45

Ala Asp Ile Asn Thr Ser Gly Asp Ser Thr Thr Tyr Ala Asp Ser Val
 50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Asn Arg Tyr Thr Gln Glu Arg Gly Gln Gly Thr Gln Val Thr Val
            100                 105                 110
```

Ser Ser

<210> SEQ ID NO 108
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 108

Asp Val Val Leu Thr Gln Thr Pro Gly Ser Leu Ser Val Val Pro Gly
1               5                   10                  15

Glu Ala Ala Ser Ile Ser Cys Lys Pro Gly Arg Thr Leu Val His Thr
            20                  25                  30

Asp Gly Arg Thr Tyr Leu Tyr Trp Leu Gln Gln Lys Pro Gly Gln Arg
        35                  40                  45

Pro Gln Leu Leu Ile Tyr Gln Val Ser Asn Arg Gly Ser Gly Val Pro
    50                  55                  60

Asp Arg Phe Thr Gly Ser Gly Ser Gly Thr Asp Phe Thr Leu Lys Ile
65                  70                  75                  80

Ser Gly Val Lys Ala Glu Asp Ala Gly Val Tyr Tyr Cys Ala Gln Ala
                85                  90                  95

Thr Tyr Tyr Pro Leu Thr Phe Gly Ser Gly Thr Arg Leu Glu Ile Lys
            100                 105                 110

<210> SEQ ID NO 109
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 109

Gln Val Gln Leu Val Glu Ser Gly Gly Gly Leu Val Gln Pro Gly Gly
1               5                   10                  15

Ser Leu Arg Val Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Ala Ile Asn Ser Gly Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Val Gln Asn Gly Gly Ile Trp Ser Phe Gly Ser Trp Gly Gln Gly Thr
            100                 105                 110

Gln Val Thr Val Ser Ser
        115

<210> SEQ ID NO 110
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 110

Ser Ser Ala Leu Thr Gln Pro Ser Ala Ile Ser Val Ser Leu Gly Gln

```
                1               5                      10                     15
Thr Ala Arg Ile Thr Cys Gln Gly Gly Asn Phe Gly Tyr Tyr Tyr Val
                20                     25                     30

Ser Trp Tyr Gln Gln Lys Pro Gly Gln Ala Pro Val Gln Val Ile Tyr
                35                     40                     45

Gly Asp Ser Asn Arg Pro Ser Gly Ile Pro Glu Arg Phe Ser Gly Ser
        50                     55                     60

Ser Ser Gly Gly Thr Ala Thr Leu Thr Ile Ser Gly Ala Gln Ala Glu
65                     70                     75                     80

Asp Glu Ala Asp Tyr Tyr Cys Leu Ser Tyr Glu Ser Ser Asp Tyr Pro
                        85                     90                     95

Val Phe Gly Gly Gly Thr His Leu Thr Val Leu
                100                    105

<210> SEQ ID NO 111
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 111

Glu Val Gln Leu Val Glu Ser Gly Gly Gly Leu Val Gln Pro Gly Gly
1               5                      10                     15

Ser Leu Arg Leu Ser Cys Ala Ala Ser Gly Phe Thr Phe Ser Ser Tyr
                20                     25                     30

Ala Met Ser Trp Val Arg Gln Ala Pro Gly Lys Gly Leu Glu Trp Val
            35                     40                     45

Ser Pro Ile Asn Ser Gly Ser Asp Ser Ala Ser Tyr Val Asp Ser Val
        50                     55                     60

Lys Gly Arg Phe Thr Ile Ser Arg Asp Asn Ala Lys Asn Thr Leu Tyr
65                     70                     75                     80

Leu Gln Met Asn Ser Leu Lys Pro Glu Asp Thr Ala Val Tyr Tyr Cys
                        85                     90                     95

Ala Lys Ala Arg Thr Ser Val Val Ala Gly Gly Met Asp Tyr Trp Gly
                100                    105                    110

Lys Gly Thr Leu Val Thr Val Ser Ser
            115                    120

<210> SEQ ID NO 112
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 112

Gln Ser Ala Leu Thr Gln Pro Ser Ala Val Ser Val Ser Leu Gly Gln
1               5                      10                     15

Thr Ala Arg Ile Thr Cys Gln Gly Gly Lys Phe Gly Ser Tyr Tyr Val
                20                     25                     30

Ser Trp Tyr Gln Gln Lys Pro Gly Gln Ala Pro Val Met Val Ile Tyr
                35                     40                     45

Lys Asp Asn Glu Arg Pro Ser Gly Ile Pro Glu Arg Phe Ser Gly Ser
        50                     55                     60

Ser Ser Gly Ser Thr Ser Thr Leu Thr Ile Ser Gly Ala Gln Ala Glu
65                     70                     75                     80
```

```
Asp Glu Gly Thr Tyr Tyr Cys Gln Ser Gly Ser Ser Asp Asn Ile
                85                  90                  95

Val Phe Gly Gly Gly Thr Glu Leu Thr Val Phe
            100                 105

<210> SEQ ID NO 113
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 113

Gln Leu Gln Val Val Glu Ser Gly Gly Gly Leu Val Gln Thr Gly Gly
1               5                   10                  15

Ser Leu Thr Leu Ser Cys Thr Thr Ser Gly Phe Thr Phe Ser Arg Tyr
            20                  25                  30

Trp Met Ile Trp Val Arg Gln Ala Pro Gly Lys Gly Leu Glu Trp Val
        35                  40                  45

Ser Ser Ile Tyr Asn Asp Gly Gly Asn Thr Tyr Tyr Ala Asp Ser Val
    50                  55                  60

Lys Gly Arg Phe Thr Ile Ser Arg Asp Asn Ser Glu Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Leu Lys Ala Ala Tyr Tyr Gly Met Asp Tyr Trp Gly Lys Gly
            100                 105                 110

Thr Leu Val Thr Val Ser Ser
        115

<210> SEQ ID NO 114
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 114

Ser Ser Ala Leu Thr Gln Pro Ser Ala Val Ser Val Ser Leu Gly Gln
1               5                   10                  15

Thr Ala Arg Ile Thr Cys Gln Gly Ala Asn Leu Gly Arg Tyr Tyr Gly
            20                  25                  30

Ile Trp Tyr Gln Gln Lys Pro Gly Gln Ala Pro Val Gln Val Ile Tyr
        35                  40                  45

Gly Asp Ser Asn Arg Pro Ser Gly Ile Pro Glu Arg Phe Ser Gly Ser
    50                  55                  60

Ser Ser Gly Gly Thr Ala Thr Leu Thr Ile Ser Gly Ala Gln Ala Glu
65                  70                  75                  80

Asp Glu Ala Asp Tyr Tyr Cys Gln Ser Tyr Glu Ser Ser Thr Ser Pro
                85                  90                  95

Val Phe Gly Gly Gly Thr His Leu Thr Val Leu
            100                 105

<210> SEQ ID NO 115
<211> LENGTH: 124
<212> TYPE: PRT
<213> ORGANISM: Artificial sequence
<220> FEATURE:
<223> OTHER INFORMATION: Synthetic polypeptide
```

<400> SEQUENCE: 115

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asn Ile Asn Ser Gly Gly Ser Thr Gly Tyr Ala Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Met Ala Val Tyr Tyr Cys
                85                  90                  95

Ala Lys Tyr Leu Arg Thr Tyr Tyr Pro Asn Ala Ala Phe Gly Met Asp
            100                 105                 110

Tyr Trp Gly Lys Gly Thr Leu Val Thr Val Ser Ser
        115                 120

<210> SEQ ID NO 116
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 116

Gln Ala Val Leu Thr Gln Pro Ser Ala Val Ser Val Ser Leu Gly Gln
1               5                   10                  15

Thr Ala Arg Ile Thr Cys Gln Gly Gly Asn Phe Gly Arg Tyr Tyr Ala
            20                  25                  30

Ser Trp Tyr Gln Gln Lys Pro Gly Gln Ala Pro Val Leu Val Ile Tyr
        35                  40                  45

Arg Asp Ser Glu Arg Pro Ser Gly Ile Pro Glu Arg Phe Ser Gly Ser
    50                  55                  60

Ser Ser Gly Asp Thr Ala Thr Leu Thr Ile Ser Gly Ala Gln Ala Glu
65                  70                  75                  80

Asp Glu Ala Asp Tyr Tyr Cys Gln Ser Gly Arg Ser Ser Asp Asn Ala
                85                  90                  95

Val Phe Gly Gly Gly Thr His Leu Thr Gly Leu
            100                 105

<210> SEQ ID NO 117
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 117

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Tyr Trp Val Arg Gln Ala Pro Gly Lys Gly Leu Glu Trp Val
        35                  40                  45

Ser Ala Ile Asp Val Gly Gly Gly Thr Thr Asp Tyr Ala Gly Ser Val
50                  55                  60

```
Lys Gly Arg Phe Thr Ile Ser Arg Asp Asn Thr Lys Ser Thr Val Tyr
 65                  70                  75                  80

Leu Gln Met Asn Thr Leu Lys Pro Glu Asp Thr Ala Leu Tyr Tyr Cys
             85                  90                  95

Leu Arg Gly Gly Ser Tyr Tyr Gly Gly Met Asp Tyr Trp Gly Lys Gly
            100                 105                 110

Thr Leu Val Thr Val Ser Ser
            115
```

<210> SEQ ID NO 118
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 118

```
Gln Ser Ala Leu Thr Gln Pro Ser Ala Val Ser Val Ser Leu Gly Gln
 1               5                  10                  15

Thr Ala Arg Ile Thr Cys Gln Gly Ala Lys Leu Gly Arg Tyr Tyr Gly
             20                  25                  30

Ile Trp Tyr Gln Gln Lys Pro Gly Gln Ala Pro Val Gln Val Ile Tyr
             35                  40                  45

Gly Asp Ser Asn Arg Pro Ser Gly Ile Pro Glu Arg Phe Ser Gly Ser
 50                  55                  60

Ser Ser Gly Gly Thr Ala Thr Leu Thr Ile Ser Gly Ala Gln Ala Glu
 65                  70                  75                  80

Asp Glu Ala Asp Tyr Tyr Cys Gln Ser Tyr Glu Ser Ser Thr Ser Pro
             85                  90                  95

Val Phe Gly Gly Gly Thr His Leu Thr Val Leu
            100                 105
```

<210> SEQ ID NO 119
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 119

```
Glu Leu Gln Leu Val Glu Ser Gly Gly Gly Leu Val Gln Pro Gly Gly
 1               5                  10                  15

Ser Leu Arg Leu Ser Cys Ser Ala Ser Gly Phe Thr Phe Gly Ala Tyr
             20                  25                  30

Ala Met Asn Trp Val Arg Gln Ala Pro Gly Lys Gly Leu Glu Trp Val
             35                  40                  45

Ser Gly Val Asn Ser Gly Gly Leu Thr Ser Tyr Gly Glu Ser Val
             50                  55                  60

Lys Gly Arg Phe Thr Ile Ser Arg Asp Asn Ala Lys Asn Thr Leu Tyr
 65                  70                  75                  80

Leu Gln Met Asn Arg Leu Asn Pro Asp Asp Thr Ala Val Tyr Tyr Cys
             85                  90                  95

Ala Lys Ser Lys Arg Gly Ala Val Ala Gly Thr Gly Asp Asp Tyr
            100                 105                 110

Trp Gly Gln Gly Thr Gln Val Thr Val Ser Ser
            115                 120
```

<210> SEQ ID NO 120

<211> LENGTH: 107
<212> TYPE: PRT
<213> ORGANISM: Artificial sequence
<220> FEATURE:
<223> OTHER INFORMATION: Synthetic polypeptide

<400> SEQUENCE: 120

Ser Ser Ala Leu Thr Gln Pro Ser Ala Val Ser Val Ser Leu Gly Gln
1               5                   10                  15
Thr Ala Arg Ile Thr Cys Gln Gly Gly Asn Phe Gly Arg Tyr Tyr Val
            20                  25                  30
Ser Trp Tyr Gln Gln Lys Pro Gly Gln Ala Pro Val Leu Val Ile Tyr
        35                  40                  45
Lys Asp Ser Glu Arg Pro Ser Gly Ile Pro Glu Arg Phe Ser Gly Ser
50                  55                  60
Ser Ser Gly Asp Thr Ala Thr Leu Thr Ile Ser Gly Ala Gln Ala Glu
65                  70                  75                  80
Asp Glu Ala Asp Tyr Tyr Cys Gln Ser Gly Ser Ser Ser Asp Asn Ala
                85                  90                  95
Val Phe Gly Gly Gly Thr His Leu Thr Val Leu
            100                 105

<210> SEQ ID NO 121
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 121

Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Asp Asp Tyr
            20                  25                  30
Ala Met Ser Trp Val Arg Gln Ala Pro Gly Lys Gly Leu Glu Trp Val
        35                  40                  45
Ser Ala Ile Ser Trp Asn Gly Gly Ser Thr Tyr Tyr Ala Glu Ser Met
50                  55                  60
Lys Gly Arg Phe Thr Ile Ser Arg Asp Asn Ala Lys Asn Thr Leu Tyr
65                  70                  75                  80
Leu Gln Met Asn Ser Leu Lys Ser Glu Asp Ala Ala Val Tyr Tyr Cys
                85                  90                  95
Ala Lys Asp Leu Ser Ala Ser Gly Ser Tyr Tyr His Thr Phe Gly Ser
            100                 105                 110
Trp Gly Gln Gly Thr Gln Val Thr Val Ser Ser
        115                 120

<210> SEQ ID NO 122
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 122

Gln Ala Gly Leu Thr Gln Pro Pro Ser Val Ala Gly Thr Leu Gly Lys
1               5                   10                  15
Thr Val Thr Ile Ser Cys Ala Gly Thr Ser Ser Asp Val Gly Tyr Gly
            20                  25                  30

Asp Tyr Val Ser Trp Tyr Gln His Ile Pro Gly Thr Ala Pro Lys Leu
            35                  40                  45

Leu Ile Tyr Lys Val Lys Thr Arg Ala Ser Gly Ile Pro Asp Arg Phe
50                  55                  60

Ser Gly Ser Lys Ser Gly Asn Thr Ala Ser Leu Thr Ile Ser Gly Leu
65                  70                  75                  80

Gln Ser Gly Asp Glu Ser Asp Tyr Tyr Cys Ala Ser Tyr Lys Asn Gly
                85                  90                  95

Gly Thr Ala Val Phe Gly Gly Gly Thr His Leu Thr Val Leu
            100                 105                 110

<210> SEQ ID NO 123
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 123

Gln Val Gln Arg Gln Glu Ser Gly Pro Gly Leu Val Lys Pro Ser Gln
1               5                   10                  15

Thr Leu Ser Val Thr Cys Thr Val Ser Gly Gly Ser Ile Thr Thr Gly
            20                  25                  30

Pro Tyr Ser Trp Ser Trp Ile Arg Gln Pro Pro Gly Lys Gly Leu Glu
        35                  40                  45

Trp Ile Gly Tyr Ile Gly Tyr Ser Gly Ser Thr Tyr Tyr Ser Pro Ser
    50                  55                  60

Leu Lys Ser Arg Thr Ser Ile Ser Arg Asp Thr Ser Asn Asn Gln Phe
65                  70                  75                  80

Ser Leu Gln Leu Ser Ser Val Thr Pro Glu Asp Thr Ala Val Tyr Tyr
                85                  90                  95

Cys Ala Arg Ser Arg Ser Ser Pro Thr Thr Phe Gly Met Asp Tyr Trp
            100                 105                 110

Gly Lys Gly Thr Leu Val Thr Val Ser Ser
        115                 120

<210> SEQ ID NO 124
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 124

Ser Ser Ala Leu Thr Gln Pro Ser Ala Val Ser Val Ser Leu Gly Gln
1               5                   10                  15

Thr Ala Arg Ile Thr Cys Gln Gly Gly Asp Phe Gly Arg Tyr Tyr Val
            20                  25                  30

Ala Trp Tyr Thr Gln Lys Pro Gly Gln Ala Pro Val Leu Val Ile Tyr
        35                  40                  45

Gln Asp Ser Glu Arg Pro Ser Gly Ile Pro Glu Arg Phe Ser Gly Ser
    50                  55                  60

Ser Ser Gly Asp Thr Ala Thr Leu Thr Ile Ser Gly Ala Gln Ala Glu
65                  70                  75                  80

Asp Glu Ala Glu Tyr Tyr Cys Gln Ser Gly Ile Ser Ser Asp Asn Ile
                85                  90                  95

Val Phe Gly Gly Gly Thr His Leu Thr Val Leu
            100                 105

<210> SEQ ID NO 125
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 125

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Asn
            20                  25                  30

Tyr Tyr Tyr Trp Ser Trp Ile Arg Gln Pro Pro Gly Lys Gly Leu Glu
        35                  40                  45

Trp Met Gly Ala Ile Ala Tyr Ser Gly Ser Thr Tyr Tyr Ser Pro Ser
    50                  55                  60

Leu Lys Ser Arg Thr Ser Ile Ser Arg Asp Thr Ser Lys Asn Gln Phe
65                  70                  75                  80

Thr Leu Gln Leu Ser Ser Val Thr Pro Glu Asp Thr Ala Val Tyr Tyr
                85                  90                  95

Cys Ala Arg Ala Pro Tyr Gly Ile Ser Arg Glu Tyr Asp Tyr Trp Gly
            100                 105                 110

Gln Gly Thr Gln Val Thr Val Ser Ser
        115                 120
```

<210> SEQ ID NO 126
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 126

```
His Ser Ala Val Thr Gln Pro Ser Ala Val Ser Val Ser Leu Gly Gln
1               5                   10                  15

Thr Ala Arg Ile Thr Cys Gln Gly Gly Lys Phe Gly Arg Tyr Tyr Ala
            20                  25                  30

Ser Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Asp Thr Ala Thr Leu Ser Ile Ser Gly Ala Gln Ala Glu
65                  70                  75                  80

Asp Glu Ala Asp Tyr Phe Cys Gln Ser Gly Arg Ser Ser Asp Asn Ala
                85                  90                  95

Val Phe Gly Gly Gly Thr His Leu Thr Val Leu
            100                 105
```

<210> SEQ ID NO 127
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 127

```
Gln Leu Gln Leu Val Glu Ser Gly Gly Gly Leu Val Gln Pro Gly Gly
1               5                   10                  15
```

```
Ser Leu Arg Leu Ser Cys Val Ala Ser Gly Phe Thr Phe Arg Asn Tyr
            20                  25                  30

Pro Met Thr Trp Val Arg Gln Ala Pro Gly Lys Gly Pro Glu Trp Val
        35                  40                  45

Ser Ala Ile Asn Gly Gly Asp Ile Pro Tyr Tyr Ala Asp Ser Val
    50                  55                  60

Lys Gly Arg Phe Thr Ile Ser Arg Asp Asn Ala Lys Asn Thr Val Tyr
 65                 70                  75                  80

Leu Gln Met Asp Ser Leu Lys Pro Glu Asp Thr Ala Met Tyr Tyr Cys
                85                  90                  95

Ala Lys Gln Lys Trp Gly Tyr Asp Pro Arg Arg Thr Asp Phe Glu Phe
            100                 105                 110

Arg Gly Gln Gly Thr Gln Val Thr Val Ser Ser
            115                 120
```

```
<210> SEQ ID NO 128
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 128

Glu Thr Val Pro Thr Gln Ser Pro Ser Val Thr Ala Ser Val Gly
1               5                   10                  15

Glu Lys Val Thr Ile Thr Cys Lys Ser Ser Gln Ser Val Arg Ile Glu
            20                  25                  30

Ser Asn His Lys Thr Tyr Leu Asn Trp Tyr Gln Gln Arg Pro Gly Arg
        35                  40                  45

Gly Pro Arg Leu Leu Ile Tyr Asp Ala Ser Ser Arg Glu Ser Gly Ile
    50                  55                  60

Pro Asp Arg Phe Ser Gly Ser Gly Ser Thr Ser Asp Phe Thr Leu Thr
 65                 70                  75                  80

Ile Ser Ser Val Gln Pro Glu Asp Ala Ala Val Tyr Tyr Cys Gln Gln
                85                  90                  95

Ala Tyr Ala Ala Pro Thr Phe Gly Gln Gly Thr Lys Leu Glu Ile Lys
            100                 105                 110
```

```
<210> SEQ ID NO 129
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 129

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ser Gly Gly Gly Trp Thr Ser Tyr Val Asp Ser Val
    50                  55                  60

Lys Gly Arg Phe Thr Ile Ser Arg Asp Asn Ala Lys Asn Thr Leu Tyr
 65                 70                  75                  80

Leu Gln Met Asp Ser Leu Lys Pro Glu Asp Thr Ala Val Tyr Tyr Cys
                85                  90                  95
```

```
Thr Lys Tyr Ser Gly Pro Glu Leu Asn Thr Gln Tyr Gly Met Asp Tyr
            100                 105                 110

Trp Gly Lys Gly Thr Leu Val Thr Val Ser Ser
            115                 120
```

<210> SEQ ID NO 130
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 130

```
Asn Phe Met Leu Thr Gln Pro Ser Ala Val Ser Val Ser Leu Gly Gln
1               5                   10                  15

Thr Ala Arg Ile Thr Cys Gln Gly Gly Asn Phe Gly Ser Tyr Tyr Ala
            20                  25                  30

Ser Trp Tyr Gln Gln Lys Pro Gly Gln Ala Pro Val Leu Val Ile Tyr
        35                  40                  45

Arg Asp Ser Gly Arg Pro Ser Gly Ile Pro Glu Arg Phe Ser Gly Ser
    50                  55                  60

Ser Ser Gly Asp Thr Ala Thr Leu Thr Ile Ser Gly Ala Gln Ala Glu
65                  70                  75                  80

Asp Glu Ala Asp Tyr Tyr Cys Gln Ser Gly Ser Ser Ser Asp Asn Thr
                85                  90                  95

Val Phe Gly Gly Gly Thr His Leu Thr Val Leu
            100                 105
```

<210> SEQ ID NO 131
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 131

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Ala Ile Asn Arg Gly Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Ala Ala Val Tyr Tyr Cys
                85                  90                  95

Ala Thr Pro Gly Asp Arg Leu Tyr Tyr Arg Tyr Asp Tyr Trp Gly
            100                 105                 110

Gln Gly Ala Gln Val Thr Val Ser Ser
        115                 120
```

<210> SEQ ID NO 132
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 132

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Gly Trp Tyr Gln Gln Thr Pro Gly Gln Ala Pro Arg Leu
        35                  40                  45

Leu Ile Tyr Asn Thr Asn Ser Arg Tyr Ser Gly Val Pro Asn Arg Phe
    50                  55                  60

Ser Gly Ser Ile Ser Gly Asn Lys Ala Ala Leu Ile Ile Ser Gly Ala
65                  70                  75                  80

Gln Pro Glu Asp Glu Ala Asp Tyr His Cys Ala Leu Asn Arg Val Arg
                85                  90                  95

Gly Thr Tyr Arg Val Phe Gly Gly Gly Thr His Leu Thr Val Leu
            100                 105                 110

<210> SEQ ID NO 133
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 133

Gln Val Gln Val Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Asn
            20                  25                  30

Tyr Phe Tyr Trp Ser Trp Ile Arg Gln Ser Pro Gly Lys Gly Leu Glu
        35                  40                  45

Trp Ile Gly Ala Ile Ala Tyr Ser Gly Arg Thr Tyr Tyr Ser Pro Ser
    50                  55                  60

Leu Lys Ser Arg Thr Ser Ile Ser Arg Asp Thr Ser Asn Asn Gln Phe
65                  70                  75                  80

Thr Leu Gln Leu Ser Ser Val Thr Pro Glu Asp Thr Ala Val Tyr Tyr
                85                  90                  95

Cys Ala Arg Gly Pro Lys Gly Leu Ala Ser Tyr Tyr Asp Tyr Trp Gly
            100                 105                 110

Gln Gly Thr Gln Val Thr Val Ser Ser
        115                 120

<210> SEQ ID NO 134
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 134

Ser Ser Ala Leu Thr Gln Pro Ser Ala Val Ser Val Ser Leu Gly Gln
1               5                   10                  15

Thr Ala Arg Ile Thr Cys Gln Gly Gly Asn Phe Gly Tyr Tyr Tyr Val
            20                  25                  30

Ser Trp Tyr Gln Gln Lys Pro Gly Gln Ala Pro Val Leu Val Ile Tyr
        35                  40                  45

Arg Asp Ser Gly Arg Pro Ser Gly Ile Pro Glu Arg Phe Ser Gly Ser
    50                  55                  60

```
Ser Ser Gly Asp Thr Ala Thr Leu Thr Ile Ser Gly Ala Gln Ala Glu
 65                  70                  75                  80

Asp Glu Ala Asp Tyr Tyr Cys Gln Ser Gly Ser Ser Asp Asn Thr
                 85                  90                  95

Val Phe Gly Gly Gly Thr His Leu Thr Val Leu
                100                 105

<210> SEQ ID NO 135
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 135

Gln Val Gln Leu Val Glu Ser Gly Gly Gly Leu Val Gln Pro Gly Gly
  1               5                  10                  15

Ser Leu Arg Leu Ser Cys Ala Ala Ser Glu Phe Thr Phe Ser Arg Tyr
             20                  25                  30

Ser Met Ser Trp Val Arg Gln Ala Pro Gly Lys Gly Leu Glu Trp Val
         35                  40                  45

Ser Thr Ile Asn Ser Gly Gly Gly Ser Thr Ser Tyr Val Asp Ser Val
     50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                 85                  90                  95

Thr Lys Ser Gln Gly Gly Ile Ser Phe Ser Thr Gln Tyr Gly Met Asp
                100                 105                 110

Tyr Trp Gly Lys Gly Thr Leu Val Thr Val Ser Ser
            115                 120

<210> SEQ ID NO 136
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 136

Asn Phe Met Leu Thr Gln Pro Ser Ala Val Ser Val Ser Leu Gly Gln
  1               5                  10                  15

Thr Ala Arg Ile Thr Cys Gln Gly Gly Asn Phe Gly Arg Tyr Tyr Ala
             20                  25                  30

Asn Trp Tyr Gln Gln Lys Pro Gly Gln Ala Pro Val Leu Val Ile Tyr
         35                  40                  45

Lys Asp Ser Glu Arg Pro Ser Gly Ile Pro Glu Arg Phe Ser Gly Ser
     50                  55                  60

Ser Ser Gly Asp Thr Ala Thr Leu Thr Ile Ser Gly Ala Gln Ala Glu
 65                  70                  75                  80

Asp Glu Ser Asp Tyr Tyr Cys Gln Ser Gly Ser Val Ser Asp Asn Ala
                 85                  90                  95

Val Phe Gly Gly Gly Thr His Leu Ala Val Leu
                100                 105

<210> SEQ ID NO 137
<211> LENGTH: 122
<212> TYPE: PRT
```

<213> ORGANISM: Artificial sequence
<220> FEATURE:
<223> OTHER INFORMATION: Synthetic polypeptide

<400> SEQUENCE: 137

```
Gln Val Gln Arg Gln Glu Ser Gly Pro Gly Leu Val Lys Pro Ser Gln
1               5                   10                  15
Thr Leu Ser Leu Thr Cys Thr Val Ser Gly Gly Ser Ile Thr Thr Asn
            20                  25                  30
Tyr Tyr Ser Trp Ser Trp Ile Arg Gln Pro Pro Gly Lys Gly Leu Glu
        35                  40                  45
Trp Ile Gly Tyr Ile Ala Tyr Ser Gly Ser Thr Ser Tyr Ser Pro Ser
    50                  55                  60
Leu Lys Ser Arg Thr Ser Ile Ser Arg Asp Thr Ser Asn Asn Gln Phe
65                  70                  75                  80
Ser Leu Gln Leu Ser Ser Val Thr Pro Glu Asp Thr Ala Val Tyr Tyr
                85                  90                  95
Cys Ala Arg Ser Arg Ser Ser Pro Thr Thr Phe Gly Met Asp Tyr Trp
            100                 105                 110
Gly Lys Gly Thr Leu Val Thr Val Ser Ser
        115                 120
```

<210> SEQ ID NO 138
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 138

```
Ser Ser Ala Leu Thr Gln Pro Ser Ala Val Ser Val Ser Leu Gly Gln
1               5                   10                  15
Thr Ala Arg Ile Thr Cys Gln Gly Gly Asn Phe Gly Arg Tyr Tyr Val
            20                  25                  30
Ser Trp Tyr Thr Gln Lys Pro Gly Gln Ala Pro Val Leu Val Ile Tyr
        35                  40                  45
Gln Asp Ser Glu Arg Pro Thr Gly Ile Pro Glu Arg Phe Ser Gly Ser
    50                  55                  60
Ser Ser Gly Asp Thr Ala Thr Leu Thr Ile Ser Gly Ala Gln Ala Glu
65                  70                  75                  80
Asp Glu Ala Asp Tyr Tyr Cys Gln Ser Gly Thr Ser Ser Asp Asn Ile
                85                  90                  95
Val Phe Gly Gly Gly Thr His Leu Thr Val Leu
            100                 105
```

<210> SEQ ID NO 139
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 139

```
Gln Leu Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Trp Met Tyr Trp Val Arg Gln Ala Pro Gly Lys Gly Leu Glu Trp Val
        35                  40                  45
```

```
Ser Ala Ile Asn Thr Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Leu Tyr Tyr Cys
                 85                  90                  95

Ala Arg Ala Gly Ser Gly Val Ala Gly Thr Gly Tyr Asp Tyr Trp Gly
            100                 105                 110

Gln Gly Thr Gln Val Thr Val Ser Ser
            115                 120

<210> SEQ ID NO 140
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 140

Gln Pro Val Leu Asn Gln Pro Ser Ala Val Ser Val Ser Leu Gly Gln
  1               5                  10                  15

Thr Ala Arg Ile Thr Cys Gln Gly Gly Asn Phe Gly Tyr Tyr Tyr Val
                 20                  25                  30

Ser Trp Tyr Gln Gln Lys Pro Gly Gln Ala Pro Val Leu Val Ile Tyr
             35                  40                  45

Arg Asp Ser Gly Arg Pro Ser Gly Ile Pro Glu Arg Phe Ser Gly Ser
 50                  55                  60

Ser Ser Gly Asp Thr Ala Thr Leu Thr Ile Ser Gly Ala Gln Ala Glu
 65                  70                  75                  80

Asp Glu Ala Asp Tyr Tyr Cys Gln Ser Gly Ser Ser Asp Asn Ala
                 85                  90                  95

Val Phe Gly Gly Gly Thr His Leu Thr Val Leu
            100                 105

<210> SEQ ID NO 141
<211> LENGTH: 142
<212> TYPE: PRT
<213> ORGANISM: Homo sapiens

<400> SEQUENCE: 141

Met Ser Leu Leu Pro Val Pro Tyr Thr Glu Ala Ala Ser Leu Ser Thr
  1               5                  10                  15

Gly Ser Thr Val Thr Ile Lys Gly Arg Pro Leu Ala Cys Phe Leu Asn
                 20                  25                  30

Glu Pro Tyr Leu Gln Val Asp Phe His Thr Glu Met Lys Glu Glu Ser
             35                  40                  45

Asp Ile Val Phe His Phe Gln Val Cys Phe Gly Arg Arg Val Val Met
 50                  55                  60

Asn Ser Arg Glu Tyr Gly Ala Trp Lys Gln Val Glu Ser Lys Asn
 65                  70                  75                  80

Met Pro Phe Gln Asp Gly Gln Glu Phe Glu Leu Ser Ile Ser Val Leu
                 85                  90                  95

Pro Asp Lys Tyr Gln Val Met Val Asn Gly Gln Ser Ser Tyr Thr Phe
            100                 105                 110

Asp His Arg Ile Lys Pro Glu Ala Val Lys Met Val Gln Val Trp Arg
            115                 120                 125
```

Asp Ile Ser Leu Thr Lys Phe Asn Val Ser Tyr Leu Lys Arg
            130                 135                 140

<210> SEQ ID NO 142
<211> LENGTH: 10
<212> TYPE: PRT
<213> ORGANISM: Homo sapiens

<400> SEQUENCE: 142

Glu Pro Lys Ser Cys Asp Lys Thr His Thr
1               5                   10

<210> SEQ ID NO 143
<211> LENGTH: 5
<212> TYPE: PRT
<213> ORGANISM: Artificial sequence
<220> FEATURE:
<223> OTHER INFORMATION: Synthetic peptide

<400> SEQUENCE: 143

Cys Pro Pro Cys Pro
1               5

<210> SEQ ID NO 144
<211> LENGTH: 8
<212> TYPE: PRT
<213> ORGANISM: Homo sapiens

<400> SEQUENCE: 144

Ala Pro Glu Leu Leu Gly Gly Pro
1               5

<210> SEQ ID NO 145
<211> LENGTH: 12
<212> TYPE: PRT
<213> ORGANISM: Homo sapiens

<400> SEQUENCE: 145

Glu Leu Lys Thr Pro Leu Gly Asp Thr Thr His Thr
1               5                   10

<210> SEQ ID NO 146
<211> LENGTH: 50
<212> TYPE: PRT
<213> ORGANISM: Artificial sequence
<220> FEATURE:
<223> OTHER INFORMATION: Synthetic polypeptide

<400> SEQUENCE: 146

Cys Pro Arg Cys Pro Glu Pro Lys Ser Cys Asp Thr Pro Pro Pro Cys
1               5                   10                  15

Pro Arg Cys Pro Glu Pro Lys Ser Cys Asp Thr Pro Pro Pro Cys Pro
                20                  25                  30

Arg Cys Pro Glu Pro Lys Ser Cys Asp Thr Pro Pro Pro Cys Pro Arg
            35                  40                  45

Cys Pro
    50

<210> SEQ ID NO 147
<211> LENGTH: 8
<212> TYPE: PRT
<213> ORGANISM: Homo sapiens

<400> SEQUENCE: 147

```
Ala Pro Glu Leu Leu Gly Gly Pro
1               5

<210> SEQ ID NO 148
<211> LENGTH: 7
<212> TYPE: PRT
<213> ORGANISM: Homo sapiens

<400> SEQUENCE: 148

Glu Ser Lys Tyr Gly Pro Pro
1               5

<210> SEQ ID NO 149
<211> LENGTH: 5
<212> TYPE: PRT
<213> ORGANISM: Artificial sequence
<220> FEATURE:
<223> OTHER INFORMATION: Synthetic peptide

<400> SEQUENCE: 149

Cys Pro Ser Cys Pro
1               5

<210> SEQ ID NO 150
<211> LENGTH: 8
<212> TYPE: PRT
<213> ORGANISM: Homo sapiens

<400> SEQUENCE: 150

Ala Pro Glu Phe Leu Gly Gly Pro
1               5

<210> SEQ ID NO 151
<211> LENGTH: 3
<212> TYPE: PRT
<213> ORGANISM: Homo sapiens

<400> SEQUENCE: 151

Glu Arg Lys
1

<210> SEQ ID NO 152
<211> LENGTH: 10
<212> TYPE: PRT
<213> ORGANISM: Artificial sequence
<220> FEATURE:
<223> OTHER INFORMATION: Synthetic peptide

<400> SEQUENCE: 152

Cys Cys Val Glu Cys Pro Pro Cys Pro
1               5                   10

<210> SEQ ID NO 153
<211> LENGTH: 7
<212> TYPE: PRT
<213> ORGANISM: Homo sapiens

<400> SEQUENCE: 153

Ala Pro Pro Val Ala Gly Pro
1               5

<210> SEQ ID NO 154
<211> LENGTH: 34
<212> TYPE: PRT
<213> ORGANISM: Artificial sequence
<220> FEATURE:
```

<223> OTHER INFORMATION: Synthetic polypeptide

<400> SEQUENCE: 154

Gly Ala Thr Gly Ala Ala Cys Thr Cys Thr Cys Gly Thr Gly Ala Ala
1               5                   10                  15

Gly Ala Ala Gly Gly Thr Gly Cys Ala Thr Gly Ala Ala Ala Cys
            20                  25                  30

Ala Gly

<210> SEQ ID NO 155
<211> LENGTH: 34
<212> TYPE: PRT
<213> ORGANISM: Artificial sequence
<220> FEATURE:
<223> OTHER INFORMATION: Synthetic polypeptide

<400> SEQUENCE: 155

Cys Thr Gly Thr Thr Thr Cys Cys Ala Thr Gly Cys Ala Cys Cys Thr
1               5                   10                  15

Thr Cys Thr Thr Cys Ala Cys Gly Ala Gly Ala Gly Thr Thr Cys Ala
            20                  25                  30

Thr Cys

<210> SEQ ID NO 156
<211> LENGTH: 23
<212> TYPE: PRT
<213> ORGANISM: Artificial sequence
<220> FEATURE:
<223> OTHER INFORMATION: Synthetic polypeptide

<400> SEQUENCE: 156

Cys Thr Cys Cys Gly Thr Cys Thr Thr Ala Gly Thr Cys Ala Ala Thr
1               5                   10                  15

Ala Ala Cys Cys Ala Cys Cys
            20

<210> SEQ ID NO 157
<211> LENGTH: 23
<212> TYPE: PRT
<213> ORGANISM: Artificial sequence
<220> FEATURE:
<223> OTHER INFORMATION: Synthetic polypeptide

<400> SEQUENCE: 157

Gly Gly Ala Ala Cys Thr Cys Gly Thr Thr Gly Gly Ala Thr Thr Thr
1               5                   10                  15

Thr Gly Gly Ala Cys Thr Gly
            20

<210> SEQ ID NO 158
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 158

Ala Cys Ala Ala Ala Ala Thr Gly Gly Thr Gly Ala Ala Gly Gly Thr
1               5                   10                  15

Cys Gly Gly Thr Gly
            20

-continued

```
<210> SEQ ID NO 159
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 159

Thr Gly Gly Cys Ala Ala Cys Ala Ala Thr Cys Thr Cys Ala Cys
1               5                   10                  15

Thr Thr Thr Gly Cys
            20

<210> SEQ ID NO 160
<211> LENGTH: 5
<212> TYPE: PRT
<213> ORGANISM: Artificial sequence
<220> FEATURE:
<223> OTHER INFORMATION: Synthetic peptide

<400> SEQUENCE: 160

Ser Tyr Asp Met Ser
1               5

<210> SEQ ID NO 161
<211> LENGTH: 17
<212> TYPE: PRT
<213> ORGANISM: Artificial sequence
<220> FEATURE:
<223> OTHER INFORMATION: Synthetic peptide

<400> SEQUENCE: 161

Ala Ile Lys Asn Gly Gly Gly Ile Thr Tyr Tyr Ala Asp Ser Val Lys
1               5                   10                  15

Gly

<210> SEQ ID NO 162
<211> LENGTH: 11
<212> TYPE: PRT
<213> ORGANISM: Artificial sequence
<220> FEATURE:
<223> OTHER INFORMATION: Synthetic peptide

<400> SEQUENCE: 162

Thr His Gly Ile Gly Thr Leu Gly Phe Gly Ser
1               5                   10

<210> SEQ ID NO 163
<211> LENGTH: 5
<212> TYPE: PRT
<213> ORGANISM: Artificial sequence
<220> FEATURE:
<223> OTHER INFORMATION: Synthetic peptide

<400> SEQUENCE: 163

Thr Asn Tyr Met Asn
1               5

<210> SEQ ID NO 164
<211> LENGTH: 17
<212> TYPE: PRT
<213> ORGANISM: Artificial sequence
<220> FEATURE:
<223> OTHER INFORMATION: Synthetic peptide

<400> SEQUENCE: 164
```

```
Gly Ile Thr Ser Gly Gly Gly Arg Thr Tyr Tyr Ala Asp Ser Val Lys
1               5                   10                  15

Gly

<210> SEQ ID NO 165
<211> LENGTH: 8
<212> TYPE: PRT
<213> ORGANISM: Artificial sequence
<220> FEATURE:
<223> OTHER INFORMATION: Synthetic peptide

<400> SEQUENCE: 165

Thr Asp His Ala Trp Leu Asp Ala
1               5

<210> SEQ ID NO 166
<211> LENGTH: 5
<212> TYPE: PRT
<213> ORGANISM: Artificial sequence
<220> FEATURE:
<223> OTHER INFORMATION: Synthetic peptide

<400> SEQUENCE: 166

Asn Tyr Asp Met Ser
1               5

<210> SEQ ID NO 167
<211> LENGTH: 17
<212> TYPE: PRT
<213> ORGANISM: Artificial sequence
<220> FEATURE:
<223> OTHER INFORMATION: Synthetic peptide

<400> SEQUENCE: 167

Asp Ile Asn Ser Gly Gly Gly Ser Thr Tyr Tyr Ala Asp Ser Val Lys
1               5                   10                  15

Gly

<210> SEQ ID NO 168
<211> LENGTH: 7
<212> TYPE: PRT
<213> ORGANISM: Artificial sequence
<220> FEATURE:
<223> OTHER INFORMATION: Synthetic peptide

<400> SEQUENCE: 168

Gly Tyr Thr Gly Tyr Tyr Tyr
1               5

<210> SEQ ID NO 169
<211> LENGTH: 5
<212> TYPE: PRT
<213> ORGANISM: Artificial sequence
<220> FEATURE:
<223> OTHER INFORMATION: Synthetic peptide

<400> SEQUENCE: 169

Tyr His Tyr Met Asn
1               5

<210> SEQ ID NO 170
<211> LENGTH: 17
<212> TYPE: PRT
<213> ORGANISM: Artificial sequence
<220> FEATURE:
<223> OTHER INFORMATION: Synthetic peptide
```

```
<400> SEQUENCE: 170

Gly Ile Ser Ala Gly Gly Gly Arg Thr Tyr Tyr Ala Asp Ser Val Lys
1               5                   10                  15

Gly

<210> SEQ ID NO 171
<211> LENGTH: 8
<212> TYPE: PRT
<213> ORGANISM: Artificial sequence
<220> FEATURE:
<223> OTHER INFORMATION: Synthetic peptide

<400> SEQUENCE: 171

Val His Gly Ile Thr Asn Asp Tyr
1               5

<210> SEQ ID NO 172
<211> LENGTH: 5
<212> TYPE: PRT
<213> ORGANISM: Artificial sequence
<220> FEATURE:
<223> OTHER INFORMATION: Synthetic peptide

<400> SEQUENCE: 172

Ser Tyr Tyr Met Ser
1               5

<210> SEQ ID NO 173
<211> LENGTH: 17
<212> TYPE: PRT
<213> ORGANISM: Artificial sequence
<220> FEATURE:
<223> OTHER INFORMATION: Synthetic peptide

<400> SEQUENCE: 173

Gly Ile Val Thr Gly Gly Gly Arg Thr His Tyr Thr Asp Ser Val Lys
1               5                   10                  15

Gly

<210> SEQ ID NO 174
<211> LENGTH: 10
<212> TYPE: PRT
<213> ORGANISM: Artificial sequence
<220> FEATURE:
<223> OTHER INFORMATION: Synthetic peptide

<400> SEQUENCE: 174

Val Asn Gly Val Val Thr Asn Tyr Asp Tyr
1               5                   10

<210> SEQ ID NO 175
<211> LENGTH: 17
<212> TYPE: PRT
<213> ORGANISM: Artificial sequence
<220> FEATURE:
<223> OTHER INFORMATION: Synthetic peptide

<400> SEQUENCE: 175

Gly Ile Thr Ser His Gly Ala Arg Thr Tyr Tyr Ala Asp Ser Val Lys
1               5                   10                  15

Gly

<210> SEQ ID NO 176
```

```
<211> LENGTH: 8
<212> TYPE: PRT
<213> ORGANISM: Artificial sequence
<220> FEATURE:
<223> OTHER INFORMATION: Synthetic peptide

<400> SEQUENCE: 176

Thr Asp His Ala Ser Leu Asp Ala
1               5

<210> SEQ ID NO 177
<211> LENGTH: 11
<212> TYPE: PRT
<213> ORGANISM: Artificial sequence
<220> FEATURE:
<223> OTHER INFORMATION: Synthetic peptide

<400> SEQUENCE: 177

Asp Gly Asn Asn Ile Gly Ser Lys Ser Ala Gln
1               5                   10

<210> SEQ ID NO 178
<211> LENGTH: 7
<212> TYPE: PRT
<213> ORGANISM: Artificial sequence
<220> FEATURE:
<223> OTHER INFORMATION: Synthetic peptide

<400> SEQUENCE: 178

Ala Asp Glu Tyr Arg Pro Glu
1               5

<210> SEQ ID NO 179
<211> LENGTH: 9
<212> TYPE: PRT
<213> ORGANISM: Artificial sequence
<220> FEATURE:
<223> OTHER INFORMATION: Synthetic peptide

<400> SEQUENCE: 179

Gln Val Trp Asp Gly Ser Ala Ala Val
1               5

<210> SEQ ID NO 180
<211> LENGTH: 14
<212> TYPE: PRT
<213> ORGANISM: Artificial sequence
<220> FEATURE:
<223> OTHER INFORMATION: Synthetic peptide

<400> SEQUENCE: 180

Ala Gly Thr Ser Ser Asp Val Gly Tyr Gly Asn Tyr Val Ser
1               5                   10

<210> SEQ ID NO 181
<211> LENGTH: 7
<212> TYPE: PRT
<213> ORGANISM: Artificial sequence
<220> FEATURE:
<223> OTHER INFORMATION: Synthetic peptide

<400> SEQUENCE: 181

Ala Val Ser Thr Arg Ala Ser
1               5

<210> SEQ ID NO 182
<211> LENGTH: 10
```

```
<212> TYPE: PRT
<213> ORGANISM: Artificial sequence
<220> FEATURE:
<223> OTHER INFORMATION: Synthetic peptide

<400> SEQUENCE: 182

Ala Ser Tyr Arg Ser Ser Asn Asn Tyr Val
1               5                   10

<210> SEQ ID NO 183
<211> LENGTH: 14
<212> TYPE: PRT
<213> ORGANISM: Artificial sequence
<220> FEATURE:
<223> OTHER INFORMATION: Synthetic peptide

<400> SEQUENCE: 183

Gly Leu Ser Ser Gly Ser Val Thr Ser Ser Asn Tyr Pro Ala
1               5                   10

<210> SEQ ID NO 184
<211> LENGTH: 7
<212> TYPE: PRT
<213> ORGANISM: Artificial sequence
<220> FEATURE:
<223> OTHER INFORMATION: Synthetic peptide

<400> SEQUENCE: 184

Ser Ile Asn Ser Arg His Ser
1               5

<210> SEQ ID NO 185
<211> LENGTH: 12
<212> TYPE: PRT
<213> ORGANISM: Artificial sequence
<220> FEATURE:
<223> OTHER INFORMATION: Synthetic peptide

<400> SEQUENCE: 185

Thr Leu Tyr Met Gly Thr Gly Ser Asn Asn Val Val
1               5                   10

<210> SEQ ID NO 186
<211> LENGTH: 7
<212> TYPE: PRT
<213> ORGANISM: Artificial sequence
<220> FEATURE:
<223> OTHER INFORMATION: Synthetic peptide

<400> SEQUENCE: 186

Glu Val Asn Lys Arg Ala Ser
1               5

<210> SEQ ID NO 187
<211> LENGTH: 10
<212> TYPE: PRT
<213> ORGANISM: Artificial sequence
<220> FEATURE:
<223> OTHER INFORMATION: Synthetic peptide

<400> SEQUENCE: 187

Ala Ser Tyr Arg Asn Ser Asn Asn Trp Val
1               5                   10

<210> SEQ ID NO 188
<211> LENGTH: 7
<212> TYPE: PRT
```

```
<213> ORGANISM: Artificial sequence
<220> FEATURE:
<223> OTHER INFORMATION: Synthetic peptide

<400> SEQUENCE: 188

Asp Val Asn Lys Arg Ala Ser
1               5

<210> SEQ ID NO 189
<211> LENGTH: 10
<212> TYPE: PRT
<213> ORGANISM: Artificial sequence
<220> FEATURE:
<223> OTHER INFORMATION: Synthetic peptide

<400> SEQUENCE: 189

Ala Ser Tyr Arg Ser Pro Asn Asn Val Val
1               5                   10

<210> SEQ ID NO 190
<211> LENGTH: 14
<212> TYPE: PRT
<213> ORGANISM: Artificial sequence
<220> FEATURE:
<223> OTHER INFORMATION: Synthetic peptide

<400> SEQUENCE: 190

Gly Leu Ser Ser Gly Ser Val Thr Ser Ser Asn Tyr Pro Gly
1               5                   10

<210> SEQ ID NO 191
<211> LENGTH: 7
<212> TYPE: PRT
<213> ORGANISM: Artificial sequence
<220> FEATURE:
<223> OTHER INFORMATION: Synthetic peptide

<400> SEQUENCE: 191

Asn Thr Asn Ser Arg Tyr Ser
1               5

<210> SEQ ID NO 192
<211> LENGTH: 12
<212> TYPE: PRT
<213> ORGANISM: Artificial sequence
<220> FEATURE:
<223> OTHER INFORMATION: Synthetic peptide

<400> SEQUENCE: 192

Ala Leu Tyr Met Gly Ser Ser Tyr Asn Thr Val
1               5                   10

<210> SEQ ID NO 193
<211> LENGTH: 10
<212> TYPE: PRT
<213> ORGANISM: Artificial sequence
<220> FEATURE:
<223> OTHER INFORMATION: Synthetic peptide

<400> SEQUENCE: 193

Ala Ser Tyr Ser Val Arg Asn Asn Val Val
1               5                   10

<210> SEQ ID NO 194
<211> LENGTH: 120
<212> TYPE: PRT
<213> ORGANISM: Artificial sequence
```

<220> FEATURE:
<223> OTHER INFORMATION: Synthetic polypeptide

<400> SEQUENCE: 194

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Asp Met Ser Trp Val Arg Gln Ala Pro Gly Lys Gly Pro Glu Trp Val
        35                  40                  45

Ser Ala Ile Lys Asn Gly Gly Gly Ile Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Thr Thr His Gly Ile Gly Thr Leu Gly Phe Gly Ser Trp Gly Gln
            100                 105                 110

Gly Thr Gln Val Thr Val Ser Ser
        115                 120

<210> SEQ ID NO 195
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 195

Ser Tyr Glu Leu Thr Gln Ser Ala Ser Val Ser Val Ala Leu Thr Gln
1               5                   10                  15

Thr Ala Lys Ile Thr Cys Asp Gly Asn Asn Ile Gly Ser Lys Ser Ala
            20                  25                  30

Gln Trp Tyr Gln Gln Lys Pro Gly Gln Ala Pro Ala Leu Val Ile Tyr
        35                  40                  45

Ala Asp Glu Tyr Arg Pro Glu Gly Ile Pro Glu Arg Phe Ser Gly Ser
    50                  55                  60

Asn Ser Gly Asn Thr Ala Thr Leu Ile Ile Ser Gly Ala Gln Ala Glu
65                  70                  75                  80

Asp Glu Ala Asp Tyr Tyr Cys Gln Val Trp Asp Gly Ser Ala Ala Val
                85                  90                  95

Phe Gly Arg Gly Thr His Leu Thr Val Leu
            100                 105

<210> SEQ ID NO 196
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 196

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Asn
            20                  25                  30

Tyr Met Asn Trp Val Arg Gln Ala Pro Gly Lys Gly Leu Glu Trp Val
        35                  40                  45

```
Ser Gly Ile Thr Ser Gly Gly Gly Arg Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Leu Tyr Tyr Cys
                85                  90                  95

Ala Arg Thr Asp His Ala Trp Leu Asp Ala Trp Gly Gln Gly Thr Leu
                100                 105                 110

Val Thr Val Ser Ser
            115

<210> SEQ ID NO 197
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 197

Gln Ala Gly Leu Thr Gln Pro Pro Ser Val Ser Gly Thr Leu Gly Lys
1               5                   10                  15

Thr Val Thr Ile Ser Cys Ala Gly Thr Ser Ser Asp Val Gly Tyr Gly
                20                  25                  30

Asn Tyr Val Ser Trp Tyr Gln Gln Leu Pro Gly Thr Ala Pro Lys Leu
                35                  40                  45

Leu Ile Tyr Ala Val Ser Thr Arg Ala Ser Gly Ile Pro Asp Arg Phe
    50                  55                  60

Ser Gly Ser Lys Ser Gly Asn Thr Ala Ser Leu Thr Ile Ser Gly Leu
65                  70                  75                  80

Leu Ser Glu Asp Glu Ala Asp Tyr Tyr Cys Ala Ser Tyr Arg Ser Ser
                85                  90                  95

Asn Asn Tyr Val Phe Gly Gly Gly Thr Lys Leu Thr Val Leu
                100                 105                 110

<210> SEQ ID NO 198
<211> LENGTH: 116
<212> TYPE: PRT
<213> ORGANISM: Artificial sequence
<220> FEATURE:
<223> OTHER INFORMATION: Synthetic polypeptide

<400> SEQUENCE: 198

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Asn Tyr
                20                  25                  30

Asp Met Ser Trp Val Arg Gln Ala Pro Gly Lys Gly Pro Glu Trp Val
                35                  40                  45

Ser Asp Ile Asn Ser Gly Gly Gly Ser Thr Tyr Tyr Ala Asp Ser Val
    50                  55                  60

Lys Gly Arg Phe Thr Ile Ser Arg Asp Asn Ala Lys Asn Ser Leu Leu
65                  70                  75                  80

Leu Gln Met Asn Ser Leu Lys Pro Glu Asp Thr Ala Val Tyr Tyr Cys
                85                  90                  95

Ala Thr Gly Tyr Thr Gly Tyr Tyr Tyr Trp Gly Gln Gly Thr Gln Val
                100                 105                 110

Thr Val Ser Ser
            115
```

```
<210> SEQ ID NO 199
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 199

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Ala Trp Tyr Gln Gln Thr Pro Gly Gln Ala Pro Arg Ala
        35                  40                  45

Leu Ile Tyr Ser Ile Asn Ser Arg His Ser Gly Val Pro Asp Arg Phe
    50                  55                  60

Ser Gly Ser Ile Ser Gly Asn Lys Ala Ala Leu Thr Ile Thr Gly Ala
65                  70                  75                  80

Gln Ala Glu Asp Glu Ala Asp Tyr Tyr Cys Thr Leu Tyr Met Gly Thr
                85                  90                  95

Gly Ser Asn Asn Val Val Phe Gly Gly Gly Thr His Leu Thr Val Leu
            100                 105                 110

<210> SEQ ID NO 200
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 200

Gln Val Gln Leu Val Glu Ser Gly Gly Gly Leu Val Gln Pro Gly Gly
1               5                   10                  15

Ser Leu Arg Val Ser Cys Ala Ala Ser Gly Phe Thr Phe Ser Tyr His
            20                  25                  30

Tyr Met Asn Trp Val Arg Gln Ala Pro Gly Lys Gly Leu Glu Trp Val
        35                  40                  45

Ser Gly Ile Ser Ala Gly Gly Arg Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Asn Ala Glu Asp Thr Ala Leu Tyr Tyr Cys
                85                  90                  95

Ala Arg Val His Gly Ile Thr Asn Asp Tyr Trp Gly Gln Gly Thr Gln
            100                 105                 110

Val Thr Val Ser Ser
        115

<210> SEQ ID NO 201
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 201

Gln Ser Ala Leu Thr Gln Pro Pro Ser Val Ser Gly Ser Pro Gly Lys
1               5                   10                  15
```

```
Thr Val Thr Ile Ser Cys Ala Gly Thr Ser Ser Asp Val Gly Tyr Gly
            20                  25                  30

Asn Tyr Val Ser Trp Tyr Gln Gln Leu Pro Gly Met Ala Pro Lys Leu
            35                  40                  45

Leu Ile Tyr Glu Val Asn Lys Arg Ala Ser Gly Ile Thr Asp Arg Phe
        50                  55                  60

Ser Gly Ser Lys Ser Gly Asn Thr Ala Phe Leu Thr Ile Ser Gly Leu
65                  70                  75                  80

Gln Ser Glu Asp Glu Ala Asp Tyr Tyr Cys Ala Ser Tyr Arg Asn Ser
                85                  90                  95

Asn Asn Trp Val Phe Gly Gly Gly Thr His Leu Thr Val Leu
            100                 105                 110

<210> SEQ ID NO 202
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 202

Glu Val Gln Leu Val Glu Ser Gly Gly Gly Leu Val Gln Pro Gly Gly
1               5                   10                  15

Ser Leu Arg Val Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
            35                  40                  45

Ser Gly Ile Val Thr Gly Gly Arg Thr His Tyr Thr Asp Ser Val
        50                  55                  60

Lys Gly Arg Phe Thr Ile Thr Arg Asp Asn Ala Lys Asn Thr Leu Tyr
65                  70                  75                  80

Leu Gln Met Asn Ser Leu Arg Pro Glu Asp Thr Ala Leu Tyr Tyr Cys
                85                  90                  95

Ala Arg Val Asn Gly Val Val Thr Asn Tyr Asp Tyr Trp Gly Gln Gly
            100                 105                 110

Thr Gln Val Thr Val Ser Ser
        115

<210> SEQ ID NO 203
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 203

Gln Ala Val Leu Thr Gln Pro Pro Ser Val Ser Gly Ser Pro Gly Lys
1               5                   10                  15

Thr Val Thr Ile Ser Cys Ala Gly Thr Ser Ser Asp Val Gly Tyr Gly
            20                  25                  30

Asn Tyr Val Ser Trp Tyr Gln Gln Leu Pro Gly Met Ala Pro Lys Leu
            35                  40                  45

Leu Ile Tyr Asp Val Asn Lys Arg Ala Ser Gly Ile Thr Asp Arg Phe
        50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Phe Cys Ala Ser Tyr Arg Ser Pro
                85                  90                  95
```

```
Asn Asn Val Val Phe Gly Gln Gly Thr His Leu Thr Val Leu
                100                 105                 110
```

<210> SEQ ID NO 204
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 204

```
Glu Leu Gln Val Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Asn
            20                  25                  30

Tyr Met Asn Trp Val Arg Gln Ala Pro Gly Lys Gly Leu Glu Trp Val
        35                  40                  45

Ser Gly Ile Thr Ser His Gly Ala Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Pro Glu Asp Thr Ala Leu Tyr Tyr Cys
                85                  90                  95

Ala Arg Thr Asp His Ala Ser Leu Asp Ala Trp Gly Gln Gly Thr Leu
            100                 105                 110

Val Thr Val Ser Ser
        115
```

<210> SEQ ID NO 205
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 205

```
Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Gly Trp Tyr Gln Gln Lys Pro Gly Gln Ala Pro Arg Thr
        35                  40                  45

Leu Ile Tyr Asn Thr Asn Ser Arg Tyr Ser Gly Val Pro Asn Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ala Leu Tyr Met Gly Ser
                85                  90                  95

Ser Ser Tyr Asn Thr Val Phe Gly Gly Gly Thr His Leu Thr Val Leu
            100                 105                 110
```

<210> SEQ ID NO 206
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 206

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Thr Asn
            20                  25                  30

Tyr Met Asn Trp Val Arg Gln Ala Pro Gly Lys Gly Leu Glu Trp Val
        35                  40                  45

Ser Gly Ile Thr Ser Gly Gly Arg Thr Tyr Tyr Ala Asp Ser Val
    50              55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Leu Tyr Tyr Cys
                85                  90                  95

Ala Arg Thr Asp His Ala Trp Leu Asp Ala Trp Gly Gln Gly Thr Leu
            100                 105                 110

Val Thr Val Ser Ser
            115

<210> SEQ ID NO 207
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 207

His Ser Ala Val Thr Gln Pro Pro Ser Val Ser Gly Thr Leu Gly Lys
1               5                   10                  15

Thr Val Thr Ile Ser Cys Ala Gly Thr Ser Ser Asp Val Gly Tyr Gly
            20                  25                  30

Asn Tyr Val Ser Trp Tyr Gln His Leu Pro Gly Thr Ala Pro Lys Leu
        35                  40                  45

Leu Ile Tyr Ala Val Ser Thr Arg Ala Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Gly Asp Tyr Tyr Cys Ala Ser Tyr Ser Val Arg
                85                  90                  95

Asn Asn Val Val Phe Gly Gly Gly Thr Arg Leu Thr Val Leu
            100                 105                 110

<210> SEQ ID NO 208
<211> LENGTH: 5
<212> TYPE: PRT
<213> ORGANISM: Artificial sequence
<220> FEATURE:
<223> OTHER INFORMATION: Synthetic peptide

<400> SEQUENCE: 208

Ala Tyr Ser Met Gly
1               5

<210> SEQ ID NO 209
<211> LENGTH: 16
<212> TYPE: PRT
<213> ORGANISM: Artificial sequence
<220> FEATURE:
<223> OTHER INFORMATION: Synthetic peptide

<400> SEQUENCE: 209

Val Ile Ser Trp Ser Gly Gly Ser His Tyr Asp Asp Ser Val Lys Gly

<210> SEQ ID NO 210
<211> LENGTH: 13
<212> TYPE: PRT
<213> ORGANISM: Artificial sequence
<220> FEATURE:
<223> OTHER INFORMATION: Synthetic peptide

<400> SEQUENCE: 210

Gly Thr Leu Tyr Ser Phe Arg Tyr Arg Asp Tyr Asp Tyr
1               5                   10

<210> SEQ ID NO 211
<211> LENGTH: 5
<212> TYPE: PRT
<213> ORGANISM: Artificial sequence
<220> FEATURE:
<223> OTHER INFORMATION: Synthetic peptide

<400> SEQUENCE: 211

Thr Tyr Ala Met Asp
1               5

<210> SEQ ID NO 212
<211> LENGTH: 16
<212> TYPE: PRT
<213> ORGANISM: Artificial sequence
<220> FEATURE:
<223> OTHER INFORMATION: Synthetic peptide

<400> SEQUENCE: 212

Ala Ile Ser Trp His Ser Ala Ile Tyr Tyr Ala Asp Ala Val Lys Gly
1               5                   10                  15

<210> SEQ ID NO 213
<211> LENGTH: 13
<212> TYPE: PRT
<213> ORGANISM: Artificial sequence
<220> FEATURE:
<223> OTHER INFORMATION: Synthetic peptide

<400> SEQUENCE: 213

Ala Leu Arg Tyr Arg Phe Asn Pro Ser Ala Met Glu Tyr
1               5                   10

<210> SEQ ID NO 214
<211> LENGTH: 5
<212> TYPE: PRT
<213> ORGANISM: Artificial sequence
<220> FEATURE:
<223> OTHER INFORMATION: Synthetic peptide

<400> SEQUENCE: 214

Gly Tyr Ala Val Gly
1               5

<210> SEQ ID NO 215
<211> LENGTH: 16
<212> TYPE: PRT
<213> ORGANISM: Artificial sequence
<220> FEATURE:
<223> OTHER INFORMATION: Synthetic peptide

<400> SEQUENCE: 215

Ile Ile Ser Trp Asn Gly Gly Thr His Tyr Ala Asp Ser Val Lys Gly
1               5                   10                  15

-continued

```
<210> SEQ ID NO 216
<211> LENGTH: 13
<212> TYPE: PRT
<213> ORGANISM: Artificial sequence
<220> FEATURE:
<223> OTHER INFORMATION: Synthetic peptide

<400> SEQUENCE: 216

Ser Pro Lys Tyr Tyr Phe Ser Pro Glu Thr Tyr Asn Tyr
1               5                   10

<210> SEQ ID NO 217
<211> LENGTH: 5
<212> TYPE: PRT
<213> ORGANISM: Artificial sequence
<220> FEATURE:
<223> OTHER INFORMATION: Synthetic peptide

<400> SEQUENCE: 217

Ser Tyr Ser Met Gly
1               5

<210> SEQ ID NO 218
<211> LENGTH: 16
<212> TYPE: PRT
<213> ORGANISM: Artificial sequence
<220> FEATURE:
<223> OTHER INFORMATION: Synthetic peptide

<400> SEQUENCE: 218

Thr Ile Ser Trp Ser Gly Gly Phe Tyr Tyr Asp Asp Ser Val Lys Gly
1               5                   10                  15

<210> SEQ ID NO 219
<211> LENGTH: 13
<212> TYPE: PRT
<213> ORGANISM: Artificial sequence
<220> FEATURE:
<223> OTHER INFORMATION: Synthetic peptide

<400> SEQUENCE: 219

Gly Thr Arg Phe Ser Phe Ser Tyr Arg Glu Tyr His Tyr
1               5                   10

<210> SEQ ID NO 220
<211> LENGTH: 5
<212> TYPE: PRT
<213> ORGANISM: Artificial sequence
<220> FEATURE:
<223> OTHER INFORMATION: Synthetic peptide

<400> SEQUENCE: 220

Ala Tyr Ser Met Ala
1               5

<210> SEQ ID NO 221
<211> LENGTH: 16
<212> TYPE: PRT
<213> ORGANISM: Artificial sequence
<220> FEATURE:
<223> OTHER INFORMATION: Synthetic peptide

<400> SEQUENCE: 221

Ala Ile Thr Trp Ser Gly Gly Ser His His Asp Asp Ser Val Lys Gly
1               5                   10                  15
```

```
<210> SEQ ID NO 222
<211> LENGTH: 13
<212> TYPE: PRT
<213> ORGANISM: Artificial sequence
<220> FEATURE:
<223> OTHER INFORMATION: Synthetic peptide

<400> SEQUENCE: 222

Gly Thr Leu Tyr Ser Phe Ser Tyr Arg Asp Tyr Asp Tyr
1               5                   10

<210> SEQ ID NO 223
<211> LENGTH: 5
<212> TYPE: PRT
<213> ORGANISM: Artificial sequence
<220> FEATURE:
<223> OTHER INFORMATION: Synthetic peptide

<400> SEQUENCE: 223

Pro Tyr Ala Met Gly
1               5

<210> SEQ ID NO 224
<211> LENGTH: 17
<212> TYPE: PRT
<213> ORGANISM: Artificial sequence
<220> FEATURE:
<223> OTHER INFORMATION: Synthetic peptide

<400> SEQUENCE: 224

Val Ile Ser Leu Ser Gly Ala Tyr Thr Tyr Asn Val Asn Ala Val Lys
1               5                   10                  15

Gly

<210> SEQ ID NO 225
<211> LENGTH: 14
<212> TYPE: PRT
<213> ORGANISM: Artificial sequence
<220> FEATURE:
<223> OTHER INFORMATION: Synthetic peptide

<400> SEQUENCE: 225

Ser Arg Thr Tyr Tyr Arg Thr Asp Glu Ser Thr Tyr Glu Tyr
1               5                   10

<210> SEQ ID NO 226
<211> LENGTH: 5
<212> TYPE: PRT
<213> ORGANISM: Artificial sequence
<220> FEATURE:
<223> OTHER INFORMATION: Synthetic peptide

<400> SEQUENCE: 226

Ser Tyr His Met Met
1               5

<210> SEQ ID NO 227
<211> LENGTH: 16
<212> TYPE: PRT
<213> ORGANISM: Artificial sequence
<220> FEATURE:
<223> OTHER INFORMATION: Synthetic peptide

<400> SEQUENCE: 227

Ala Leu Ala Trp Arg Gly Gly Thr Tyr Cys Ala Asn Ser Val Lys Gly
1               5                   10                  15
```

<210> SEQ ID NO 228
<211> LENGTH: 13
<212> TYPE: PRT
<213> ORGANISM: Artificial sequence
<220> FEATURE:
<223> OTHER INFORMATION: Synthetic peptide

<400> SEQUENCE: 228

Ser Arg Arg Tyr Val Phe Asp Pro Ser Ala Met Asp Tyr
1               5                   10

<210> SEQ ID NO 229
<211> LENGTH: 5
<212> TYPE: PRT
<213> ORGANISM: Artificial sequence
<220> FEATURE:
<223> OTHER INFORMATION: Synthetic peptide

<400> SEQUENCE: 229

Ser Tyr Ser Met Ser
1               5

<210> SEQ ID NO 230
<211> LENGTH: 16
<212> TYPE: PRT
<213> ORGANISM: Artificial sequence
<220> FEATURE:
<223> OTHER INFORMATION: Synthetic peptide

<400> SEQUENCE: 230

Ile Ile Ser Trp Ser Gly Gly Thr Tyr Tyr Asp Asp Ser Val Lys Gly
1               5                   10                  15

<210> SEQ ID NO 231
<211> LENGTH: 13
<212> TYPE: PRT
<213> ORGANISM: Artificial sequence
<220> FEATURE:
<223> OTHER INFORMATION: Synthetic peptide

<400> SEQUENCE: 231

Gly Thr Gln Phe Ser Phe Ser Tyr Arg Glu Tyr Asp Tyr
1               5                   10

<210> SEQ ID NO 232
<211> LENGTH: 5
<212> TYPE: PRT
<213> ORGANISM: Artificial sequence
<220> FEATURE:
<223> OTHER INFORMATION: Synthetic peptide

<400> SEQUENCE: 232

Thr Tyr Ser Met Ala
1               5

<210> SEQ ID NO 233
<211> LENGTH: 16
<212> TYPE: PRT
<213> ORGANISM: Artificial sequence
<220> FEATURE:
<223> OTHER INFORMATION: Synthetic peptide

<400> SEQUENCE: 233

Ala Ile Thr Arg Ser Gly Gly Asn Thr Tyr Ala Asp Ser Val Lys Gly
1               5                   10                  15

```
<210> SEQ ID NO 234
<211> LENGTH: 13
<212> TYPE: PRT
<213> ORGANISM: Artificial sequence
<220> FEATURE:
<223> OTHER INFORMATION: Synthetic peptide

<400> SEQUENCE: 234

Gly Gly Thr Tyr Ser Phe Val Pro Arg Ser Tyr Asn Tyr
1               5                   10

<210> SEQ ID NO 235
<211> LENGTH: 16
<212> TYPE: PRT
<213> ORGANISM: Artificial sequence
<220> FEATURE:
<223> OTHER INFORMATION: Synthetic peptide

<400> SEQUENCE: 235

Ala Ile Ala Trp Arg Gly Gly Thr Tyr Cys Ala Asn Ser Val Lys Gly
1               5                   10                  15

<210> SEQ ID NO 236
<211> LENGTH: 13
<212> TYPE: PRT
<213> ORGANISM: Artificial sequence
<220> FEATURE:
<223> OTHER INFORMATION: Synthetic peptide

<400> SEQUENCE: 236

Ser Leu Arg Tyr Val Phe Asp Pro Ser Ala Met Asp Tyr
1               5                   10

<210> SEQ ID NO 237
<211> LENGTH: 17
<212> TYPE: PRT
<213> ORGANISM: Artificial sequence
<220> FEATURE:
<223> OTHER INFORMATION: Synthetic peptide

<400> SEQUENCE: 237

Ala Ile Thr Trp Ala Gly Gly Tyr Thr Tyr Gly Ala Asp Ser Glu Lys
1               5                   10                  15

Gly

<210> SEQ ID NO 238
<211> LENGTH: 13
<212> TYPE: PRT
<213> ORGANISM: Artificial sequence
<220> FEATURE:
<223> OTHER INFORMATION: Synthetic peptide

<400> SEQUENCE: 238

Gly Arg Leu Phe Thr Ser Gln Ser Ser Ala Tyr Gln Tyr
1               5                   10

<210> SEQ ID NO 239
<211> LENGTH: 5
<212> TYPE: PRT
<213> ORGANISM: Artificial sequence
<220> FEATURE:
<223> OTHER INFORMATION: Synthetic peptide

<400> SEQUENCE: 239

Pro Tyr Thr Met Gly
1               5
```

```
<210> SEQ ID NO 240
<211> LENGTH: 16
<212> TYPE: PRT
<213> ORGANISM: Artificial sequence
<220> FEATURE:
<223> OTHER INFORMATION: Synthetic peptide

<400> SEQUENCE: 240

Val Val Ser Ser Gly Gly Gly Thr Tyr Tyr Ala Asn Ser Val Lys Gly
1               5                   10                  15

<210> SEQ ID NO 241
<211> LENGTH: 13
<212> TYPE: PRT
<213> ORGANISM: Artificial sequence
<220> FEATURE:
<223> OTHER INFORMATION: Synthetic peptide

<400> SEQUENCE: 241

Gly Ser Ile Phe Arg Trp Ser Pro Met Ser Tyr Asp Tyr
1               5                   10

<210> SEQ ID NO 242
<211> LENGTH: 5
<212> TYPE: PRT
<213> ORGANISM: Artificial sequence
<220> FEATURE:
<223> OTHER INFORMATION: Synthetic peptide

<400> SEQUENCE: 242

Ile Ser Arg Met Gly
1               5

<210> SEQ ID NO 243
<211> LENGTH: 16
<212> TYPE: PRT
<213> ORGANISM: Artificial sequence
<220> FEATURE:
<223> OTHER INFORMATION: Synthetic peptide

<400> SEQUENCE: 243

Ile Ile Phe Ser Asp Ala Ser Thr Asp Tyr Ala Asp Ser Val Lys Gly
1               5                   10                  15

<210> SEQ ID NO 244
<211> LENGTH: 13
<212> TYPE: PRT
<213> ORGANISM: Artificial sequence
<220> FEATURE:
<223> OTHER INFORMATION: Synthetic peptide

<400> SEQUENCE: 244

Val Leu Arg Ala Ala Gly Tyr Gly Tyr Phe Asn Gln Tyr
1               5                   10

<210> SEQ ID NO 245
<211> LENGTH: 5
<212> TYPE: PRT
<213> ORGANISM: Artificial sequence
<220> FEATURE:
<223> OTHER INFORMATION: Synthetic peptide

<400> SEQUENCE: 245

Thr Tyr Ala Met Gly
1               5
```

<210> SEQ ID NO 246
<211> LENGTH: 17
<212> TYPE: PRT
<213> ORGANISM: Artificial sequence
<220> FEATURE:
<223> OTHER INFORMATION: Synthetic peptide

<400> SEQUENCE: 246

Ala Ile Thr Arg Ala Gly Gly Asn Thr Tyr Asn Ala Asp Ser Val Lys
1               5                   10                  15

Gly

<210> SEQ ID NO 247
<211> LENGTH: 13
<212> TYPE: PRT
<213> ORGANISM: Artificial sequence
<220> FEATURE:
<223> OTHER INFORMATION: Synthetic peptide

<400> SEQUENCE: 247

Gly Pro Arg Tyr Ser Thr Ile Ser Thr Met Phe Pro Tyr
1               5                   10

<210> SEQ ID NO 248
<211> LENGTH: 16
<212> TYPE: PRT
<213> ORGANISM: Artificial sequence
<220> FEATURE:
<223> OTHER INFORMATION: Synthetic peptide

<400> SEQUENCE: 248

Thr Ile Ser Trp Ser Gly Gly Asn Tyr Val Asp Asn Ser Val Lys Gly
1               5                   10                  15

<210> SEQ ID NO 249
<211> LENGTH: 13
<212> TYPE: PRT
<213> ORGANISM: Artificial sequence
<220> FEATURE:
<223> OTHER INFORMATION: Synthetic peptide

<400> SEQUENCE: 249

Gly Thr Gln Phe Ser Phe Ser Tyr Arg Gln Tyr Asp Tyr
1               5                   10

<210> SEQ ID NO 250
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 250

Gln Leu Gln Val Val Glu Ser Gly Gly Gly Leu Val Gln Ala Gly Gly
1               5                   10                  15

Ser Leu Arg Leu Ser Cys Ala Ala Ser Ser Ala Tyr Ser Met Gly
                20                  25                  30

Trp Phe Arg Gln Ala Pro Gly Lys Glu Arg Glu Phe Val Ala Val Ile
            35                  40                  45

Ser Trp Ser Gly Gly Ser His Tyr Asp Asp Ser Val Lys Gly Arg Phe
        50                  55                  60

Thr Ile Ser Arg Asp Gly Ala Lys Asn Thr Val Tyr Leu Gln Met Asn
65                  70                  75                  80

-continued

Ser Leu Lys Pro Glu Asp Thr Ala Val Tyr Tyr Cys Ala Val Gly Thr
            85                  90                  95

Leu Tyr Ser Phe Arg Tyr Arg Asp Tyr Asp Trp Gly Gln Gly Thr
            100                 105                 110

Gln Val Thr Val Ser Ser
        115

<210> SEQ ID NO 251
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 251

Gln Leu Gln Leu Val Glu Ser Gly Gly Gly Leu Val Gln Ala Gly Gly
1               5                   10                  15

Ser Leu Arg Leu Ser Cys Val Ala Ser Gly Arg Thr Phe Ser Thr Tyr
            20                  25                  30

Ala Met Asp Trp Phe Arg Gln Ala Pro Gly Lys Glu Arg Glu Phe Val
        35                  40                  45

Ala Ala Ile Ser Trp His Ser Ala Ile Tyr Tyr Ala Asp Ala Val Lys
    50                  55                  60

Gly Arg Phe Thr Ile Ser Arg Asp Asn Gly Lys Asn Thr Met Tyr Leu
65                  70                  75                  80

Gln Met Asn Asn Leu Lys Pro Glu Asp Thr Ala Val Tyr Phe Cys Ala
                85                  90                  95

Ala Ala Leu Arg Tyr Arg Phe Asn Pro Ser Ala Met Glu Tyr Trp Gly
            100                 105                 110

Lys Gly Thr Leu Val Thr Val Ser Ser
        115                 120

<210> SEQ ID NO 252
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 252

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Gly Tyr
            20                  25                  30

Ala Val Gly Trp Phe Arg Gln Ala Pro Gly Lys Glu Arg Glu Phe Val
        35                  40                  45

Thr Ile Ile Ser Trp Asn Gly Thr His Tyr Ala Asp Ser Val Lys
    50                  55                  60

Gly Arg Phe Ala Ile Ser Arg Asp Asn Ala Lys Asn Thr Val Tyr Leu
65                  70                  75                  80

Gln Met Asn Asn Leu Lys Pro Glu Asp Thr Ala Val Tyr Tyr Cys Ala
                85                  90                  95

Val Ser Pro Lys Tyr Tyr Phe Pro Glu Tyr Asn Tyr Trp Gly
            100                 105                 110

Gln Gly Thr Gln Val Thr Val Ser Ser
        115                 120

<210> SEQ ID NO 253

```
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 253

Gln Leu Gln Leu Val Glu Ser Gly Gly Gly Leu Val Gln Ala Gly Gly
1               5                   10                  15

Ser Leu Arg Leu Ser Cys Ala Ala Ser Ser Ser Tyr Ser Met Gly
            20                  25                  30

Trp Phe Arg Gln Ala Pro Gly Lys Glu Arg Glu Phe Val Ala Thr Ile
        35                  40                  45

Ser Trp Ser Gly Gly Phe Tyr Tyr Asp Asp Ser Val Lys Gly Arg Phe
    50                  55                  60

Thr Val Ser Arg Asp Asn Ala Lys Asn Thr Val Tyr Leu Gln Met Asn
65                  70                  75                  80

Ser Leu Lys Pro Glu Asp Thr Ala Val Tyr Tyr Cys Ala Ala Gly Thr
                85                  90                  95

Arg Phe Ser Phe Ser Tyr Arg Glu Tyr His Tyr Trp Gly Gln Gly Thr
            100                 105                 110

Gln Val Thr Val Ser Ser
        115

<210> SEQ ID NO 254
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 254

Gln Leu Gln Val Val Glu Ser Gly Gly Gly Leu Val Gln Ala Gly Gly
1               5                   10                  15

Ser Leu Arg Leu Ser Cys Ala Ala Ser Ser Ser Ala Tyr Ser Met Ala
            20                  25                  30

Trp Phe Arg Gln Ala Pro Gly Lys Glu Arg Glu Phe Val Ala Ala Ile
        35                  40                  45

Thr Trp Ser Gly Gly Ser His His Asp Asp Ser Val Lys Gly Arg Phe
    50                  55                  60

Thr Ile Ser Arg Asp Gly Ala Lys Asn Thr Val Tyr Leu Gln Met Asn
65                  70                  75                  80

Ser Leu Lys Pro Glu Asp Thr Ala Val Tyr Tyr Cys Ala Val Gly Thr
                85                  90                  95

Leu Tyr Ser Phe Ser Tyr Arg Asp Tyr Asp Tyr Trp Gly Gln Gly Thr
            100                 105                 110

Gln Val Thr Val Ser Ser
        115

<210> SEQ ID NO 255
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 255

Glu Leu Gln Leu Val Glu Ser Gly Gly Gly Leu Val Gln Ala Gly Gly
1               5                   10                  15
```

```
Ser Leu Arg Leu Ser Cys Ala Ala Ser Glu Gly Thr Phe Arg Pro Tyr
            20                  25                  30

Ala Met Gly Trp Phe Arg Gln Ala Pro Arg Lys Glu Arg Glu Phe Val
        35                  40                  45

Ala Val Ile Ser Leu Ser Gly Ala Tyr Thr Tyr Asn Val Asn Ala Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Thr Pro Glu Asp Thr Ala Ile Tyr Tyr Cys
                85                  90                  95

Gly Ala Ser Arg Thr Tyr Tyr Arg Thr Asp Glu Ser Tyr Tyr Glu Tyr
            100                 105                 110

Trp Gly Gln Gly Thr Gln Val Thr Val Ser Ser
        115                 120

<210> SEQ ID NO 256
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 256

Gln Leu Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

His Met Met Trp Phe Arg Gln Ala Pro Gly Lys Glu Arg Glu Phe Val
        35                  40                  45

Ala Ala Leu Ala Trp Arg Gly Gly Thr Tyr Cys Ala Asn Ser Val Lys
    50                  55                  60

Gly Arg Cys Thr Ile Ser Arg Asp Asn Ala Gln Asp Thr Val Tyr Leu
65                  70                  75                  80

Gln Met Asn Ser Leu Lys Pro Glu Asp Thr Ala Val Tyr Phe Cys Ala
                85                  90                  95

Ala Ser Arg Arg Tyr Val Phe Asp Pro Ser Ala Met Asp Tyr Trp Ala
            100                 105                 110

Lys Gly Thr Leu Val Thr Val Ser Ser
        115                 120

<210> SEQ ID NO 257
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 257

Gln Val Gln Leu Val Glu Ser Gly Gly Gly Leu Val Gln Ala Gly Gly
1               5                   10                  15

Ser Leu Arg Leu Ser Cys Ala Ala Ser Ser Ser Ser Tyr Ser Met Ser
            20                  25                  30

Trp Phe Arg Gln Ala Pro Gly Lys Glu Arg Glu Phe Val Ala Ile Ile
        35                  40                  45

Ser Trp Ser Gly Gly Thr Tyr Tyr Asp Asp Ser Val Lys Gly Arg Phe
    50                  55                  60

Thr Val Ser Arg Asp Asn Ala Lys Asn Thr Val Tyr Leu Gln Met Asn
65                  70                  75                  80
```

Ser Leu Lys Pro Glu Asp Thr Ala Val Tyr Tyr Cys Ala Ala Gly Thr
            85                  90                  95

Gln Phe Ser Phe Ser Tyr Arg Glu Tyr Asp Tyr Trp Gly Gln Gly Thr
            100                 105                 110

Gln Val Thr Val Ser Ser
        115

<210> SEQ ID NO 258
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 258

Glu Leu Gln Val Val Glu Ser Gly Gly Gly Leu Val Gln Ala Gly Gly
1               5                   10                  15

Ser Leu Arg Leu Ser Cys Ala Ala Ser Gly Arg Thr Phe Ser Thr Tyr
            20                  25                  30

Ser Met Ala Trp Phe Arg Gln Ala Pro Gly Lys Glu Arg Glu Phe Val
        35                  40                  45

Ala Ala Ile Thr Arg Ser Gly Gly Asn Thr Tyr Ala Asp Ser Val Lys
    50                  55                  60

Gly Arg Phe Thr Ile Ser Arg Asp Asn Ala Lys Asn Thr Val Thr Leu
65                  70                  75                  80

Gln Met Asn Ser Leu Lys Pro Glu Asp Thr Ala Ala Tyr His Cys Ala
                85                  90                  95

Ala Gly Gly Thr Tyr Ser Phe Val Pro Arg Ser Tyr Asn Tyr Trp Gly
            100                 105                 110

Gln Gly Thr Gln Val Thr Val Ser Ser
        115                 120

<210> SEQ ID NO 259
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 259

Gln Val Gln Val Gln Glu Ser Gly Gly Gly Leu Val Gln Ala Gly Asn
1               5                   10                  15

Ser Leu Arg Leu Ser Cys Ala Ala Ser Gly Arg Thr Phe Ser Ser Tyr
            20                  25                  30

His Met Met Trp Phe Arg Gln Ala Pro Gly Lys Glu Arg Glu Phe Val
        35                  40                  45

Ala Ala Ile Ala Trp Arg Gly Gly Thr Tyr Cys Ala Asn Ser Val Lys
    50                  55                  60

Gly Arg Cys Thr Ile Ser Arg Asp Asn Ala Lys Asp Thr Val Tyr Leu
65                  70                  75                  80

Gln Met Asn Ser Leu Lys Pro Glu Asp Thr Ala Val Tyr Phe Cys Ala
                85                  90                  95

Ala Ser Leu Arg Tyr Val Phe Asp Pro Ser Ala Met Asp Tyr Trp Gly
            100                 105                 110

Lys Gly Thr Leu Val Thr Val Ser Ser
        115                 120

<210> SEQ ID NO 260
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 260

Gln Val Gln Leu Val Glu Ser Gly Gly Gly Leu Ala Gln Ala Gly Gly
1               5                   10                  15

Ser Leu Arg Leu Ser Cys Val Ala Ser Gly Arg Ala Ala Gly Thr Tyr
            20                  25                  30

Ser Met Ala Trp Phe Arg Gln Ala Pro Gly Lys Glu Arg Glu Phe Val
        35                  40                  45

Ala Ala Ile Thr Trp Ala Gly Gly Tyr Thr Tyr Gly Ala Asp Ser Glu
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Ser Cys
                85                  90                  95

Ala Gly Gly Arg Leu Phe Thr Ser Gln Ser Ser Ala Tyr Gln Tyr Trp
            100                 105                 110

Gly Gln Gly Thr Gln Val Thr Val Ser Ser
        115                 120

<210> SEQ ID NO 261
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 261

Gln Leu Gln Leu Val Glu Ser Gly Gly Gly Leu Val Gln Ala Gly Gly
1               5                   10                  15

Ser Leu Lys Leu Ser Cys Ala Ala Ser Gly Arg Thr Phe Asn Pro Tyr
            20                  25                  30

Thr Met Gly Trp Phe Arg Gln Ala Pro Gly Lys Glu Arg Glu Phe Val
        35                  40                  45

Ala Val Val Ser Ser Gly Gly Gly Thr Tyr Tyr Ala Asn Ser Val Lys
    50                  55                  60

Gly Arg Phe Thr Ile Ser Arg Asp Asn Ala Lys Ala Thr Val Tyr Leu
65                  70                  75                  80

Gln Met Asn Ser Leu Lys Pro Glu Asp Thr Ala Val Tyr Tyr Cys Ala
                85                  90                  95

Ala Gly Ser Ile Phe Arg Trp Ser Pro Met Ser Tyr Asp Tyr Trp Gly
            100                 105                 110

Gln Gly Thr Gln Val Thr Val Ser Ser
        115                 120

<210> SEQ ID NO 262
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 262

Glu Leu Gln Val Val Glu Ser Gly Gly Gly Leu Val Gln Ala Gly Asp
1               5                   10                  15

-continued

```
Ser Leu Arg Leu Ser Cys Ala Val Ser Gly Arg Thr Phe Ser Ser Tyr
        20                  25                  30

His Met Met Trp Phe Arg Gln Ala Pro Gly Lys Glu Arg Glu Phe Val
            35                  40                  45

Ala Ala Ile Ala Trp Arg Gly Gly Thr Tyr Cys Ala Asn Ser Val Lys
 50                  55                  60

Gly Arg Cys Thr Ile Ser Arg Asp Asn Ala Lys Asp Thr Val Tyr Leu
 65                  70                  75                  80

Gln Met Asn Ser Leu Lys Pro Glu Asp Thr Ala Val Tyr Phe Cys Ala
                85                  90                  95

Ala Ser Leu Arg Tyr Val Phe Asp Pro Ser Ala Met Asp Tyr Trp Gly
            100                 105                 110

Lys Gly Thr Leu Val Thr Val Ser Ser
            115                 120
```

<210> SEQ ID NO 263
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 263

```
Gln Val Gln Leu Val Glu Ser Gly Gly Gly Leu Val Gln Pro Gly Gly
 1               5                  10                  15

Ser Leu Arg Leu Ser Cys Ala Ala Ser Gly Ser Ile Phe Ser Ile Ser
            20                  25                  30

Arg Met Gly Trp Tyr Arg Gln Ala Pro Gly Lys Gln Arg Glu Leu Val
        35                  40                  45

Ala Ile Ile Phe Ser Asp Ala Ser Thr Asp Tyr Ala Asp Ser Val Lys
 50                  55                  60

Gly Arg Phe Thr Ile Ser Arg Ser Asn Ala Lys Asn Thr Val Tyr Leu
 65                  70                  75                  80

Gln Met Asn Ser Leu Lys Pro Glu Asp Thr Ala Val Tyr Tyr Cys Lys
                85                  90                  95

Ser Val Leu Arg Ala Ala Gly Tyr Gly Tyr Phe Asn Gln Tyr Trp Gly
            100                 105                 110

Gln Gly Thr Gln Val Thr Val Ser Ser
            115                 120
```

<210> SEQ ID NO 264
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 264

```
Gln Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Phe Ser Thr Tyr
            20                  25                  30

Ser Met Ala Trp Phe Arg Gln Ala Pro Gly Lys Glu Arg Glu Phe Val
        35                  40                  45

Ala Ala Ile Thr Arg Ser Gly Gly Asn Thr Tyr Ala Asp Ser Val Lys
 50                  55                  60

Gly Arg Phe Thr Ile Ser Arg Asp Asn Ala Lys Asn Thr Val Thr Leu
```

```
                65                  70                  75                  80
Gln Met Asn Ser Leu Lys Pro Glu Asp Thr Ala Ala Tyr His Cys Ala
                    85                  90                  95

Ala Gly Gly Thr Tyr Ser Phe Val Pro Arg Ser Tyr Asn Tyr Trp Gly
                100                 105                 110

Gln Gly Thr Gln Val Thr Val Ser Ser
                115                 120

<210> SEQ ID NO 265
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 265

Gln Leu Gln Leu Val Glu Ser Gly Gly Gly Leu Val Gln Pro Gly Gly
1               5                   10                  15

Ser Leu Arg Leu Ser Cys Ala Ala Ser Glu Asn Ser Val Ser Thr Tyr
                20                  25                  30

Ala Met Gly Trp Phe Arg Gln Ala Pro Gly Lys Glu Arg Glu Phe Val
                35                  40                  45

Ala Ala Ile Thr Arg Ala Gly Gly Asn Thr Tyr Asn Ala Asp Ser Val
            50                  55                  60

Lys Gly Arg Phe Thr Ile Ser Arg Asp Asn Ala Glu Asn Thr Ile Tyr
65                  70                  75                  80

Leu Gln Met Asn Ser Leu Lys Pro Glu Asp Thr Ala Val Tyr Ser Cys
                85                  90                  95

Ala Ala Gly Pro Arg Tyr Ser Thr Ile Ser Thr Met Phe Pro Tyr Trp
                100                 105                 110

Gly Gln Gly Thr Gln Val Thr Val Ser Ser
                115                 120

<210> SEQ ID NO 266
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 266

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ser Tyr Ser Met Gly
                20                  25                  30

Trp Phe Arg Gln Ala Pro Gly Lys Glu Arg Glu Phe Val Ala Thr Ile
                35                  40                  45

Ser Trp Ser Gly Gly Asn Tyr Val Asp Asn Ser Val Lys Gly Arg Phe
            50                  55                  60

Thr Val Ser Arg Asp Asn Ala Lys Asn Thr Val Tyr Leu Gln Met Asn
65                  70                  75                  80

Ser Leu Lys Pro Glu Asp Thr Ala Val Tyr Tyr Cys Ala Ala Gly Thr
                85                  90                  95

Gln Phe Ser Phe Ser Tyr Arg Gln Tyr Asp Tyr Trp Gly Gln Gly Thr
                100                 105                 110

Gln Val Thr Val Ser Ser
                115
```

<210> SEQ ID NO 267
<211> LENGTH: 139
<212> TYPE: PRT
<213> ORGANISM: Macaca fascicularis

<400> SEQUENCE: 267

Met Ser Leu Leu Ser Val Pro His Thr Glu Ser Val Ser Leu Ser Thr
1               5                   10                  15

Gly Ser Thr Val Thr Ile Lys Gly Arg Pro Leu Val Cys Phe Leu Asn
            20                  25                  30

Glu Pro His Leu Gln Val Asp Phe His Thr Glu Met Lys Glu Asp Ser
        35                  40                  45

Asp Ile Ala Phe His Phe Gln Val Tyr Phe Gly Asn Arg Val Val Met
    50                  55                  60

Asn Ser Arg Glu Phe Lys Ile Trp Lys Glu Val Glu Ser Lys Asn
65                  70                  75                  80

Met Pro Phe Gln Asp Gly Gln Glu Phe Glu Leu Ser Ile Leu Val Leu
                85                  90                  95

Glu Asp Lys Tyr Gln Val Met Val Asn Gly Gln Ala Tyr Tyr Asn Phe
            100                 105                 110

Asn His Arg Ile Pro Val Ser Ser Val Lys Met Val Gln Val Trp Arg
        115                 120                 125

Asp Ile Ser Leu Thr Lys Phe Asn Val Ser Asn
    130                 135

<210> SEQ ID NO 268
<211> LENGTH: 139
<212> TYPE: PRT
<213> ORGANISM: Macaca fascicularis

<400> SEQUENCE: 268

Met Ser Leu Leu Ser Val Pro His Thr Glu Ser Val Ser Leu Ser Thr
1               5                   10                  15

Gly Ser Thr Val Thr Ile Lys Gly Arg Pro Leu Val Cys Phe Phe Asn
            20                  25                  30

Glu Pro His Leu Gln Val Asp Phe His Thr Glu Met Lys Glu Asp Ser
        35                  40                  45

Asp Ile Ala Phe His Phe Gln Val Tyr Phe Gly Asn Arg Val Val Met
    50                  55                  60

Asn Ser Arg Glu Phe Lys Ile Trp Lys Glu Val Glu Ser Lys Asn
65                  70                  75                  80

Met Pro Phe Gln Asp Gly Gln Glu Phe Glu Leu Ser Ile Leu Val Leu
                85                  90                  95

Glu Asp Lys Tyr Gln Val Met Val Asn Gly Gln Ala Tyr Tyr Asn Phe
            100                 105                 110

Asn His Arg Ile Pro Val Ser Ser Val Lys Met Val Gln Val Trp Arg
        115                 120                 125

Asp Ile Ser Leu Thr Lys Phe Asn Val Ser Asn
    130                 135

<210> SEQ ID NO 269
<211> LENGTH: 139
<212> TYPE: PRT
<213> ORGANISM: Macaca fascicularis

<400> SEQUENCE: 269

Met Ser Leu Leu Ser Val Pro His Thr Glu Ser Val Ser Leu Ser Thr

```
            1               5                  10                 15
Gly Ser Thr Val Thr Ile Glu Ala Arg Pro Leu Val Cys Phe Phe Asn
                20                 25                 30
Glu Pro His Leu Gln Val Asp Phe His Thr Glu Met Lys Glu Asp Ser
                35                 40                 45
Asp Ile Ala Phe His Phe Gln Val Tyr Phe Gly Asn Arg Val Val Met
                50                 55                 60
Asn Ser Arg Glu Tyr Arg Thr Trp Lys Glu Val Glu Ser Lys Asn
 65                 70                 75                 80
Met Pro Phe Gln Asp Gly Gln Glu Phe Glu Leu Arg Ile Leu Val Leu
                85                 90                 95
Glu Asp Lys Tyr Gln Val Met Val Asn Gly Gln Ala Tyr Tyr Asn Phe
                100                105                110
Asn His Arg Ile Pro Val Ser Ser Val Lys Met Val Gln Val Trp Arg
                115                120                125
Asp Ile Ser Leu Thr Lys Phe Asn Val Ser Asn
                130                135
```

<210> SEQ ID NO 270
<211> LENGTH: 5
<212> TYPE: PRT
<213> ORGANISM: Artificial sequence
<220> FEATURE:
<223> OTHER INFORMATION: Synthetic peptide

<400> SEQUENCE: 270

```
Glu Glu Glu Glu Lys
1               5
```

<210> SEQ ID NO 271
<211> LENGTH: 8
<212> TYPE: PRT
<213> ORGANISM: Artificial sequence
<220> FEATURE:
<223> OTHER INFORMATION: Synthetic peptide

<400> SEQUENCE: 271

```
Glu Asn Leu Tyr Phe Gln Gly Ser
1               5
```

<210> SEQ ID NO 272
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 272

```
Met Ala Ser Thr Thr His His His His His His Asp Thr Asp Ile Pro
1               5                  10                 15
Thr Thr Gly Gly Gly Ser Arg Pro Asp Asp Asp Lys Glu Asn Leu
                20                 25                 30
Tyr Phe Gln Gly His Met
                35
```

GALECTIN-10 ANTIBODIES

RELATED APPLICATIONS

This application is a division of U.S. patent application Ser. No. 16/382,997, filed Apr. 12, 2019, which claims benefit of Great Britain Provisional Application No. 1806099.6, filed Apr. 13, 2018, and Great Britain Provisional Application No. 1901648.4, filed Feb. 6, 2019, the entire contents of each of which are incorporated herein by reference.

SEQUENCE LISTING

The instant application contains a Sequence Listing which has been submitted electronically in ASCII format and is hereby incorporated by reference in its entirety. Said ASCII copy, created on Mar. 8, 2021, is named 715925_AGX5-047DIV_ST25.txt, and is 127,850 bytes in size.

FIELD OF THE INVENTION

The present invention relates to antagonists, particularly antibodies and antigen binding fragments thereof, that bind to the protein galectin-10, particularly human galectin-10. The galectin-10 antagonists, particularly the antibodies and antigen binding fragments of the invention, disrupt the crystallization of galectin-10 and are therefore useful in methods of preventing and treating diseases and conditions wherein the pathology is linked to the formation/presence of Charcot-Leyden crystals (CLCs).

BACKGROUND TO THE INVENTION

Charcot-Leyden crystals (CLCs) were first described in 1853 and are microscopic, colourless crystals found in patients with certain conditions including allergic asthma and parasitic infections. CLCs are frequently observed in human tissues and secretions associated with an eosinophilic inflammatory response. In addition to asthma and parasitic infections, these crystals have been found in patients with cancer, for example myeloid leukemia. Structurally, CLCs accumulate as extracellular hexagonal bipyramidal crystals with a length of 20-40 µm and a width of 2-4 µm. The protein forming these crystals has been identified as galectin-10.

Galectin-10 (also known as Charcot Leyden Crystal Protein) is a small (16.5 kDa), hydrophobic, glycan-binding protein expressed abundantly in the bone marrow, primarily by eosinophils (Chua et al. (2012) *PLoS One.* 7(8): e42549). Galectin-10 is also produced to a lesser extent by basophils and Foxp3-positive Tregs (Kubach et al. (2007) *Blood* 110(5): 1550-8). This protein is among the most abundant of eosinophil constituents, representing 7%-10% of total cellular protein. Galectin-10 is only found in humans, it lacks a secretion peptide signal and transmembrane domain, and is secreted under certain conditions by non-classical and novel apocrine mechanisms.

Despite abundant reports showing the appearance of CLCs in tissues from patients with eosinophilic disorders, the common view is that these crystals are merely a marker of eosinophil demise.

SUMMARY OF THE INVENTION

The in vivo function of galectin-10 and the significance of CLC formation have remained elusive, particularly because mice do not carry a LGALS10 gene encoding galectin-10. It is reported herein how galectin-10 crystals can induce a pro-inflammatory response in vivo and how this response can be suppressed by the administration of galectin-10 antibodies capable of disrupting galectin-10 crystallization. It is reported herein how galectin-10 antibodies and antigen binding fragments, including IgGs, VHH antibodies and Fabs, can prevent crystallization of galectin-10 and also dissolve pre-existing galectin-10 crystals. Importantly, galectin-10 antibodies were able to dissolve CLCs from patient mucus samples. Taken together, this demonstrates how agents that target galectin-10 crystallization can be used to treat conditions and disorders where the pathology is linked to the presence of CLCs.

In a first aspect, the present invention provides an antagonist that binds to galectin-10, wherein the antagonist binds to an epitope of galectin-10 and thereby shields a crystal packing interface of galectin-10. The antagonist preferably binds to human galectin-10. The present invention further provides an antagonist that binds to galectin-10, which, when bound to soluble galectin-10, inhibits the crystallization of galectin-10. The present invention further provides an antagonist that binds to galectin-10, which, when bound to crystalline galectin-10, promotes the dissolution of crystalline galectin-10.

In certain embodiments, the antagonists that bind to galectin-10 and thereby shield a crystal packing interface of galectin-10 inhibit crystallization of the galectin-10 when bound to soluble galectin-10. Alternatively or in addition, the galectin-10 antagonists, when bound to crystalline galectin-10, may promote dissolution of crystalline galectin-10.

The antagonists of the present invention preferably bind to human galectin-10. In certain embodiments, the antagonist binds to an epitope comprising one or more amino acids from the crystal packing interfaces of galectin-10. Said epitope may comprise one or more amino acids selected from the group consisting of: Ser2, Leu3, Leu4, Tyr8, Thr9, Glu10, Ala11, Ala12, Ser13, Thr16, Thr42, Glu43, Met44, Lys45, Asp49, Ile50, Glu68, Tyr69, Gly70, Ala71, Lys73, Gln74, Gln75, Val76, Glu77, Ser78, Lys79, Asn80, Met81, Leu96, Pro97, Asp98, Lys99, Gln101, Met103, Gly106, Gln107, Ser108, Ser109, Tyr110, Thr111, Asp113, His114, Arg115, Ile116, Lys117, Ala120, Gln125, Thr133, Lys134, Phe135, Asn136, Val137, Ser138, Tyr139, Leu140 and Lys141. The amino acid positions of galectin-10 are defined with reference to the human protein sequence identified herein as SEQ ID NO: 141.

In certain embodiments, the antagonist binds to an epitope comprising Tyr69 or an epitope comprising an amino acid adjacent to Tyr69. In preferred embodiments, the antagonist binds to an epitope comprising Tyr69. In a further preferred embodiment, the antagonist binds to an epitope comprising Glu68, Tyr69 and Gly70, wherein the amino acid positions are identified with reference to SEQ ID NO: 141. In certain embodiments, the antagonist binds to an epitope comprising the amino acids Thr42, Glu43, Lys45, Asp49, Glu68, Tyr69, Gly70, Ala71, Lys73, His114, Arg115, Ile116, Lys117 and Ala120. In certain embodiments, the antagonist binds to an epitope comprising the amino acids Thr42, Glu43, Lys45, Asp49, Glu68, Tyr69, Gly70, Ala71, Lys73, His114, Arg115, Ile116, Lys117, GLu119, Ala120 and Lys122. The epitope may additionally comprise Gln74 and/or Asp98.

In certain embodiments, the antagonist binds to an epitope comprising Glu33, Gly59, Arg60 and Lys79. The epitope may additionally comprise Gln74, Gln75 and Glu77. In certain embodiments, the epitope comprises or consists of Leu31, Glu33, Gly59, Arg60, Ser78, Lys79, Asn80, Met81, Pro82 and Gln84. In certain embodiments, the epitope comprises or consists of Glu33, Gly59, Arg60, Gln74, Gln75, Val76, Glu77, Ser78, Lys79, Asn80, Met81, Pro82 and Ser109. In certain embodiments, the epitope comprises or consists of Glu33, Gly59, Arg60, Trp72, Gln74, Gln75, Val76, Glu77, Lys79, Asn80, Met81, Pro82, Gln84 and Ser109. In certain embodiments, the epitope comprises or consists of Glu33, Gly59, Arg60, Gln74, Gln75, Val76, Glu77, Ser78, Lys79, Asn80, Met81, Pro82, Phe83, Gln84. In certain embodiments, the epitope comprises or consist of Thr42, Asp49, Glu68, Tyr69, Gly70, Ala71, Lys73, Arg115, Ile116, Lys117, Glu119 and Ala120. In certain embodiments, the epitope comprises or consists of Glu43, Asp49, Glu68, Tyr69, Lys73, Asp98, Asp113, His114, Arg115, Lys117, Glu119 and Ala120. In certain embodiments, the epitope comprises or consists of Asp49, Glu68, Tyr69, Lys73, Gln74, Asp98, Asp113, His114, Arg115, Ile116 and Lys117. In certain embodiments, the epitope comprises or consists of Ser2, Leu3, Leu4, Pro5, Pro7, Tyr8, Thr9, Glu10, Ala11, Lys23, Arg25, Met44, Gly86, Gln87, Glu88, Phe89, Glu90, Asn105, Gln125, Thr133, Lys134 and Phe135. The amino acid positions of galectin-10 are defined with reference to the human protein sequence identified herein as SEQ ID NO: 141.

The galectin-10 antagonist may bind to an epitope consisting of amino acids from the crystal packing interfaces of galectin-10. In such embodiments, the epitope may consist of one or more amino acids selected from the group consisting of: Ser2, Leu3, Leu4, Tyr8, Thr9, Glu10, Ala11, Ala12, Ser13, Thr16, Thr42, Glu43, Met44, Lys45, Asp49, Ile50, Glu68, Tyr69, Gly70, Ala71, Lys73, Gln74, Gln75, Val76, Glu77, Ser78, Lys79, Asn80, Met81, Leu96, Pro97, Asp98, Lys99, Gln101, Met103, Gly106, Gln107, Ser108, Ser109, Tyr110, Thr111, Asp113, His114, Arg115, Ile116, Lys117, Ala120, Gln125, Thr133, Lys134, Phe135, Asn136, Val137, Ser138, Tyr139, Leu140 and Lys141. The amino acid positions of galectin-10 are defined with reference to the human protein sequence identified herein as SEQ ID NO: 141.

Alternatively or in addition, the antagonist may bind to an epitope comprising one or more amino acids from the dimerization interface of galectin-10. In such embodiments, the antagonist may bind to an epitope comprising one or more amino acids selected from the group consisting of: Pro5, Pro7, Leu27, Ala28, Cys29, Leu31, Asn32, Glu33, Pro34, Tyr35, Gln37, His41, Glu46, Glu47, Gln55, Arg60, Arg61, Arg67, Trp72, Gln75, Trp127, Arg128 and Asp129.

In certain embodiments, the antagonist is a small molecule, an inhibitory polypeptide or an antibody mimetic. In preferred embodiments, the antagonist is an antibody or antigen binding fragment thereof, as defined elsewhere herein. The antibody may be an immunoglobulin, preferably an immunoglobulin of the IgG class, more preferably IgG1. The antibody may be a VHH antibody. The antibody or antigen binding fragment thereof may be a humanised or germlined variant of a non-human antibody, for example a camelid-derived antibody. The antibody or antigen binding fragment may comprise the CH1 domain, hinge region, CH2 domain and/or CH3 domain of a human IgG, preferably IgG1.

In certain embodiments, the antigen binding fragment is selected from the group consisting of: an antibody light chain variable domain (VL); an antibody heavy chain variable domain (VH); a single chain antibody (scFv); a F(ab')2 fragment; a Fab fragment; an Fd fragment; an Fv fragment; a one-armed (monovalent) antibody; diabodies, triabodies, tetrabodies, or any antigen binding molecule formed by combination, assembly or conjugation of such antigen binding fragments. In preferred embodiments, the antigen binding fragment is a Fab.

The present invention provides, in further aspects, antibodies and antigen binding fragments that bind galectin-10. These antibodies may be defined exclusively with respect to their structural characteristics as described below. In certain embodiments, the antibody or antigen binding fragment comprises a variable heavy chain domain (VH) and a variable light chain domain (VL) wherein the VH and VL domains comprise the complementarity determining region (CDR) sequences selected from the group consisting of:

(i) HCDR3 comprising or consisting of SEQ ID NO: 3; HCDR2 comprising or consisting of SEQ ID NO: 2; HCDR1 comprising or consisting of SEQ ID NO: 1; LCDR3 comprising or consisting of SEQ ID NO: 58; LCDR2 comprising or consisting of SEQ ID NO: 57; LCDR1 comprising or consisting of SEQ ID NO: 56;

(ii) HCDR3 comprising or consisting of SEQ ID NO: 6; HCDR2 comprising or consisting of SEQ ID NO: 5; HCDR1 comprising or consisting of SEQ ID NO: 4; LCDR3 comprising or consisting of SEQ ID NO: 61; LCDR2 comprising or consisting of SEQ ID NO: 60; LCDR1 comprising or consisting of SEQ ID NO: 59;

(iii) HCDR3 comprising or consisting of SEQ ID NO: 9; HCDR2 comprising or consisting of SEQ ID NO: 8; HCDR1 comprising or consisting of SEQ ID NO: 7; LCDR3 comprising or consisting of SEQ ID NO: 64; LCDR2 comprising or consisting of SEQ ID NO: 63; LCDR1 comprising or consisting of SEQ ID NO: 62;

(iv) HCDR3 comprising or consisting of SEQ ID NO: 12; HCDR2 comprising or consisting of SEQ ID NO: 11; HCDR1 comprising or consisting of SEQ ID NO: 10; LCDR3 comprising or consisting of SEQ ID NO: 67; LCDR2 comprising or consisting of SEQ ID NO: 66; LCDR1 comprising or consisting of SEQ ID NO: 65;

(v) HCDR3 comprising or consisting of SEQ ID NO: 15; HCDR2 comprising or consisting of SEQ ID NO: 14; HCDR1 comprising or consisting of SEQ ID NO: 13; LCDR3 comprising or consisting of SEQ ID NO: 70; LCDR2 comprising or consisting of SEQ ID NO: 69; LCDR1 comprising or consisting of SEQ ID NO: 68;

(vi) HCDR3 comprising or consisting of SEQ ID NO: 18; HCDR2 comprising or consisting of SEQ ID NO: 17; HCDR1 comprising or consisting of SEQ ID NO: 16; LCDR3 comprising or consisting of SEQ ID NO: 72; LCDR2 comprising or consisting of SEQ ID NO: 66; LCDR1 comprising or consisting of SEQ ID NO: 71;

(vii) HCDR3 comprising or consisting of SEQ ID NO: 20; HCDR2 comprising or consisting of SEQ ID NO: 19; HCDR1 comprising or consisting of SEQ ID NO: 4; LCDR3 comprising or consisting of SEQ ID NO: 75; LCDR2 comprising or consisting of SEQ ID NO: 74; LCDR1 comprising or consisting of SEQ ID NO: 73;

(viii) HCDR3 comprising or consisting of SEQ ID NO: 23; HCDR2 comprising or consisting of SEQ ID NO: 22; HCDR1 comprising or consisting of SEQ ID NO: 21; LCDR3 comprising or consisting of SEQ ID NO: 67; LCDR2 comprising or consisting of SEQ ID NO: 66; LCDR1 comprising or consisting of SEQ ID NO: 65;

(ix) HCDR3 comprising or consisting of SEQ ID NO: 25; HCDR2 comprising or consisting of SEQ ID NO: 24; HCDR1 comprising or consisting of SEQ ID NO: 4; LCDR3 comprising or consisting of SEQ ID NO: 78; LCDR2 comprising or consisting of SEQ ID NO: 77; LCDR1 comprising or consisting of SEQ ID NO: 76;

(x) HCDR3 comprising or consisting of SEQ ID NO: 28; HCDR2 comprising or consisting of SEQ ID NO: 27; HCDR1 comprising or consisting of SEQ ID NO: 26; LCDR3 comprising or consisting of SEQ ID NO: 67; LCDR2 comprising or consisting of SEQ ID NO: 66; LCDR1 comprising or consisting of SEQ ID NO: 79;

(xi) HCDR3 comprising or consisting of SEQ ID NO: 31; HCDR2 comprising or consisting of SEQ ID NO: 30; HCDR1 comprising or consisting of SEQ ID NO: 29; LCDR3 comprising or consisting of SEQ ID NO: 81; LCDR2 comprising or consisting of SEQ ID NO: 63; LCDR1 comprising or consisting of SEQ ID NO: 80;

(xii) HCDR3 comprising or consisting of SEQ ID NO: 33; HCDR2 comprising or consisting of SEQ ID NO: 32; HCDR1 comprising or consisting of SEQ ID NO: 1; LCDR3 comprising or consisting of SEQ ID NO: 84; LCDR2 comprising or consisting of SEQ ID NO: 83; LCDR1 comprising or consisting of SEQ ID NO: 82;

(xiii) HCDR3 comprising or consisting of SEQ ID NO: 36; HCDR2 comprising or consisting of SEQ ID NO: 35; HCDR1 comprising or consisting of SEQ ID NO: 34; LCDR3 comprising or consisting of SEQ ID NO: 87; LCDR2 comprising or consisting of SEQ ID NO: 86; LCDR1 comprising or consisting of SEQ ID NO: 85;

(xiv) HCDR3 comprising or consisting of SEQ ID NO: 38; HCDR2 comprising or consisting of SEQ ID NO: 11; HCDR1 comprising or consisting of SEQ ID NO: 37; LCDR3 comprising or consisting of SEQ ID NO: 78; LCDR2 comprising or consisting of SEQ ID NO: 63; LCDR1 comprising or consisting of SEQ ID NO: 88;

(xv) HCDR3 comprising or consisting of SEQ ID NO: 41; HCDR2 comprising or consisting of SEQ ID NO: 40; HCDR1 comprising or consisting of SEQ ID NO: 39; LCDR3 comprising or consisting of SEQ ID NO: 91; LCDR2 comprising or consisting of SEQ ID NO: 90; LCDR1 comprising or consisting of SEQ ID NO: 89;

(xvi) HCDR3 comprising or consisting of SEQ ID NO: 43; HCDR2 comprising or consisting of SEQ ID NO: 42; HCDR1 comprising or consisting of SEQ ID NO: 4; LCDR3 comprising or consisting of SEQ ID NO: 94; LCDR2 comprising or consisting of SEQ ID NO: 93; LCDR1 comprising or consisting of SEQ ID NO: 92;

(xvii) HCDR3 comprising or consisting of SEQ ID NO: 6; HCDR2 comprising or consisting of SEQ ID NO: 44; HCDR1 comprising or consisting of SEQ ID NO: 4; LCDR3 comprising or consisting of SEQ ID NO: 97; LCDR2 comprising or consisting of SEQ ID NO: 96; LCDR1 comprising or consisting of SEQ ID NO: 95;

(xviii) HCDR3 comprising or consisting of SEQ ID NO: 47; HCDR2 comprising or consisting of SEQ ID NO: 46; HCDR1 comprising or consisting of SEQ ID NO: 45; LCDR3 comprising or consisting of SEQ ID NO: 94; LCDR2 comprising or consisting of SEQ ID NO: 93; LCDR1 comprising or consisting of SEQ ID NO: 71;

(xix) HCDR3 comprising or consisting of SEQ ID NO: 50; HCDR2 comprising or consisting of SEQ ID NO: 49; HCDR1 comprising or consisting of SEQ ID NO: 48; LCDR3 comprising or consisting of SEQ ID NO: 96; LCDR2 comprising or consisting of SEQ ID NO: 63; LCDR1 comprising or consisting of SEQ ID NO: 95;

(xx) HCDR3 comprising or consisting of SEQ ID NO: 36; HCDR2 comprising or consisting of SEQ ID NO: 52; HCDR1 comprising or consisting of SEQ ID NO: 51; LCDR3 comprising or consisting of SEQ ID NO: 98; LCDR2 comprising or consisting of SEQ ID NO: 97; LCDR1 comprising or consisting of SEQ ID NO: 80; and (xxi) HCDR3 comprising or consisting of SEQ ID NO: 55; HCDR2 comprising or consisting of SEQ ID NO: 54; HCDR1 comprising or consisting of SEQ ID NO: 53; LCDR3 comprising or consisting of SEQ ID NO: 81; LCDR2 comprising or consisting of SEQ ID NO: 93; LCDR1 comprising or consisting of SEQ ID NO: 71.

In certain embodiments, the antibody or antigen binding fragment thereof comprises a combination of a heavy chain variable domain (VH) and a light chain variable domain (VL) selected from the following:

(i) a VH comprising the amino acid sequence of SEQ ID NO: 99 or an amino acid sequence at least 90%, 95%, 97%, 98% or 99% identical thereto and a VL comprising the amino acid sequence of SEQ ID NO: 100 or an amino acid sequence at least 90%, 95%, 97%, 98% or 99% identical thereto;

(ii) a VH comprising the amino acid sequence of SEQ ID NO: 101 or an amino acid sequence at least 90%, 95%, 97%, 98% or 99% identical thereto and a VL comprising the amino acid sequence of SEQ ID NO: 102 or an amino acid sequence at least 90%, 95%, 97%, 98% or 99% identical thereto;

(iii) a VH comprising the amino acid sequence of SEQ ID NO: 103 or an amino acid sequence at least 90%, 95%, 97%, 98% or 99% identical thereto and a VL comprising the amino acid sequence of SEQ ID NO: 104 or an amino acid sequence at least 90%, 95%, 97%, 98% or 99% identical thereto;

(iv) a VH comprising the amino acid sequence of SEQ ID NO: 105 or an amino acid sequence at least 90%, 95%, 97%, 98% or 99% identical thereto and a VL comprising the amino acid sequence of SEQ ID NO: 106 or an amino acid sequence at least 90%, 95%, 97%, 98% or 99% identical thereto;

(v) a VH comprising the amino acid sequence of SEQ ID NO: 107 or an amino acid sequence at least 90%, 95%, 97%, 98% or 99% identical thereto and a VL comprising the amino acid sequence of SEQ ID NO: 108 or an amino acid sequence at least 90%, 95%, 97%, 98% or 99% identical thereto;

(vi) a VH comprising the amino acid sequence of SEQ ID NO: 109 or an amino acid sequence at least 90%, 95%, 97%, 98% or 99% identical thereto and a VL comprising the amino acid sequence of SEQ ID NO: 110 or an amino acid sequence at least 90%, 95%, 97%, 98% or 99% identical thereto;

(vii) a VH comprising the amino acid sequence of SEQ ID NO: 111 or an amino acid sequence at least 90%, 95%, 97%, 98% or 99% identical thereto and a VL comprising the amino acid sequence of SEQ ID NO: 112 or an amino acid sequence at least 90%, 95%, 97%, 98% or 99% identical thereto;

(viii) a VH comprising the amino acid sequence of SEQ ID NO: 113 or an amino acid sequence at least 90%, 95%, 97%, 98% or 99% identical thereto and a VL comprising the amino acid sequence of SEQ ID NO: 114 or an amino acid sequence at least 90%, 95%, 97%, 98% or 99% identical thereto;

(ix) a VH comprising the amino acid sequence of SEQ ID NO: 115 or an amino acid sequence at least 90%, 95%, 97%, 98% or 99% identical thereto and a VL comprising the amino acid sequence of SEQ ID NO: 116 or an amino acid sequence at least 90%, 95%, 97%, 98% or 99% identical thereto;

(x) a VH comprising the amino acid sequence of SEQ ID NO: 117 or an amino acid sequence at least 90%, 95%, 97%, 98% or 99% identical thereto and a VL comprising the amino acid sequence of SEQ ID NO: 118 or an amino acid sequence at least 90%, 95%, 97%, 98% or 99% identical thereto;

(xi) a VH comprising the amino acid sequence of SEQ ID NO: 119 or an amino acid sequence at least 90%, 95%, 97%, 98% or 99% identical thereto and a VL comprising the amino acid sequence of SEQ ID NO: 120 or an amino acid sequence at least 90%, 95%, 97%, 98% or 99% identical thereto;

(xii) a VH comprising the amino acid sequence of SEQ ID NO: 121 or an amino acid sequence at least 90%, 95%, 97%, 98% or 99% identical thereto and a VL comprising the amino acid sequence of SEQ ID NO: 122 or an amino acid sequence at least 90%, 95%, 97%, 98% or 99% identical thereto;

(xiii) a VH comprising the amino acid sequence of SEQ ID NO: 123 or an amino acid sequence at least 90%, 95%, 97%, 98% or 99% identical thereto and a VL comprising the amino acid sequence of SEQ ID NO: 124 or an amino acid sequence at least 90%, 95%, 97%, 98% or 99% identical thereto;

(xiv) a VH comprising the amino acid sequence of SEQ ID NO: 125 or an amino acid sequence at least 90%, 95%, 97%, 98% or 99% identical thereto and a VL comprising the amino acid sequence of SEQ ID NO: 126 or an amino acid sequence at least 90%, 95%, 97%, 98% or 99% identical thereto;

(xv) a VH comprising the amino acid sequence of SEQ ID NO: 127 or an amino acid sequence at least 90%, 95%, 97%, 98% or 99% identical thereto and a VL comprising the amino acid sequence of SEQ ID NO: 128 or an amino acid sequence at least 90%, 95%, 97%, 98% or 99% identical thereto;

(xvi) a VH comprising the amino acid sequence of SEQ ID NO: 129 or an amino acid sequence at least 90%, 95%, 97%, 98% or 99% identical thereto and a VL comprising the amino acid sequence of SEQ ID NO: 130 or an amino acid sequence at least 90%, 95%, 97%, 98% or 99% identical thereto;

(xvii) a VH comprising the amino acid sequence of SEQ ID NO: 131 or an amino acid sequence at least 90%, 95%, 97%, 98% or 99% identical thereto and a VL comprising the amino acid sequence of SEQ ID NO: 132 or an amino acid sequence at least 90%, 95%, 97%, 98% or 99% identical thereto;

(xviii) a VH comprising the amino acid sequence of SEQ ID NO: 133 or an amino acid sequence at least 90%, 95%, 97%, 98% or 99% identical thereto and a VL comprising the amino acid sequence of SEQ ID NO: 134 or an amino acid sequence at least 90%, 95%, 97%, 98% or 99% identical thereto;

(xix) a VH comprising the amino acid sequence of SEQ ID NO: 135 or an amino acid sequence at least 90%, 95%, 97%, 98% or 99% identical thereto and a VL comprising the amino acid sequence of SEQ ID NO: 136 or an amino acid sequence at least 90%, 95%, 97%, 98% or 99% identical thereto;

(xx) a VH comprising the amino acid sequence of SEQ ID NO: 137 or an amino acid sequence at least 90%, 95%, 97%, 98% or 99% identical thereto and a VL comprising the amino acid sequence of SEQ ID NO: 138 or an amino acid sequence at least 90%, 95%, 97%, 98% or 99% identical thereto; and (xxi) a VH comprising the amino acid sequence of SEQ ID NO: 139 or an amino acid sequence at least 90%, 95%, 97%, 98% or 99% identical thereto and a VL comprising the amino acid sequence of SEQ ID NO: 140 or an amino acid sequence at least 90%, 95%, 97%, 98% or 99% identical thereto.

For embodiments wherein the domains of the antibodies or antigen binding fragments are defined by a particular percentage sequence identity to a reference sequence, the VH and/or VL domains may retain identical CDR sequences to those present in the reference sequence such that the variation is present only within the framework regions.

In certain embodiments, the antibody or antigen binding fragment comprises a variable heavy chain domain (VH) and a variable light chain domain (VL) wherein the VH and VL domains comprise the CDR sequences selected from the group consisting of:

(i) HCDR3 comprising or consisting of SEQ ID NO: 162; HCDR2 comprising or consisting of SEQ ID NO: 161; HCDR1 comprising or consisting of SEQ ID NO: 160; LCDR3 comprising or consisting of SEQ ID NO: 179; LCDR2 comprising or consisting of SEQ ID NO: 178; LCDR1 comprising or consisting of SEQ ID NO: 177;

(ii) HCDR3 comprising or consisting of SEQ ID NO: 165; HCDR2 comprising or consisting of SEQ ID NO: 164; HCDR1 comprising or consisting of SEQ ID NO: 163; LCDR3 comprising or consisting of SEQ ID NO: 182; LCDR2 comprising or consisting of SEQ ID NO: 181; LCDR1 comprising or consisting of SEQ ID NO: 180;

(iii) HCDR3 comprising or consisting of SEQ ID NO: 168; HCDR2 comprising or consisting of SEQ ID NO: 167; HCDR1 comprising or consisting of SEQ ID NO: 166; LCDR3 comprising or consisting of SEQ ID NO: 185; LCDR2 comprising or consisting of SEQ ID NO: 184; LCDR1 comprising or consisting of SEQ ID NO: 183;

(iv) HCDR3 comprising or consisting of SEQ ID NO: 171; HCDR2 comprising or consisting of SEQ ID NO: 170; HCDR1 comprising or consisting of SEQ ID NO: 169; LCDR3 comprising or consisting of SEQ ID NO: 187; LCDR2 comprising or consisting of SEQ ID NO: 186; LCDR1 comprising or consisting of SEQ ID NO: 180;

(v) HCDR3 comprising or consisting of SEQ ID NO: 174; HCDR2 comprising or consisting of SEQ ID NO: 173; HCDR1 comprising or consisting of SEQ ID NO: 172; LCDR3 comprising or consisting of SEQ ID NO: 189; LCDR2 comprising or consisting of SEQ ID NO: 188; LCDR1 comprising or consisting of SEQ ID NO: 180;

(vi) HCDR3 comprising or consisting of SEQ ID NO: 176; HCDR2 comprising or consisting of SEQ ID NO: 175; HCDR1 comprising or consisting of SEQ ID NO: 163; LCDR3 comprising or consisting of SEQ ID NO: 192; LCDR2 comprising or consisting of SEQ ID NO: 191; LCDR1 comprising or consisting of SEQ ID NO: 190; and (vii) HCDR3 comprising or consisting of SEQ ID NO: 165; HCDR2 comprising or consisting of SEQ ID NO: 164; HCDR1 comprising or consisting of SEQ ID NO: 163; LCDR3 comprising or consisting of SEQ ID NO: 193; LCDR2 comprising or consisting of SEQ ID NO: 181; LCDR1 comprising or consisting of SEQ ID NO: 180.

In certain embodiments, the antibody or antigen binding fragment thereof comprises a combination of a heavy chain variable domain (VH) and a light chain variable domain (VL) selected from the following:

(i) a VH comprising the amino acid sequence of SEQ ID NO: 194 or an amino acid sequence at least 90%, 95%, 97%, 98% or 99% identical thereto and a VL comprising the amino acid sequence of SEQ ID NO: 195 or an amino acid sequence at least 90%, 95%, 97%, 98% or 99% identical thereto;

(ii) a VH comprising the amino acid sequence of SEQ ID NO: 196 or an amino acid sequence at least 90%, 95%, 97%, 98% or 99% identical thereto and a VL comprising the amino acid sequence of SEQ ID NO: 197 or an amino acid sequence at least 90%, 95%, 97%, 98% or 99% identical thereto;

(iii) a VH comprising the amino acid sequence of SEQ ID NO: 198 or an amino acid sequence at least 90%, 95%, 97%, 98% or 99% identical thereto and a VL comprising the amino acid sequence of SEQ ID NO: 199 or an amino acid sequence at least 90%, 95%, 97%, 98% or 99% identical thereto;

(iv) a VH comprising the amino acid sequence of SEQ ID NO: 200 or an amino acid sequence at least 90%, 95%, 97%, 98% or 99% identical thereto and a VL comprising the amino acid sequence of SEQ ID NO: 201 or an amino acid sequence at least 90%, 95%, 97%, 98% or 99% identical thereto;

(v) a VH comprising the amino acid sequence of SEQ ID NO: 202 or an amino acid sequence at least 90%, 95%, 97%, 98% or 99% identical thereto and a VL comprising the amino acid sequence of SEQ ID NO: 203 or an amino acid sequence at least 90%, 95%, 97%, 98% or 99% identical thereto;

(vi) a VH comprising the amino acid sequence of SEQ ID NO: 204 or an amino acid sequence at least 90%, 95%, 97%, 98% or 99% identical thereto and a VL comprising the amino acid sequence of SEQ ID NO: 205 or an amino acid sequence at least 90%, 95%, 97%, 98% or 99% identical thereto; and (vii) a VH comprising the amino acid sequence of SEQ ID NO: 206 or an amino acid sequence at least 90%, 95%, 97%, 98% or 99% identical thereto and a VL comprising the amino acid sequence of SEQ ID NO: 207 or an amino acid sequence at least 90%, 95%, 97%, 98% or 99% identical thereto.

For embodiments wherein the domains of the antibodies or antigen binding fragments are defined by a particular percentage sequence identity to a reference sequence, the VH and/or VL domains may retain identical CDR sequences to those present in the reference sequence such that the variation is present only within the framework regions.

In certain embodiments, the antibody is a VHH antibody comprising CDR sequences selected from the group consisting of:

(i) CDR3 comprising or consisting of SEQ ID NO: 210; CDR2 comprising or consisting of SEQ ID NO: 209; CDR1 comprising or consisting of SEQ ID NO: 208;

(ii) CDR3 comprising or consisting of SEQ ID NO: 213; CDR2 comprising or consisting of SEQ ID NO: 212; CDR1 comprising or consisting of SEQ ID NO: 211;

(iii) CDR3 comprising or consisting of SEQ ID NO: 216; CDR2 comprising or consisting of SEQ ID NO: 215; CDR1 comprising or consisting of SEQ ID NO: 214;

(iv) CDR3 comprising or consisting of SEQ ID NO: 219; CDR2 comprising or consisting of SEQ ID NO: 218; CDR1 comprising or consisting of SEQ ID NO: 217;

(v) CDR3 comprising or consisting of SEQ ID NO: 222; CDR2 comprising or consisting of SEQ ID NO: 221; CDR1 comprising or consisting of SEQ ID NO: 220;

(vi) CDR3 comprising or consisting of SEQ ID NO: 225; CDR2 comprising or consisting of SEQ ID NO: 224; CDR1 comprising or consisting of SEQ ID NO: 223;

(vii) CDR3 comprising or consisting of SEQ ID NO: 228; CDR2 comprising or consisting of SEQ ID NO: 227; CDR1 comprising or consisting of SEQ ID NO: 226;

(viii) CDR3 comprising or consisting of SEQ ID NO: 231; CDR2 comprising or consisting of SEQ ID NO: 230; CDR1 comprising or consisting of SEQ ID NO: 229;

(ix) CDR3 comprising or consisting of SEQ ID NO: 234; CDR2 comprising or consisting of SEQ ID NO: 233; CDR1 comprising or consisting of SEQ ID NO: 232;

(x) CDR3 comprising or consisting of SEQ ID NO: 236; CDR2 comprising or consisting of SEQ ID NO: 235; CDR1 comprising or consisting of SEQ ID NO: 226;

(xi) CDR3 comprising or consisting of SEQ ID NO: 238; CDR2 comprising or consisting of SEQ ID NO: 237; CDR1 comprising or consisting of SEQ ID NO: 232;

(xii) CDR3 comprising or consisting of SEQ ID NO: 241; CDR2 comprising or consisting of SEQ ID NO: 240; CDR1 comprising or consisting of SEQ ID NO: 239;

(xiii) CDR3 comprising or consisting of SEQ ID NO: 236; CDR2 comprising or consisting of SEQ ID NO: 235; CDR1 comprising or consisting of SEQ ID NO: 226;

(xiv) CDR3 comprising or consisting of SEQ ID NO: 244; CDR2 comprising or consisting of SEQ ID NO: 243; CDR1 comprising or consisting of SEQ ID NO: 242;

(xv) CDR3 comprising or consisting of SEQ ID NO: 234; CDR2 comprising or consisting of SEQ ID NO: 233; CDR1 comprising or consisting of SEQ ID NO: 232;

(xvi) CDR3 comprising or consisting of SEQ ID NO: 247; CDR2 comprising or consisting of SEQ ID NO: 246; CDR1 comprising or consisting of SEQ ID NO: 245; and (xvii) CDR3 comprising or consisting of SEQ ID NO: 249; CDR2 comprising or consisting of SEQ ID NO: 248; CDR1 comprising or consisting of SEQ ID NO: 217.

In certain embodiments, the antibody is a VHH antibody wherein the VHH domain comprises or consists of the amino acid sequence represented by any one of SEQ ID NOs: 250, 251, 252, 253, 254, 255, 256, 257, 258, 259, 260, 261, 262, 263, 264, 265 or 266, or an amino acid sequence at least 90%, 95%, 97%, 98% or 99% identical thereto.

For embodiments wherein the VHH domains are defined by a particular percentage sequence identity to a reference sequence, the VHH domain may retain identical CDR sequences to those present in the reference sequence such that the variation is present only within the framework regions.

The invention further provides an antibody or antigen binding fragment thereof, which binds to the same epitope as the antibodies or antigen binding fragments defined herein with reference to specific SEQ ID NOs. Also provided are isolated polynucleotides encoding the antibodies or antigen binding fragments thereof, including polynucleotides encoding the VH and/or VL domains of the antibodies and antigen binding fragments described herein. The invention further provides an expression vector comprising the afore-mentioned polynucleotides operably linked to regulatory sequences which permit expression of the antibody, antigen binding fragment, variable heavy chain domain or variable light chain domain in a host cell or cell-free expression system. Also provided are host cells or cell-free expression systems containing the afore-mentioned expression vectors.

The present invention also provides a pharmaceutical composition comprising an antagonist in accordance with the first aspect of the invention, particularly an antibody or antigen binding fragment thereof, and at least one pharmaceutically acceptable carrier or excipient.

Further provided is an antagonist in accordance with the first aspect of the invention, particularly an antibody or antigen binding fragment thereof, or a pharmaceutical composition in accordance with the invention for use as a medicament.

In a further aspect, the present invention provides a method of treating a subject in need thereof, wherein the method comprises administering to the subject a therapeutically effective amount of an antagonist according to the first aspect of the invention, particularly an antibody or antigen binding fragment thereof, or a pharmaceutical composition in accordance with the invention. The antagonist, antibody, antigen binding fragment or pharmaceutical composition may be administered to treat a disease or condition associated with the presence or formation of galectin-10 crystals. In certain embodiments, the disease or condition is selected from: asthma; chronic rhinosinusitis; celiac disease; helminth infection; gastrointestinal eosinophilic inflammation; cystic fibrosis (CF); allergic bronchopulmonary aspergillosis (ABPA); Churg-Strauss vasculitis; chronic eosinophilic pneumonia; and acute myeloid leukemia. In preferred embodiments, the antagonists, antibodies, antigen binding fragments or pharmaceutical compositions are administered to treat asthma.

The present invention also provides use of an antagonist according to the first aspect of the invention, particularly an antibody or antigen binding fragment thereof, for the detection of galectin-10 in a sample obtained from a patient. The antagonist, antibody or antigen binding fragment is preferably used for the detection of crystalline galectin-10. The patient sample may be a sputum sample.

The invention also provides a kit comprising a galectin-10 antagonist in accordance with the first aspect of the invention, preferably a galectin-10 antibody or antigen binding fragment thereof, and optionally instructions for use.

BRIEF DESCRIPTION OF DRAWINGS

(FIG. 1A) SDS PAGE of His-tagged Gal10 before and after addition of TEV protease to remove the His-Tag. (FIG. 1B) Multi-angle laser scattering (MALLS) reveals a molecular mass of appr. 40 kDa, representing a dimeric form of His-tagged Gal10 in solution. (FIG. 1C) After cleavage by TEV protease, the protein solution spontaneously crystallizes into needle-shaped crystals. (FIG. 1D) Original drawing of Charcot (1853) describing the various shapes of crystals seen in the airways of asthmatics. (FIG. 1E) Snapshots of various forms of crystals taken form a fluorescently labeled batch of recombinant Gal10 crystals. All macroscopic forms of crystals originally described by Charcot and von Leyden are found.

(FIG. 2B) Immunostaining for Gal10 shows copious amounts of crystalline material in the allergic sticky mucin. Similar mucus is also found in the airways of asthmatics and ABPA patients. (FIG. 2C) Ex vivo obtained crystal mounted for X-ray diffraction studies. (FIG. 2D) X-ray diffraction pattern of a patient-derived crystal. (FIG. 2E) Crystal structure of patient-derived CLC crystal reveals a dimeric nature. (FIG. 2F) comparison of the obtained ex vivo crystal structure to recombinantly-produced Gal10 crystals and published recrystallized CLC crystals obtained from a human eosinophil cell line (AML14.3D10) reveals complete similarity (root mean square of distance (RMSD) difference of 0.2 Angstrom), showing that the recombinant Gal10 crystals are biosimilar to CLCs.

(FIG. 3C) Spontaneous crystallization experiment of wild-type and mutein Gal10 protein after removal of the His tag by TEV protease. The Tyr69Glu (Y96E) mutein was completely resistant to autocrystallization and was used throughout the disclosure as crystallization-resistant soluble Gal10 mutein. (FIG. 3D) X-ray structure of the Gal10 Tyr69Glu mutein. This structure was used to model the scattering profile in a small-angle X-ray scattering in solution (SAXS) experiment of Tyr69Glu mutein in solution. (FIG. 3E) The experimental data of the SAXS experiment overlap with the modeled data, essentially showing that the mutein forms a dimer in solution. (FIG. 3F) Overlap of the structures of wild type with Y69E Gal10 mutant based on the SAXS data.

C57Bl/6 mice were injected intratracheally with Gal10 crystals, soluble Gal10mut or with control PBS. (FIG. 4A) Number of neutrophils (left panel) and monocytes (right panel) recovered from the lungs 6 and 24 hours after the treatment. (FIG. 4B) Levels of IL-6 (left panel) and TNFα (right panel) in the bronchoalveolar lavage 6 and 24 hours after the treatment. (FIG. 4C) Levels of IL-1β and CCL-2 in the lung 6 and 24 hours after the treatment. NS implies a p value >0.12; * implies a p value <0.033;  implies a p value <0.002; * implies a p value <0.0002; **** implies a p value <0.0001.

(FIG. 7B) Number of human CD45$^+$ leukocytes recovered from the left lungs of mice treated as described under (FIG. 7A). (FIG. 7C) Levels of human IgE measured in the serum of mice treated as described under (FIG. 7A).

(FIG. 8B) overview of the activity of various scFv-Fc and IgG1 antibodies.

(FIG. 9B) Kinetic dissolution curve of crystals upon addition of crystal-dissolving antibodies. The total area of refractive crystalline material in the high power view of the spinning disk microscope was integrated and normalized to 1 prior to addition of the crystals.

(FIGS. 10A-10C) Crystals of a mixture of Fab fragments and recombinant Gal10 were formed using a crystallization robot, and subsequently analyzed by X-ray diffraction. The Gal10 crystal structure is depicted as a cartoon model (black). The Light Chain (LC) and Heavy Chain (HC) of the Fab fragments are shown in surface mode with the LC colored white and the HC colored dark grey. (FIGS. 10D-10F) The three clones from which co-crystallization structure could be obtained all target the crucial Tyr69 residue of Gal10.

(FIG. 12B) Hematoxylin eosin staining of lung sections. (FIG. 12C) Levels of human IgE measured in the serum. (FIG. 12D) Mucin Muc5ac mRNA expression in lungs of mice treated as described under (FIG. 12A). (FIG. 12E) Investigator-blinded quantitative image analysis of number of inflammatory cells extending into a 500 μm perimeter region from the basement membrane, expressed per length of basement membrane. (FIG. 12F) Bronchoconstriction measured as dynamic airway resistance (Rrs) after inhalation of increasing concentrations of the bronchoconstrictor methacoline.

The galectin-10 binding capacity of scFv periplasmic extracts was determined by binding ELISA as described herein. Absorbance was measured at 450 nm (reference at 620 nm). For each periplasmic Master plate (PMP), a blank control and negative control (periplasmic extract binding to irrelevant target) were included. The raw data (OD values) were plotted on GraphPad Prism 7.01. A binder was defined as an scFv showed a binding capacity higher than 0.5 OD value on ELISA binding.

Figure 14:
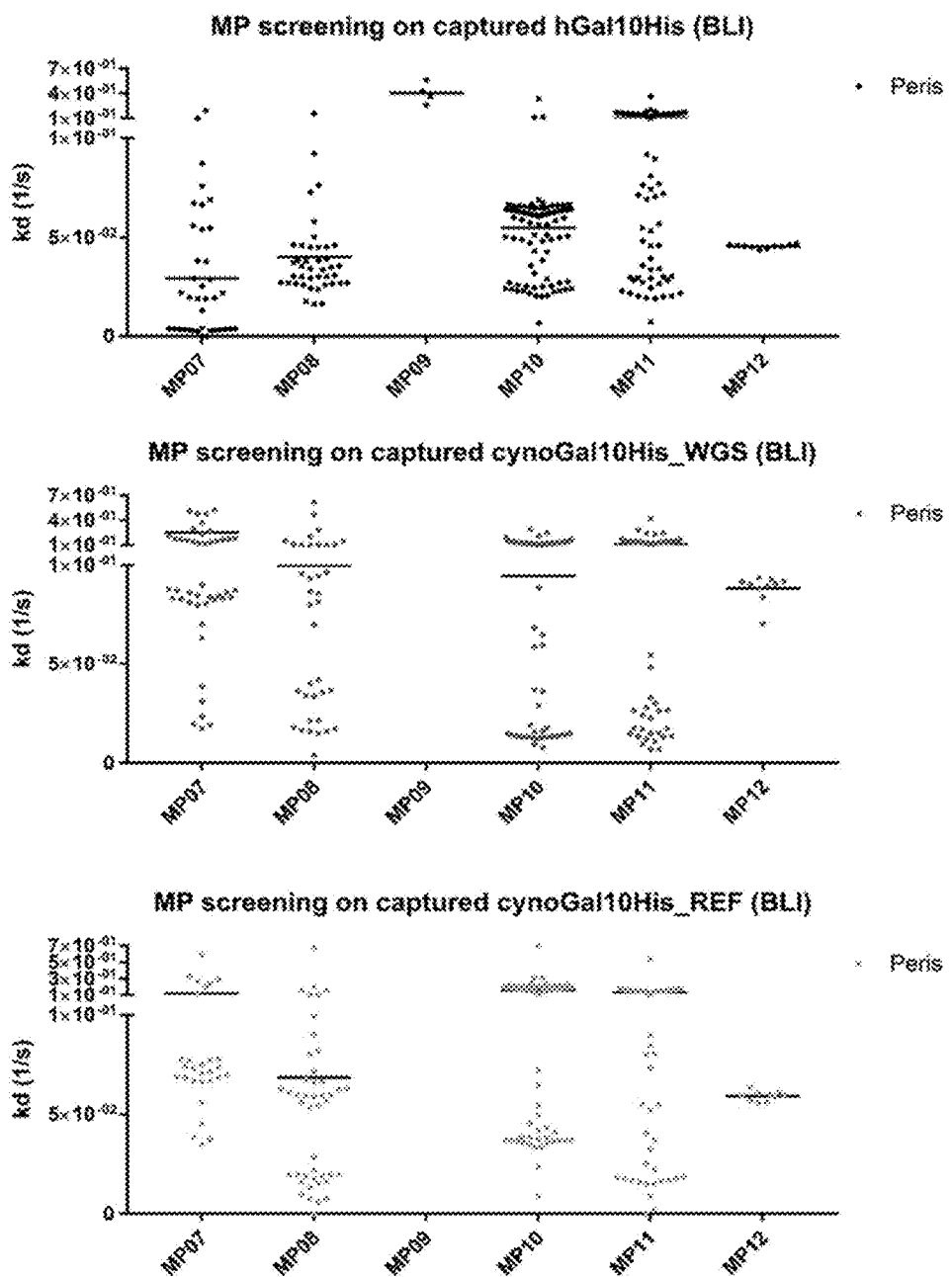

FIG. 14: Screening of scFv periplasmic extracts using BLI technology

The galectin-10 binding capacity of selected scFv periplasmic extracts was analyzed on BLI technology by using an Octet Red96. A capture approach was used, where human and cynomolgus (WGS or REF isoforms) galectin-10-His were immobilized on anti-His1K biosensors before being incubated with diluted selected scFv periplasmic extracts. The off-rate of each scFv clone plotted on GraphPad Prism 7.01.

Figure 15:
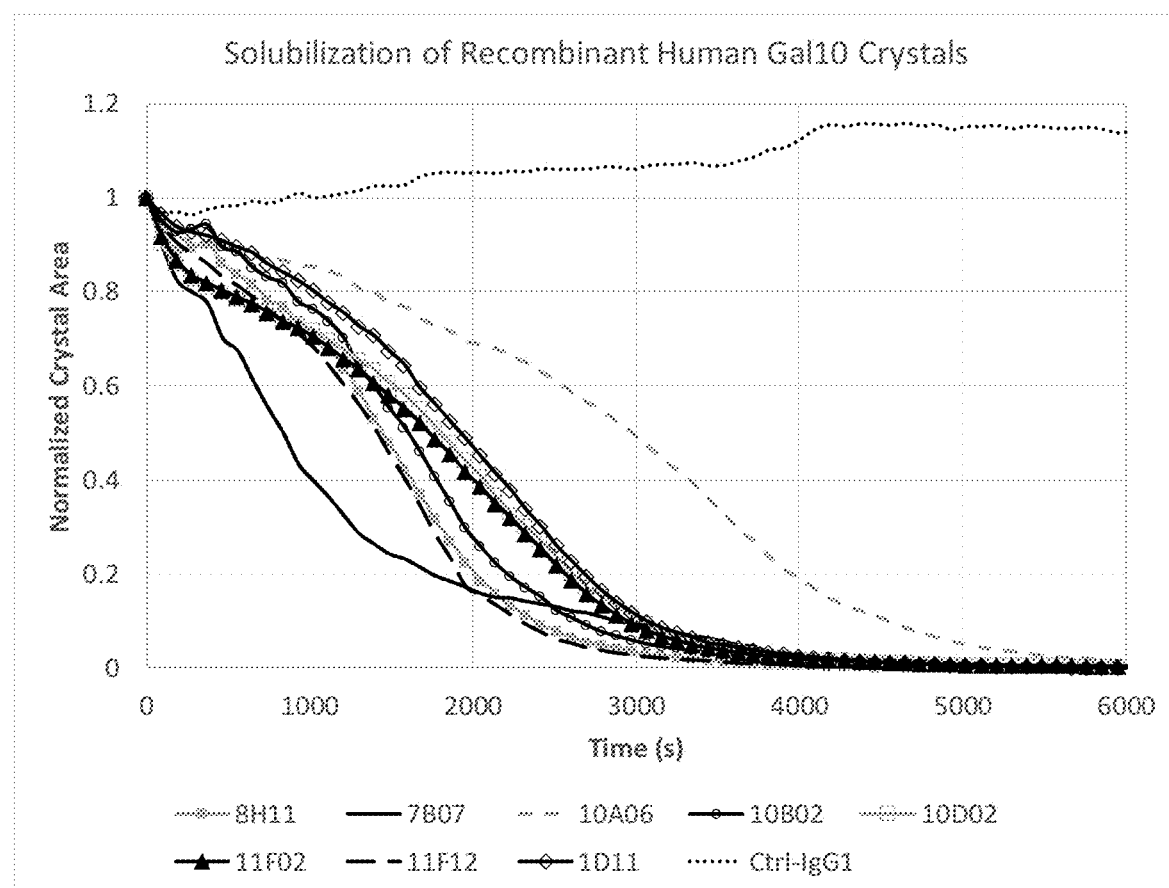

FIG. 15: Crystal dissolution by Gal10 IgG1 antibodies

To study if Gal10 antibodies can dissolve existing crystals, clones were added to in vitro grown recombinant human Gal10 crystals, and observed using spinning disk confocal microscopy. The 8 clones all completely dissolved crystals over the time-course studied, whereas irrelevant isotype antibody did not.

Figure 16:
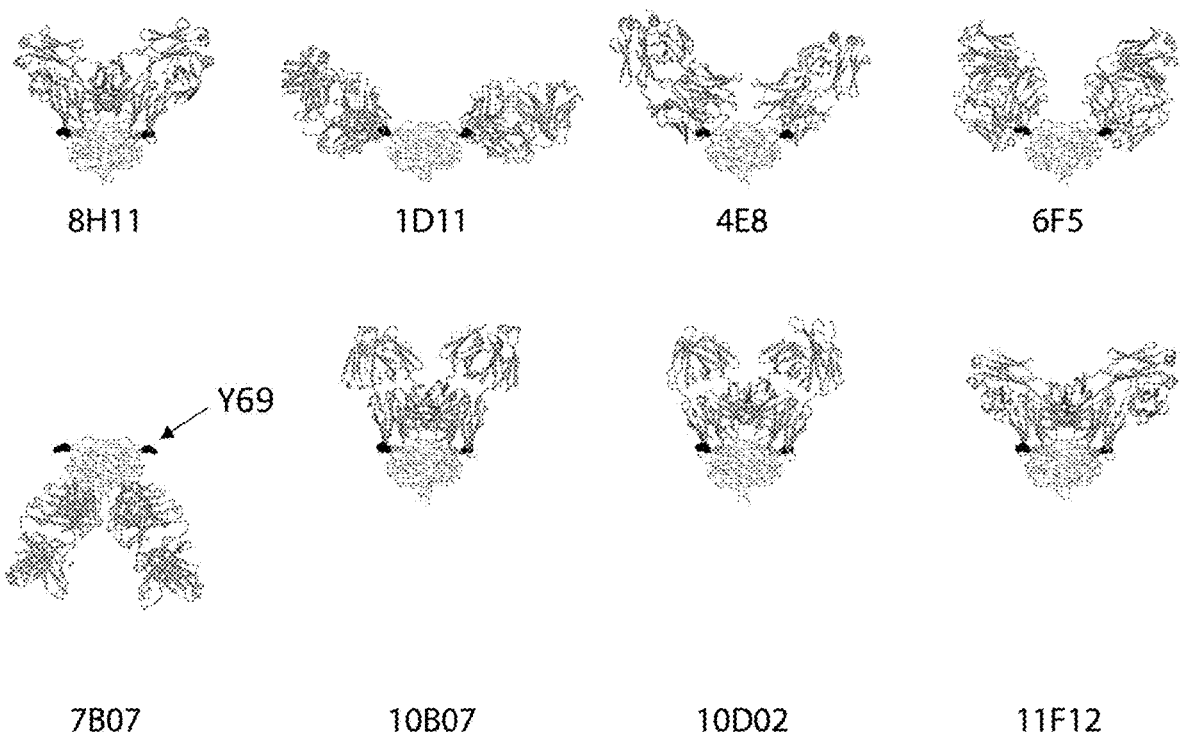

FIG. 16: Crystal structure of Fab fragments of crystal dissolving clones in complex with Gal10

Crystals of a mixture of Fab-fragments and recombinant Gal10 were formed using a crystallization robot, and subsequently analyzed by X-ray diffraction.

Figure 17:
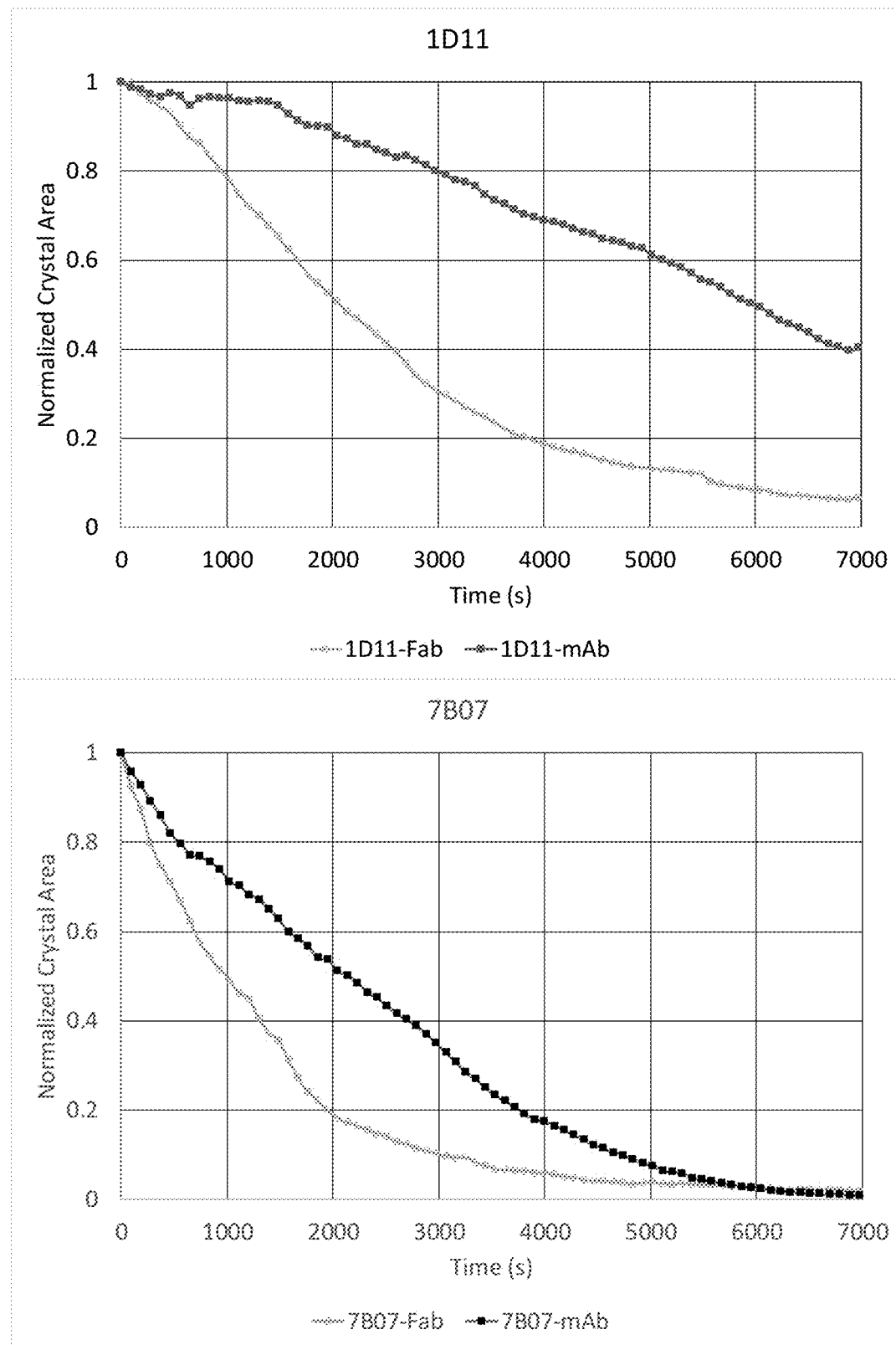
Figure 17:
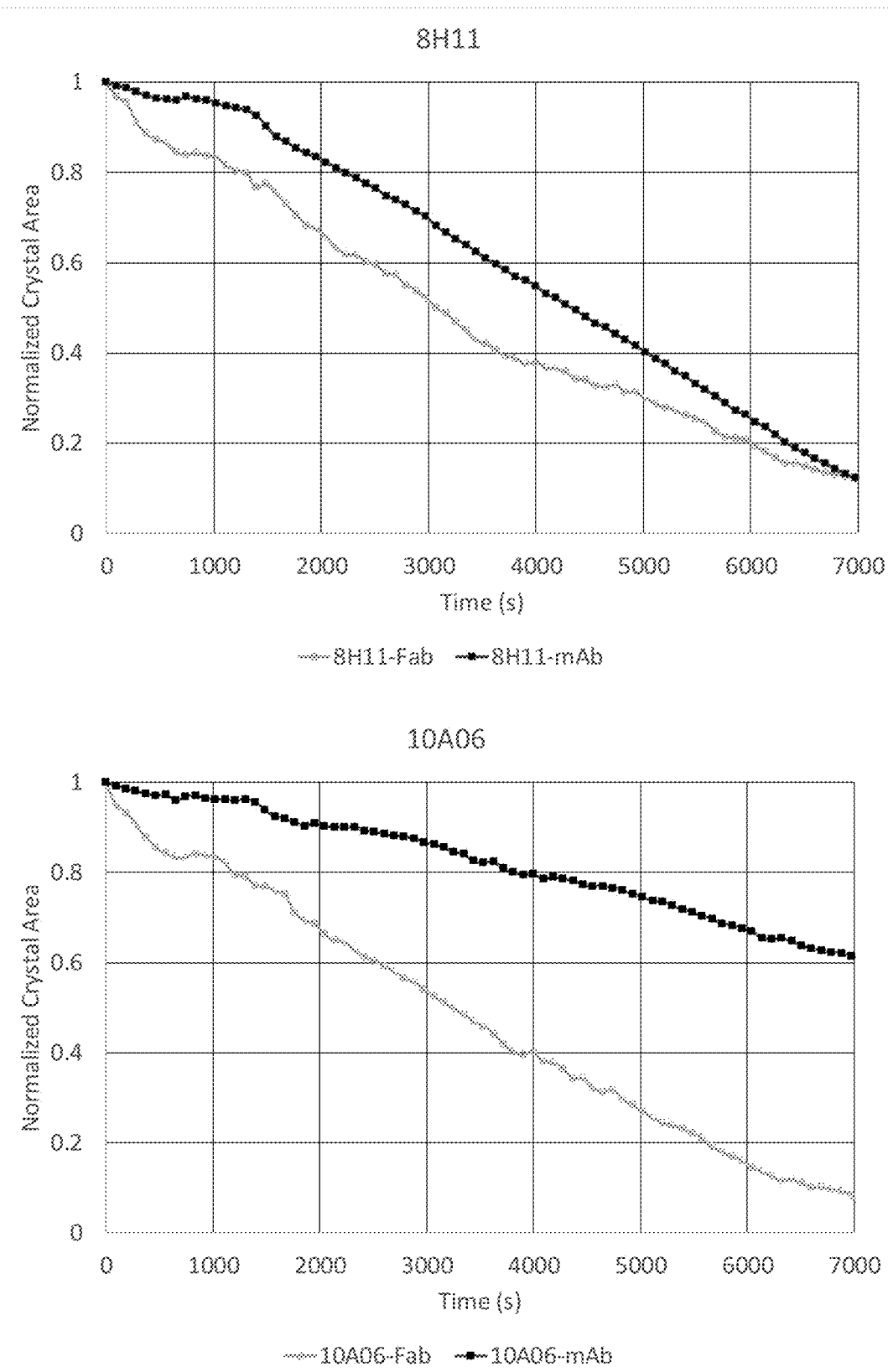
Figure 17:
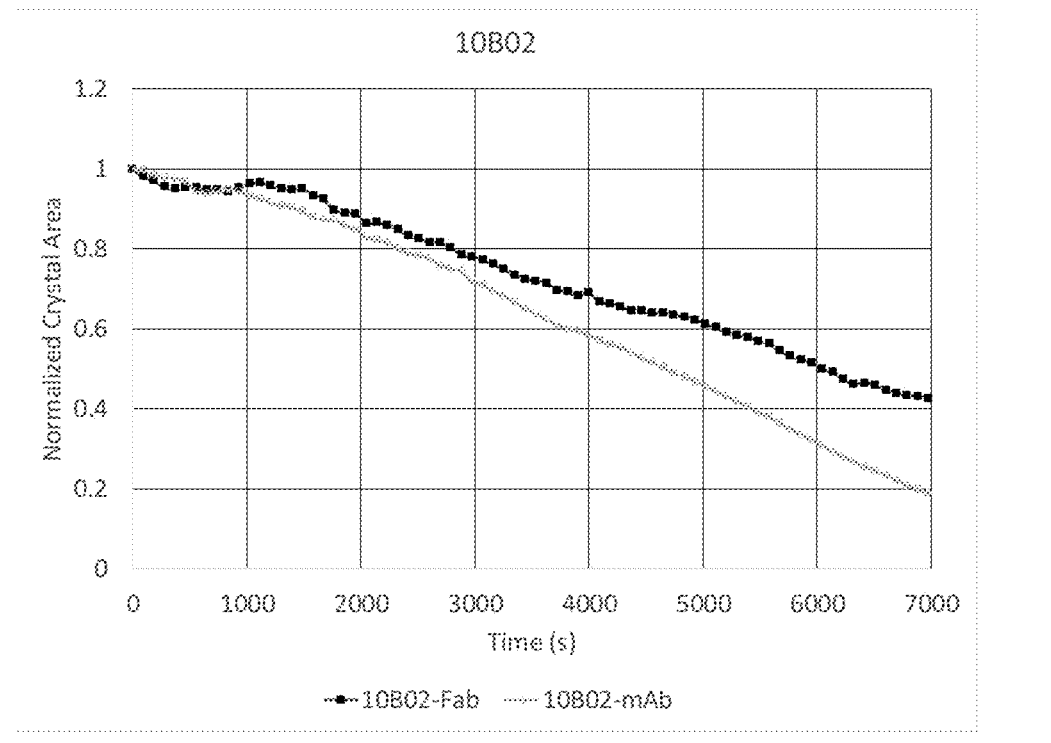
Figure 17:
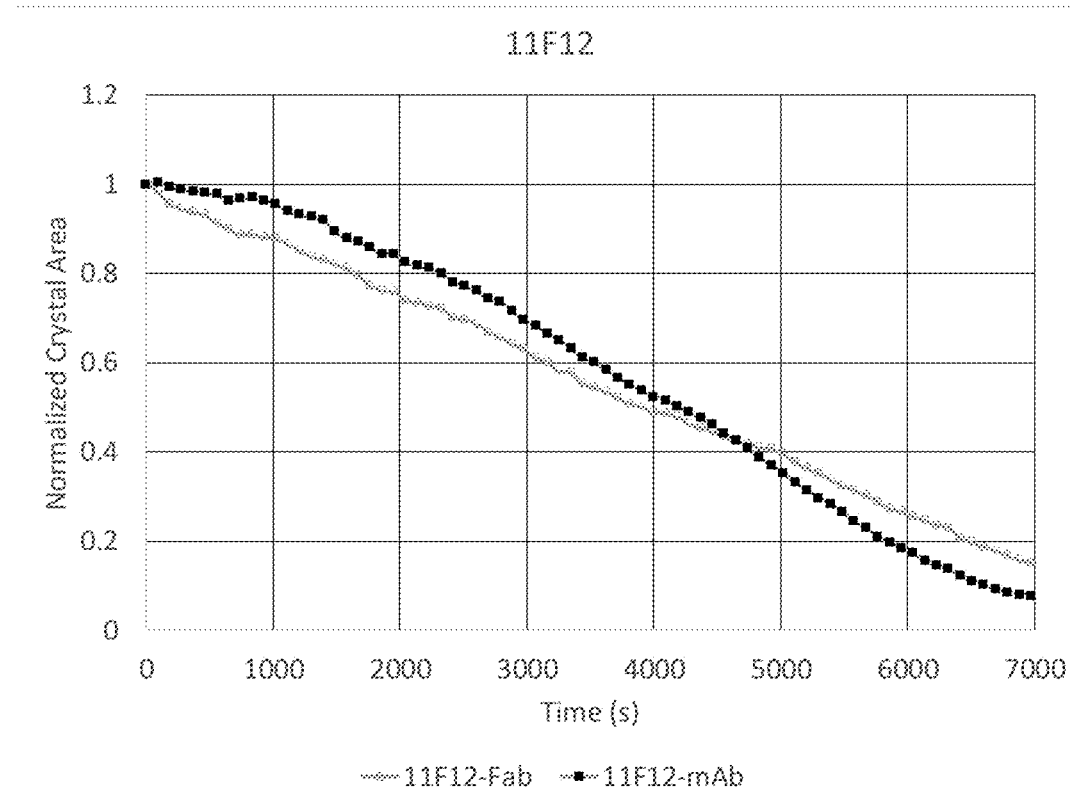
Figure 17:
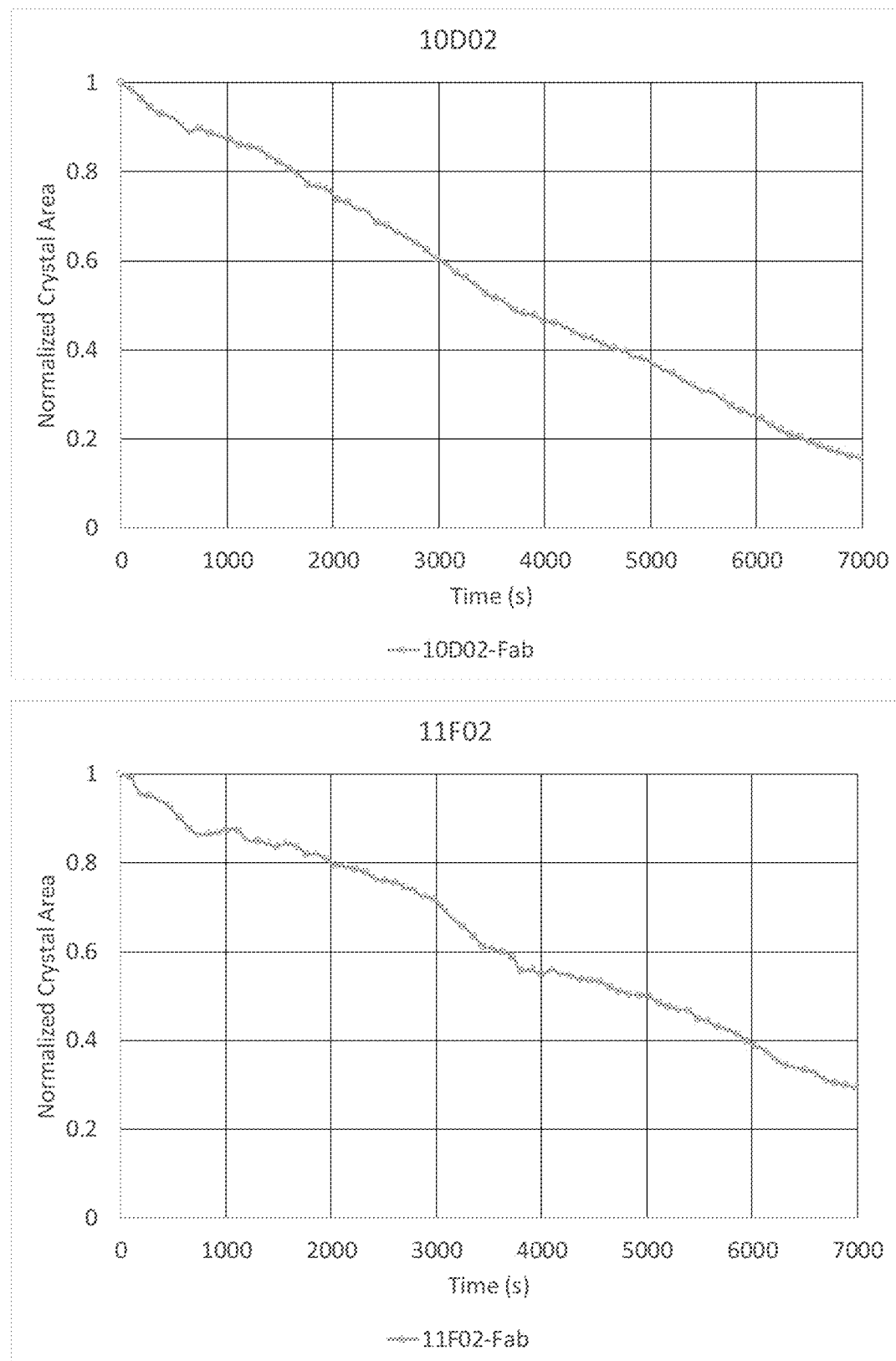

FIG. 17: Crystal dissolution by Gal10 IgG1 antibodies and Fab fragments

CLC dissolution experiments using pre-formed recombinant human CLCs were carried out over a time-course in the presence of Gal10 mAbs and Gal10 Fabs. The dissolution of crystals was observed using spinning disk confocal microscopy.

Figure 18:
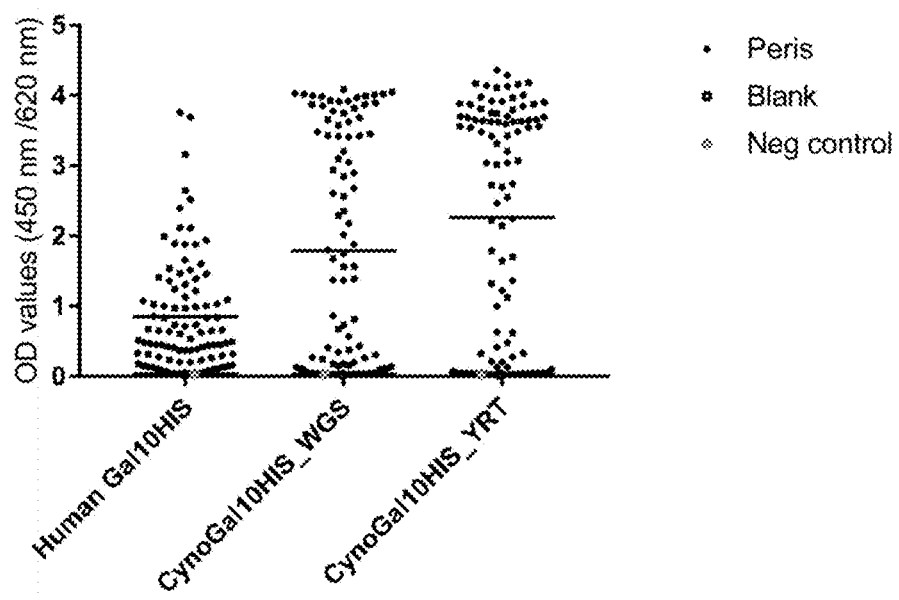
Figure 18:
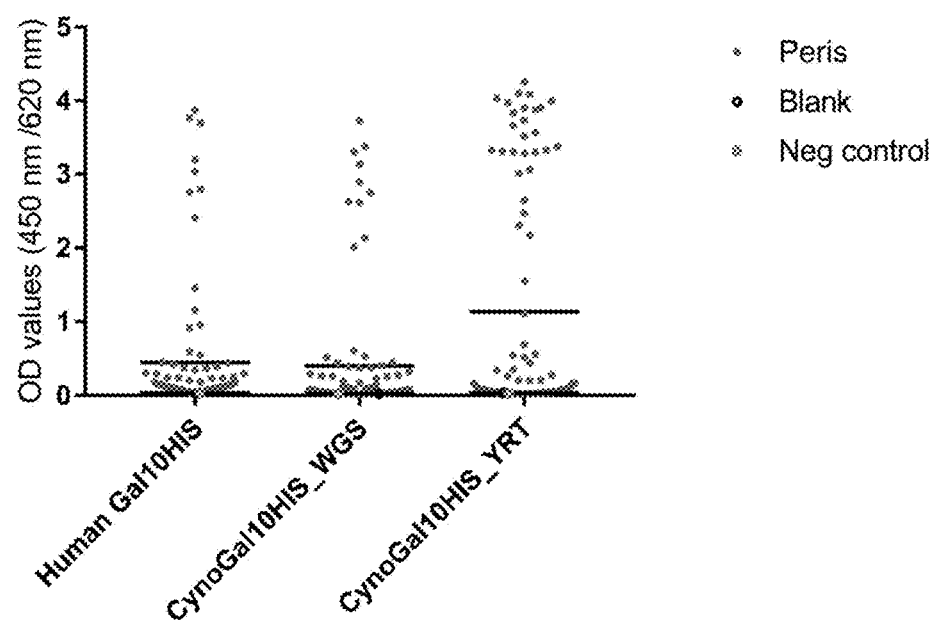

FIG. 18: Screening of VHH periplasmic extracts by ELISA

The galectin-10 binding capacity of VHH periplasmic extracts was measured by binding ELISA as described herein. Absorbance was measured at 450 nm (reference at 620 nm). For each periplasmic Master plate (PMP), a blank control and negative control (VHH periplasmic extract binding to irrelevant target) were included. The raw data (OD values) were plotted on GraphPad Prism 7.01.

Figure 19:
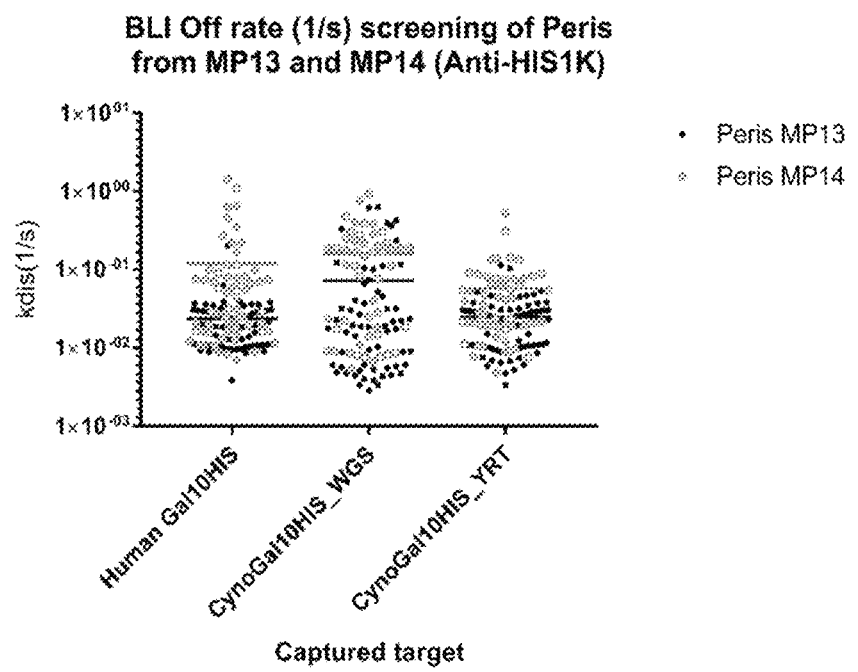
Figure 19:
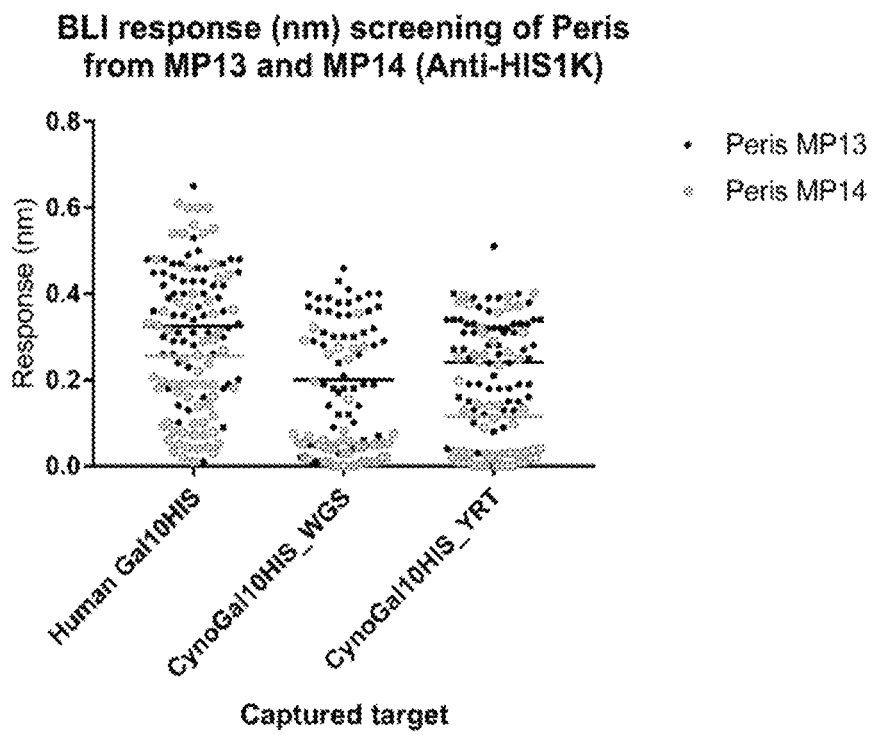

FIG. 19: Screening of VHH periplasmic extracts using BLI technology

The binding capacity of selected VHH periplasmic extracts was analysed on BLI technology by using an Octet Red96. For this purpose, a capture approach was used, where human and cynomolgus (WGS or YRT isoforms) galectin-10-His were immobilized on anti-His1K biosensors before being incubated with diluted selected VHH periplasmic extracts. The off-rate (1/s) and response (nm) of each VHH clone were plotted on GraphPad Prism 7.01.

Figure 20:
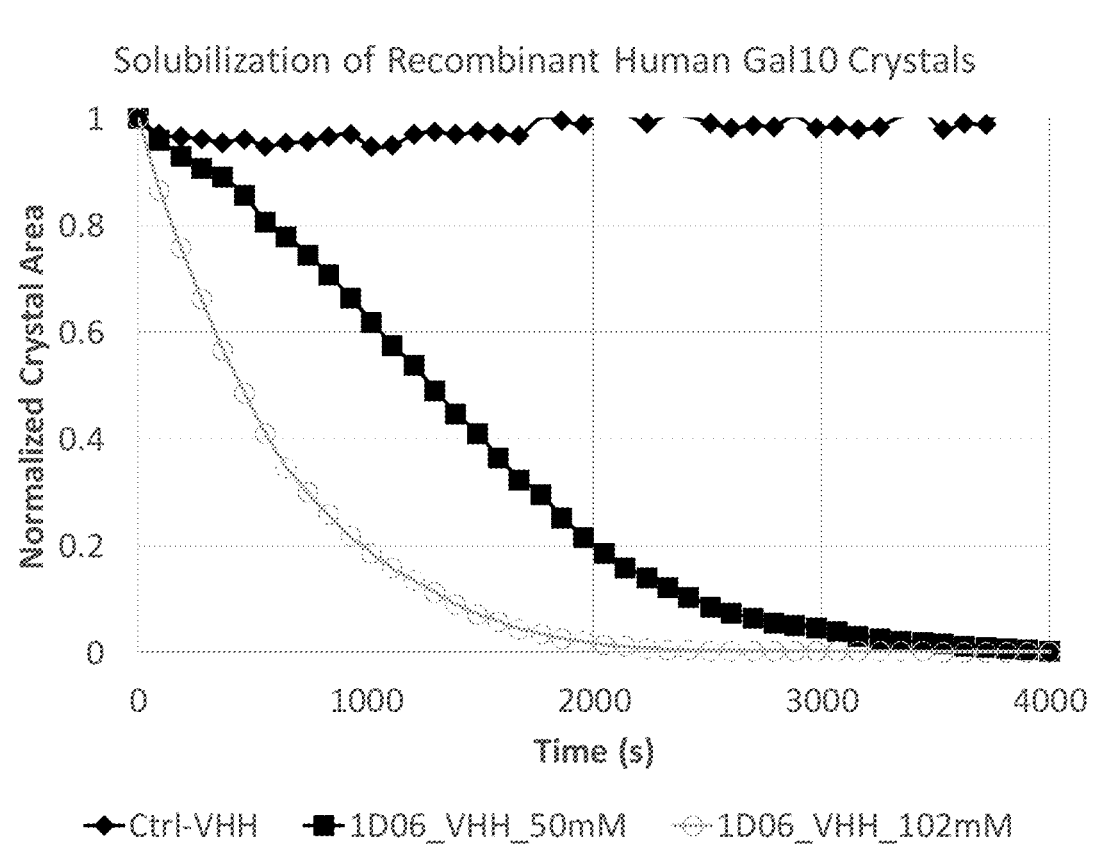

FIG. 20: Crystal dissolution by Gal10 VHH antibodies

CLC dissolution experiments using pre-formed recombinant human CLCs were carried out over a time-course in the presence of Gal10 VHH antibodies. The dissolution of crystals was observed using spinning disk confocal microscopy.

DETAILED DESCRIPTION

A. Definitions

Unless defined otherwise, all technical and scientific terms used herein have the same meaning as is commonly understood by one skilled in the art in the technical field of the invention.

"Antagonist"—As used herein, the term "antagonist" means any agent capable of binding to galectin-10 and shielding a crystal packing interface. By shielding or "obscuring" a crystal packing interface, the function of the antagonist is to disrupt crystallization of galectin-10 molecules. Antagonists in accordance with the present invention will typically bind specifically or "specifically bind" to galectin-10. The term "specifically bind" refers to the ability of an antagonist to preferentially bind to its target, in this case galectin-10. Agents capable of binding to protein targets, particularly agents capable of exhibiting binding specificity for a given protein target, are known to those skilled in the art. Such agents include but are not limited to small molecule inhibitors, biological molecules including inhibitory peptides, antibodies, antigen-binding fragments of antibodies, and antibody mimetics such as affibodies, affilins, affitins, adnectins, atrimers, evasins, DARPins, anticalins, avimers, fynomers, versabodies and duocalins. Preferred antagonists in accordance with the present invention are antibodies and antigen binding fragments thereof.

"Antibody" or "Immunoglobulin"—As used herein, the term "immunoglobulin" includes a polypeptide having a combination of two heavy and two light chains whether or not it possesses any relevant specific immunoreactivity. "Antibodies" refer to such assemblies which have significant known specific immunoreactive activity to an antigen of interest (herein galectin-10). The term "galectin-10 antibodies" is used herein to refer to antibodies which exhibit immunological specificity for the galectin-10 protein, including human galectin-10, and in some cases species homologues thereof. Antibodies and immunoglobulins comprise light and heavy chains, with or without an interchain covalent linkage between them. Basic immunoglobulin structures in vertebrate systems are relatively well understood.

The generic term "immunoglobulin" comprises five distinct classes of antibody (IgG, IgM, IgA, IgD, and IgE) that can be distinguished biochemically. All five classes of antibodies are within the scope of the present invention. The following discussion will generally be directed to the IgG class of immunoglobulin molecules. With regard to IgG, immunoglobulins comprise two identical light polypeptide chains of molecular weight approximately 23,000 Daltons, and two identical heavy chains of molecular weight 53,000-70,000 Daltons. The four chains are joined by disulfide bonds in a "Y" configuration wherein the light chains bracket the heavy chains starting at the mouth of the "Y" and continuing through the variable region.

The light chains of an antibody are classified as either kappa or lambda (κ,λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA, IgD or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernible to the skilled artisan in view of the instant disclosure and, accordingly, are within the scope of the instant invention.

As indicated above, the variable region of an antibody allows the antibody to selectively recognize and specifically bind epitopes on antigens. That is, the VL domain and VH domain of an antibody combine to form the variable region that defines a three dimensional antigen binding site. This quaternary antibody structure forms the antigen binding site present at the end of each arm of the Y. More specifically, the antigen binding site is defined by three complementary determining regions (CDRs) on each of the VH and VL chains.

The term "antibody" as used herein is also intended to encompass "VHH antibodies" or "heavy-chain only antibodies".

"VHH antibodies"—As used herein the term "VHH antibody" or "heavy-chain only antibody" refers to a type of antibody produced only by species of the Camelidae family, which includes camels, llama, alpaca. Heavy chain-only antibodies or VHH antibodies are composed of two heavy chains and are devoid of light chains. Each heavy chain has a variable domain at the N-terminus, and these variable domains are referred to as "VHH" domains in order to distinguish them from the variable domains of the heavy chains of the conventional heterotetrameric antibodies described above.

"Galectin-10"—As used herein, the term "galectin-10" (or Gal10 or Gal-10) refers to the small, hydrophobic glycan binding protein that autocrystallizes to form Charcot-Leyden crystals. Galectin-10 is also referred to as Charcot-Leyden crystal protein (CLCP), eosinophil lysophospholipase and lysolecithin acylhydrolase. The term "galectin-10" is broad enough to cover the human protein and any species homologues. The amino acid sequence of the full-length human galectin-10 is represented by SEQ ID NO: 141 (see below). This sequence corresponds to the sequence deposited in the UniProt database as human galectin-10, accession number Q05315. Also encompassed within the term "galectin-10" are naturally occurring variants of the human sequence, for example the Ala→Val variant on position 28.

```
                                          SEQ ID NO: 141
1         10         20         30         40
MSLLPVPYTE AASLSTGSTV TIKGRPLACF LNEPYLQVDF 50         60         70         80
HTEMKEESDI VFHFQVCFGR RVVMNSREYG AWKQQVESKN 90        100        110        120
MPFQDGQEFE LSISVLPDKY QVMVNGQSSY TFDHRIKPEA 130        140
VKMVQVWRDI SLTKFNVSYL KR
```

"Galectin-10 crystals" or "Charcot-Leyden crystals"—The terms "galectin-10 crystals", "Charcot-Leyden crystals" and "CLCs" are used herein interchangeably to refer to crystals formed of galectin-10. The crystals formed by galectin-10 are typically bi-pyramidal hexagonal crystals and are approximately 20-40 µm in length and approximately 2-4 µm width. These crystals have been associated with eosinophilic inflammatory disorders.

"Crystal packing interface"—A "crystal packing interface" of galectin-10 refers to a set of amino acids forming a surface patch on galectin-10 that contacts one or more neighbouring galectin-10 molecules in the crystalline lattice. CLCs have different crystal packing interfaces and the amino acids forming these crystal packing interfaces have been characterised as: Ser2, Leu3, Leu4, Tyr8, Thr9, Glu10, Ala11, Ala12, Ser13, Thr16, Thr42, Glu43, Met44, Lys45, Asp49, Ile50, Glu68, Tyr69, Gly70, Ala71, Lys73, Gln74, Gln75, Val76, Glu77, Ser78, Lys79, Asn80, Met81, Leu96, Pro97, Asp98, Lys99, Gln101, Met103, Gly106, Gln107, Ser108, Ser109, Tyr110, Thr111, Asp113, His114, Arg115, Ile116, Lys117, Ala120, Gln125, Thr133, Lys134, Phe135, Asn136, Val137, Ser138, Tyr139, Leu140 and Lys141, wherein the positions are defined with reference to SEQ ID NO: 141 above.

"Epitope"—As used herein in reference to galectin-10, the term "epitope" means the region of the galectin-10 protein to which the antagonist binds. An antagonist will typically bind to its respective galectin-10 epitope via a complementary binding site on the antagonist. The epitope to which the antagonist binds will typically comprise one or more amino acids from the full-length galectin-10 protein. The epitope may include amino acids that are contiguous in the galectin-10 protein, i.e., a linear epitope, or may include amino acids that are non-contiguous in the galectin-10 protein, i.e., a conformational epitope.

"Binding Site"—As used herein, the term "binding site" comprises a region of a polypeptide which is responsible for selectively binding to a target antigen of interest (e.g. galectin-10). Binding domains comprise at least one binding site. Exemplary binding domains include an antibody variable domain. The antibody molecules of the invention may comprise a single binding site or multiple (e.g., two, three or four) binding sites.

"Derived From"—As used herein the term "derived from" a designated protein (e.g. a camelid antibody or antigen binding fragment thereof) refers to the origin of the polypeptide or amino acid sequence. In one embodiment, the polypeptide or amino acid sequence which is derived from a particular starting polypeptide is a CDR sequence or sequence related thereto. In one embodiment, the amino acid sequence which is derived from a particular starting polypeptide is not contiguous. For example, in one embodiment, one, two, three, four, five, or six CDRs are derived from a starting antibody. In one embodiment, the polypeptide or amino acid sequence which is derived from a particular starting polypeptide or amino acid sequence has an amino acid sequence that is essentially identical to that of the starting sequence, or a portion thereof wherein the portion consists of at least 3-5 amino acids, at least 5-10 amino acids, at least 10-20 amino acids, at least 20-30 amino acids, or at least 30-50 amino acids, or which is otherwise identifiable to one of ordinary skill in the art as having its origin in the starting sequence. In one embodiment, the one or more CDR sequences derived from the starting antibody are altered to produce variant CDR sequences, e.g. affinity variants, wherein the variant CDR sequences maintain target antigen binding activity.

"Camelid-Derived"—In certain preferred embodiments, the antibodies of the invention comprise framework amino acid sequences and/or CDR amino acid sequences derived from a camelid conventional antibody or a VHH antibody raised by active immunisation of a camelid. However, antibodies of the invention comprising camelid-derived amino acid sequences may be engineered to comprise framework and/or constant region sequences derived from a human amino acid sequence (i.e. a human antibody) or other non-camelid mammalian species. For example, a human or non-human primate framework region, heavy chain portion, and/or hinge portion may be included in the galectin-10 antibodies. In one embodiment, one or more non-camelid amino acids may be present in the framework region of a "camelid-derived" antibody, e.g., a camelid framework amino acid sequence may comprise one or more amino acid mutations in which the corresponding human or non-human primate amino acid residue is present. Moreover, camelid-derived VH and VL domains, or humanised variants thereof, may be linked to the constant domains of human antibodies to produce a chimeric molecule, as described elsewhere herein.

"Conservative amino acid substitution"—A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a non-essential amino acid residue in an immunoglobulin polypeptide may be replaced with another amino acid residue from the same side chain family. In another embodiment, a string of amino acids can be replaced with a structurally similar string that differs in order and/or composition of side chain family members.

"Heavy chain portion"—As used herein, the term "heavy chain portion" includes amino acid sequences derived from the constant domains of an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. In one embodiment, an antibody or antigen binding fragment of the invention may comprise the Fc portion of an immunoglobulin heavy chain (e.g., a hinge portion, a CH2 domain, and a CH3 domain). In another embodiment, an antibody or antigen binding fragment of the invention may lack at least a portion of a constant domain (e.g., all or part of a CH2 domain). In certain embodiments, at least one, and preferably all, of the constant domains are derived from a human immunoglobulin heavy chain. For example, in one preferred embodiment, the heavy chain portion comprises a fully human hinge domain. In other preferred embodiments, the heavy chain portion comprises a fully human Fc portion (e.g., hinge, CH2 and CH3 domain sequences from a human immunoglobulin).

In certain embodiments, the constituent constant domains of the heavy chain portion are from different immunoglobulin molecules. For example, a heavy chain portion of a polypeptide may comprise a CH2 domain derived from an IgG1 molecule and a hinge region derived from an IgG3 or IgG4 molecule. In other embodiments, the constant domains are chimeric domains comprising portions of different immunoglobulin molecules. For example, a hinge may comprise a first portion from an IgG1 molecule and a second portion from an IgG3 or IgG4 molecule. As set forth above, it will be understood by one of ordinary skill in the art that the constant domains of the heavy chain portion may be modified such that they vary in amino acid sequence from the naturally occurring (wild-type) immunoglobulin molecule. That is, the polypeptides of the invention disclosed herein may comprise alterations or modifications to one or more of the heavy chain constant domains (CH1, hinge, CH2 or CH3) and/or to the light chain constant region domain (CL). Exemplary modifications include additions, deletions or substitutions of one or more amino acids in one or more domains.

"Chimeric"—A "chimeric" protein comprises a first amino acid sequence linked to a second amino acid sequence with which it is not naturally linked in nature. The amino acid sequences may normally exist in separate proteins that are brought together in the fusion polypeptide or they may normally exist in the same protein but are placed in a new arrangement in the fusion polypeptide. A chimeric protein may be created, for example, by chemical synthesis, or by creating and translating a polynucleotide in which the peptide regions are encoded in the desired relationship. Exemplary chimeric antibodies of the invention include fusion proteins comprising camelid-derived VH and VL domains, or humanised variants thereof, fused to the constant domains of a human antibody, e.g. human IgG1, IgG2, IgG3 or IgG4.

"Variable region" or "variable domain"—The terms "variable region" and "variable domain" are used herein interchangeably and are intended to have equivalent meaning. The term "variable" refers to the fact that certain portions of the variable domains VH and VL differ extensively in sequence among antibodies and are used in the binding and specificity of each particular antibody for its target antigen. However, the variability is not evenly distributed throughout the variable domains of antibodies. It is concentrated in three segments called "hypervariable loops" in each of the VL domain and the VH domain which form part of the antigen binding site. The first, second and third hypervariable loops of the VLambda light chain domain are referred to herein as L1(λ), L2(λ) and L3(λ) and may be defined as comprising residues 24-33 (L1(λ), consisting of 9, 10 or 11 amino acid residues), 49-53 (L2(λ), consisting of 3 residues) and 90-96 (L3(λ), consisting of 5 residues) in the VL domain (Morea et al., Methods 20:267-279 (2000)). The first, second and third hypervariable loops of the VKappa light chain domain are referred to herein as L1(κ), L2(κ) and L3(κ) and may be defined as comprising residues 25-33 (L1(κ), consisting of 6, 7, 8, 11, 12 or 13 residues), 49-53 (L2(κ), consisting of 3 residues) and 90-97 (L3(κ), consisting of 6 residues) in the VL domain (Morea et al., Methods 20:267-279 (2000)). The first, second and third hypervariable loops of the VH domain are referred to herein as H1, H2 and H3 and may be defined as comprising residues 25-33 (H1, consisting of 7, 8 or 9 residues), 52-56 (H2, consisting of 3 or 4 residues) and 91-105 (H3, highly variable in length) in the VH domain (Morea et al., Methods 20:267-279 (2000)).

Unless otherwise indicated, the terms L1, L2 and L3 respectively refer to the first, second and third hypervariable loops of a VL domain, and encompass hypervariable loops obtained from both Vkappa and Vlambda isotypes. The terms H1, H2 and H3 respectively refer to the first, second and third hypervariable loops of the VH domain, and encompass hypervariable loops obtained from any of the known heavy chain isotypes, including γ, μ, α, δ, or ε.

The hypervariable loops L1, L2, L3, H1, H2 and H3 may each comprise part of a "complementarity determining region" or "CDR", as defined below. The terms "hypervariable loop" and "complementarity determining region" are not strictly synonymous, since the hypervariable loops (HVs) are defined on the basis of structure, whereas complementarity determining regions (CDRs) are defined based on sequence variability (Kabat et al., Sequences of Proteins of Immunological Interest, 5th Ed. Public Health Service, National Institutes of Health, Bethesda, Md., 1983) and the limits of the HVs and the CDRs may be different in some VH and VL domains.

The CDRs of the VL and VH domains can typically be defined as comprising the following amino acids: residues 24-34 (LCDR1), 50-56 (LCDR2) and 89-97 (LCDR3) in the light chain variable domain, and residues 31-35 or 31-35b (HCDR1), 50-65 (HCDR2) and 95-102 (HCDR3) in the heavy chain variable domain; (Kabat et al., Sequences of Proteins of Immunological Interest, 5th Ed. Public Health Service, National Institutes of Health, Bethesda, Md. (1991)). Thus, the HVs may be comprised within the corresponding CDRs and references herein to the "hypervariable loops" of VH and VL domains should be interpreted as also encompassing the corresponding CDRs, and vice versa, unless otherwise indicated.

The more highly conserved portions of variable domains are called the framework region (FR), as defined below. The variable domains of native heavy and light chains each comprise four FRs (FR1, FR2, FR3 and FR4, respectively), largely adopting a β-sheet configuration, connected by the three hypervariable loops. The hypervariable loops in each chain are held together in close proximity by the FRs and, with the hypervariable loops from the other chain, contribute to the formation of the antigen binding site of antibodies. Structural analysis of antibodies revealed the relationship between the sequence and the shape of the binding site formed by the complementarity determining regions (Chothia et al., J. Mol. Biol. 227: 799-817 (1992)); Tramontano et al., J. Mol. Biol, 215:175-182 (1990)). Despite their high sequence variability, five of the six loops adopt just a small repertoire of main-chain conformations, called "canonical structures". These conformations are first of all determined by the length of the loops and secondly by the presence of key residues at certain positions in the loops and in the framework regions that determine the conformation through their packing, hydrogen bonding or the ability to assume unusual main-chain conformations.

"CDR"—As used herein, the term "CDR" or "complementarity determining region" means the non-contiguous antigen binding sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth for comparison. Preferably, the term "CDR" is a CDR as defined by Kabat based on sequence comparisons.

TABLE 1

CDR definitions

| | CDR Definitions | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra "Framework region"—The term "framework region" or "FR region" as used herein, includes the amino acid residues that are part of the variable region, but are not part of the CDRs (e.g., using the Kabat definition of CDRs). Therefore, a variable region framework is between about 100-120 amino acids in length but includes only those amino acids outside of the CDRs. For the specific example of a heavy chain variable domain and for the CDRs as defined by Kabat et al., framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94, and framework region 4 corresponds to the domain of the variable region from amino acids 103 to the end of the variable region. The framework regions for the light chain are similarly separated by each of the light chain variable region CDRs. Similarly, using the definition of CDRs by Chothia et al. or McCallum et al. the framework region boundaries are separated by the respective CDR termini as described above. In preferred embodiments the CDRs are as defined by Kabat.

In naturally occurring antibodies, the six CDRs present on each monomeric antibody are short, non-contiguous sequences of amino acids that are specifically positioned to form the antigen binding site as the antibody assumes its three dimensional configuration in an aqueous environment. The remainder of the heavy and light variable domains show less inter-molecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

"Hinge region"—As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux K. H. et al. J. Immunol. 161:4083-90 1998). Antibodies of the invention comprising a "fully human" hinge region may contain one of the hinge region sequences shown in Table 2 below.

TABLE 2

Human hinge sequences

| IgG | Upper hinge | Middle hinge | Lower hinge |
|---|---|---|---|
| IgG1 | EPKSCDKTHT (SEQ ID NO: 142) | CPPCP (SEQ ID NO: 143) | APELLGGP (SEQ ID NO: 144) |
| IgG3 | ELKTPLGDTTHT (SEQ ID NO: 145) | CPRCP(EPKSCDTPPPCPRCP)$_3$ (SEQ ID NO: 146) | APELLGGP (SEQ ID NO: 147) |
| IgG4 | ESKYGPP (SEQ ID NO: 148) | CPSCP (SEQ ID NO: 149) | APEFLGGP (SEQ ID NO: 150) |
| IgG42 | ERK (SEQ ID NO: 151) | CCVECPPPCP (SEQ ID NO: 152) | APPVAGP (SEQ ID NO: 153) |

"CH2 domain"—As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system, Kabat E A et al. Sequences of Proteins of Immunological Interest. Bethesda, US Department of Health and Human Services, NIH. 1991). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

"Fragment"—The term "fragment", as used in the context of antibodies of the invention, refers to a part or portion of an antibody or antibody chain comprising fewer amino acid residues than an intact or complete antibody or antibody chain. The term "antigen binding fragment" refers to a polypeptide fragment of an immunoglobulin or antibody that binds antigen or competes with intact antibody (i.e., with the intact antibody from which they were derived) for antigen binding (i.e., specific binding to galectin-10). As used herein, the term "fragment" of an antibody molecule includes antigen binding fragments of antibodies, for example, an antibody light chain variable domain (VL), an antibody heavy chain variable domain (VH), a single chain antibody (scFv), a F(ab')2 fragment, a Fab fragment, an Fd fragment, an Fv fragment, a one-armed (monovalent) antibody, diabodies, triabodies, tetrabodies or any antigen binding molecule formed by combination, assembly or conjugation of such antigen binding fragments. The term "antigen binding fragment" as used herein is further intended to encompass antibody fragments selected from the group consisting of unibodies, domain antibodies and nanobodies. Fragments can be obtained, e.g., via chemical or enzymatic treatment of an intact or complete antibody or antibody chain or by recombinant means.

"Fab"—A "Fab" or "Fab fragment" refers to a molecule composed of a heavy chain and light chain wherein the light chain consists of the VL domain and the one constant domain (CL, Cκ or Cλ) and the heavy chain consists of the VH domain and the CH1 domain only. A Fab fragment is typically one arm of a Y-shaped immunoglobulin molecule. A Fab fragment can be generated from an immunoglobulin molecule by the action of the enzyme papain. Papain cleaves immunoglobulin molecules in the region of the hinge so as yield two Fab fragments and a separate Fc region.

"scFv" or "scFv fragment"—An scFv or scFv fragment means a single chain variable fragment. An scFv is a fusion protein of a VH domain and a VL domain of an antibody connected via a linker.

"Valency"—As used herein the term "valency" refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different ligands or different antigens, or different epitopes on the same antigen).

"Specificity"—The term "specificity" refers to the ability to bind (e.g., immunoreact with) a given target, e.g. galectin-10. A polypeptide may be monospecific and contain one or more binding sites which specifically bind a target or a polypeptide may be multispecific and contain two or more binding sites which specifically bind the same or different targets.

"Synthetic"—As used herein the term "synthetic" with respect to polypeptides includes polypeptides which comprise an amino acid sequence that is not naturally occurring. For example, non-naturally occurring polypeptides which are modified forms of naturally occurring polypeptides (e.g., comprising a mutation such as an addition, substitution or deletion) or which comprise a first amino acid sequence (which may or may not be naturally occurring) that is linked in a linear sequence of amino acids to a second amino acid sequence (which may or may not be naturally occurring) to which it is not naturally linked in nature.

"Engineered"—As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques). Preferably, the antibodies of the invention are engineered, including for example, humanized and/or chimeric antibodies, and antibodies which have been engineered to improve one or more properties, such as antigen binding, stability/half-life or effector function.

"Modified antibody"—As used herein, the term "modified antibody" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules and the like. scFv molecules are known in the art and are described, e.g., in U.S. Pat. No. 5,892,019. In addition, the term "modified antibody" includes multivalent forms of antibodies (e.g., trivalent, tetravalent, etc., antibodies that bind to three or more copies of the same antigen). In another embodiment, a modified antibody of the invention is a fusion protein comprising at least one heavy chain portion lacking a CH2 domain and comprising a binding domain of a polypeptide comprising the binding portion of one member of a receptor ligand pair.

The term "modified antibody" may also be used herein to refer to amino acid sequence variants of the antibodies of the invention as structurally defined herein. It will be understood by one of ordinary skill in the art that an antibody may be modified to produce a variant antibody which varies in amino acid sequence in comparison to the antibody from which it was derived. For example, nucleotide or amino acid substitutions leading to conservative substitutions or changes at "non-essential" amino acid residues may be made (e.g., in CDR and/or framework residues). Amino acid substitutions can include replacement of one or more amino acids with a naturally occurring or non-natural amino acid.

"Humanising substitutions"—As used herein, the term "humanising substitutions" refers to amino acid substitutions in which the amino acid residue present at a particular position in the VH or VL domain of an antibody (for example a camelid-derived galectin-10 antibody) is replaced with an amino acid residue which occurs at an equivalent position in a reference human VH or VL domain. The reference human VH or VL domain may be a VH or VL domain encoded by the human germline. Humanising substitutions may be made in the framework regions and/or the CDRs of the antibodies, defined herein.

"Humanised variants"—As used herein the term "humanised variant" refers to a variant antibody which contains one or more "humanising substitutions" compared to a reference antibody, wherein a portion of the reference antibody (e.g. the VH domain and/or the VL domain or parts thereof containing at least one CDR) has an amino acid derived from a non-human species, and the "humanising substitutions" occur within the amino acid sequence derived from a non-human species.

"Germlined variants"—The term "germlined variant" is used herein to refer specifically to "humanised variants" in which the "humanising substitutions" result in replacement of one or more amino acid residues present at a particular position (s) in the VH or VL domain of an antibody (for example a camelid-derived galectin-10 antibody) with an amino acid residue which occurs at an equivalent position in a reference human VH or VL domain encoded by the human germline. It is typical that for any given "germlined variant", the replacement amino acid residues substituted into the germlined variant are taken exclusively, or predominantly, from a single human germline-encoded VH or VL domain. The terms "humanised variant" and "germlined variant" are often used interchangeably herein. Introduction of one or more "humanising substitutions" into a camelid-derived (e.g. llama derived) VH or VL domain results in production of a "humanised variant" of the camelid (llama)-derived VH or VL domain. If the amino acid residues substituted in are derived predominantly or exclusively from a single human germline-encoded VH or VL domain sequence, then the result may be a "human germlined variant" of the camelid (llama)-derived VH or VL domain.

"Affinity variants"—As used herein, the term "affinity variant" refers to a variant antibody which exhibits one or more changes in amino acid sequence compared to a reference antibody, wherein the affinity variant exhibits an altered affinity for the target antigen in comparison to the reference antibody. For example, affinity variants will exhibit a changed affinity for galectin-10, as compared to the reference galectin-10 antibody. Preferably the affinity variant will exhibit improved affinity for the target antigen, e.g. galectin-10, as compared to the reference antibody. Affinity variants typically exhibit one or more changes in amino acid sequence in the CDRs, as compared to the reference antibody. Such substitutions may result in replacement of the original amino acid present at a given position in the CDRs with a different amino acid residue, which may be a naturally occurring amino acid residue or a non-naturally occurring amino acid residue. The amino acid substitutions may be conservative or non-conservative.

"High human homology"—An antibody comprising a heavy chain variable domain (VH) and a light chain variable domain (VL) may be considered as having high human homology if the VH domains and the VL domains, taken together, exhibit at least 90% amino acid sequence identity to the closest matching human germline VH and VL sequences. Antibodies having high human homology may include antibodies comprising VH and VL domains of native non-human antibodies which exhibit sufficiently high % sequence identity to human germline sequences, including for example antibodies comprising VH and VL domains of camelid conventional antibodies, as well as engineered, especially humanised or germlined, variants of such antibodies and also "fully human" antibodies.

In one embodiment the VH domain of the antibody with high human homology may exhibit an amino acid sequence identity or sequence homology of 80% or greater with one or more human VH domains across the framework regions FR1, FR2, FR3 and FR4. In other embodiments the amino acid sequence identity or sequence homology between the VH domain of the polypeptide of the invention and the closest matching human germline VH domain sequence may be 85% or greater, 90% or greater, 95% or greater, 97% or greater, or up to 99% or even 100%.

In one embodiment the VH domain of the antibody with high human homology may contain one or more (e.g. 1 to 10) amino acid sequence mis-matches across the framework regions FR1, FR2, FR3 and FR4, in comparison to the closest matched human VH sequence.

In another embodiment the VL domain of the antibody with high human homology may exhibit a sequence identity or sequence homology of 80% or greater with one or more human VL domains across the framework regions FR1, FR2, FR3 and FR4. In other embodiments the amino acid sequence identity or sequence homology between the VL domain of the polypeptide of the invention and the closest matching human germline VL domain sequence may be 85% or greater 90% or greater, 95% or greater, 97% or greater, or up to 99% or even 100%.

In one embodiment the VL domain of the antibody with high human homology may contain one or more (e.g. 1 to 10) amino acid sequence mis-matches across the framework regions FR1, FR2, FR3 and FR4, in comparison to the closest matched human VL sequence.

B. Galectin-10 Antagonists

In a first aspect, the present invention provides an antagonist which binds to galectin-10, wherein the antagonist binds to an epitope of galectin-10 and thereby shields a crystal packing interface of galectin-10. The present invention further provides an antagonist that binds to galectin-10, which, when bound to soluble galectin-10, inhibits the crystallization of galectin-10. The present invention further provides an antagonist that binds to galectin-10, which, when bound to crystalline galectin-10, promotes the dissolution of crystalline galectin-10. The antagonists of the invention preferably bind to human galectin-10.

The protein galectin-10 is a relatively small (16.5 kDa) glycan-binding protein. Galectin-10 proteins form dimers in solution and can also form insoluble hexagonal bipyramidal crystals. These crystals were first observed in patients with allergic asthma and parasitic infections, and are otherwise known as Charcot-Leyden crystals (or CLCs).

The antagonists of the present invention bind to an epitope of galectin-10. The epitope may be a linear epitope, i.e., it may consist of two or more consecutive amino acids in the galectin-10 primary protein sequence. Alternatively, the epitope may be a conformational epitope comprising or consisting of two or more amino acids that are not located adjacent to each other in the galectin-10 primary protein sequence. For embodiments in which the antagonist binds to a conformational epitope, the two or more amino acids of the epitope will typically be located in close proximity within the 3-dimensional structure of the galectin-10 protein. The epitopes to which the galectin-10 antagonists of the invention bind may comprise or consist of at least two amino acids, at least three amino acids, at least four amino acids, at least five amino acids, at least six amino acids, or at least seven amino acids. In certain embodiments, the epitopes to which the galectin-10 antagonists bind comprise or consist of 5, 6, 7, 8, 9, 10, 11, 12, 13, 14, 15, 16, 17, 18, 19 or 20 amino acids.

The antagonists of the invention bind to an epitope of galectin-10 and thereby shield a crystal packing interface of galectin-10. As defined elsewhere herein, a crystal packing interface of galectin-10 is a surface patch of amino acids that contacts one or more neighbouring galectin-10 molecules in the crystalline lattice. By binding to an epitope of galectin-10 that serves to shield a crystal packing interface of galectin-10, the antagonists of the invention disrupt the crystallization of galectin-10. It follows, that the antagonists of the invention may shield a crystal packing interface fully or partially, provided that the antagonist disrupts the crystallization of galectin-10. In certain embodiments, the antagonists, when bound to soluble galectin-10, inhibit crystallization of galectin-10. In certain embodiments, the antagonists, when bound to crystalline galectin-10, promote dissolution of galectin-10.

The antagonistic properties of the galectin-10 antagonists described herein may be measured in accordance with the assays described herein. For example, galectin-10 antagonists, including galectin-10 antibodies, may be incubated with soluble galectin-10 under experimental conditions that favour galectin-10 crystallization and the ability of the antagonists to inhibit this process may be measured. The inhibitory activity of the galectin-10 antagonists may be measured relative to a control, for example an antagonist that does not bind to galectin-10. The inhibitory activity of the galectin-10 antagonists may also be measured relative to a control that is a galectin-10 binding molecule without crystallization inhibitory activity. The galectin-10 antagonists may inhibit crystallization of galectin-10 by 100% relative to control, by at least 90% relative to control, by at least 80% relative to control, or by at least 70% relative to control.

Alternatively, galectin-10 antagonists, including galectin-10 antibodies and antigen binding fragments, may be incubated with pre-formed galectin-10 crystals and the ability of the antagonists to dissolve the crystals may be measured over a suitable time-course. The galectin-10 crystals may be recombinant crystals formed from recombinant galectin-10 produced in vitro. Alternatively, the galectin-10 crystals may be crystals obtained from a patient sample, for example crystals obtained from polyps within the nasal or sinus cavities of a patient. In certain embodiments, the galectin-10 antagonists of the invention may be capable of dissolving pre-formed galectin-10 crystals over a period of up to 10 hours, up to 12 hours, up to 14 hours, up to 16 hours, up to 18 hours, up to 20 hours. The galectin-10 antagonists may dissolve the crystals completely, i.e. by 100%. Alternatively, the galectin-10 antagonists may dissolve the crystals such that over 50% of the crystals are dissolved, over 60% or the crystals are dissolved, over 70% of the crystals are dissolved, over 80% of the crystals are dissolved, or over 90% of the crystals are dissolved over the time-course.

In certain embodiments, the galectin-10 antagonist shields a crystal packing interface by binding to an epitope comprising one or more amino acids from the crystal packing interfaces of galectin-10. The amino acids of galectin-10 that form the crystal packing interfaces are typically identified as: Ser2, Leu3, Leu4, Tyr8, Thr9, Glu10, Ala11, Ala12, Ser13, Thr16, Thr42, Glu43, Met44, Lys45, Asp49, Ile50, Glu68, Tyr69, Gly70, Ala71, Lys73, Gln74, Gln75, Val76, Glu77, Ser78, Lys79, Asn80, Met81, Leu96, Pro97, Asp98, Lys99, Gln101, Met103, Gly106, Gln107, Ser108, Ser109, Tyr110, Thr111, Asp113, His114, Arg115, Ile116, Lys117, Ala120, Gln125, Thr133, Lys134, Phe135, Asn136, Val137, Ser138, Tyr139, Leu140 and Lys141, wherein the positions are defined with reference to SEQ ID NO: 141. Thus, in certain embodiments, the galectin-10 antagonists of the invention bind to an epitope comprising one or more, two or more, three or more, four or more, five or more, six or more, seven or more, eight or more, nine or more, ten or more amino acids selected from the group consisting of: Ser2, Leu3, Leu4, Tyr8, Thr9, Glu10, Ala11, Ala12, Ser13, Thr16, Thr42, Glu43, Met44, Lys45, Asp49, Ile50, Glu68, Tyr69, Gly70, Ala71, Lys73, Gln74, Gln75, Val76, Glu77, Ser78, Lys79, Asn80, Met81, Leu96, Pro97, Asp98, Lys99, Gln101, Met103, Gly106, Gln107, Ser108, Ser109, Tyr110, Thr111, Asp113, His114, Arg115, Ile116, Lys117, Ala120, Gln125, Thr133, Lys134, Phe135, Asn136, Val137, Ser138, Tyr139, Leu140 and Lys141. In certain embodiments, the epitope consists entirely of amino acids from the crystal packing interfaces of galectin-10. For example, the epitope may consist of 5, 6, 7, 8, 9, 10, 11, 12, 13, 14, 15, 16, 17, 18, 19 or 20 amino acids from the crystal packing interfaces of galectin-10. Alternatively, the epitope may comprise amino acids from the crystal packing interfaces and additionally comprise at least one amino acid from outside the amino acids of the crystal packing interfaces of galectin-10.

In preferred embodiments, the antagonist binds to an epitope comprising Tyr69. Alternatively or in addition, the antagonist may preferably bind to an epitope comprising an amino acid adjacent to Tyr69, specifically Glu68 or Gly70. In one embodiment, the antagonist binds to an epitope comprising Glu68, Tyr69 and Gly70.

In a particular embodiment, the antagonist binds to an epitope comprising or consisting of the amino acids: Thr42, Glu43, Lys45, Asp49, Glu68, Tyr69, Gly70, Ala71, Lys73, His114, Arg115, Ile116, Lys117 and Ala120. In a particular embodiment, the antagonist binds to an epitope comprising or consisting of the amino acids: Thr42, Glu43, Lys45, Asp49, Glu68, Tyr69, Gly70, Ala71, Lys73, His114, Arg115, Ile116, Lys117, GLu119, Ala120 and Lys122. In a particular embodiment, the antagonist binds to an epitope comprising or consisting of the amino acids: Thr42, Glu43, Lys45, Asp49, Glu68, Tyr69, Gly70, Ala71, Lys73, Gln74, Asp98, His114, Arg115, Ile116, Lys117, GLu119, Ala120 and Lys122. The amino acid positions of galectin-10 are identified with respect to SEQ ID NO: 141.

In certain embodiments, the antagonist binds to an epitope comprising one or more amino acids from the dimerization interface of galectin-10. The amino acids of galectin-10 that form the dimerization domain may differ from the amino acids that participate in the crystal packing interfaces. However, it is possible for an antagonist that binds to amino acids located in the dimerization interface to also shield the crystal packing interfaces and thereby disrupt crystallization of galectin-10. The amino acids of galectin-10 that form the dimerization interface are typically identified as: Pro5, Pro7, Leu27, Ala28, Cys29, Leu31, Asn32, Glu33, Pro34, Tyr35, Gln37, His41, Glu46, Glu47, Gln55, Arg60, Arg61, Arg67, Trp72, Gln75, Trp127, Arg128 and Asp129. Thus, in certain embodiments, the galectin-10 antagonists of the invention bind to an epitope comprising or consisting of one or more, two or more, three or more, four or more, five or more, six or more, seven or more, eight or more, nine or more, ten or more amino acids selected from the group consisting of: Pro5, Pro7, Leu27, Ala28, Cys29, Leu31, Asn32, Glu33, Pro34, Tyr35, Gln37, His41, Glu46, Glu47, Gln55, Arg60, Arg61, Arg67, Trp72, Gln75, Trp127, Arg128 and Asp129. The amino acid positions of galectin-10 are identified with respect to SEQ ID NO: 141.

In certain embodiments, the galectin-10 antagonists of the invention bind to an epitope of galectin-10 comprising one or more amino acids from the crystal packing interfaces and one or more amino acids from the dimerization interface. The one or more amino acids from the crystal packing interfaces and the one or more amino acids from the dimerization interface may be any of the specific amino acids identified above. In preferred embodiments, the antagonists of the invention bind to an epitope comprising Glu68, Tyr69 and Gly70.

C. Galectin-10 Antibodies and Antigen Binding Fragments Thereof

In preferred embodiments, the galectin-10 antagonists of the present invention are antibodies or antigen binding fragments thereof. The term "antibody" herein is used in the broadest sense and encompasses, but is not limited to, monoclonal antibodies (including full length monoclonal antibodies), polyclonal antibodies, multispecific antibodies (e.g., bispecific antibodies), VHH antibodies, so long as they exhibit the appropriate immunological specificity for the galectin-10 protein. The galectin-10 antibodies and antigen binding fragments described herein may exhibit immunological specificity for any of the galectin-10 epitopes described in section B above.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes) on the antigen, each monoclonal antibody is directed against a single determinant or epitope on the antigen. "Antibody fragments" or "antigen binding fragments" comprise a portion of a full length antibody, generally the antigen binding or variable domain thereof. Antibody fragments are described elsewhere herein and examples of antibody fragments include Fab, Fab', F(ab')2, bi-specific Fab's, and Fv fragments, diabodies, linear antibodies, single-chain antibody molecules, a single chain variable fragment (scFv) and multispecific antibodies formed from antibody fragments (see Holliger and Hudson, Nature Biotechnol. 23:1126-36 (2005), the contents of which are incorporated herein by reference).

The galectin-10 antibodies and antigen binding fragments described herein are intended for human therapeutic use and therefore, will typically be immunoglobulins of the IgA, IgD, IgE, IgG, IgM type, often of the IgG type, in which case they can belong to any of the four sub-classes IgG1, IgG2a and b, IgG3 or IgG4. In preferred embodiments, the galectin-10 antibodies are IgG antibodies. Particularly preferred are IgG1 antibodies. Monoclonal antibodies are preferred since they are highly specific, being directed against a single antigenic site. In certain preferred embodiments, the galectin-10 antigen binding fragments are Fab fragments or "Fabs".

The galectin-10 antibodies and antigen binding fragments thereof may exhibit high human homology as defined elsewhere herein. Such antibody molecules having high human homology may include antibodies comprising VH and VL domains of native non-human antibodies which exhibit sufficiently high % sequence identity to human germline sequences. In certain embodiments, the antibodies or antigen binding fragments thereof are humanised or germlined variants of non-human antibodies.

In certain embodiments, the galectin-10 antibodies and antigen binding fragments described herein may be camelid-derived. Camelid-derived antibodies may be heavy-chain only antibodies i.e. VHH antibodies or may be conventional heterotetrameric antibodies. In preferred embodiments, the galectin-10 antibodies and antigen binding fragments are derived from camelid heterotetrameric antibodies. In further preferred embodiments, the galectin-10 antibodies are VHH antibodies or are derived from VHH antibodies.

For example, the galectin-10 antibodies and antigen binding fragments may be selected from immune libraries obtained by a method comprising the step of immunizing a camelid with the target of interest i.e. galectin-10. The camelid may be immunized with the target protein or polypeptide fragment thereof, or with an mRNA molecule or cDNA molecule expressing the protein or a polypeptide fragment thereof. Methods for producing antibodies in camelid species and selecting antibodies against preferred targets from camelid immune libraries are described in, for example, International patent application no. WO2010/001251, incorporated herein by reference.

In certain embodiments, the galectin-10 antibodies and antigen binding fragments may be camelid-derived in that they comprise at least one hypervariable (HV) loop or complementarity determining region obtained from a VH domain or a VL domain of a species in the family Camelidae. In particular, the galectin-10 antibodies and antigen binding fragments may comprise VH and/or VL domains, or CDRs thereof, obtained by active immunisation of outbred camelids, e.g. llamas, with galectin-10.

The term "obtained from" in this context implies a structural relationship, in the sense that the HVs or CDRs of the antibodies embody an amino acid sequence (or minor variants thereof) which was originally encoded by a Camelidae immunoglobulin gene. However, this does not necessarily imply a particular relationship in terms of the production process used to prepare the antibodies or antigen binding fragments thereof.

Camelid-derived antibodies or antigen binding fragments thereof may be derived from any camelid species, including inter alia, llama, dromedary, alpaca, vicuna, guanaco or camel.

Antibody molecules comprising camelid-derived VH and VL domains, or CDRs thereof, are typically recombinantly expressed polypeptides, and may be chimeric polypeptides. The term "chimeric polypeptide" refers to an artificial (non-naturally occurring) polypeptide which is created by juxtaposition of two or more peptide fragments which do not otherwise occur contiguously. Included within this definition are "species" chimeric polypeptides created by juxtaposition of peptide fragments encoded by two or more species, e.g. camelid and human.

In certain embodiments, the entire VH domain and/or the entire VL domain may be obtained from a species in the family Camelidae. The camelid-derived VH domain and/or the camelid-derived VL domain may then be subject to protein engineering, in which one or more amino acid substitutions, insertions or deletions are introduced into the camelid amino acid sequence. These engineered changes preferably include amino acid substitutions relative to the camelid sequence. Such changes include "humanisation" or "germlining" wherein one or more amino acid residues in a camelid-encoded VH or VL domain are replaced with equivalent residues from a homologous human-encoded VH or VL domain.

Isolated camelid VH and VL domains obtained by active immunisation of a camelid (e.g. llama) with galectin-10 can be used as a basis for engineering galectin-10 antibodies and antigen binding fragments in accordance with the present invention. Starting from intact camelid VH and VL domains, it is possible to engineer one or more amino acid substitutions, insertions or deletions which depart from the starting camelid sequence. In certain embodiments, such substitutions, insertions or deletions may be present in the framework regions of the VH domain and/or the VL domain.

In other embodiments, there are provided "chimeric" antibody molecules comprising camelid-derived VH and VL domains (or engineered variants thereof) and one or more constant domains from a non-camelid antibody, for example human-encoded constant domains (or engineered variants thereof). In such embodiments it is preferred that both the VH domain and the VL domain are obtained from the same species of camelid, for example both VH and VL may be from *Lama glama* or both VH and VL may be from *Lama pacos* (prior to introduction of engineered amino acid sequence variation). In such embodiments both the VH and the VL domain may be derived from a single animal, particularly a single animal which has been actively immunised with the antigen of interest.

As an alternative to engineering changes in the primary amino acid sequence of Camelidae VH and/or VL domains, individual camelid-derived hypervariable loops or CDRs, or combinations thereof, can be isolated from camelid VH/VL domains and transferred to an alternative (i.e. non-Camelidae) framework, e.g. a human VH/VL framework, by CDR grafting.

In non-limiting embodiments, the galectin-10 antibodies may comprise CH1 domains and/or CL domains (from the heavy chain and light chain, respectively), the amino acid sequence of which is fully or substantially human. For antibody molecules intended for human therapeutic use, it is typical for the entire constant region of the antibody, or at least a part thereof, to have fully or substantially human amino acid sequence. Therefore, one or more or any combination of the CH1 domain, hinge region, CH2 domain, CH3 domain and CL domain (and CH4 domain if present) may be fully or substantially human with respect to its amino acid sequence. The CH1 domain, hinge region, CH2 domain, CH3 domain and/or CL domain (and/or CH4 domain if present) may be derived from a human antibody, preferably a human IgG antibody, more preferably a human IgG1 antibody of subtype IgG1, IgG2, IgG3 or IgG4.

Advantageously, the CH1 domain, hinge region, CH2 domain, CH3 domain and CL domain (and CH4 domain if present) may all have fully or substantially human amino acid sequence. In the context of the constant region of a humanised or chimeric antibody, or an antibody fragment, the term "substantially human" refers to an amino acid sequence identity of at least 90%, or at least 92%, or at least 95%, or at least 97%, or at least 99% with a human constant region. The term "human amino acid sequence" in this context refers to an amino acid sequence which is encoded by a human immunoglobulin gene, which includes germline, rearranged and somatically mutated genes. The invention also contemplates polypeptides comprising constant domains of "human" sequence which have been altered, by one or more amino acid additions, deletions or substitutions with respect to the human sequence, excepting those embodiments where the presence of a "fully human" hinge region is expressly required.

The galectin-10 antibodies may have one or more amino acid substitutions, insertions or deletions within the constant region of the heavy and/or the light chain, particularly within the Fc region. Amino acid substitutions may result in replacement of the substituted amino acid with a different naturally occurring amino acid, or with a non-natural or modified amino acid. Other structural modifications are also permitted, such as for example changes in glycosylation pattern (e.g. by addition or deletion of N- or O-linked glycosylation sites).

The galectin-10 antibodies may be modified within the Fc region to increase binding affinity for the neonatal Fc receptor FcRn. The increased binding affinity may be measurable at acidic pH (for example from about approximately pH 5.5 to approximately pH 6.0). The increased binding affinity may also be measurable at neutral pH (for example from approximately pH 6.9 to approximately pH 7.4). By "increased binding affinity" is meant increased binding affinity to FcRn relative to the unmodified Fc region. Typically, the unmodified Fc region will possess the wild-type amino acid sequence of human IgG1, IgG2, IgG3 or IgG4. In such embodiments, the increased FcRn binding affinity of the antibody molecule having the modified Fc region will be measured relative to the binding affinity of wild-type IgG1, IgG2, IgG3 or IgG4 for FcRn.

In certain embodiments, one or more amino acid residues within the Fc region may be substituted with a different amino acid so as to increase binding to FcRn. Several Fc substitutions have been reported that increase FcRn binding and thereby improve antibody pharmacokinetics. Such substitutions are reported in, for example, Zalevsky et al. (2010) Nat. Biotechnol. 28(2):157-9; Hinton et al. (2006) J Immunol. 176:346-356; Yeung et al. (2009) J Immunol. 182:7663-7671; Presta L G. (2008) Curr. Op. Immunol. 20:460-470; and Vaccaro et al. (2005) Nat. Biotechnol. 23(10):1283-88, the contents of which are incorporated herein in their entirety.

In certain embodiments, the galectin-10 antibodies comprise a modified human IgG Fc domain comprising or consisting of the amino acid substitutions H433K and N434F, wherein the Fc domain numbering is in accordance with EU numbering. In a further embodiment, the galectin-10 antibodies described herein comprise a modified human IgG Fc domain comprising or consisting of the amino acid substitutions M252Y, S254T, T256E, H433K and N434F, wherein the Fc domain numbering is in accordance with EU numbering.

In certain embodiments, the galectin-10 antibodies comprise a modified human IgG Fc domain consisting of up to 2, up to 3, up to 4, up to 5, up to 6, up to 7, up to 8, up to 9, up to 10, up to 12, up to 15, up to 20 substitutions relative to the corresponding wild-type IgG sequence.

The galectin-10 antibodies may also be modified so as to form immunoconjugates comprising an antibody conjugated to a cytotoxic agent such as a chemotherapeutic agent, toxin (e.g., an enzymatically active toxin of bacterial, fungal, plant or animal origin, or fragments thereof), or a radioactive isotope (i.e., a radioconjugate). Fc regions may also be engineered for half-life extension, as described by Chan and Carter (2010) Nature Reviews: Immunology 10:301-316, incorporated herein by reference.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids.

In particular embodiments, the Fc region may be engineered such that there is no effector function. In certain embodiments, the antibody molecules of the invention may have an Fc region derived from naturally-occurring IgG isotypes having reduced effector function, for example IgG4. Fc regions derived from IgG4 may be further modified to increase therapeutic utility, for example by the introduction of modifications that minimise the exchange of arms between IgG4 molecules in vivo. Fc regions derived from IgG4 may be modified to include the S228P substitution.

In certain embodiments, the antibody molecules are modified with respect to glycosylation. For example, an aglycosylated antibody can be made (i.e., the antibody lacks glycosylation). Glycosylation can be altered to, for example, increase the affinity of the antibody for the target antigen. Such carbohydrate modifications can be accomplished by; for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen.

Also envisaged are variant galectin-10 antibodies having an altered type of glycosylation, such as a hypofucosylated antibody having reduced amounts of fucosyl residues or a fully or partially de-fucosylated antibody (as described by Natsume et al., Drug Design Development and Therapy, Vol. 3, pp 7-16, 2009) or an antibody having increased bisecting GlcNAc structures. Such altered glycosylation patterns have been demonstrated to increase the ADCC activity of antibodies, producing typically 10-fold enhancement of ADCC relative to an equivalent antibody comprising a "native" human Fc domain. Such carbohydrate modifications can be accomplished by, for example, expressing the antibody in a host cell with altered glycosylation enzymatic machinery (as described by Yamane-Ohnuki and Satoh, mAbs 1:3, 230-236, 2009). Examples of non-fucosylated antibodies with enhanced ADCC function are those produced using the Potelligent™ technology of BioWa Inc.

D. Exemplary Galectin-10 Antibodies

The present invention provides exemplary galectin-10 antibodies and antigen binding fragments thereof. These galectin-10 antibodies and antigen binding fragments serve as preferred galectin-10 antagonists in accordance with the invention. The exemplary galectin-10 antibodies and antigen binding fragments of the invention may be defined exclusively with respect to their structural characteristics, as described below.

Provided herein is an antibody or antigen binding fragment thereof which binds to galectin-10, wherein the antibody or antigen binding fragment comprises a variable heavy chain domain (VH) and a variable light chain domain (VL) wherein the VH and VL domains comprise the CDR sequences selected from the group consisting of:

(i) HCDR3 comprising or consisting of SEQ ID NO: 3; HCDR2 comprising or consisting of SEQ ID NO: 2; HCDR1 comprising or consisting of SEQ ID NO: 1; LCDR3 comprising or consisting of SEQ ID NO: 58; LCDR2 comprising or consisting of SEQ ID NO: 57; LCDR1 comprising or consisting of SEQ ID NO: 56;

(ii) HCDR3 comprising or consisting of SEQ ID NO: 6; HCDR2 comprising or consisting of SEQ ID NO: 5; HCDR1 comprising or consisting of SEQ ID NO: 4; LCDR3 comprising or consisting of SEQ ID NO: 61; LCDR2 comprising or consisting of SEQ ID NO: 60; LCDR1 comprising or consisting of SEQ ID NO: 59;

(iii) HCDR3 comprising or consisting of SEQ ID NO: 9; HCDR2 comprising or consisting of SEQ ID NO: 8; HCDR1 comprising or consisting of SEQ ID NO: 7; LCDR3 comprising or consisting of SEQ ID NO: 64; LCDR2 comprising or consisting of SEQ ID NO: 63; LCDR1 comprising or consisting of SEQ ID NO: 62;

(iv) HCDR3 comprising or consisting of SEQ ID NO: 12; HCDR2 comprising or consisting of SEQ ID NO: 11; HCDR1 comprising or consisting of SEQ ID NO: 10; LCDR3 comprising or consisting of SEQ ID NO: 67; LCDR2 comprising or consisting of SEQ ID NO: 66; LCDR1 comprising or consisting of SEQ ID NO: 65;

(v) HCDR3 comprising or consisting of SEQ ID NO: 15; HCDR2 comprising or consisting of SEQ ID NO: 14; HCDR1 comprising or consisting of SEQ ID NO: 13; LCDR3 comprising or consisting of SEQ ID NO: 70; LCDR2 comprising or consisting of SEQ ID NO: 69; LCDR1 comprising or consisting of SEQ ID NO: 68;

(vi) HCDR3 comprising or consisting of SEQ ID NO: 18; HCDR2 comprising or consisting of SEQ ID NO: 17; HCDR1 comprising or consisting of SEQ ID NO: 16; LCDR3 comprising or consisting of SEQ ID NO: 72; LCDR2 comprising or consisting of SEQ ID NO: 66; LCDR1 comprising or consisting of SEQ ID NO: 71;

(vii) HCDR3 comprising or consisting of SEQ ID NO: 20; HCDR2 comprising or consisting of SEQ ID NO: 19; HCDR1 comprising or consisting of SEQ ID NO: 4; LCDR3 comprising or consisting of SEQ ID NO: 75; LCDR2 comprising or consisting of SEQ ID NO: 74; LCDR1 comprising or consisting of SEQ ID NO: 73;

(viii) HCDR3 comprising or consisting of SEQ ID NO: 23; HCDR2 comprising or consisting of SEQ ID NO: 22; HCDR1 comprising or consisting of SEQ ID NO: 21; LCDR3 comprising or consisting of SEQ ID NO: 67; LCDR2 comprising or consisting of SEQ ID NO: 66; LCDR1 comprising or consisting of SEQ ID NO: 65;

(ix) HCDR3 comprising or consisting of SEQ ID NO: 25; HCDR2 comprising or consisting of SEQ ID NO: 24; HCDR1 comprising or consisting of SEQ ID NO: 4; LCDR3 comprising or consisting of SEQ ID NO: 78; LCDR2 comprising or consisting of SEQ ID NO: 77; LCDR1 comprising or consisting of SEQ ID NO: 76;

(x) HCDR3 comprising or consisting of SEQ ID NO: 28; HCDR2 comprising or consisting of SEQ ID NO: 27; HCDR1 comprising or consisting of SEQ ID NO: 26; LCDR3 comprising or consisting of SEQ ID NO: 67; LCDR2 comprising or consisting of SEQ ID NO: 66; LCDR1 comprising or consisting of SEQ ID NO: 79;

(xi) HCDR3 comprising or consisting of SEQ ID NO: 31; HCDR2 comprising or consisting of SEQ ID NO: 30; HCDR1 comprising or consisting of SEQ ID NO: 29; LCDR3 comprising or consisting of SEQ ID NO: 81; LCDR2 comprising or consisting of SEQ ID NO: 63; LCDR1 comprising or consisting of SEQ ID NO: 80;

(xii) HCDR3 comprising or consisting of SEQ ID NO: 33; HCDR2 comprising or consisting of SEQ ID NO: 32; HCDR1 comprising or consisting of SEQ ID NO: 1; LCDR3 comprising or consisting of SEQ ID NO: 84; LCDR2 comprising or consisting of SEQ ID NO: 83; LCDR1 comprising or consisting of SEQ ID NO: 82;

(xiii) HCDR3 comprising or consisting of SEQ ID NO: 36; HCDR2 comprising or consisting of SEQ ID NO: 35; HCDR1 comprising or consisting of SEQ ID NO: 34; LCDR3 comprising or consisting of SEQ ID NO: 87; LCDR2 comprising or consisting of SEQ ID NO: 86; LCDR1 comprising or consisting of SEQ ID NO: 85;

(xiv) HCDR3 comprising or consisting of SEQ ID NO: 38; HCDR2 comprising or consisting of SEQ ID NO: 11; HCDR1 comprising or consisting of SEQ ID NO: 37; LCDR3 comprising or consisting of SEQ ID NO: 78; LCDR2 comprising or consisting of SEQ ID NO: 63; LCDR1 comprising or consisting of SEQ ID NO: 88;

(xv) HCDR3 comprising or consisting of SEQ ID NO: 41; HCDR2 comprising or consisting of SEQ ID NO: 40; HCDR1 comprising or consisting of SEQ ID NO: 39; LCDR3 comprising or consisting of SEQ ID NO: 91; LCDR2 comprising or consisting of SEQ ID NO: 90; LCDR1 comprising or consisting of SEQ ID NO: 89;

(xvi) HCDR3 comprising or consisting of SEQ ID NO: 43; HCDR2 comprising or consisting of SEQ ID NO: 42; HCDR1 comprising or consisting of SEQ ID NO: 4; LCDR3 comprising or consisting of SEQ ID NO: 94; LCDR2 comprising or consisting of SEQ ID NO: 93; LCDR1 comprising or consisting of SEQ ID NO: 92;

(xvii) HCDR3 comprising or consisting of SEQ ID NO: 6; HCDR2 comprising or consisting of SEQ ID NO: 44; HCDR1 comprising or consisting of SEQ ID NO: 4; LCDR3 comprising or consisting of SEQ ID NO: 97; LCDR2 comprising or consisting of SEQ ID NO: 96; LCDR1 comprising or consisting of SEQ ID NO: 95;

(xviii) HCDR3 comprising or consisting of SEQ ID NO: 47; HCDR2 comprising or consisting of SEQ ID NO: 46; HCDR1 comprising or consisting of SEQ ID NO: 45; LCDR3 comprising or consisting of SEQ ID NO: 94; LCDR2 comprising or consisting of SEQ ID NO: 93; LCDR1 comprising or consisting of SEQ ID NO: 71;

(xix) HCDR3 comprising or consisting of SEQ ID NO: 50; HCDR2 comprising or consisting of SEQ ID NO: 49; HCDR1 comprising or consisting of SEQ ID NO: 48; LCDR3 comprising or consisting of SEQ ID NO: 96; LCDR2 comprising or consisting of SEQ ID NO: 63; LCDR1 comprising or consisting of SEQ ID NO: 95;

(xx) HCDR3 comprising or consisting of SEQ ID NO: 36; HCDR2 comprising or consisting of SEQ ID NO: 52; HCDR1 comprising or consisting of SEQ ID NO: 51; LCDR3 comprising or consisting of SEQ ID NO: 98; LCDR2 comprising or consisting of SEQ ID NO: 97; LCDR1 comprising or consisting of SEQ ID NO: 80; and (xxi) HCDR3 comprising or consisting of SEQ ID NO: 55; HCDR2 comprising or consisting of SEQ ID NO: 54; HCDR1 comprising or consisting of SEQ ID NO: 53; LCDR3 comprising or consisting of SEQ ID NO: 81; LCDR2 comprising or consisting of SEQ ID NO: 93; LCDR1 comprising or consisting of SEQ ID NO: 71.

In certain embodiments, there is provided an antibody or antigen binding fragment thereof, which binds galectin-10, said antibody or antigen binding fragment comprising a heavy chain variable domain and a light chain variable domain, wherein the variable heavy chain CDR3 sequence comprises or consists of SEQ ID NO:3 [DRNLGYRLGYPYDY] or sequence variant thereof;

the variable heavy chain CDR2 sequence comprises or consists SEQ ID NO:2 [GISWNGGSTYYAESMKG] or sequence variant thereof;

the variable heavy chain CDR1 sequence comprises or consists of SEQ ID NO:1 [DYAMS] or sequence variant thereof;

the variable light chain CDR3 sequence comprises or consists of SEQ ID NO:58 [ASYRSSNNAV] or sequence variant thereof;

the variable light chain CDR2 sequence comprises or consists SEQ ID NO:57 [EVNKRAS] or sequence variant thereof;

the variable light chain CDR1 sequence comprises or consists of SEQ ID NO:56 [AGTSSDVGYGNYVS] or sequence variant thereof; and wherein the sequence variant comprises one, two or three amino acid substitutions (e.g., conservative substitutions, humanising substitutions or affinity variants) in the recited sequence.

In certain embodiments, there is provided an antibody or antigen binding fragment thereof, which binds galectin-10, said antibody or antigen binding fragment comprising a heavy chain variable domain and a light chain variable domain, wherein the variable heavy chain CDR3 sequence comprises or consists of SEQ ID NO:6 [PGDRLWYYRYDY] or sequence variant thereof;

the variable heavy chain CDR2 sequence comprises or consists SEQ ID NO:5 [AINSGGGSTSYADSVKG] or sequence variant thereof;

the variable heavy chain CDR1 sequence comprises or consists of SEQ ID NO:4 [SYAMS] or sequence variant thereof;

the variable light chain CDR3 sequence comprises or consists of SEQ ID NO:61 [ASYRYRNNVV] or sequence variant thereof;

the variable light chain CDR2 sequence comprises or consists SEQ ID NO:60 [KVSRRAS] or sequence variant thereof;

the variable light chain CDR1 sequence comprises or consists of SEQ ID NO:59 [AGTSSDIGYGNYVS] or sequence variant thereof; and wherein the sequence variant comprises one, two or three amino acid substitutions (e.g., conservative substitutions, humanising substitutions or affinity variants) in the recited sequence.

In certain embodiments, there is provided an antibody or antigen binding fragment thereof, which binds galectin-10, said antibody or antigen binding fragment comprising a heavy chain variable domain and a light chain variable domain, wherein the variable heavy chain CDR3 sequence comprises or consists of SEQ ID NO:9 [YIRGSSWSGWSAYDY] or sequence variant thereof;

the variable heavy chain CDR2 sequence comprises or consists SEQ ID NO:8 [VIASDGSTYYSPSLKS] or sequence variant thereof;

the variable heavy chain CDR1 sequence comprises or consists of SEQ ID NO:7 [TSYYAWS] or sequence variant thereof;

the variable light chain CDR3 sequence comprises or consists of SEQ ID NO:64 [QSADSSDNPV] or sequence variant thereof;

the variable light chain CDR2 sequence comprises or consists SEQ ID NO:63 [KDSERPS] or sequence variant thereof;

the variable light chain CDR1 sequence comprises or consists of SEQ ID NO:62 [QGGNFGYYYGS] or sequence variant thereof; and wherein the sequence variant comprises one, two or three amino acid substitutions (e.g., conservative substitutions, humanising substitutions or affinity variants) in the recited sequence.

In certain embodiments, there is provided an antibody or antigen binding fragment thereof, which binds galectin-10, said antibody or antigen binding fragment comprising a heavy chain variable domain and a light chain variable domain, wherein the variable heavy chain CDR3 sequence comprises or consists of SEQ ID NO:12 [RPNWYRALDA] or sequence variant thereof;

the variable heavy chain CDR2 sequence comprises or consists SEQ ID NO:11 [AIAYSGSTYYSPSLKS] or sequence variant thereof;

the variable heavy chain CDR1 sequence comprises or consists of SEQ ID NO:10 [TNSYYWS] or sequence variant thereof;

the variable light chain CDR3 sequence comprises or consists of SEQ ID NO:67 [QSYESSTSPV] or sequence variant thereof;

the variable light chain CDR2 sequence comprises or consists SEQ ID NO:66 [GDSNRPS] or sequence variant thereof;

the variable light chain CDR1 sequence comprises or consists of SEQ ID NO:65 [QGANLGRYYGI] or sequence variant thereof; and wherein the sequence variant comprises one, two or three amino acid substitutions (e.g., conservative substitutions, humanising substitutions or affinity variants) in the recited sequence.

In certain embodiments, the antibodies and antigen binding fragments that bind to galectin-10 are selected from antibody molecules comprising or consisting of a variable heavy chain domain (VH) and a variable light chain domain (VL) selected from the following:

(i) a VH comprising or consisting of the amino acid sequence of SEQ ID NO: 99 or an amino acid sequence at least 90%, 95%, 97%, 98% or 99% identical thereto and a VL comprising or consisting of the amino acid sequence of SEQ ID NO: 100 or an amino acid sequence at least 90%, 95%, 97%, 98% or 99% identical thereto;

(ii) a VH comprising or consisting of the amino acid sequence of SEQ ID NO: 101 or an amino acid sequence at least 90%, 95%, 97%, 98% or 99% identical thereto and a VL comprising or consisting of the amino acid sequence of SEQ ID NO: 102 or an amino acid sequence at least 90%, 95%, 97%, 98% or 99% identical thereto;

(iii) a VH comprising or consisting of the amino acid sequence of SEQ ID NO: 103 or an amino acid sequence at least 90%, 95%, 97%, 98% or 99% identical thereto and a VL comprising or consisting of the amino acid sequence of SEQ ID NO: 104 or an amino acid sequence at least 90%, 95%, 97%, 98% or 99% identical thereto;

(iv) a VH comprising or consisting of the amino acid sequence of SEQ ID NO: 105 or an amino acid sequence at least 90%, 95%, 97%, 98% or 99% identical thereto and a VL comprising or consisting of the amino acid sequence of SEQ ID NO: 106 or an amino acid sequence at least 90%, 95%, 97%, 98% or 99% identical thereto;

(v) a VH comprising or consisting of the amino acid sequence of SEQ ID NO: 107 or an amino acid sequence at least 90%, 95%, 97%, 98% or 99% identical thereto and a VL comprising or consisting of the amino acid sequence of SEQ ID NO: 108 or an amino acid sequence at least 90%, 95%, 97%, 98% or 99% identical thereto;

(vi) a VH comprising or consisting of the amino acid sequence of SEQ ID NO: 109 or an amino acid sequence at least 90%, 95%, 97%, 98% or 99% identical thereto and a VL comprising or consisting of the amino acid sequence of SEQ ID NO: 110 or an amino acid sequence at least 90%, 95%, 97%, 98% or 99% identical thereto;

(vii) a VH comprising or consisting of the amino acid sequence of SEQ ID NO: 111 or an amino acid sequence at least 90%, 95%, 97%, 98% or 99% identical thereto and a VL comprising or consisting of the amino acid sequence of SEQ ID NO: 112 or an amino acid sequence at least 90%, 95%, 97%, 98% or 99% identical thereto;

(viii) a VH comprising or consisting of the amino acid sequence of SEQ ID NO: 113 or an amino acid sequence at least 90%, 95%, 97%, 98% or 99% identical thereto and a VL comprising or consisting of the amino acid sequence of SEQ ID NO: 114 or an amino acid sequence at least 90%, 95%, 97%, 98% or 99% identical thereto;

(ix) a VH comprising or consisting of the amino acid sequence of SEQ ID NO: 115 or an amino acid sequence at least 90%, 95%, 97%, 98% or 99% identical thereto and a VL comprising or consisting of the amino acid sequence of SEQ ID NO: 116 or an amino acid sequence at least 90%, 95%, 97%, 98% or 99% identical thereto;

(x) a VH comprising or consisting of the amino acid sequence of SEQ ID NO: 117 or an amino acid sequence at least 90%, 95%, 97%, 98% or 99% identical thereto and a VL comprising or consisting of the amino acid sequence of SEQ ID NO: 118 or an amino acid sequence at least 90%, 95%, 97%, 98% or 99% identical thereto;

(xi) a VH comprising or consisting of the amino acid sequence of SEQ ID NO: 119 or an amino acid sequence at least 90%, 95%, 97%, 98% or 99% identical thereto and a VL comprising or consisting of the amino acid sequence of SEQ ID NO: 120 or an amino acid sequence at least 90%, 95%, 97%, 98% or 99% identical thereto;

(xii) a VH comprising or consisting of the amino acid sequence of SEQ ID NO: 121 or an amino acid sequence at least 90%, 95%, 97%, 98% or 99% identical thereto and a VL comprising or consisting of the amino acid sequence of SEQ ID NO: 122 or an amino acid sequence at least 90%, 95%, 97%, 98% or 99% identical thereto;

(xiii) a VH comprising or consisting of the amino acid sequence of SEQ ID NO: 123 or an amino acid sequence at least 90%, 95%, 97%, 98% or 99% identical thereto and a VL comprising or consisting of the amino acid sequence of SEQ ID NO: 124 or an amino acid sequence at least 90%, 95%, 97%, 98% or 99% identical thereto;

(xiv) a VH comprising or consisting of the amino acid sequence of SEQ ID NO: 125 or an amino acid sequence at least 90%, 95%, 97%, 98% or 99% identical thereto and a VL comprising or consisting of the amino acid sequence of SEQ ID NO: 126 or an amino acid sequence at least 90%, 95%, 97%, 98% or 99% identical thereto;

(xv) a VH comprising or consisting of the amino acid sequence of SEQ ID NO: 127 or an amino acid sequence at least 90%, 95%, 97%, 98% or 99% identical thereto and a VL comprising or consisting of the amino acid sequence of SEQ ID NO: 128 or an amino acid sequence at least 90%, 95%, 97%, 98% or 99% identical thereto;

(xvi) a VH comprising or consisting of the amino acid sequence of SEQ ID NO: 129 or an amino acid sequence at least 90%, 95%, 97%, 98% or 99% identical thereto and a VL comprising or consisting of the amino acid sequence of SEQ ID NO: 130 or an amino acid sequence at least 90%, 95%, 97%, 98% or 99% identical thereto;

(xvii) a VH comprising or consisting of the amino acid sequence of SEQ ID NO: 131 or an amino acid sequence at least 90%, 95%, 97%, 98% or 99% identical thereto and a VL comprising or consisting of the amino acid sequence of SEQ ID NO: 132 or an amino acid sequence at least 90%, 95%, 97%, 98% or 99% identical thereto;

(xviii) a VH comprising or consisting of the amino acid sequence of SEQ ID NO: 133 or an amino acid sequence at least 90%, 95%, 97%, 98% or 99% identical thereto and a VL comprising or consisting of the amino acid sequence of SEQ ID NO: 134 or an amino acid sequence at least 90%, 95%, 97%, 98% or 99% identical thereto;

(xix) a VH comprising or consisting of the amino acid sequence of SEQ ID NO: 135 or an amino acid sequence at least 90%, 95%, 97%, 98% or 99% identical thereto and a VL comprising or consisting of the amino acid sequence of SEQ ID NO: 136 or an amino acid sequence at least 90%, 95%, 97%, 98% or 99% identical thereto;

(xx) a VH comprising or consisting of the amino acid sequence of SEQ ID NO: 137 or an amino acid sequence at least 90%, 95%, 97%, 98% or 99% identical thereto and a VL comprising or consisting of the amino acid sequence of SEQ ID NO: 138 or an amino acid sequence at least 90%, 95%, 97%, 98% or 99% identical thereto; and (xxi) a VH comprising or consisting of the amino acid sequence of SEQ ID NO: 139 or an amino acid sequence at least 90%, 95%, 97%, 98% or 99% identical thereto and a VL comprising or consisting of the amino acid sequence of SEQ ID NO: 140 or an amino acid sequence at least 90%, 95%, 97%, 98% or 99% identical thereto.

Provided herein is an antibody or antigen binding fragment thereof which binds to galectin-10, wherein the antibody or antigen binding fragment comprises a variable heavy chain domain (VH) and a variable light chain domain (VL) wherein the VH and VL domains comprise the CDR sequences selected from the group consisting of:

(i) HCDR3 comprising or consisting of SEQ ID NO: 162; HCDR2 comprising or consisting of SEQ ID NO: 161; HCDR1 comprising or consisting of SEQ ID NO: 160; LCDR3 comprising or consisting of SEQ ID NO: 179; LCDR2 comprising or consisting of SEQ ID NO: 178; LCDR1 comprising or consisting of SEQ ID NO: 177;

(ii) HCDR3 comprising or consisting of SEQ ID NO: 165; HCDR2 comprising or consisting of SEQ ID NO: 164; HCDR1 comprising or consisting of SEQ ID NO: 163; LCDR3 comprising or consisting of SEQ ID NO: 182; LCDR2 comprising or consisting of SEQ ID NO: 181; LCDR1 comprising or consisting of SEQ ID NO: 180;

(iii) HCDR3 comprising or consisting of SEQ ID NO: 168; HCDR2 comprising or consisting of SEQ ID NO: 167; HCDR1 comprising or consisting of SEQ ID NO: 166; LCDR3 comprising or consisting of SEQ ID NO: 185; LCDR2 comprising or consisting of SEQ ID NO: 184; LCDR1 comprising or consisting of SEQ ID NO: 183;

(iv) HCDR3 comprising or consisting of SEQ ID NO: 171; HCDR2 comprising or consisting of SEQ ID NO: 170; HCDR1 comprising or consisting of SEQ ID NO: 169; LCDR3 comprising or consisting of SEQ ID NO: 187; LCDR2 comprising or consisting of SEQ ID NO: 186; LCDR1 comprising or consisting of SEQ ID NO: 180;

(v) HCDR3 comprising or consisting of SEQ ID NO: 174; HCDR2 comprising or consisting of SEQ ID NO: 173; HCDR1 comprising or consisting of SEQ ID NO: 172; LCDR3 comprising or consisting of SEQ ID NO: 189; LCDR2 comprising or consisting of SEQ ID NO: 188; LCDR1 comprising or consisting of SEQ ID NO: 180;

(vi) HCDR3 comprising or consisting of SEQ ID NO: 176; HCDR2 comprising or consisting of SEQ ID NO: 175; HCDR1 comprising or consisting of SEQ ID NO: 163; LCDR3 comprising or consisting of SEQ ID NO: 192; LCDR2 comprising or consisting of SEQ ID NO: 191; LCDR1 comprising or consisting of SEQ ID NO: 190; and (vii) HCDR3 comprising or consisting of SEQ ID NO: 165; HCDR2 comprising or consisting of SEQ ID NO: 164; HCDR1 comprising or consisting of SEQ ID NO: 163; LCDR3 comprising or consisting of SEQ ID NO: 193; LCDR2 comprising or consisting of SEQ ID NO: 181; LCDR1 comprising or consisting of SEQ ID NO: 180.

In certain embodiments, the antibodies and antigen binding fragments that bind to galectin-10 are selected from antibody molecules comprising or consisting of a variable heavy chain domain (VH) and a variable light chain domain (VL) selected from the following:

(i) a VH comprising the amino acid sequence of SEQ ID NO: 194 or an amino acid sequence at least 90%, 95%, 97%, 98% or 99% identical thereto and a VL comprising the amino acid sequence of SEQ ID NO: 195 or an amino acid sequence at least 90%, 95%, 97%, 98% or 99% identical thereto;

(ii) a VH comprising the amino acid sequence of SEQ ID NO: 196 or an amino acid sequence at least 90%, 95%, 97%, 98% or 99% identical thereto and a VL comprising the amino acid sequence of SEQ ID NO: 197 or an amino acid sequence at least 90%, 95%, 97%, 98% or 99% identical thereto;

(iii) a VH comprising the amino acid sequence of SEQ ID NO: 198 or an amino acid sequence at least 90%, 95%, 97%, 98% or 99% identical thereto and a VL comprising the amino acid sequence of SEQ ID NO: 199 or an amino acid sequence at least 90%, 95%, 97%, 98% or 99% identical thereto;

(iv) a VH comprising the amino acid sequence of SEQ ID NO: 200 or an amino acid sequence at least 90%, 95%, 97%, 98% or 99% identical thereto and a VL comprising the amino acid sequence of SEQ ID NO: 201 or an amino acid sequence at least 90%, 95%, 97%, 98% or 99% identical thereto;

(v) a VH comprising the amino acid sequence of SEQ ID NO: 202 or an amino acid sequence at least 90%, 95%, 97%, 98% or 99% identical thereto and a VL comprising the amino acid sequence of SEQ ID NO: 203 or an amino acid sequence at least 90%, 95%, 97%, 98% or 99% identical thereto;

(vi) a VH comprising the amino acid sequence of SEQ ID NO: 204 or an amino acid sequence at least 90%, 95%, 97%, 98% or 99% identical thereto and a VL comprising the amino acid sequence of SEQ ID NO: 205 or an amino acid sequence at least 90%, 95%, 97%, 98% or 99% identical thereto; and (vii) a VH comprising the amino acid sequence of SEQ ID NO: 206 or an amino acid sequence at least 90%, 95%, 97%, 98% or 99% identical thereto and a VL comprising the amino acid sequence of SEQ ID NO: 207 or an amino acid sequence at least 90%, 95%, 97%, 98% or 99% identical thereto.

For embodiments wherein the domains of the antibodies or antigen binding fragments are defined by a particular percentage sequence identity to a reference sequence, the VH and/or VL domains may retain identical CDR sequences to those present in the reference sequence such that the variation is present only within the framework regions.

Provided herein is an antibody or antigen binding fragment thereof which binds to galectin-10, wherein the antibody is a VHH antibody and wherein the VHH domain comprises the CDR sequences selected from the group consisting of:

(i) CDR3 comprising or consisting of SEQ ID NO: 210; CDR2 comprising or consisting of SEQ ID NO: 209; CDR1 comprising or consisting of SEQ ID NO: 208;

(ii) CDR3 comprising or consisting of SEQ ID NO: 213; CDR2 comprising or consisting of SEQ ID NO: 212; CDR1 comprising or consisting of SEQ ID NO: 211;

(iii) CDR3 comprising or consisting of SEQ ID NO: 216; CDR2 comprising or consisting of SEQ ID NO: 215; CDR1 comprising or consisting of SEQ ID NO: 214;

(iv) CDR3 comprising or consisting of SEQ ID NO: 219; CDR2 comprising or consisting of SEQ ID NO: 218; CDR1 comprising or consisting of SEQ ID NO: 217;

(v) CDR3 comprising or consisting of SEQ ID NO: 222; CDR2 comprising or consisting of SEQ ID NO: 221; CDR1 comprising or consisting of SEQ ID NO: 220;

(vi) CDR3 comprising or consisting of SEQ ID NO: 225; CDR2 comprising or consisting of SEQ ID NO: 224; CDR1 comprising or consisting of SEQ ID NO: 223;

(vii) CDR3 comprising or consisting of SEQ ID NO: 228; CDR2 comprising or consisting of SEQ ID NO: 227; CDR1 comprising or consisting of SEQ ID NO: 226;

(viii) CDR3 comprising or consisting of SEQ ID NO: 231; CDR2 comprising or consisting of SEQ ID NO: 230; CDR1 comprising or consisting of SEQ ID NO: 229;

(ix) CDR3 comprising or consisting of SEQ ID NO: 234; CDR2 comprising or consisting of SEQ ID NO: 233; CDR1 comprising or consisting of SEQ ID NO: 232;

(x) CDR3 comprising or consisting of SEQ ID NO: 236; CDR2 comprising or consisting of SEQ ID NO: 235; CDR1 comprising or consisting of SEQ ID NO: 226;

(xi) CDR3 comprising or consisting of SEQ ID NO: 238; CDR2 comprising or consisting of SEQ ID NO: 237; CDR1 comprising or consisting of SEQ ID NO: 232;

(xii) CDR3 comprising or consisting of SEQ ID NO: 241; CDR2 comprising or consisting of SEQ ID NO: 240; CDR1 comprising or consisting of SEQ ID NO: 239;

(xiii) CDR3 comprising or consisting of SEQ ID NO: 236; CDR2 comprising or consisting of SEQ ID NO: 235; CDR1 comprising or consisting of SEQ ID NO: 226;

(xiv) CDR3 comprising or consisting of SEQ ID NO: 244; CDR2 comprising or consisting of SEQ ID NO: 243; CDR1 comprising or consisting of SEQ ID NO: 242;

(xv) CDR3 comprising or consisting of SEQ ID NO: 234; CDR2 comprising or consisting of SEQ ID NO: 233; CDR1 comprising or consisting of SEQ ID NO: 232;

(xvi) CDR3 comprising or consisting of SEQ ID NO: 247; CDR2 comprising or consisting of SEQ ID NO: 246; CDR1 comprising or consisting of SEQ ID NO: 245; and (xvii) CDR3 comprising or consisting of SEQ ID NO: 249; CDR2 comprising or consisting of SEQ ID NO: 248; CDR1 comprising or consisting of SEQ ID NO: 217.

In certain embodiments, the VHH antibodies that bind to galectin-10 comprise a VHH domain comprising or consisting of an selected from antibody molecules comprising or consisting of the amino acid sequence represented by any one of SEQ ID NOs: 250, 251, 252, 253, 254, 255, 256, 257, 258, 259, 260, 261, 262, 263, 264, 265 or 266, or an amino acid sequence at least 90%, 95%, 97%, 98% or 99% identical thereto.

For embodiments wherein the VHH domains are defined by a particular percentage sequence identity to a reference sequence, the VHH domain may retain identical CDR sequences to those present in the reference sequence such that the variation is present only within the framework regions.

The invention also provides antibodies or antigen binding fragments thereof, which bind to the same epitope as the galectin-10 antibodies exemplified herein.

In certain embodiments, the exemplary galectin-10 antibodies and antigen binding fragments thereof defined as having the CDR sequences recited above or defined as having a particular percentage identity to the specific VH/VL/VHH domain amino acid sequences recited above are humanised, germlined or affinity variants of the antibodies or antigen binding fragments thereof from which the CDR, VH, VL and/or VHH sequences derive.

In a preferred embodiment, the exemplary galectin-10 antibody molecules having the CDR sequences recited above exhibit high human homology, for example are humanised or germlined variants of the antibodies or antigen binding fragments thereof from which the CDR sequences derive.

In non-limiting embodiments, the exemplary galectin-10 antibodies and antigen binding fragments thereof having the CDR, VH and/or VL sequences described herein may comprise CH1 domains and/or CL domains (from the heavy chain and light chain, respectively), the amino acid sequence of which is fully or substantially human. For antibody molecules intended for human therapeutic use, it is typical for the entire constant region of the antibody, or at least a part thereof, to have fully or substantially human amino acid sequence. Therefore, one or more or any combination of the CH1 domain, hinge region, CH2 domain, CH3 domain and CL domain (and CH4 domain if present) may be fully or substantially human with respect to its amino acid sequence.

Advantageously, the CH1 domain, hinge region, CH2 domain, CH3 domain and CL domain (and CH4 domain if present) may all have fully or substantially human amino acid sequence. In the context of the constant region of a humanised or chimeric antibody, or an antibody fragment, the term "substantially human" refers to an amino acid sequence identity of at least 90%, or at least 92%, or at least 95%, or at least 97%, or at least 99% with a human constant region. The term "human amino acid sequence" in this context refers to an amino acid sequence which is encoded by a human immunoglobulin gene, which includes germline, rearranged and somatically mutated genes. The invention also contemplates polypeptides comprising constant domains of "human" sequence which have been altered, by one or more amino acid additions, deletions or substitutions with respect to the human sequence, excepting those embodiments where the presence of a "fully human" hinge region is expressly required. Any of the exemplary Fc region modifications described herein may be incorporated into the galectin-10 antibodies having the CDR and/or VH/VL domain sequences recited above. In certain embodiments, the galectin-10 antibodies having the CDR and/or VH/VL domain sequences recited above comprise a modified human IgG Fc domain comprising or consisting of the amino acid substitutions H433K and N434F, wherein the Fc domain numbering is in accordance with EU numbering. In certain embodiments, the galectin-10 antibodies having the CDR and/or VH/VL domain sequences recited above comprise a modified human IgG Fc domain comprising or consisting of the amino acid substitutions M252Y, S254T, T256E, H433K and N434F.

Unless otherwise stated in the present application, % sequence identity between two amino acid sequences may be determined by comparing these two sequences aligned in an optimum manner and in which the amino acid sequence to be compared can comprise additions or deletions with respect to the reference sequence for an optimum alignment between these two sequences. The percentage of identity is calculated by determining the number of identical positions for which the amino acid residue is identical between the two sequences, dividing this number of identical positions by the total number of positions in the comparison window and multiplying the result obtained by 100 in order to obtain the percentage of identity between these two sequences. For example, it is possible to use the BLAST program, "BLAST 2 sequences" (Tatusova et al, "Blast 2 sequences—a new tool for comparing protein and nucleotide sequences", FEMS Microbiol Lett. 174:247-250) available on the site <<blast.ncbi.nlm.nih.gov>>, the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program.

E. Polynucleotides Encoding Galectin-10 Antibodies

The invention also provides polynucleotide molecules encoding the galectin-10 antibodies of the invention or fragments thereof. Polynucleotide molecules encoding the full-length galectin-10 antibodies are provided, together with polynucleotide molecules encoding fragments, for example the VH, VL and/or VHH domains of the galectin-10 antibodies described herein. Also provided are expression vectors containing said nucleotide sequences of the invention operably linked to regulatory sequences which permit expression of the antibodies or fragments thereof in a host cell or cell-free expression system, and a host cell or cell-free expression system containing this expression vector.

Polynucleotide molecules encoding galectin-10 antibodies of the invention include, for example, recombinant DNA molecules. The terms "nucleic acid", "polynucleotide" or a "polynucleotide molecule" as used herein interchangeably and refer to any DNA or RNA molecule, either single- or double-stranded and, if single-stranded, the molecule of its complementary sequence. In discussing nucleic acid molecules, a sequence or structure of a particular nucleic acid molecule may be described herein according to the normal convention of providing the sequence in the 5' to 3' direction. In some embodiments of the invention, nucleic acids or polynucleotides are "isolated." This term, when applied to a nucleic acid molecule, refers to a nucleic acid molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or non-human host organism. When applied to RNA, the term "isolated polynucleotide" refers primarily to an RNA molecule encoded by an isolated DNA molecule as defined above. Alternatively, the term may refer to an RNA molecule that has been purified/separated from other nucleic acids with which it would be associated in its natural state (i.e., in cells or tissues). An isolated polynucleotide (either DNA or RNA) may further represent a molecule produced directly by biological or synthetic means and separated from other components present during its production.

For recombinant production of a galectin-10 antibody according to the invention, a recombinant polynucleotide encoding it or recombinant polynucleotides encoding the different chains or domains may be prepared (using standard molecular biology techniques) and inserted into a replicable vector for expression in a chosen host cell, or a cell-free expression system. Suitable host cells may be prokaryote, yeast, or higher eukaryote cells, specifically mammalian cells. Examples of useful mammalian host cell lines are monkey kidney CV1 line transformed by SV40 (COS-7, ATCC CRL 1651); human embryonic kidney line (HEK293 or 293 cells subcloned for growth in suspension culture, Graham et al., J. Gen. Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); mouse myeloma cells SP2/0-AG14 (ATCC CRL 1581; ATCC CRL 8287) or NS0 (HPA culture collections no. 85110503); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), as well as DSM's PERC-6 cell line. Expression vectors suitable for use in each of these host cells are also generally known in the art.

It should be noted that the term "host cell" generally refers to a cultured cell line. Whole human beings into which an expression vector encoding an antigen binding polypeptide according to the invention has been introduced are explicitly excluded from the definition of a "host cell".

F. Antibody Production

In a further aspect, the invention also provides a method of producing antibodies of the invention which comprises culturing a host cell (or cell free expression system) containing polynucleotide (e.g. an expression vector) encoding the antibody under conditions which permit expression of the antibody, and recovering the expressed antibody. This recombinant expression process can be used for large scale production of antibodies, including galectin-10 antibodies according to the invention, including monoclonal antibodies intended for human therapeutic use. Suitable vectors, cell lines and production processes for large scale manufacture of recombinant antibodies suitable for in vivo therapeutic use are generally available in the art and will be well known to the skilled person.

G. Pharmaceutical Compositions

The scope of the invention includes pharmaceutical compositions, containing one or a combination of galectin-10 antibodies or antigen binding fragments thereof, formulated with one or more pharmaceutically acceptable carriers or excipients. Such compositions may include one or a combination of (e.g., two or more different) galectin-10 antibodies. Techniques for formulating monoclonal antibodies for human therapeutic use are well known in the art and are reviewed, for example, in Wang et al., J. Pharm. Sci., 96:1-26, 2007, the contents of which are incorporated herein in their entirety.

Pharmaceutically acceptable excipients that may be used to formulate the compositions include, but are not limited to: ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (for example sodium carboxymethylcellulose), polyethylene glycol, polyacrylates, waxes, polyethylene-polyoxypropylene block copolymers, polyethylene glycol and wool fat.

In certain embodiments, the compositions are formulated for administration to a subject via any suitable route of administration including but not limited to intramuscular, intravenous, intradermal, intraperitoneal injection, subcutaneous, epidural, nasal, oral, rectal, topical, inhalational, buccal (e.g., sublingual), and transdermal administration.

H. Methods of Treatment

The galectin-10 antagonists, particularly the galectin-10 antibodies and antigen binding fragments described herein, may be used in methods of treatment. Thus, provided herein is a galectin-10 antagonist in accordance with the first aspect of the invention for use as a medicament. Alternatively, provided herein is a galectin-10 antagonist in accordance with the first aspect of the invention for use in a method of treatment. In preferred embodiments, the invention provides galectin-10 antibodies and antigen binding fragments as described elsewhere herein for use as medicaments. Alternatively, the invention provides galectin-10 antibodies and antigen binding fragments as described elsewhere herein for use in a method of treatment. The galectin-10 antagonists, including the galectin-10 antibodies and antigen binding fragments thereof, for use as medicaments are typically formulated as pharmaceutical compositions. Importantly, all embodiments described above in relation to the galectin-10 antagonists, particularly the galectin-10 antibodies and antigen binding fragments thereof, are equally applicable to the methods described herein.

The present invention also provides methods of treating a subject in need thereof, wherein the method comprises administering to the subject a therapeutically effective amount of a galectin-10 antagonist in accordance with the first aspect of the invention. In preferred embodiments, the galectin-10 antagonist is a galectin-10 antibody or antigen binding fragment thereof as described elsewhere herein. In such methods of treatment, the galectin-10 antagonists, including the galectin-10 antibodies and antigen binding fragments thereof, are typically formulated as pharmaceutical compositions. As used herein, the term "therapeutically effective amount" is intended to mean the quantity or dose of galectin-10 antagonist, e.g. antibody, that is sufficient to produce a therapeutic effect, for example, the quantity or dose of antagonist required to eradicate or at least alleviate the symptoms associated with a disease or condition. An appropriate amount or dose can be determined by animal studies and/or a physician, as appropriate. For example, the dose can be adjusted based on factors such as the size or weight of a subject to be treated, the age of the subject to be treated, the general physical condition of the subject to be treated, the condition to be treated, and the route of administration.

For clinical use, in certain embodiments, the galectin-10 antagonist is a galectin-10 antibody or antigen binding fragment thereof as described elsewhere herein and it is administered to a subject as one or more doses of about 0.1 mg/kg body weight to about 20 mg/kg body weight. In certain embodiments, the galectin-10 antagonist is a galectin-10 antibody or antigen binding fragment thereof as described elsewhere herein and it is administered to a subject in a dose of about 0.1 mg/kg body weight to about 10 mg/kg body weight. In certain embodiments, the galectin-10 antagonist is a galectin-10 antibody or antigen binding fragment thereof as described elsewhere herein and it is administered to a subject in a dose of about 0.5 mg/kg body weight to about 10 mg/kg body weight. In certain embodiments, the galectin-10 antagonist is a galectin-10 antibody or antigen binding fragment thereof as described elsewhere herein and it is administered to a subject in a dose of about 1 mg/kg body weight to about 10 mg/kg body weight.

The galectin-10 antagonists, particularly the galectin-10 antibodies and antigen binding fragments thereof, are useful in therapeutic methods, for the reason that they can disrupt galectin-10 crystallization. As explained elsewhere herein, the galectin-10 antagonists of the present invention bind to an epitope of galectin-10 thereby shielding a crystal packing interface and consequently disrupting the crystallization of galectin-10. In certain embodiments, the galectin-10 antagonists inhibit the crystallization of galectin-10. In certain embodiments, the galectin-10 antagonists promote dissolution of crystalline galectin-10.

The galectin-10 antagonists, including the galectin-10 antibodies and antigen binding fragments thereof, may be for use in preventing or treating diseases or conditions associated with the presence or formation of galectin-10 crystals or CLCs. Provided herein are methods of preventing or treating a disease or condition associated with the presence or formation of galectin-10 crystals or CLCs in a patient or subject in need thereof by administering an effective amount of a galectin-10 antagonist as described herein, particularly a galectin-10 antibody or antigen binding fragment thereof.

As used herein, a method of "preventing" a disease or condition means preventing the onset of the disease, preventing the worsening of symptoms, preventing the progression of the disease or condition or reducing the risk of a subject developing the disease or condition. As used herein, a method of "treating" a disease or condition means curing a disease or condition and/or alleviating or eradicating the symptoms associated with the disease or condition such that the patient's suffering is reduced.

For patients having diseases or conditions characterised by the presence of galectin-10 crystals, the methods of treatment will typically involve the administration of a galectin-10 antagonist, preferably a galectin-10 antibody or antigen binding fragment thereof, capable of dissolving the galectin-10 crystals located in the patient's tissues and/or body fluids. For patients identified as "at risk" of developing a disease or condition characterised by the formation of galectin-10 crystals, the methods of prevention may involve the administration of a galectin-10 antagonist, preferably a galectin-10 antibody or antigen binding fragment thereof, capable of inhibiting the crystallization of galectin-10.

Galectin-10 crystals or CLCs have been observed in patients having a range of diseases and conditions. It follows that the galectin-10 antagonists described herein may be used to prevent or treat a disease or condition selected from the group consisting of: asthma; chronic rhinosinusitis; celiac disease; helminth infection; gastrointestinal eosinophilic inflammation; cystic fibrosis (CF); allergic bronchopulmonary aspergillosis (ABPA); Churg-Strauss vasculitis; chronic eosinophilic pneumonia; and acute myeloid leukemia. In preferred embodiments, galectin-10 antibodies or antigen binding fragments thereof are used to prevent or treat a disease or condition selected from the group consisting of: asthma; chronic rhinosinusitis; celiac disease; helminth infection; gastrointestinal eosinophilic inflammation; cystic fibrosis (CF); allergic bronchopulmonary aspergillosis (ABPA); Churg-Strauss vasculitis; chronic eosinophilic pneumonia; and acute myeloid leukemia.

As noted above, galectin-10 crystals or CLCs are particularly associated with diseases or conditions characterised by eosinophilic inflammation. In preferred embodiments, the galectin-10 antagonists described herein, preferably galectin-10 antibodies or antigen binding fragments thereof described herein, are used to treat disorders or conditions associated with eosinophilic inflammation.

In particularly preferred embodiments, the galectin-10 antagonists described herein, preferably galectin-10 antibodies or antigen binding fragments thereof described herein, are used to prevent or treat asthma.

The results presented herein highlight the important role of CLCs in inducing an innate immune response and inducing airway inflammation in vivo. These effects were successfully reversed by exemplary galectin-10 antibodies described herein. The inflammation observed in the mouse model described herein was found to be independent of the NLRP3 inflammasome complex. These results indicate for the first time a causative role for CLCs in inflammatory responses mediated via a pathway independent of the NLRP3 inflammasome i.e. the inflammatory complex previously implicated in CLC pathology. It follows, that the methods of the present invention may be used to treat inflammatory conditions or disorders, particularly inflammatory conditions or disorders of the airways. The therapeutic effect may be mediated independently of the NLRP3 inflammasome complex.

The present invention also provides use of a galectin-10 antagonist for the detection of galectin-10 in a sample obtained from a patient. In certain embodiments, a galectin-10 antibody or antigen binding fragment in accordance with the invention is used to detect galectin-10 in a sample obtained from a patient. The antagonists, antibodies or antigen binding fragments thereof are typically used to detect crystalline galectin-10. As noted above, galectin-10 crystals or CLC crystals have been observed in patients having a number of different diseases and conditions. It follows, that the patient sample may be isolated from a subject having or suspected of having any one of the following diseases or conditions: asthma, chronic rhinosinusitis, celiac disease, helminth infection, gastrointestinal eosinophilic inflammation, cystic fibrosis (CF), allergic bronchopulmonary aspergillosis (ABPA), Churg-Strauss vasculitis, chronic eosinophilic pneumonia, or acute myeloid leukemia. The detection of crystalline galectin-10 in the patient sample may be used to diagnose the disease or condition in the subject from which the sample was obtained. The sample may be any suitable patient sample, for example any fluid or tissue in which CLCs are observed in a disease state. In certain embodiments, the sample is a tissue sample obtained from a polyp, for example a nasal polyp. In certain embodiments, the sample is a mucus sample. In such embodiments, the detection of crystalline galectin-10 in the mucus sample using the antagonists of the invention may be used to detect or diagnose chronic rhinosinusitis. In preferred embodiments, the patient sample is a sputum sample. In such embodiments, the detection of crystalline galectin-10 in the sputum sample using the antagonists of the invention may be used to detect or diagnose asthma.

I. Kits

Any of the galectin-10 antagonists, antibodies or antigen binding fragments described herein can be packaged as a kit and optionally include instructions for use.

EXAMPLES

The invention will be further understood with reference to the following non-limiting examples.

Example 1. Production of Recombinant Charcot-Leyden Crystals (CLCs)

Previous studies on CLCs have been performed on crystals obtained by auto-crystallization of protein-rich lysates of primary human blood eosinophils or leukemic cell lines, which has led to co-purification of contaminating proteins like lysophospholipase (Ackerman et al., J. Immunol. 125 (5): 2118-26 (1980); Weller et al., J. Biol. Chem. 259(24): 15100-5 (1984); and Archer et al., J. Exp. Med. 122: 173-80 (1965)).

Figure 1A:
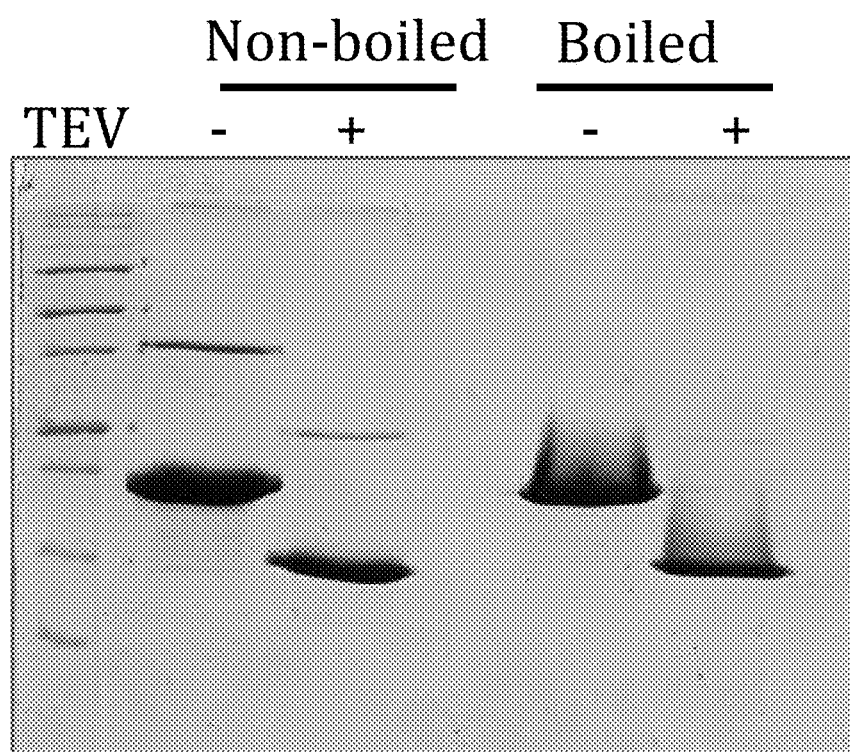
FIGS. 1A-1E: Production of recombinant Gal10 crystals resembling in vivo CLC crystals His-tagged galectin-10 (Gal10) was expressed in E coli.

To generate large amounts of pure CLC crystals for use in functional studies in vivo, human galectin-10, carrying a TEV-cleavable N-terminal His-tag, was produced in E. coli and purified by a combination of immobilized affinity chromatography and size-exclusion chromatography (FIG. 1A). A synthetic codon-optimized DNA sequence encoding human galectin-10 (residues 1-142, Uniprot Q05315) was cloned into the NcoI/XhoI sites of the pET28a bacterial expression vector (Novagen, cat #69864-3) with an His-tag and two protease cleavage sites, enterokinase (DDDDK) (SEQ ID NO: 270) and TEV protease (ENLYFQG) (SEQ ID NO: 271), at the N-terminus (MASTTHHHHHHDTDIP-TTGGGSRPDDDDKENLYFQGHM) (SEQ ID NO: 272). pET28a-galectin-10 was transformed in BL21(DE3) cells using kanamycin (25 µg/mL) as a selection marker. Expression cultures were grown at 28° C. in Luria-Bertani medium, containing kanamycin (25 µg/mL). Expression of galectin-10 was induced at a culture $OD_{600}$ of 0.6, by the addition of isopropyl-β-D-thiogalactopyranoside (ITPG) to a final concentration of 1 mM, after which the culture was allowed to grow overnight. The bacteria were harvested by centrifugation (6,000 g for 20 min at 4° C.) and the cellular paste was stored at −80° C. The bacterial pellet was thawed and resuspended in lysis buffer (50 mM $NaH_2PO_4$, 300 mM NaCl pH 7.4). The cells were lysed by sonication on a Branson sonifier (total run time of 4 min with 30 s pulses at 30% output interspersed with 30 s of down time). Cell debris was removed by centrifugation at 4° C. (20,000 g for 30 min). The supernatant was clarified by filtration using a 0.22 µm bottle top filter and loaded onto a Ni Sepharose column equilibrated with 50 mM $NaH_2PO_4$, 300 mM NaCl pH 7.4. Next the column was washed with loading buffer supplemented with 20 mM imidazole and 0.1% empigen detergent, followed by washing with loading buffer supplemented with 20 mM imidazole. Next, the protein was eluted using loading buffer supplemented with 50 mM and 500 mM imidazole. The 50 mM and 500 mM elution peaks were pooled and concentrated and injected onto a HiLoad 16/600 Superdex 200 µg column using PBS pH 7.4 as running buffer. The elution fractions corresponding to galectin-10 were pooled and stored at −80° C. Endotoxin-levels were determined with an Endosafe-PTS system (Charles River) as lower than 5 EU $mg^{-1}$ recombinant protein. The His-tagged galectin-10 protein was soluble up to 30 mg/ml.

Figure 1B:
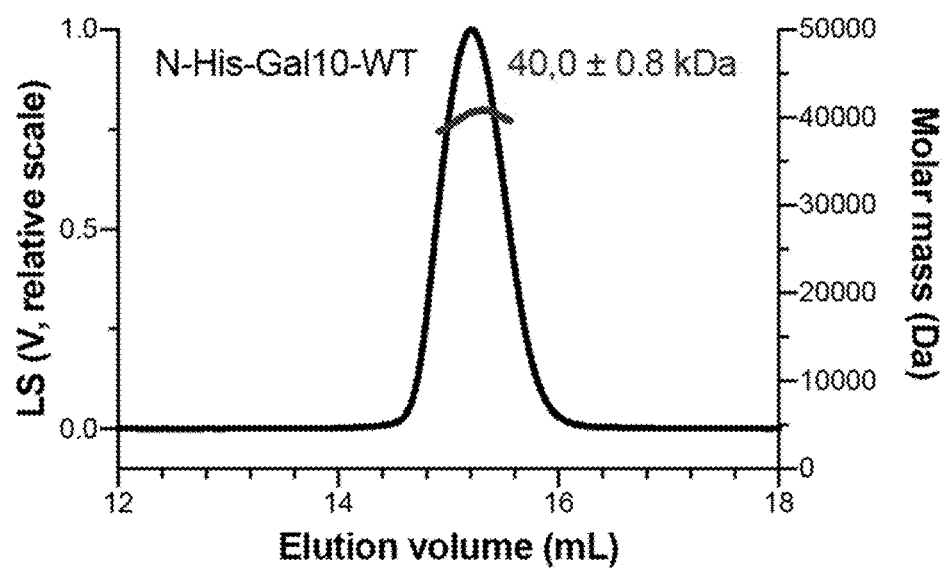

To analyse molecular mass and oligomeric state of His-tagged galectin-10, SEC-MALLS was performed (FIG. 1B). Protein samples (100 µL) were injected onto a Superdex 200 Increase 10/300 GL column (GE Healthcare), with PBS pH 7.4 as running buffer at 0.5 ml $min^{-1}$, coupled to an online UV-detector (Shimadzu), a multi-angle light scattering miniDAWN TREOS instrument (Wyatt) and a Optilab T-rEX refractometer (Wyatt) at 25° C. A refractive index increment (dn/dc) value of 0.185 ml $g^{-1}$ was used for protein concentration and molecular mass determination. Data were analyzed using the ASTRA6 software (Wyatt). Correction for band broadening was applied using parameters derived from BSA injected under identical running conditions. SEC-MALLS analysis showed that His-tagged galectin-10 is a dimer in solution (FIG. 1B). The determined molecular weight was 40±0.8 kDa, which closely matches the theoretical weight for tagged dimeric galectin-10 of 41.2 kDa.

Figure 1C:
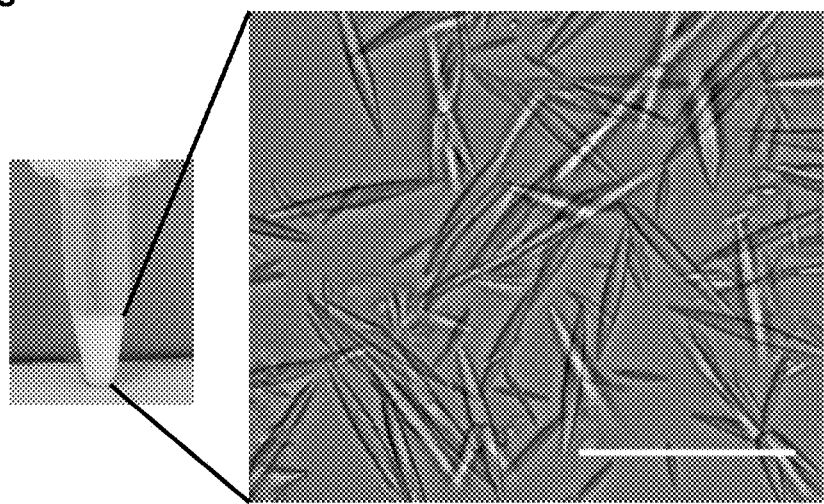
Figure 1D:
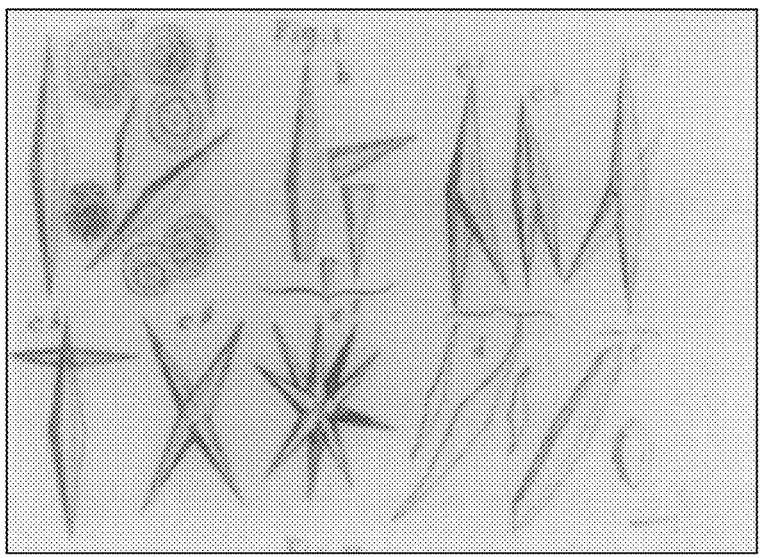

To form recombinant galectin-10 crystals, N-terminally tagged galectin-10 (at a concentration between 2 to 4.5 mg/ml) was incubated with in-house produced TEV protease (Kapust et al., 2001). The pRK793 plasmid encoding His-tagged TEV was a kind gift from David Waugh (Addgene plasmid #8827). Following overnight digestion, the protein solution was agitated by inverting it 5 times after which the solution turned cloudy in about 30 minutes due to the spontaneously formation of needle-shaped CLC crystals (FIG. 1C). Following TEV cleavage, recombinant galectin-10 autocrystallized in PBS buffer and was only soluble up to a concentration of 0.2 mg/ml. Following TEV-digestion three residues are left at the N-terminus (GHM) of recombinant galectin-10. The crystals closely resembled the various macroscopic shapes originally described by Charcot and von Leyden (FIG. 1D).

Figure 1E:
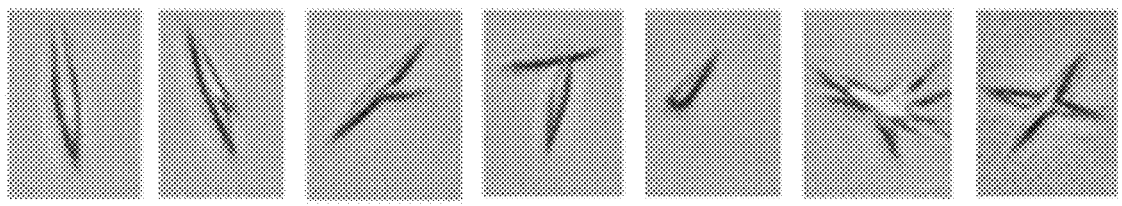

Fluorescently-labelled forms of galectin-10 crystals were also produced. Since galectin-10 contains two solvent exposed cysteine-residues (Cys29 and Cys57), the thiol-reactive fluorescent dye 5-iodoacetamidofluorescein (5-IAF) was used to fluorescently label tagged galectin-10. 5-IAF was solubilized in 100% dimethylformamide to a concentration of 100 mM. The pH of the galectin-10 protein solution (~5 mg/mL) was adjusted to pH 8.5 by adding 100 mM Tris pH 8.5 (using a 1 M Tris pH 8.5 stock solution). Next, a 10-fold molar excess of 5-IAF to galectin-10 (monomer) was added to the protein solution and the labeling reaction was kept in the dark at room temperature for 2 hours. For galectin-10 carrying an N-terminal His-tag a molar extinction coefficient of 21430 $cm^{-1}$ $M^{-1}$ was used. Next, the excess of non-reacted 5-IAF was quenched by adding 5 mM DTT (using 1 M DTT). The excess of 5-IAF was then removed by running the sample on a 50 mL HiTrap desalting column (GE Healthcare) using PBS as running buffer. Next, 5-IAF labeled galectin-10 was concentrated and injected on HiLoad 16/600 Superdex 200 μg column. The fractions of the elution peak were then pooled and stored at −80° C. The endotoxin-levels were determined with an Endosafe-PTS system (Charles River) as lower than 5 EU mg$^{-1}$ recombinant protein. To form fluorescent galectin-10 crystals the N-terminal His-tag of 5-IAF labeled galectin-10 was removed by overnight incubation as described above. These fluorescent crystals had the myriad shapes originally described by Charcot and von Leyden (FIG. 1E).

Example 2. Characterisation of In Vivo Grown CLCs

Figure 2A:
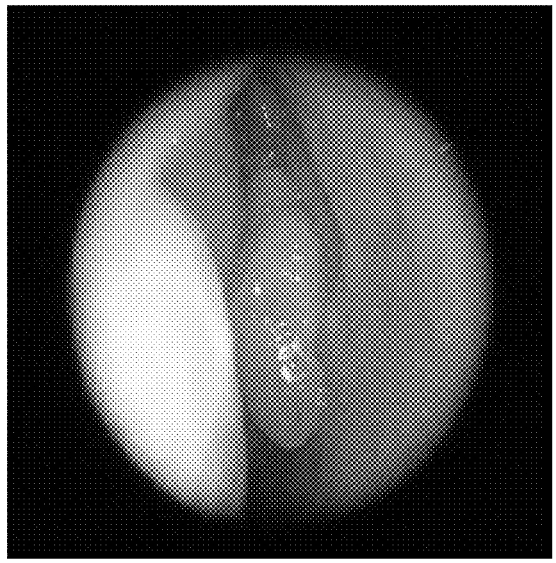
FIGS. 2A-2F: Isolation and crystal structure of in vivo grown CLC crystals of sinusitis patients (FIG. 2A) Mucus samples were collected during surgery of patients with chronic rhinosinusitis and nasal polyps (CRSwNP). Polyp tissue is shown here.

To date, there has been no description of the crystal lattice structure of in vivo grown CLC. Therefore, crystals were isolated from the sticky mucus of CRSwNP patients. Airway mucosal tissue and/or secretions were collected from patients undergoing endoscopic sinus surgery for chronic rhinosinusitis with nasal polyps (CRSwNP) (FIG. 2A). Nasal polyposis was diagnosed on the basis of symptoms, clinical examination, nasal endoscopy, and sinus computed tomography scan according to the European Position Paper on Rhinosinusitis and Nasal Polyps guidelines. All patients refrained from using oral and/or topical corticosteroids at least 4 weeks before surgery. The study and collection of samples were approved by the ethics committee of the Ghent University Hospital and an informed consent was obtained from all patients prior to enrollment in the study. Mucus "sticky allergic mucin type" obtained from patients was stored overnight at 4° C. in RPMI 1640 (Sigma-Aldrich, Bornem, Belgium) containing antibiotics (50 IU/mL penicillin and 50 mg/mL streptomycin; Invitrogen), and 0.1% BSA (Sigma).

Figure 2B:
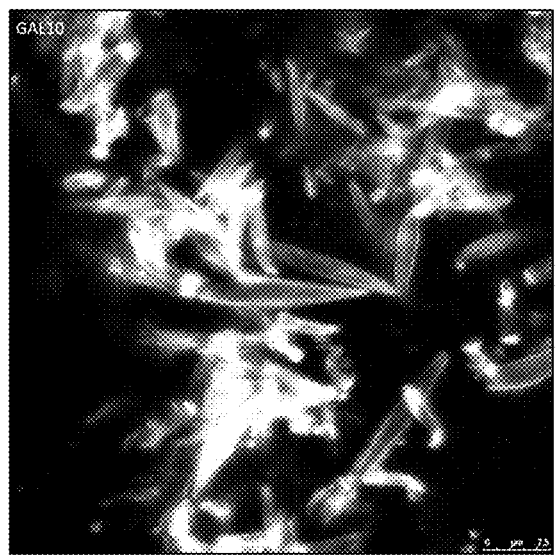

To reveal the presence and identity of CLC crystals, immunofluorescence staining was performed for galectin-10. The collected allergic mucin was fixed with 4% paraformaldehyde and embedded in paraffin. Tissue slides (5 μm) of the embedded mucin were cut, deparaffinized using xylene (3×10 minutes) and rehydrated by stepwise immersion in decreasing ethanol concentrations (100%, 90%, 60%, 30%, 0% ethanol, 2 minutes/step). After rehydration, the slides were immersed in PBS for 5 minutes and subsequently incubated for 1 h with 0.05% trypsin-EDTA (Life Technologies) at 37° C. in a moist chamber. After washing with PBS (Life Technologies) for 10 minutes, the slides were incubated for 1 h with blocking buffer (7.5% BSA (Sigma Aldrich) in PBS) in a moist chamber at RT. Subsequently, the slides were incubated overnight at 4° C. with an anti-human galectin-10 antibody (Clone EPR11197, Abcam, 1/200 dilution in blocking buffer). The next day, the slides were washed with PBS for 10 minutes and incubated with a FITC labeled secondary goat anti-rabbit antibody (A11034 Life Technologies, 1/400 dilution). After washing for 10 minutes with PBS, the slides were mounted with Vectashield containing DAPI. The slides were stored in the dark and analyzed with a confocal laser-scanning microscope (Leica) the next day. This revealed the presence of large amounts of needle shaped crystals immunoreactive for galectin-10 (FIG. 2B).

Figure 2C:
Figure 2D:
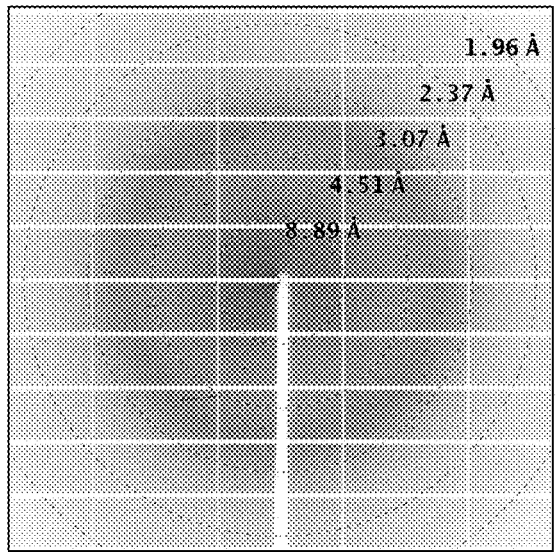
Figure 2E:
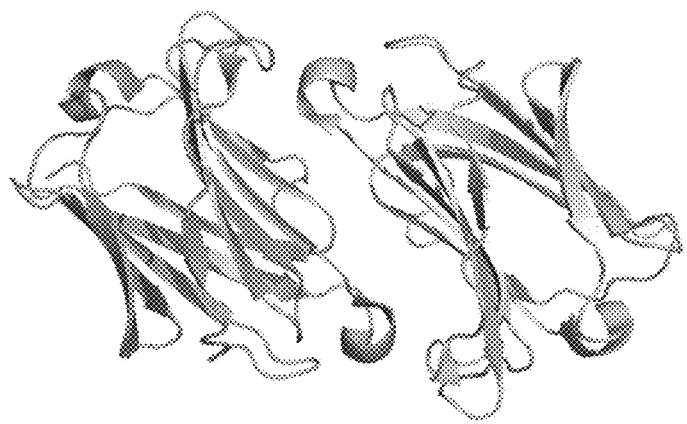
Figure 2F:
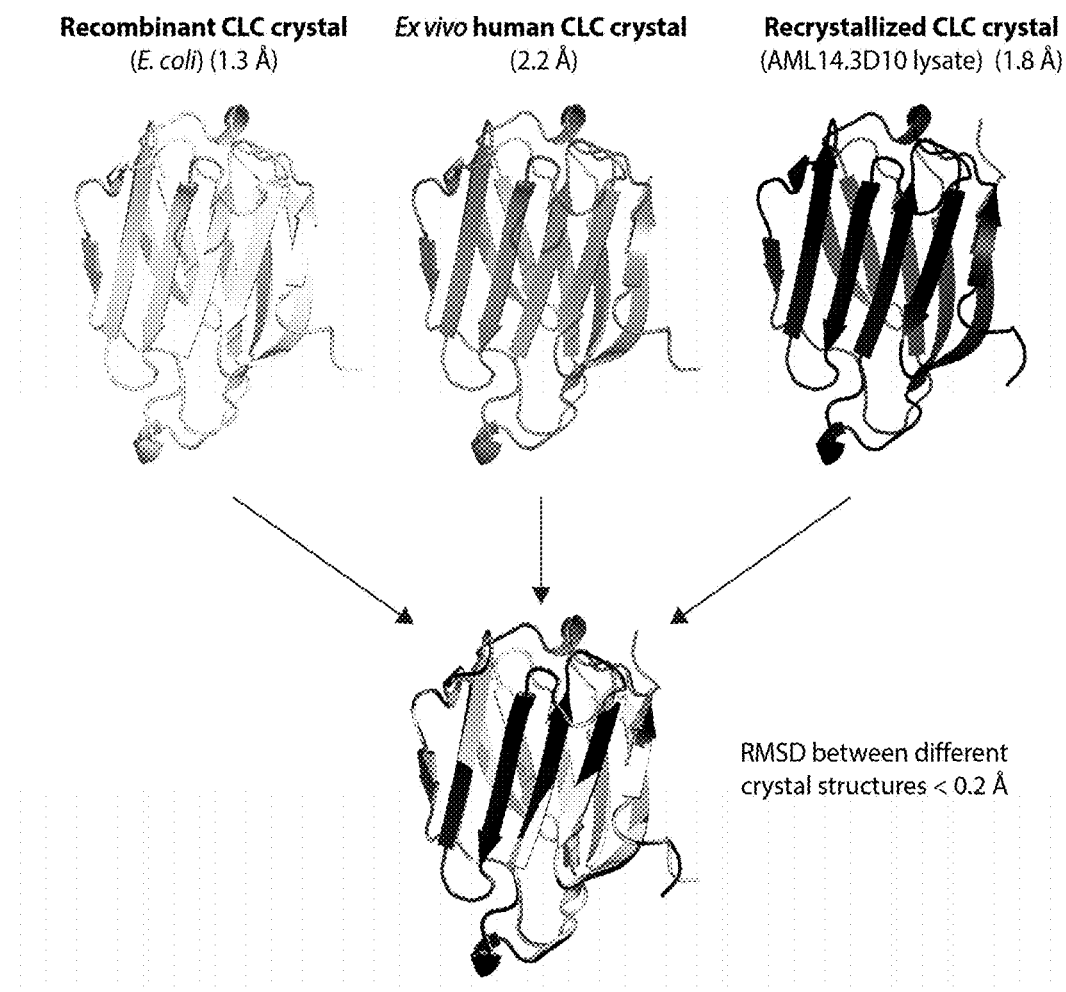

To purify crystals for ex vivo crystallography, the medium was discarded and 1 g of the mucus was cut thoroughly in 10 ml RPMI 1640 (Sigma-Aldrich, Bornem, Belgium) containing antibiotics (50 IU/mL penicillin and 50 mg/mL streptomycin; Invitrogen), 0.1% BSA (Sigma) and 1 mg/ml Collagen type 2 (Worthington). The mucus was further homogenized using a GentleMACS Dissociator (Myltenyi Biotec) and subsequently incubated at 37° C. for 45 minutes under continuous rotation. After incubation, the partly dissolved mucus was homogenized with the GentleMACS Dissociator (Myltenyi Biotec) and centrifuged at 400 g for 7 minutes at RT. After centrifugation the supernatant was discarded and the pellet was dissolved in 3 ml PBS (Life technologies) containing 50 IU/ml penicillin and 50 mg/ml streptomycin (Life technologies). 3 ml of the isolated fluid was mixed with 6 ml Ficoll-Paque (GE Healthcare) and centrifuged at 250 g for 10 minutes. After removal of the supernatant and most of the Ficoll layer, 2.8 ml PBS with antibiotics was added to the remaining fluid (200 μl) at the bottom of the tube. This precipitation process was repeated 5 more times. The final fluid containing the crystals at the bottom of the tube was resuspended in 2 ml PBS with antibiotics and centrifuged at 200 g for 5 minutes. Most of the supernatant was removed and 800 μl of PBS with antibiotics was added to the crystals in the remaining 200 μl of fluid at the bottom of the tube. Single crystals were harvested from the solution using mounted cryoloops (FIG. 2C). Before flash-freezing in liquid nitrogen the crystals were cryoprotected by a brief soak in PBS supplemented with 35% (v/v) glycerol. Diffraction experiments at 100 K were conducted on beamline P14 of PetraIII (DESY, Hamburg, Germany). All data were integrated and scaled using the XDS suite (Kabsch, 2010). Molecular replacement (MR) was performed with Phaser (McCoy et al., 2007) using search models based on the structure of galectin-10 (PDB 1LCL). Model (re)building was performed in COOT (Emsley et al., Acta Crystallogr. D Biol. Crystallogr. 66(4): 486-501 (2010)) and individual coordinate and ADP refinement was performed in PHENIX (Adams et al., Acta Crystallogr. D Biol. Crystallogr. 66(2): 213-21 (2010)) and autoBuster (Bricogne et al., 2017). Model and map validation tools in COOT and the PHENIX suite were used throughout the work flow to guide improvement and validate the quality of crystallographic models. Using this methodology, the structure of a human CLC crystal isolated from a patient suffering from nasal polyps was determined using single crystal X-ray diffraction using synchrotron radiation (to 2.2 Å resolution) (FIG. 2D, FIG. 2E, Table 17). The crystal structure obtained was compared with that of recombinant galectin-10 crystals (1.4 Å resolution), and a published structure of galectin-10 crystals obtained by eosinophil lysis and crystallization in vitro (pdb 1LCL, 1.8 A) (Leonidas et al., Structure 3: 1379-93 (1995)). The resulting analysis showed that all three galectin-10 crystal forms belong to space group P6$_5$22 with similar unit cell parameters (Table 17). Moreover, the atomic structures for recombinant galectin-10 produced in *E. coli* and for galectin-10 obtained from a human eosinophilic cell line (pdb 1LCL) can be considered virtually identical as the structure of galectin-10 in human CLC crystals (RMSD<0.2 Å) (FIG. 2F).

Figure 3A:
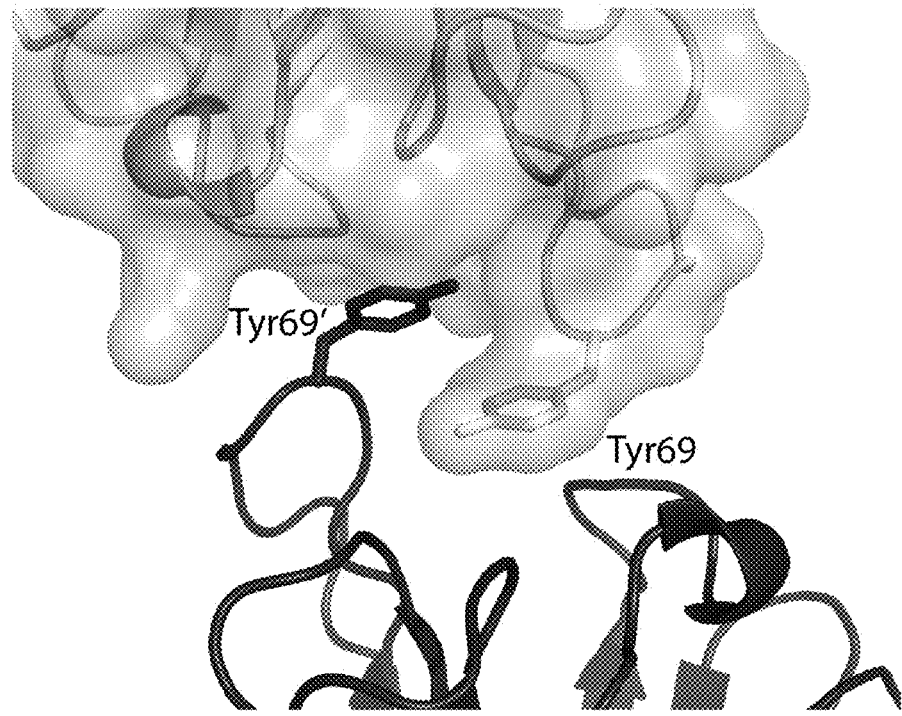
FIGS. 3A-3F: Creation of crystallization resistant Gal10 muteins by detailed analysis of the crystal packing interface of Gal10 crystals (FIG. 3A) and (FIG. 3B) are close-up views of various amino acids closely involved in the crystal packing interface between two adjacent Gal10 dimers. Highlighted amino acids were selected for a mutational analysis and creation of muteins.
Figure 3B:
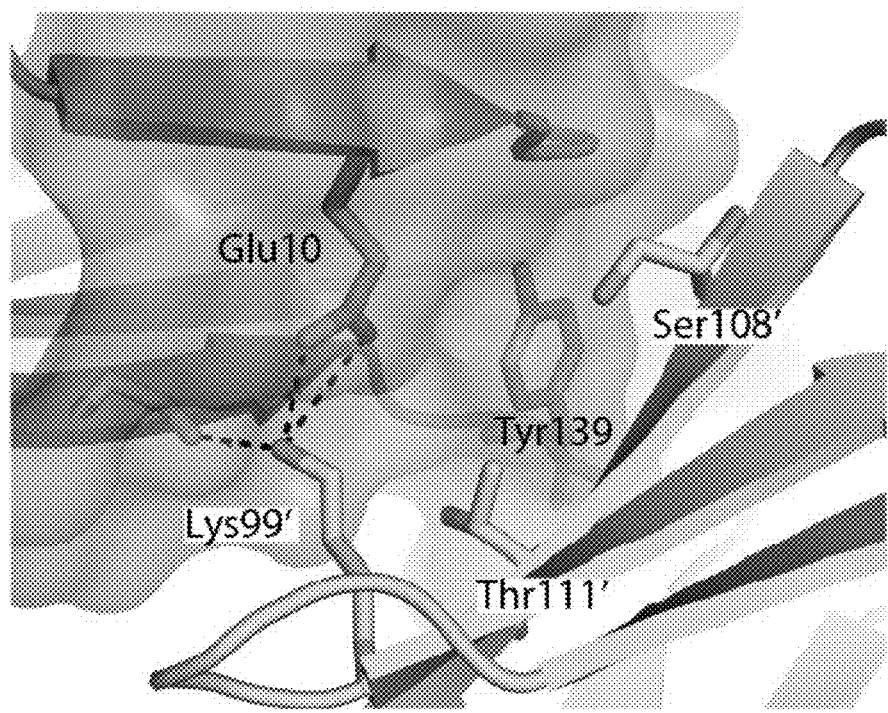
Figure 3C:
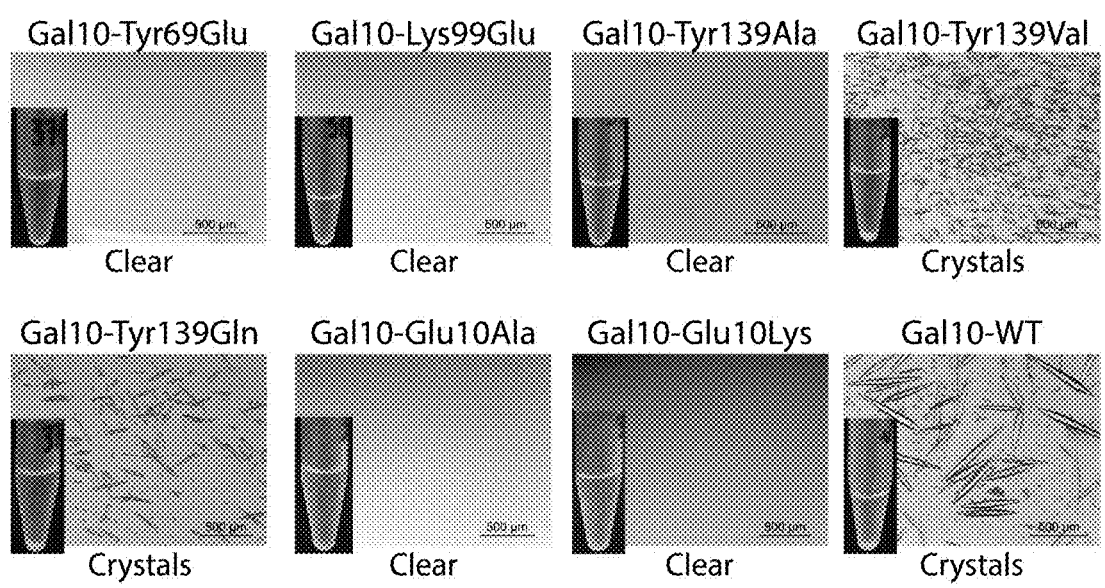

Example 3. Production of a Non-Autocrystallizinq Galectin-10 Variant, Galectin-10-Tyr69Glu In order to produce a non-autocrystallizing variant of galectin-10, the crystal packing interactions (FIG. 3A and FIG. 3B) in the reported structure for galectin-10 (PDB 1LCL) were analysed. Residue Tyr69 which engages in crystal packing interactions with a neighbouring galectin- 10-Tyr69 residue in the crystal lattice was selected as a potential key residue for autocrystallization (FIG. 3A). Accordingly, a variant of galectin-10 carrying the Tyr69Glu (Y69E) substitution was recombinantly produced following an identical protocol as for wild-type galectin-10. To produce a potentially non-autocrystallizing galectin-10 variant, residue Tyr69 was mutated to a glutamate residue using Quickchange site-directed mutagenesis (Agilent). For the mutagenesis PCR the following forward and reverse primers were used, FP: GATGAACTCTCGTGAAGAAGGTG-CATGGAAACAG (SEQ ID NO: 154) and RP: CTGTTTC-CATGCACCTTCTTCACGAGAGTTCATC (SEQ ID NO: 155). The pET28a-galectin-10 plasmid was used as a template. The resulting plasmid, pET28a-galectin-10-Y69E was used to transform BL21(DE3) cells. Protein production and purification were identical as compared to wild-type galectin-10. Following TEV-mediated removal of the N-terminal tag of galectin-10-Y69E, His-tagged TEV was removed by running the digestion mixture on a Ni-sepharose column using PBS as running buffer. Next, the column flow-through, containing galectin-10-Y69E, was concentrated and injected onto HiLoad 16/600 Superdex 200 µg column. The SEC elution fractions corresponding to galectin-10-Y69E were pooled and stored at −80° C. Endotoxin-levels were determined with an Endosafe-PTS system (Charles River) as lower than 5 EU mg$^{-1}$ recombinant protein. It was found that following TEV treatment, the Y69E galectin-10 mutein did not autocrystallize as compared to wild type galectin-10 (FIG. 3C). According to similar methodology, several other crystallization-resistant muteins were made based on predicted importance in the crystal packing interface (FIG. 3C). SEC-MALLS analysis also showed that the Y69E variant is a dimer in solution. The determined molecular weight was 32.6 kDa, which closely matches the theoretical molecular weight for TEV-cleaved dimeric galectin-10-Tyr69Glu (33.2 kDa).

A crystal structure of the non-autocrystallizing galectin-10-Y69E mutein was also obtained. For this, galectin-10-Y69E was concentrated to 6-7 mg/mL before crystallization experiments. Sitting-drop nanoliter-scale vapour diffusion crystallization experiments were set up at 293 K using a Mosquito crystallization robot (TTP Labtech) and commercially available sparse-matrix screens (Molecular Dimensions, Hampton research). Crystals of the mutant galectin-10-Y69E mutein appeared after 24 hrs in condition D12 of the PEG/Ion screen (Hampton Research—0.2 M ammonium citrate pH 5.1, 20% PEG$_{3350}$). Before flash-freezing into liquid nitrogen, crystals of galectin-10-Y69E were cryoprotected by briefly soaking the crystals in mother liquor supplement with 25% PEG 400.

Figure 3D:
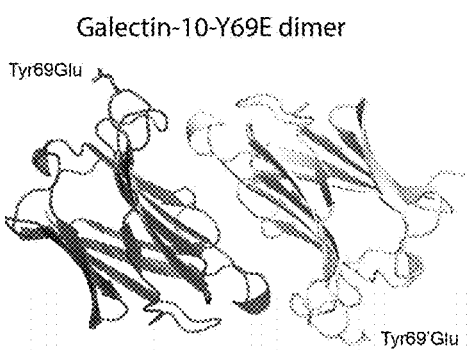
Figure 3F:
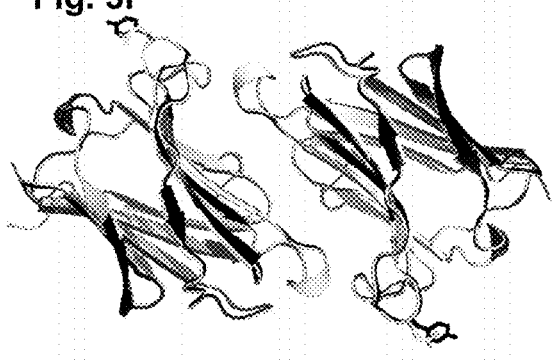

Analysis of galectin-10-Tyr69Glu by X-ray crystallography showed that the non-autocrystallizing variant adopts a virtually identical structure as the crystallographic galectin-10 dimer in pdb 1LCL (RMSD<0.3 Å) (FIG. 3D and FIG. 3F, Table 17).

Figure 3E:
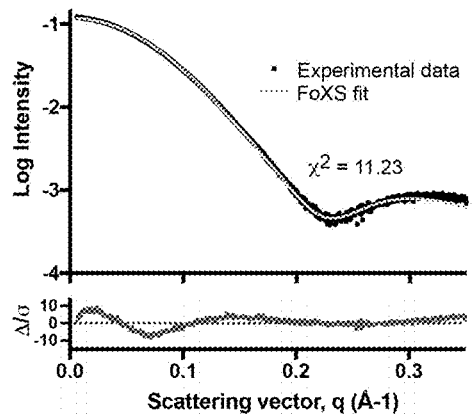

The structure of the soluble mutein in solution was also studied using small-angle X-ray scattering in solution (SAXS). For this, SAXS data were measured on the SWING beam line at the SOLEIL Synchrotron (Gif-sur-Yvette, France). 50 µl of galectin-10-Tyr69Glu was injected onto an Agilent 4.6×300 mm Bio SEC-3 column with 300 Å pore size and HBS pH 7.4 as running buffer at a flow speed of 0.3 ml min$^{-1}$ at 15° C. X-ray scattering data were collected in continuous flow mode with 1 s exposure time per frame. Data were recorded within a momentum transfer range of 0.0066 Å$^{-1}$<q<0.609 Å$^{-1}$, with q=4π sin θ/λ. Raw data were radially averaged and buffer subtracted using Foxtrot v3.3.4 (developed at Synchrotron SOLEIL and provided by Xenocs, Sassenage, France). The quality of the data was analyzed with Foxtrot by checking the stability of the radius of gyration over the length of the elution peak and by scaling all curves to the most intense scattering profile. The final scattering curve was obtained by averaging the unscaled, buffer-subtracted scattering profiles from frames 255-268, which correspond to the top of the elution peak. Structural parameters were determined with the ATSAS suite version 2.8.3 (Franke et al., J. Appl. Crystallogr. 50(4): 1212-25 (2017)). Molecular weight estimates were calculated using DATMW by methods based on the Porod volume (Petoukhov et al., J. Appl. Crystallogr. 45(2): 342-50 (2012)), the volume of correlation (Rambo et al., Nature 496(7446): 477 (2013)) and the apparent volume (Fischer et al., J. Appl. Crystallogr. 43(1): 101-9 (2010)). The theoretical SAXS profile for dimeric galectin-10-Tyr69Glu was calculated from the determined X-ray structure and fitted to the experimental data using the FoXS server (Schneidman-Duhovny et al., Nucleic Acids Res. 44(W1): W424-9 (2016)). The error-weighted residual difference plot was calculated as $\Delta/\sigma = [I_{exp}(q) - cI_{mod}(q)]/\sigma(q)$ versus q (Trewhella et al., Acta Crystallogr. D Struct. Biol. 73(9): 710-28 (2017)). SAXS analysis revealed that the dimeric assembly obtained by X-ray crystallography corresponds to the in-solution structure (FIG. 3E).

Example 4. CLCs Induce an Innate Immune Response In Vivo

To probe whether galectin-10 crystals promoted lung inflammation in vivo, naïve C57Bl/6 mice (Janvier) received an intra-tracheal injection of crystalline galectin-10 or control soluble galectin-10-Tyr69Glu mutein. For this, mice were anesthetized with isoflurane (2 l/min, 2-3%; 05260-05, Abbott Laboratories) and then injected intratracheally (i.t.) with 100 µg galectin-10 crystals or control soluble galectin-10-Tyr69Glu mutein (in 80 µl PBS). After 6 and 24 h, mice were euthanized by $CO_2$ inhalation and lungs were collected. In order to obtain single-cell suspensions, lungs were first cut with a scissor and then digested at 37° C. for 30 min in RPMI-1640 (Thermo Fisher Scientific) containing Liberase™ (1:50; 05 401 127 001, Sigma-Aldrich) and DNase I (1:1000; 04 536 282 001, Sigma-Aldrich). The obtained suspension was filtered through a 70 µm filter and depleted of red blood cells by RBC lysis buffer (0.15 M $NH_4Cl$, 1 mM $KHCO_3$, 0.1 mM $Na_2EDTA$ in MilliQ $H_2O$). Single-cell suspensions were stained for flow cytometry. The following antibodies were used: anti-CD3s FITC (145-2C11) (35-0031-U500, Tonbo Biosciences), anti-CD19 FITC (1D3) (35-0193-U500, Tonbo Biosciences), anti-CD11c FITC (HL3) (553801, BD Biosciences), anti-Siglec-F PE (552126, E50-2440) (BD Biosciences), anti-CD127 PE-CF594 (SB/199) (562419, BD Biosciences), anti-CD25 PE-Cy7 (PC61.5) (25-0251-82, ThermoFisher Scientific), anti-CD11b BD Horizon V450 (M1/70) (560455, BD Biosciences), anti-CD45 BV605 (30-F11) (563053, BD Biosciences), anti-CD90.2 APC (52-2.1) (17-0902-82, ThermoFisher Scientific), anti-Ly6G AF700 (1A8) (561236, BD Biosciences), and anti-CD117 APC-eFluor780 (2B8) (47-1171-82, ThermoFisher Scientific). Viable cells were discriminated by the use of eBioscience™ Fixable Viability Dye eFluor™506 (ThermoFisher Scientific). To block unspecific antibody binding Fc Block 2.4.G2 (1:600, Bioceros) was used. Cell surface markers were stained for 30 min at 4° C. in the dark. 123count eBeads™ Counting Beads (ThermoFisher Scientific) were added to each sample. Settings were done using UltraComp eBeads™ Compensation Beads (ThermoFisher Scientific). Data were collected on a BD LSRFortessa and were analyzed with FlowJo software (Tree Star Incorporation).

Figure 4A:
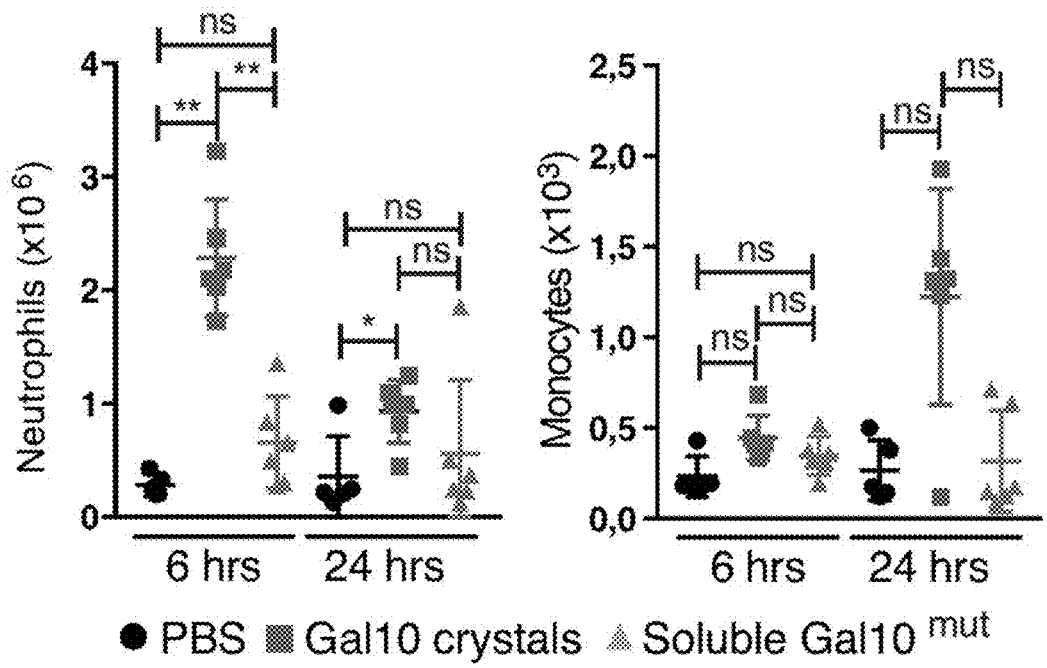
FIGS. 4A-4C: Innate airway inflammation induced by Gal10 crystals

After 6 h there was a strong influx of neutrophils in the airways of mice receiving galectin-10 crystals but not those receiving soluble galectin-10-Y69E mutein or control PBS solution (FIG. 4A). After 24 h there was a strong influx of monocytes in the airways of mice receiving galectin-10 crystals but not those receiving soluble galectin-10-Y69E mutein or control PBS solution (FIG. 4A).

Figure 4B:
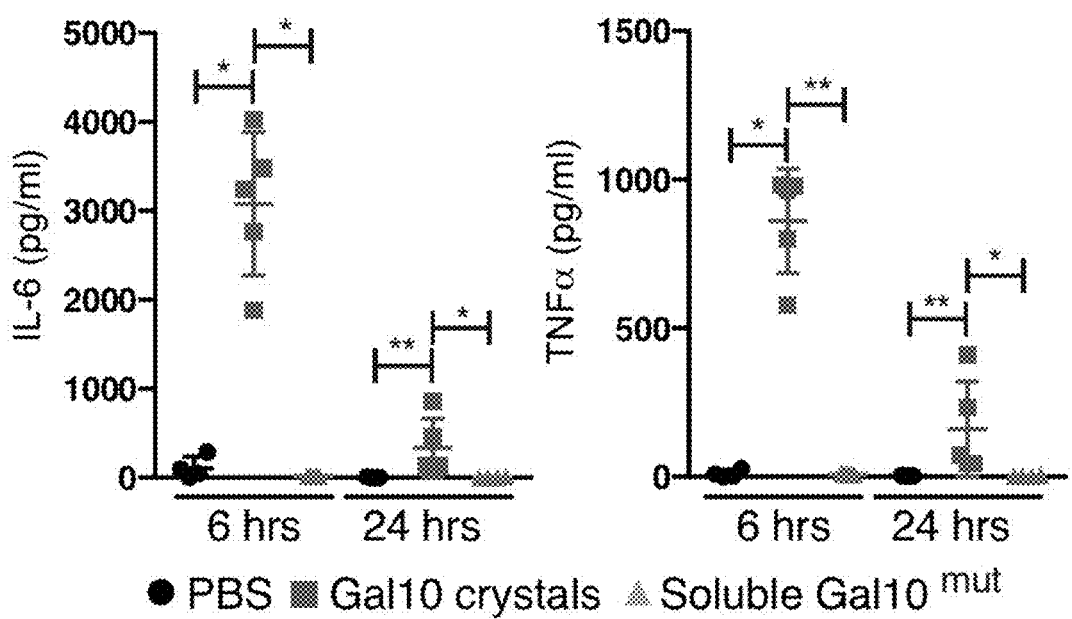
Figure 4C:
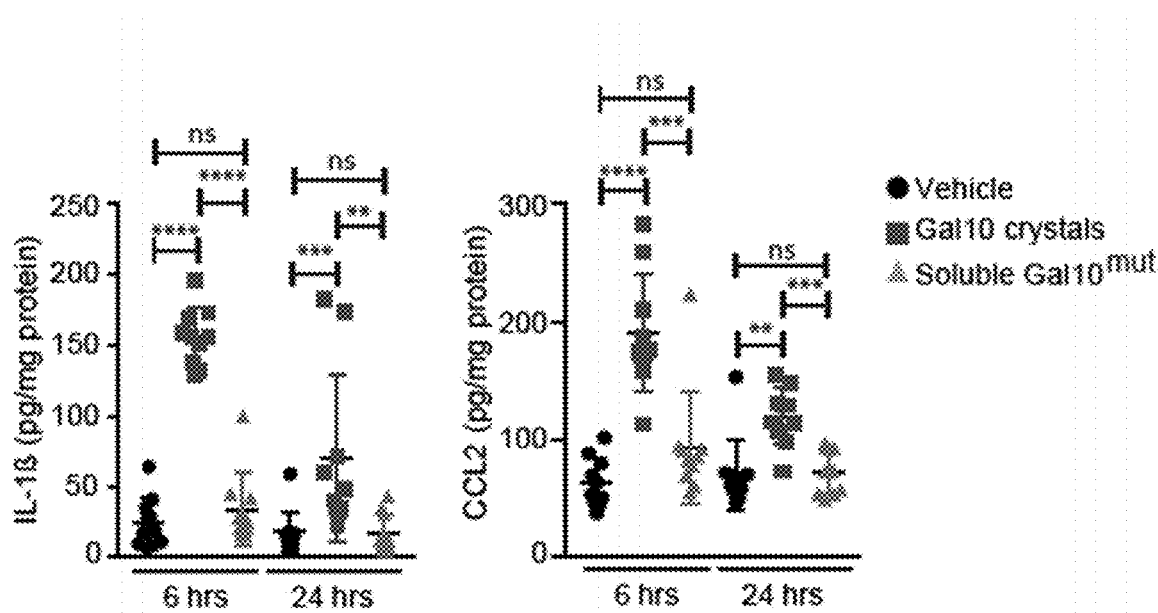

The production of pro-inflammatory cytokines in mice receiving galectin-10 crystals was also measured (FIG. 4B and FIG. 4C). The production of the chemokine CCL-2 was also measured (FIG. 4C). Mice were euthanized by an overdose of pentobarbital and bronchoalveolar lavage (BAL) was performed by injecting 1 ml of PBS containing 0.01 mM EDTA. Subsequently, BAL was spun down (400 g, 5 min, 4° C.) and supernatant was stored at −20° C. Lysates of lung tissue were also produced. For evaluation of the cytokine secretion, the Ready-Set-Go ELISA kit from ThermoFisher Scientific was used. A flatbottom 96 half area well plate (Greiner) was coated with 50 µl per well of capture antibody diluted in 1× coating buffer (00-0000-53, ThermoFisher Scientific) and incubated overnight at 4° C. The following antibodies were used: anti-mouse IL-1β capture antibody (1:250; 14-7012-68A); anti-mouse IL-6 capture antibody (1:250; 14-7061-68); anti-mouse TNFα capture antibody (1:250; 14-7423-68), using the instructions of the commercial provider ThermoFisher Scientific. 50 µl per well of the samples, the standard (mouse IL-1β standard (39-8012-60); mouse IL-6 standard (39-8061-60); mouse TNFα standard (39-8321-60), all from ThermoFisher Scientific) and a blank were added in duplicate. After incubation and washing, 50 µl per well of detection antibody (biotinylated anti-mouse IL-1β detecting antibody (1:250; 13-7112-68A); biotinylated anti-mouse IL-6 detecting antibody (1:250; 13-7062-68A); biotinylated anti-mouse TNFα detecting antibody (1:250; 13-7341-68A) all from ThermoFisher Scientific) diluted in 1× assay diluent was added, followed by another incubation of 1 h at room temperature. Subsequently, the wells were washed and streptavidin-HRP reagent (1:250; 00-4100-94, ThermoFisher Scientific) diluted in assay diluent was added. After an incubation of 30 min at room temperature, the wells were washed and TMB substrate solution (00-4201-56, ThermoFisher Scientific) was added. The reaction was stopped by 2.5 N $H_2SO_4$, and absorbance was read at 450 nm with a Perkin Elmer Multilabel counter and data were collected with Wallac 1420 Manager software. For evaluation of CCL-2 levels, the mouse CCL2 (MCP-1) ELISA Ready-SET-Go!™ kit from eBioscience was used in accordance with manufacturer's instructions (cat no. 50-112-5204).

Injection of galectin-10 crystals was accompanied by production of IL-6 and TNF-α at 6 h post injection, whereas no induction of IL-1β was observed in the BAL samples (not shown). Injection of control soluble galectin-10-Y69E mutein or PBS did not lead to cytokine production (FIG. 4B).

Injection of galectin-10 crystals was also accompanied by production of large quantities of IL-1β and CCL-2 as measured in lung tissue (FIG. 4C).

Figure 5:
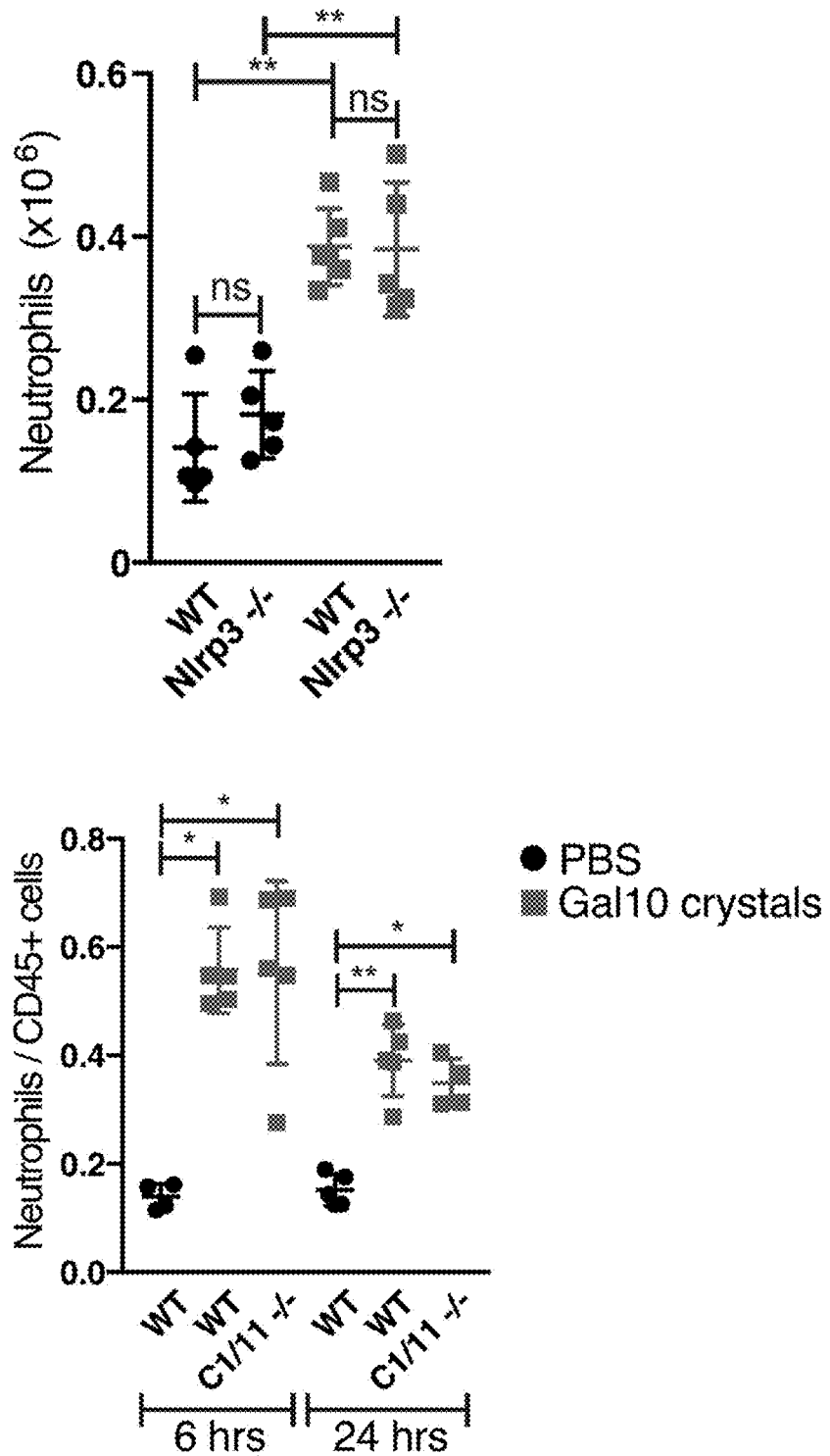
FIG. 5: Innate inflammation induced by Gal10 crystals does not depend on the NLRP3 inflammasome Nlrp3-deficient (left panel) and Caspase1/11-deficient mice (right panel) (deficient mice are referred to as −/−), and their wild type littermates (referred to as +/+) were injected intratracheally with Gal10 crystals or with control PBS. The number of neutrophils recovered from digested lungs of the different mouse strains was determined 6 and 24 hours after the treatment. NS implies a p value >0.12; * implies a p value <0.033;  implies a p value <0.002; * implies a p value <0.0002; **** implies a p value <0.0001.

Example 5. The Innate Immune Response Induced by CLCs is not Dependent on the Nlrp3 Inflammasome In Vivo Many inorganic and organic crystals have the potential to elicit IL-1β secretion from inflammatory cells through triggering of the Nlrp3 inflammasome, leading to ASC adaptor recruitment, ASC spec formation, and caspase 1 activation for pro-IL-1β processing (Kool et al., Immunity 34(4): 527-40 (2011)). A recent paper posted on BioR$_x$Iv (bioRxiv 252957; doi: <<doi.org/10.1101/252957>>) reported that Charcot-Leyden crystals purified from a human eosinophilic cell line had the potential to trigger the NLRP3 inflammasome in vitro. It was however not reported whether crystal induced inflammation was dependent on NLRP3 in vivo, which would pinpoint the inflammasome as a therapeutic target. Inflammation was studied at 24 h as in Example 4. When galectin-10 crystals were injected in the airways of Nlrp3$^{-/-}$ or Casp1/11$^{-/-}$ mice, there was no reduction in crystal-induced cellular influx compared with wild type littermate C57Bl/6 control mice (FIG. 5). Therefore, inflammasome inhibition is unlikely to be successful in inhibiting CLC-induced inflammation in vivo.

Example 6. The Innate Immune Response Induced by CLCs is Independent of Tlr4

Figure 6:
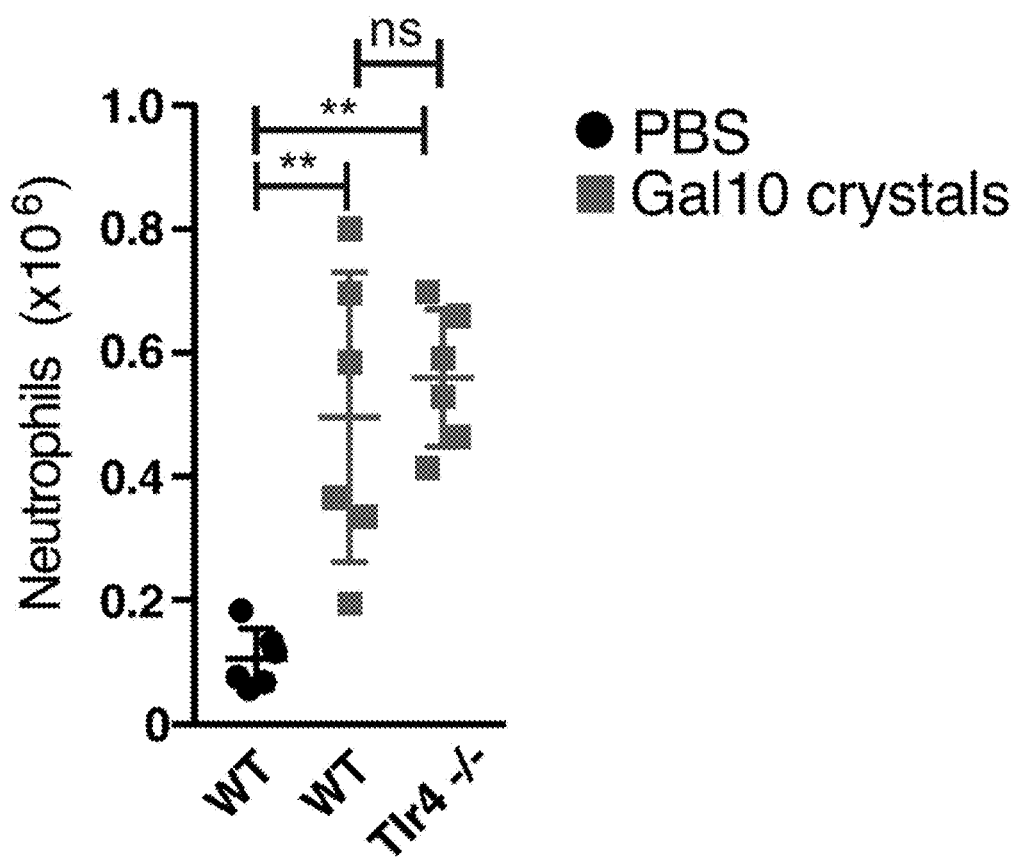
FIG. 6: Innate inflammation induced by Gal10 crystals does not depend on TLR4 Toll-like receptor 4 (TLR4)-deficient and their wild type (WT) littermates were injected intratracheally with Gal10 crystals or with control PBS. The number of neutrophils recovered from digested lungs of the different mouse strains was determined 24 hours after the treatment. NS implies a p value >0.12; * implies a p value <0.033;  implies a p value <0.002; * implies a p value <0.0002; **** implies a p value <0.0001.

Recombinant galectin-10 crystals are produced from galectin-10 protein produced in *E coli*, that has bacterial endotoxin in its cell wall. As endotoxin can trigger an innate immune response in the lungs, it was important to check the potential importance of contamination of galectin-10 crystals with endotoxin to induction of airway inflammation. For this reason, the immune response to galectin-10 crystals in Tlr4$^{-/-}$ mice that lack the receptor for endotoxin was also studied. Inflammation was studied as in Example 4. In these mice, there was no reduction in crystal-induced neutrophilic airway inflammation 24 h after injection compared with wild type littermate C57Bl/6 mice (FIG. 6).

Figure 7A:
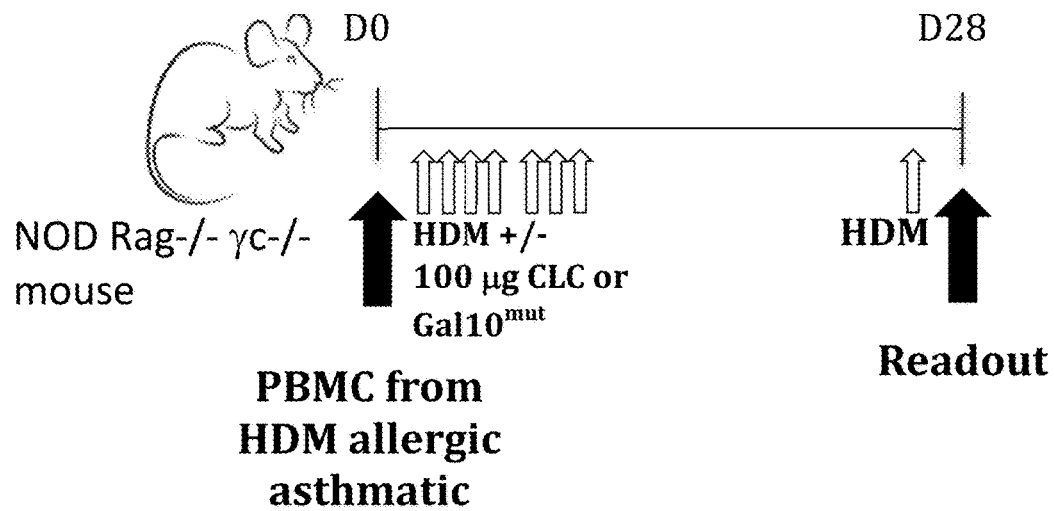
FIGS. 7A-7C: Gal10 crystals boost human asthma features in a humanized model of the disease (FIG. 7A) Experimental setup illustrating the dosing regimen of house dust mite (HDM) extracts and the different forms of galectin-10. Peripheral blood mononuclear cells (PBMCs) were injected intraperitoneally. House dust mite (HDM) extracts, Charcot-Leyden crystals (CLC) and the mutated galectin-10 (Gal10$^{mut}$) were all administered intratracheally.

Example 7. Galectin-10 Crystals Stimulate Airway Inflammation and IgE Synthesis in Humanized Mice Receiving PBMCs from Human Asthmatics Galectin-10 is a neoantigen to the mouse immune system, as mice do not carry the LGALS10 gene coding for galectin-10. Therefore, experiments were set up in humanized mice carrying the immune system of a human house dust mite (HDM) allergic asthmatic donor. To collect PBMCs, 50 ml of blood from a house dust mite allergic patient were collected in EDTA-coated tubes. The blood was diluted in RPMI 1640 (v/v) and layered over 12 ml of Ficoll. After centrifugation (1200 g, 20 min, room temperature), PBMCs were harvested and washed in PBS. Cells were counted using trypan blue to exclude dead cells. PBMCs were resuspended in PBS at a concentration of 15×10$^6$ cells/ml. On day 0, NOD Rag$^{-/-}$ γc$^{-/-}$ (NRG) mice were reconstituted by intraperitoneal injection of 3×10$^6$ PBMCs. On days 1-4 and 7-9, all mice were injected intratracheally with 20 µg of HDM extract (Greer) diluted in 50 µl of PBS. In experiments addressing the pro-inflammatory effects of galectin-10 crystals, on days 1, 3, 7 and 9 NRG mice were treated with the following regimens (FIG. 7A): Regimen 1, PBS control 30 µl; Regimen 2, 100 µg of recombinant galectin-10 crystals (1 µl of the stock) diluted in 30 µl of PBS; Regimen 3, 100 µg of recombinant galectin-10-Tyr69Glu mutein (1 µl of the stock) diluted in 30 µl of PBS.

On day 27, all mice were challenged one final time intratracheally with 20 µg of HDM extract (Greer) diluted in 80 µl of PBS. All mice were sacrificed on day 28 using an overdose of pentobarbital injected intraperitoneally. Mice were bled through the iliac vein. Blood was collected in dry tubes. These tubes were centrifuged (5000 rpm for 10 minutes) to obtain serum. To obtain single lung cell suspensions, the left lung was collected, minced using iridectomy scissors, homogenized in PBS over a 100 µm mesh, washed by adding an excess of PBS, and centrifuged at 400 g for 7 minutes. Pellets were resuspended in PBS and stored on ice until further use (flow cytometry).

The upper and lower lobes of the right lung were fixed in 4% PFA before being embedded in paraffin for histology. The middle lobe of the right lung was embedded in OCT and frozen at −80° C. until further use (qRT-PCR and immunofluorescence).

To detect human cells, single cell suspensions from the left lung of mice were incubated for 20 minutes at 4° C. with APC-labeled anti-human CD45. Dead cells were stained using the Aqua Live/Dead fixable dead cell stain kit (BD). After washing the cells in PBS, 15000 counting beads were added to each sample. Cells were then analyzed by flow cytometry on a Fortessa (BD). None of the Abs used cross-react with murine tissues.

Human IgE concentrations were measured in the serum of NRG mice using a Human IgE uncoated ELISA kit (ThermoFischer). Briefly, ELISA plates were coated overnight at 4° C. with anti-human IgE antibodies in coating buffer. After washing with an excess of PBS-0.05% Tween 20, ELISA plates were blocked for 2 hours at room temperature with the blocking buffer provided by the manufacturer. After washing, the IgE standards (1:2 serial dilution) as well as the sera from NRG mice were added to the plates (dilution 1:5 in blocking buffer), and incubated for 2 hours. The detection antibody was added for 1 hour at room temperature. The presence of human IgE was revealed by adding TMB substrate in all wells. Plates were read at 450 nm on a spectrophotometer.

Figure 7B:
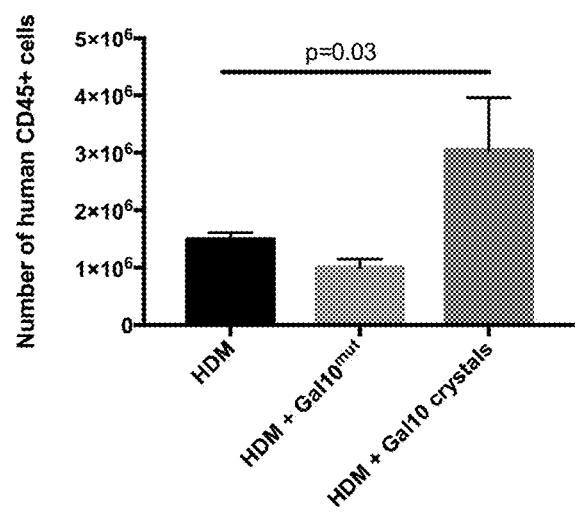
Figure 7C:
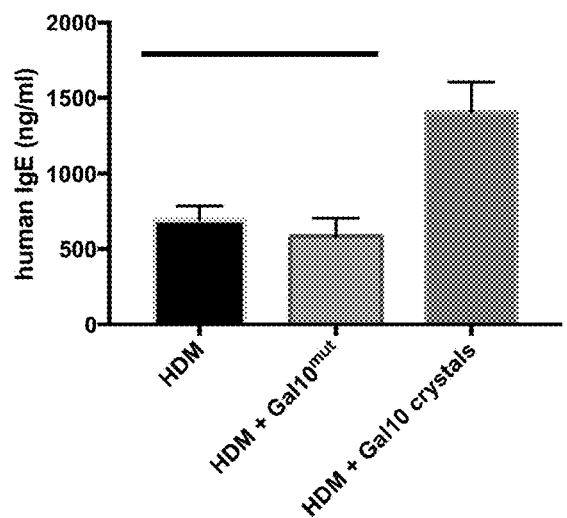

After 28 days, the degree of human CD45+ cell influx in the airways (FIG. 7B), and human IgE synthesis (FIG. 7C) was considerably higher in mice receiving 4 injections of crystalline galectin-10 compared with those receiving galectin-10-Tyr69Glu mutein or those receiving PBS during the HDM challenge period, showing that galectin-10 crystals boost human cellular influx in the lungs and IgE synthesis in an asthma model of immunodeficient mice reconstituted with the immune system of a HDM allergic donor.

Example 8. Production of Galectin-10 Antibodies

A. Immunization of Llamas

Two llamas (*Lama glama*), named Ynigo and Montoyo, were protein immunized intramuscularly with the galectin-10 crystals (1 mg/dose/llama). Protein immunization was started on day 0 and galectin-10 crystals were administered every 14 days for a total of three injections (total five weeks). Five days after the last immunization, 400 mL of blood from the immunized llamas was collected to isolate the PBMCs and allow for RNA extraction.

In order to determine the immune response of the two immunized llamas, an enzyme-linked immunosorbent assay (ELISA) setup was used. For the ELISA, a homogeneous, non-crystallized form of galectin-10 was used.

To carry out the ELISA, a Maxisorp plate was coated with galectin-10 (100 µg/mL) and blocked with casein. Serial dilutions of llama serum pre- and post-immunization were added to the wells of the plate. Then llama IgG1 bound to coated galectin-10 was detected with a mouse anti-llama CH1 specific antibody (10D12), and detection was realized with an anti-mouse IgG-HRP (DAMPO). Finally, after the addition of TMB, the reaction was stopped with 0.5M $H_2SO_4$ and absorbance was measured at 450 nm (Tecan Sunrise, Magellan software). Both immunized llamas showed a strong immune response against galectin-10, even though only 3 injections were carried out.

B. Library Construction (scFv)

scFv libraries were constructed as follows. mRNA was purified from PBMCs isolated from the blood of the immunized llamas. The mRNA was reverse transcribed with random hexamer primers to obtain cDNA. For construction of heavy and light chain libraries, a two-step PCR was carried out. First, non-tagged primers were used directly on the cDNA to amplify the VH-CH1, VL-CL and Vk-Ck regions. The PCR product was then purified and used in a second PCR with the tagged scFv primers to amplify the VH, VL and Vk and these were cloned separately in the phagemid vector to create the "Lambda" and "Kappa" llama scFv libraries, respectively. The scFv fusion protein consisted of the VH and VL sequences coupled by a $(G_4S)_3$ linker (glycine and serine residues) for a size around 25 kDa. The choice to make scFv libraries was based on the fact that scFv fragments are better expressed as protein III fusions at the tip of the phage than Fabs. This results in a better yield and diversity of the phage library during the phage display selection. However, scFv fragments tend to form aggregates, which can result in apparent better affinities, due to the avidity effect. The antibody fragments in scFv format can be secreted into the periplasmic space of *E. coli* bacteria by induction with IPTG.

Enrichment of the phage expressing specific galectin-10 scFv fragments was performed by three rounds of selection on immobilized galectin-10.

The initial selection of the appropriate scFv clones specific for galectin-10 was carried out by a biopanning approach. Briefly, galectin-10-HIS was immobilized on Maxisorp ELISA plates, then the scFv phages library (Input) was added. Unbound phages were removed via multiple washing steps. Finally, the bound phages were eluted with trypsin, and *E. coli* infection was performed in order to amplify the selected phages. This process resulted in the enrichment of the phage population expressing scFv with high affinity anti-galectin-10. At the end of the round of selection, the number of eluted phages was estimated by titration of infected *E. coli*, spotted (from $10^{-1}$ to $10^{-6}$) on Petri dishes containing solid LB medium with ampicillin and glucose. The first round of selection of the Lambda and Kappa library from both llamas resulted in a minor enrichment of specific anti-galectin-10 phages. These second and third rounds of selection resulted in an enrichment of phages expressing scFv with probably a higher affinity for galectin-10.

From the output of round 2 (Library Kappa and Lambda versus 5 µg/mL of galectin-10) and round 3 (Library Kappa versus 0.2 µg/mL and Lambda library versus 0.02 µg/mL), single clones were generated and resulted in the creation of six Master plates. From these Master plates, periplasmic master plates (PMP) were produced. For this purpose, single clones from the Master plates were first amplified in 96 well format (deep well), and production of the scFv was induced by an overnight incubation with IPTG. The next day, the bacteria were lysed by two cycles of freeze/thaw (−80° C. and −20° C.). After centrifugation, the supernatant (periplasmic extract) was collected and transferred into separate 96 wells plate in order to be tested for binding capacity (ELISA and Biacore).

C. Screening of the scFv Periplasmic Extracts by ELISA

In order to test the binding capacity of the scFvs to galectin-10, an ELISA binding assay was established. Briefly, a Maxisorp plate was coated with soluble galectin-10 (1 µg/mL), then blocked with casein, before being incubated with the periplasmic extract (dilution 1/5 in PBS) containing the scFv-Myc. Detection of the binder was carried out with an anti-Myc-HRP antibody. Absorbance was measured at 450 nm (reference at 620 nm) with Tecan instrument. A significant number of galectin-10 scFv binders were isolated after the second round of selection (45-87% of binders). For both llamas, the Lambda library showed higher numbers of galectin-10 binders than the kappa library. The third round of selection resulted in an increase in the number of scFv clones with high binding capacity to galectin-10. The scFv clones generated from the lambda library showed 74-93% binders to galectin-10, whereas the scFv generated from the kappa library showed 15-20% binders.

D. Sequencing and Reformatting of scFv Clones

Selected scFv clones that showed binding to galectin-10 were sequenced. Based on their CDR1-2-3, VH and VL sequences, each clone was classified as belonging to a particular family. This process resulted in the determination of 65 VH families, 13 VKappa families and 23 VLambda families. Twelve clones shown in Table 3 below were selected for further characterization.

clones that showed the proper insert (VH/VL) were selected and amplified in order to purify the DNA sequence (MidiPrep).

Production into mammalian cells was then initiated. Each DNA of the scFv-human Fc clone was transfected into HEK293E cells via the polyethylenimine (PEI). After 6 days, scFv-human Fc molecules were purified from the cell supernatant using the protein-A sepharose beads. Finally, SDS-PAGE analysis was carried out to assess the purity and the integrity of the scFv-human Fc molecules (~100 kDa).

E. Characterization of the scFv-Human Fc Panel

ELISA and SPR with a T3000 Biacore were used to assess the binding properties of the scFv-human Fc panel.

(i) ELISA Analysis

In a similar setup to that used during the initial screening, the relative binding properties of the 12 scFv-human Fc clones were analyzed by ELISA. Briefly, a Maxisorp plate was coated with galectin-10-His at 0.2 µg/mL and blocked with casein, before being incubated with a serial dilution of the scFv-human Fc fusion molecules. After several washing steps, detection of the bound scFv-human Fc was carried out with an anti-human Fc-HRP antibody. Absorbance was measured at 450 nm (reference at 620 nm) with Tecan instrument. Finally, the raw data (OD values) were plotted on GraphPad Prism 7.01. The EC50 value of each compound was calculated with a non-linear regression (log(agonist) vs. response Variable slope (four parameters)). The results are shown in Table 4 below.

TABLE 3 scFv clones binding to galectin-10

| Clone name | Isolated from selection round | Gal10 concentration during selection (ug/ml) | PERI-ELISA binding (OD values) | VH Family nb | Lambda Family nb | Kappa Family nb |
| --- | --- | --- | --- | --- | --- | --- |
| 1A12 | 2 | 5 | 2.134 | 32 | 4 | |
| 2B11 | 2 | 0.5 | 3.793 | 57 | 1 | |
| 2C07 | 2 | 0.5 | 3.626 | 7 | 1 | |
| 2E11 | 2 | 0.5 | 3.511 | 23 | 23 | |
| 3A03 | 3 | 0.2 | 3.4 | 65 | | 2 |
| 4B10 | 3 | 0.02 | 2.435 | 17 | 4 | |
| 4G05 | 3 | 0.2 | 3.803 | 18 | 4 | |
| 4H10 | 3 | 0.02 | 3.484 | 59 | 17 | |
| 5O12 | 3 | 0.02 | 2.415 | 64 | | 3 |
| 6A11 | 3 | 0.02 | 2.346 | 24 | 23 | |
| 6F05 | 3 | 0.2 | 3.827 | 26 | 17 | |
| 6F011 | 3 | 0.02 | 3.757 | 53 | 23 | |

The CDR, VH and VL sequences of these clones are shown in Tables 14, 15 and 16 below.

The 12 scFv clones in Table 3 were re-cloned as scFv-human Fc fusion molecules. For this purpose, the DNA of each selected scFv clone was first digested with restriction enzymes (AscI/SfiI). After extraction of the DNA from agarose gel, ligation of the DNA was performed into pre-digested vector containing the CH2-CH3 constant domains of the human IgG1 (pUPEX50: pScFv-Fc fusion vector). The transformation of each ligated product was performed using Top10 bacteria by heat shock and transfer onto LB-agarose plates with Ampicillin. After one night of incubation, ligated products showed high numbers of single bacterial colonies whereas no colonies were observed for the negative controls (empty vectors). Per scFv clone, four to eight colonies were picked and sent for sequencing. The

TABLE 4

ELISA binding characteristics of the lead panel of scFv-human Fc antibodies

| Clone name (ScFv-hFc) | Bmax (OD values) | EC50 (nM) |
| --- | --- | --- |
| 1A12 | 0.409 | ambiguous |
| 2B11 | 2.432 | 0.08 |
| 2C07 | 2.887 | 0.05 |
| 2E11 | 1.425 | 0.14 |
| 3A03 | 1.81 | 0.06 |
| 4B10 | 1.28 | 0.08 |
| 4G05 | 3.034 | 0.09 |
| 4H10 | 1.301 | 0.2 |
| 5E12 | 1.84 | 0.25 |
| 6A11 | 1.595 | 0.01 |

TABLE 4-continued

ELISA binding characteristics of the lead
panel of scFv-human Fc antibodies

| Clone name (ScFv-hFc) | Bmax (OD values) | EC50 (nM) |
|---|---|---|
| 6F05 | 2.895 | 0.02 |
| 6F11 | 1.565 | 0.48 |
| Isotype control | 0.018 | / |

Clones 2C07, 6F05, 4G05 and 2B111 showed the best relative binding capacity with EC50 values between 0.02-0.09 nM.

Clones 6F11 and 5E12 showed the lowest binding capacity (EC50 values between 0.25-0.48 nM).

One clone (1A12) showed weak binding to galectin-10, with an ambiguous fit.

In addition, the whole panel showed similar binding capacity to coated galectin-10 and galectin-10-His tagged.

(ii) SPR Analysis

In order to determine the binding properties (on-rate/off-rate) of the scFv-human Fc panel, their binding capacity to galectin-10 was analyzed on Biacore T3000. For this purpose, a capture approach was set up. A CM5 Chip was coated with polyclonal anti-human Fc at 8000 RU, then a fixed concentration of the scFv-human Fc panel (1.5 µg/mL), diluted in HBS-EP pH7.4, were captured to reach a binding signal around 150 RU. Finally, a serial dilution of galectin-10-His (serial dilution, 1 over 2 from 5 µg/mL, 6 points of dilution) diluted in HBS-EP pH7.4 was injected. Raw data were analyzed via BIA evaluation software with a blank subtraction (4-3). The kd/KD and Rmax of each scFv-human Fc for galectin-10-His was determined using the Fit Kinetics simultaneous ka/kd/Binding with mass transfer/Local Rmax on BIA evaluation software. The results are shown in Table 5 below.

TABLE 5

Characterisation of the binding properties of the
panel of scFv-human Fc antibodies on Biacore T3000

| Clone name (ScFv-hFc) | Rmax | kd 1E−04 (1/s) | KD (nM) |
|---|---|---|---|
| 1A12 | 12.4 | 31.5 | 11.7 |
| 2B11 | 37.3 | 180 | 0.875 |
| 2C07 | 41.3 | 2.59 | 0.677 |
| 2E11 | 21.6 | 111 | 1.16 |
| 3A03 | 18.3 | 111 | 1.56 |
| 4B10 | 20.6 | 128 | 1.94 |
| 4G05 | 23.6 | 437 | 0.911 |
| 4H10 | 19.6 | 27.7 | 1.55 |
| 5E12 | 6.67 | 17.7 | 4.73 |
| 6A11 | 35.6 | 1240 | 0.711 |
| 6F05 | 38 | 1.17 | 0.918 |
| 6F11 | 28.84 | 172 | 2.96 |
| Isotype control | 6.06 | / | / |

The clones 6F05 and 2C07 showed clearly the best affinity (0.9 and 0.6 nM, respectively), with off-rates of 1.17E-04 and 2.59 E-04 s$^{-1}$, respectively.

However, the other 10 clones showed fast off-rate with affinities in a nanomolar range (>17 nM).

F. Screening of the scFv Clones by Bio-Layer Interferometry (BLI) Technology (Octet)

In addition to the sequencing and characterization of clones described in sections D and E above, 272 scFv clones from the Master plates 1-6, that showed a clear binding in ELISA (screening) were selected and their binding capacity to galectin-10-His was analyzed on BLI, using the Octet RED96. The BLI is a label-free technology for measuring biomolecular interactions. It is an optical analytical technique that analyzes the interference pattern of white light reflected from two surfaces: a layer of immobilized protein on the biosensor tip, and an internal reference layer. Any change in the number of molecules bound to the biosensor tip causes a shift in the interference pattern that can be measured in real-time.

Briefly, galectin-10-His tagged diluted in Kinetic Buffer was captured on Anti-Penta His 1K sensor tips until an immobilization level of 1 nm was reached. Then, diluted periplasmic extracts (1/10) were applied and association/dissociation to immobilized galectin-10-His was measured using the ForteBio Data analysis 9.0 software (subtraction of the reference Tips, 1.1 binding model). During the screening, only the dissociation (off-rate) of the scFv can be determined since the effective concentration of the scFv is unknown and can vary a lot from clone to clone. The results confirmed that most of the selected clones within the scFv panel showed fast off-rates. However, some clones, mainly from the lambda library (round 2 and round 3 of selection), showed slow off-rate (dissociation) to captured galectin-10. Therefore, taking into consideration the ELISA and BLI data, a new panel of lead scFvs was selected.

Based on the ELISA data and BLI data, a second panel of lead scFv clones was taken forward for further characterisation. The characteristics of these scFv clones is shown in Table 6 below.

TABLE 6

Second panel of lead scFv clones

| Clone name | Isolated from selection round | Concentration of galectin-10 used for selection | ELISA binding (OD values) | BLI binding (off rate kdis(1/s)) | VH Family | Lambda Family |
|---|---|---|---|---|---|---|
| 1C08 | 2 | 5 | 3.7 | 8.2E−03 | 59 | 17 |
| 1C09 | 2 | 5 | 3.5 | 1.4E−03 | 58 | 4 |
| 1D011 | 2 | 5 | 3.3 | 5.2E−03 | 62 | 17 |
| 2C07 | 2 | 0.5 | 3.6 | 6.7E−03 | 7 | 1 |
| 2F09 | 2 | 0.5 | 3.6 | 9.9E−03 | 57 | 23 |
| 4E08 | 3 | 0.2 | 3.6 | 9.4E−03 | 56 | 1 |
| 6A08 | 3 | 0.02 | 3.5 | 8.2E−03 | 26 | 14 |

TABLE 6-continued

Second panel of lead scFv clones

| Clone name | Isolated from selection round | Concentration of galectin-10 used for selection | ELISA binding (OD values) | BLI binding (off rate kdis(1/s)) | VH Family | Lambda Family |
|---|---|---|---|---|---|---|
| 6B06 | 3 | 0.2 | 3.7 | 5.8E−03 | 53 | 23 |
| 6E10 | 3 | 0.02 | 3.7 | 1.6E−02 | 35 | 23 |
| 6F06 | 3 | 0.2 | 3.8 | 5.7E−03 | 14 | 1 |

The CDR, VH and VL sequences of these scFv clones are shown in Tables 14-16 below.

G. Reformatting of Selected scFv Clones into a Mouse IgG1 Backbone

The selected leads shown in Table 6 above were re-cloned into a mouse IgG1 backbone for further characterization. For this purpose, the VH and the VL of each clone were PCR amplified using specific primers, isolated by electrophoresis, purified and digested with restriction enzymes (BsmBi). After digestion and clean-up, ligation of the DNA (VH or VL) was performed into BsmBi pre-digested vectors containing the constant domains of the mouse lambda light chain (pUPEX116.35) or of the mouse IgG1 heavy chain (CH1-CH2-CH3, pUPEX116.33). The transformation of each ligated product was carried out using Top10 bacteria by heat shock and transfer onto agarose plates with Ampicillin (resistance gene of the vectors). After one night of incubation, ligated products showed high numbers of single bacterial colonies whereas no colonies were observed for the negative controls (empty vectors). Per clone (HC and LC), four to eight colonies were picked and sent for sequencing. The clones that showed the proper insert were selected and amplified in order to purify the DNA sequence (MidiPrep).

The production of the 10 mouse IgG1 was done by transfection with a ratio of 1 heavy chain for 3 light chains incorporated in HEK293E cells via the polyethylenimine (PEI). After 6 days, mouse monoclonal antibodies were purified from the cell supernatant using the protein-A sepharose beads. Finally, SDS-PAGE analysis was carried out to assed the purity and the integrity of the antibodies (150 kDa).

H. Characterization of the Binding Properties of the Galectin-10 Mouse IgG1 Panel Several assays were performed to evaluate the binding and functional properties of the galectin-10 mouse IgG1 panel. Both ELISA and SPR with a T3000 Biacore were used to determine the binding capacity of the lead panel.

(i) ELISA Analysis

In a similar setup to that used during the characterization of the scFv-human Fc molecules, the relative binding affinities of the 10 mouse IgG1 antibodies were analyzed by ELISA. A Maxisorp plate was coated overnight with 0.2 µg/mL of galectin-10-His. Then a serial dilution of each clone (from 100 nM, dilution 1/4, 12 points of dilutions) was incubated on coated galectin-10. After several washing steps, detection of the bound mouse IgG1 was carried out with an anti-mouse Fc-HRP antibody. Absorbance was measured at 450 nm (reference at 620 nm) with Tecan instrument. A mouse IgG1 isotype control was used as negative control. A polyclonal anti-galectin-10 antibody was used as positive control for the coating of galectin-10. The raw data (OD values) were plotted on GraphPad Prism 7.01. The EC50 values for each antibody, calculated with a non-linear regression (log(agonist) vs. response Variable slope (four parameters)), are reported in Table 7 below.

The new panel of galectin-10 mouse IgG1 antibodies showed a relative binding capacity between 3.22 nM to 0.04 nM against coated galectin-10. The clones 2F09, 6A05, 6B06 and 2C07 showed the best relative binding affinity (0.05-0.08 nM).

TABLE 7

Characterization of the binding properties of the mouse IgG1 panel by ELISA

| Constructs (mouse IgG1) | Bmax | EC50 (nM) |
|---|---|---|
| 1C09 | 2.297 | 0.13 |
| 1D011 | 1.498 | 0.1 |
| 2C07 | 2.947 | 0.08 |
| 2F09 | 3.293 | 0.05 |
| 4E08 | 2.063 | 3.22 |
| 6A05 | 1.744 | 0.07 |
| 6A08 | 3.196 | 0.15 |
| 6B06 | 3.278 | 0.08 |
| 6E10 | 2.398 | 0.17 |
| 6F06 | 2.926 | 0.08 |
| Isotype control | 0.042 | / |

(ii) SPR Analysis

The binding capacity of the mouse IgG1 antibodies to galectin-10 was analyzed on Biacore T3000. For this purpose, a capture approach was set up. A CM5 Chip was coated with polyclonal anti-mouse Fc at 8000 RU, then a fixed concentration of the mouse IgG1 antibody panel (1.5 µg/mL), diluted in HBS-EP pH7.4, was captured to reach a binding signal around 150 RU. Finally, a serial dilution of galectin-10-His (serial dilution, 1 over 2 from 5 µg/mL) diluted in HBS-EP pH7.4 was injected. Raw data were analyzed via BIA evaluation software with a blank subtraction (4-3). The kd/KD and Rmax of each mAb to galectin-10-His was determined using the Fit Kinetics simultaneous ka/kd/Binding with mass transfer/Local Rmax on BIA evaluation software.

TABLE 8

Characterization of the binding properties of the mouse IgG1 panel by Biacore T3000

| Constructs (mouse IgG1) | KD (nM) | kd 1E−04 (1/s) |
|---|---|---|
| 1C09 | 0.5 | 52.9 |
| 1D11 | 1 | 52.9 |
| 2C07 | 0.5 | 3.6 |
| 2F09 | 0.3 | 3.4 |
| 4E08 | 0.8 | 8.5 |

TABLE 8-continued

Characterization of the binding properties
of the mouse IgG1 panel by Biacore T3000

| Constructs (mouse IgG1) | KD (nM) | kd 1E−04 (1/s) |
|---|---|---|
| 6A05 | 0.6 | 48.3 |
| 6A08 | 1 | 6.7 |
| 6B06 | 0.3 | 30.6 |
| 6E10 | 0.5 | 8.2 |
| 6F06 | 0.7 | 48.7 |

In this setup, the 10 clones showed an affinity in a nanomolar up to sub-nanomolar range, with an off-rate between 3.4-53 $1^{E-04}$(1/s). In line with the ELISA binding data, the clones 2F09 and 2C07 were found on the top of the panel. The off-rate measured during the characterization of the mouse panel was not in line with the off-rate measured during the screening. This is mainly explained by the difference in the assay setup used during the screening (BLI, galectin-10-His captured by anti-His sensor tips) and the characterization (SPR, mouse IgG1 captured by polyclonal anti-mouse Fc Chip).

I. Epitope Mapping of the Galectin-10 Mouse IgG1 Panel

In order to identify the galectin-10 binding sites of the different clones, an epitope mapping method (TANDEM), using the BLI technology, was established. Briefly, the galectin-10-His was captured on anti-HIS 1K sensor tips, before incubation with an excess of one antibody (called the "saturating" antibody) then directly transferred to a solution containing the "competitor" antibody at a suboptimal concentration. If the "saturating" and the competitor antibody bind to the same binding sites, no binding of "competitor" will be detected (expressed in nm shift). If they do not share the epitope, the "competitor" antibody will be able to bind in presence of the "saturating" antibody. An isotype control was used as a negative control for "saturating" antibody, where all the clones used as "competitor" antibodies showed a clear binding to galectin-10.

A similar approach was used for the first panel of scFv-human Fc fusion. All bound on the same epitope on galectin-10 (data not shown) i.e. the same epitope as the mIgG1 anti-galectin-10.

Example 9. Characterization of Galectin-10 Antibodies for Ability to Affect Crystallization In Vitro The effects of the lead galectin-10 scFv-human Fc molecules and the lead galectin-10 mouse IgG antibodies on the formation of the recombinant CLCs described in Example 1 was tested. Because galectin-10 autocrystallization is so reproducible in vitro, a Mosquito crystallization robot (TTP Labtech) was used to screen anti-galectin-10 antibodies for their potential to block galectin-10 autocrystallization. Using this approach, clones that inhibited galectin-10 crystallization were screened. For the crystal inhibition assay, soluble TEV-cleaved wild-type recombinant galectin-10 in PBS was equilibrated overnight against a solution of 50% PEG 3350 in the presence of anti-galectin antibodies or an irrelevant antibody. To evaluate the inhibition of crystal formation, 250 nL of soluble TEV-cleaved wild-type recombinant galectin-10 in PBS at a concentration of 0.4-0.7 mg/mL was mixed with 100 nL anti-galectin-10 antibody or an irrelevant antibody. Next, the protein mixture was equilibrated against 40 microliter of 50% (v/v) PEG 3350 contained in the reservoir well of a 96-well crystallization plate. Due to the action of the PEG, the amount of water within the drop decreased and therefore the concentration of galectin-10 increased, until it reached the threshold where the galectin-10 crystallizes to form CLCs. Following overnight incubation the presence or absence of CLC crystals was evaluated using a stereomicroscope. The presence of crystal was determined as 100% crystal formation, few crystals observed equal 50% crystal formation and no crystals observed after the incubation time was set as 0% crystal formation. This experiment was not quantitative and only aimed to rank the potency of the different galectin-10 clones to block the CLC formation. Due to the experimental setup, and the high concentration of anti-galectin-10 molecules needed, only selected clones from the scFv-human Fc and the mouse IgG1 anti-galectin-10 panel were tested.

TABLE 9

Epitope mapping by competition assay

| Antibody 1 (Saturating Ab) (10 ug/mL) | Antibody 2 (competitor) at 1 ug/mL (binding signal in nm) | | | | | | | | | | |
|---|---|---|---|---|---|---|---|---|---|---|---|
| | 1C09 | 1D011 | 2F09 | 4E08 | 6A05 | 2C07 | 6A08 | 6B06 | 6E010 | 6F06 | Buffer |
| 1C09 | 0.03 | 0.01 | 0.04 | −0.02 | 0.00 | 0.00 | 0.00 | 0.01 | 0.03 | 0.00 | −0.02 |
| 1D011 | 0.10 | 0.06 | 0.12 | 0.03 | 0.04 | 0.04 | 0.05 | 0.07 | 0.10 | 0.06 | 0.02 |
| 2F09 | 0.02 | 0.02 | 0.03 | 0.01 | 0.01 | −0.01 | 0.00 | 0.00 | 0.00 | 0.00 | 0.01 |
| 4E08 | 0.08 | 0.00 | 0.10 | −0.08 | −0.03 | −0.05 | −0.05 | 0.03 | 0.10 | 0.02 | 0.01 |
| 6A05 | 0.09 | 0.06 | 0.12 | 0.03 | 0.05 | 0.04 | 0.05 | 0.06 | 0.09 | 0.05 | 0.01 |
| 6A08 | 0.04 | 0.01 | 0.07 | −0.03 | 0.00 | −0.01 | −0.04 | 0.02 | 0.04 | 0.00 | 0.01 |
| 6E010 | 0.02 | −0.01 | 0.03 | −0.05 | −0.03 | −0.04 | −0.05 | −0.02 | 0.00 | −0.03 | −0.21 |
| 2C07 | 0.03 | 0.02 | 0.05 | 0.00 | 0.01 | 0.03 | 0.05 | 0.04 | 0.06 | 0.03 | 0.02 |
| 6B06 | 0.02 | 0.00 | 0.03 | 0.00 | 0.00 | 0.04 | 0.05 | 0.03 | 0.04 | 0.03 | 0.03 |
| 6F06 | 0.04 | 0.03 | 0.06 | 0.01 | 0.02 | 0.04 | 0.05 | 0.05 | 0.07 | 0.04 | −0.05 |
| Isotype | 1.21 | 1.18 | 1.14 | 0.97 | 1.02 | 0.73 | 1.04 | 0.94 | 1.34 | 1.15 | −0.05 |
| Buffer | / | / | / | / | / | 0.80 | 1.08 | 0.98 | 1.38 | 1.22 | / |

The results showed that the 10 clones tested compete with each other, suggesting that they bind to the same binding site/epitope on galectin-10-His.

CLC crystals consistently appeared in control conditions but were absent in conditions containing anti-galectin-10 antibodies. This experimental setup is exemplified in FIG.

Figure 8A:
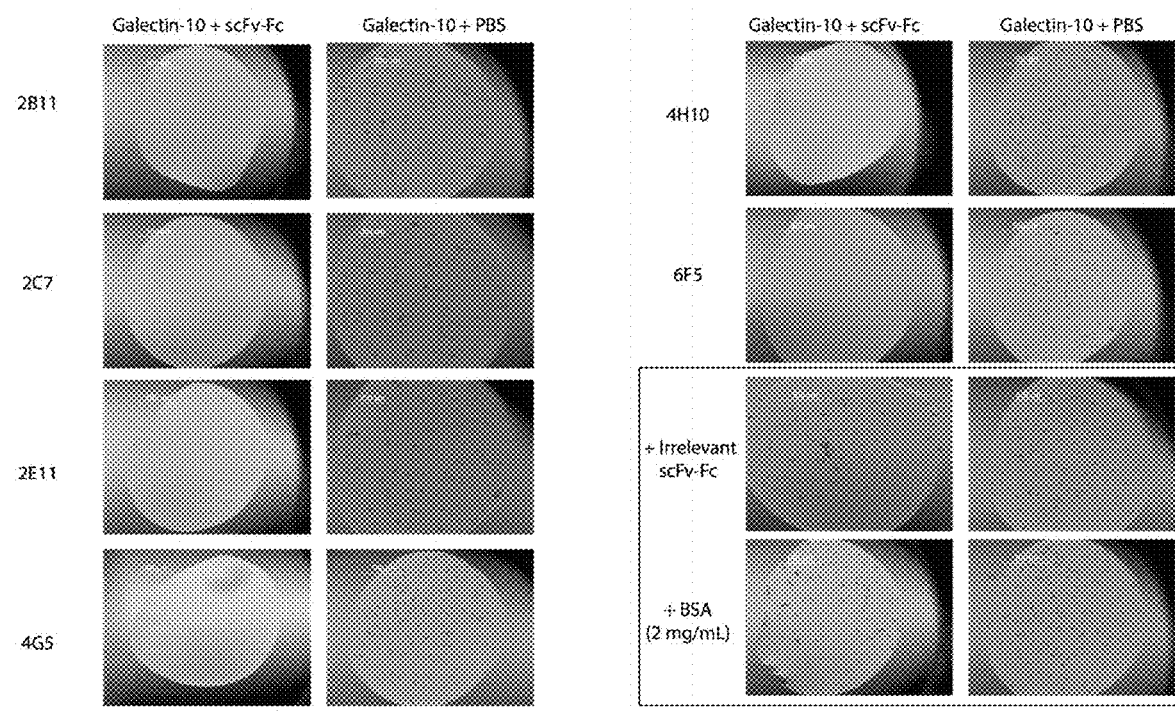
FIGS. 8A-8B: Prevention of Gal10 autocrystallization in vitro by addition of Gal10 antibodies (FIG. 8A) Gal10 was allowed to autocrystallize by removal of the HIS tag via TEV protease. This assay was performed in the presence of various Gal10-specific scFv-Fc antibody clones or irrelevant scFv-Fc antibodies, and crystal formation was observed in a crystallization robot.
Figure 8B:
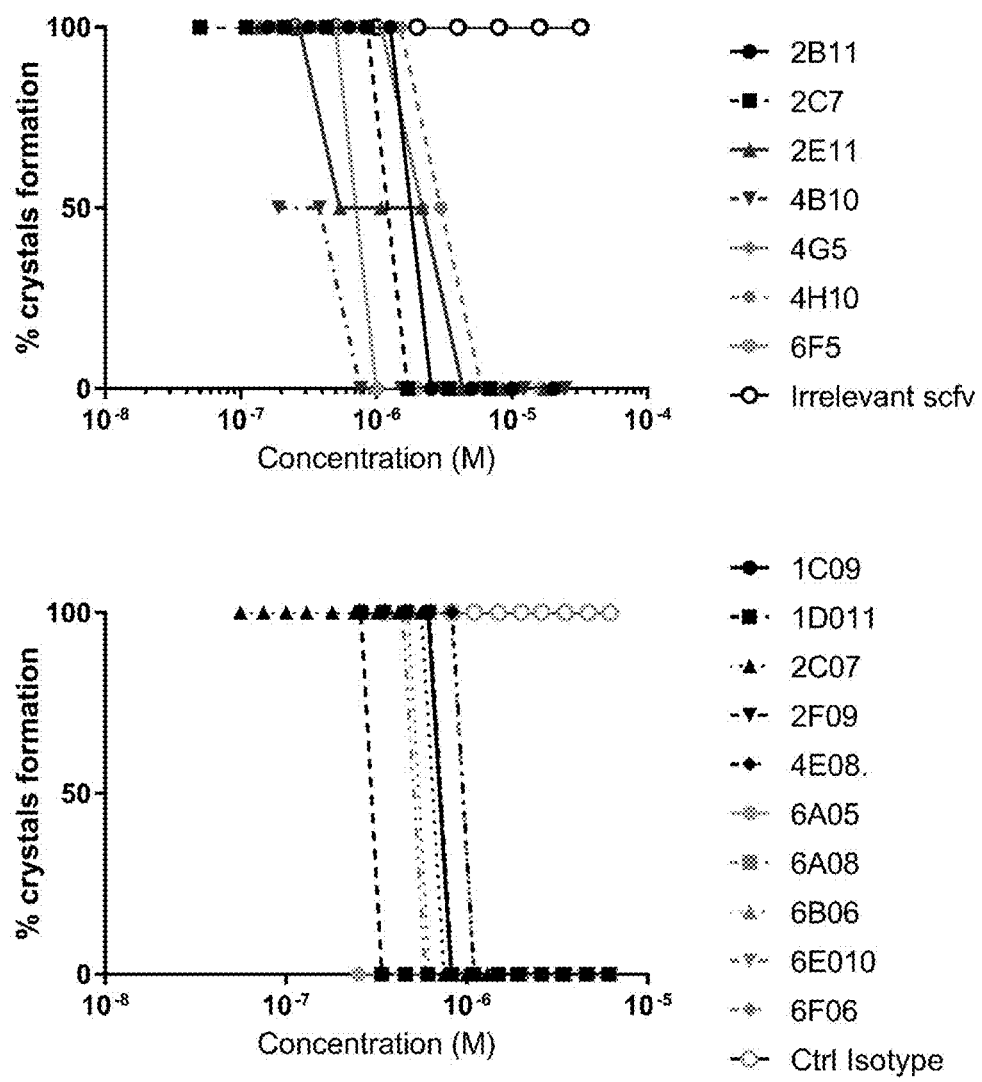

8A and effectiveness of several clones summarized in FIG. 8B.

The results show that all of the clones tested (17 in total) were able to block the CLC formation. Among the scFv-human Fc panel, the clones 4B10, 2E11 and 6F5 showed the best efficacy to block the CLC formation. The clone 1D11 showed the best potency to block the formation of the CLC among the mouse IgG1 panel. Clone 6A05 showed no CLC formation, even at the lowest ratio galectin-10/mouse IgG1 anti-galectin-10, and the reason for this is unclear. However, all the negative controls (galectin-10 incubated with irrelevant scFv-human Fc or mouse IgG1, buffer or BSA (2 mg/mL)) showed 100% CLC formation after 2 days of incubation.

Example 10. Galectin-10 Antibodies can Solubilize Pre-Existing CLCs In Vitro Using an analogous experimental setup the antibody-mediated solubilization of already formed recombinant galectin-10 crystals was evaluated using the lead galectin-10 scFv-human Fc molecules and the lead galectin-10 mouse IgG antibodies. In this assay, antibodies were added to the crystals that had formed following overnight equilibration against the PEG3350 solution (250 nL of soluble TEV-cleaved wild-type recombinant galectin-10 in PBS against 50% PEG 3350 overnight). Crystal solubilization was observed as a function of time after addition of antibodies. 100 nL of anti-galectin-10 or control antibody was added and the solubilization of galectin-10 crystals was observed under a stereomicroscope. Each condition was performed in 12 replicas. As a negative control, an irrelevant scFv-human Fc and mouse IgG1 were included, as well as buffer only.

Table 10 shows that most of the tested galectin-10 antibody clones were able to dissolve pre-existing CLCs. This dissolution happened in less than 2 hours of incubation with the anti-galectin-10 molecules.

TABLE 10

Solubilization of existing CLCs in vitro

| Clone name | Format | 100% Solubilization of CLC (Conc μM) | Clone name | Format | 100% Solubilization of CLC (Conc μM) |
|---|---|---|---|---|---|
| 1A12 | scFv-human Fc | n.t | 1C09 | mouse IgG1 | 10.48 |
| 2B11 | scFv-human Fc | 5.04 | 1D11 | mouse IgG1 | 7.86 |
| 2C07 | scFv-human Fc | 6.86 | 2C07 | mouse IgG1 | >2.2 |
| 2E11 | scFv-human Fc | 4.36 | 2F09 | mouse IgG1 | 10.67 |
| 3A03 | scFv-human Fc | n.t | 4E08 | mouse IgG1 | >10 |
| 4B10 | scFv-human Fc | 6.14 | 6A05 | mouse IgG1 | 10.1 |
| 4G05 | scFv-human Fc | 4.36 | 6A08 | mouse IgG1 | >10 |
| 4H10 | scFv-human Fc | 6 | 6B06 | mouse IgG1 | >10 |
| 5E12 | scFv-human Fc | n.t | 6E10 | mouse IgG1 | 10.48 |
| 6A11 | scFv-human Fc | n.t | 6F06 | mouse IgG1 | 7.57 |
| 6F05 | scFv-human Fc | 4 | 6F06 | mouse IgG1 | 7.57 |
| 6F11 | scFv-human Fc | n.t | Isotype | mouse IgG1 | No solubilization |
| 6F11 | scFv-human Fc | n.t | | | |
| Isotype | scFv-human Fc | No solubilization | | | |

Example 11. Further Characterization of the Crystal Dissolving Properties of Selected Galectin-10 Antibodies The four clones shown in the table below were selected for further analysis.

TABLE 11

Summary of characteristics of 6F05,1C09,1D11 and 4E08

| Clone name | Format | ELISA binding EC50 (nM) | Biacore (capture approach) KD (nM) | kd 1E−04 (1/s) | Potency in inhibition of the CLC formation and solubilization 100% Inhibition of CLC formation (Conc μM) | 100% Solubilization of CLC (Conc μM) |
|---|---|---|---|---|---|---|
| 6F05 | scFv-human Fc | 0.02 | 0.9 | 1.2 | 1.00 | 4.00 |
| 1C09 | mouse IgG1 | 0.13 | 0.5 | 52.9 | 0.82 | 10.48 |
| 1D11 | mouse IgG1 | 0.1 | 1 | 52.9 | 0.34 | 7.86 |
| 4E08 | mouse IgG1 | 3.22 | 0.8 | 8.5 | 1.11 | >10 |

A. Time-Lapse Solubilization of CLCs by 6F05, 1C09, 1D11 and 4E08

To better document and characterize the solubilization process of CLC crystals by anti-galectin-10 antibodies, time-lapse experiments on a spinning disk confocal microscope were conducted. 2.5 µL of autocrystallized CLC solution (at 0.7 mg/mL) in PBS was spotted in a well of a chamber microscope slide with glass bottom (Ibidi). Crystal solubilization was then initiated and followed overtime by the addition of 2 µL of anti-galectin-10 antibodies at a concentration of 7 mg/mL. To prevent evaporation the chamber was sealed with vacuum grease and a glass cover slide.

Figure 9A:
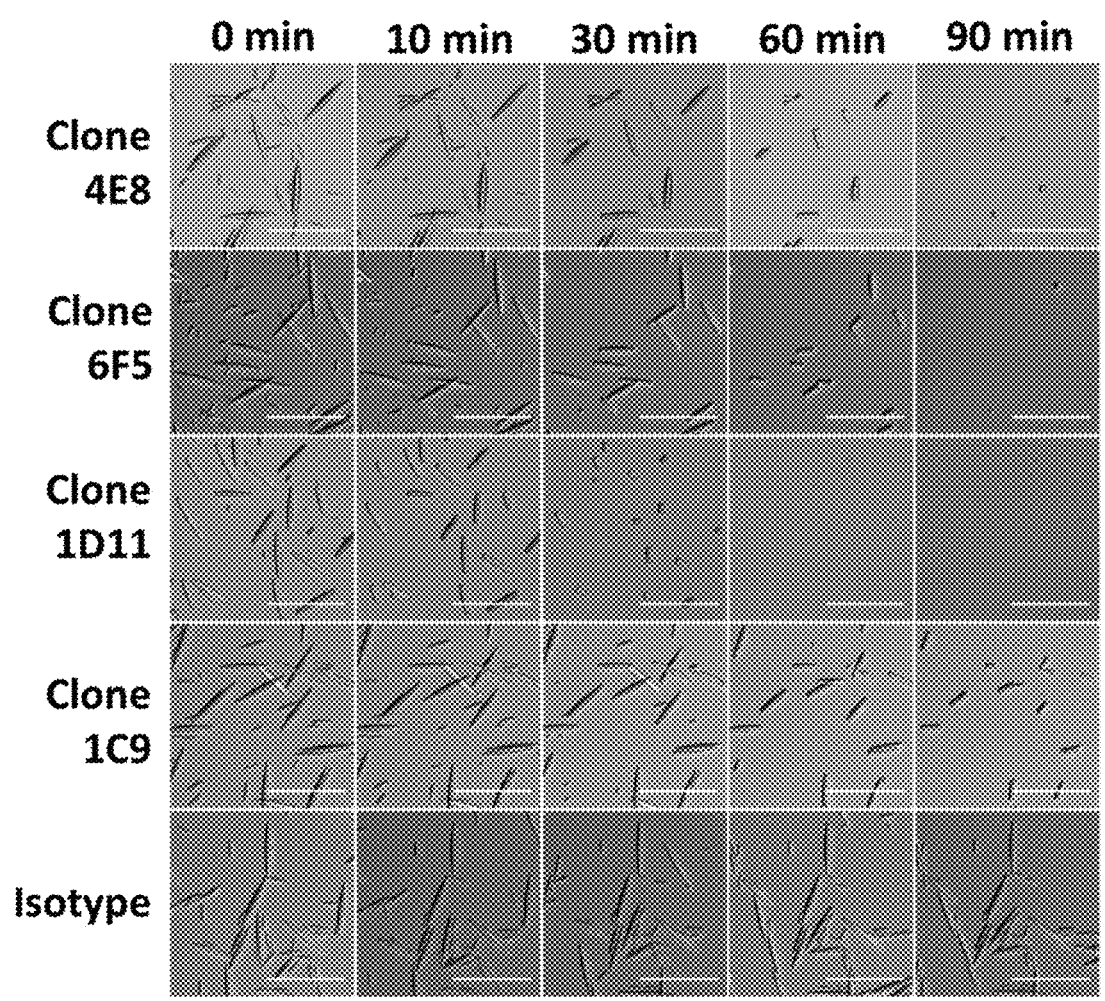
FIGS. 9A-9B: Time-lapse images of crystal dissolution by 4 clones of IgG1 antibodies (FIG. 9A) To study if antibodies can also dissolve existing crystals, clones were added to in vitro grown Gal10 crystals, and observed using spinning disk confocal microscopy. The 4 clones all completely dissolved crystals within 90 minutes, whereas irrelevant isotype antibody did not.

The CLC dissolution induced by 6F05, 1C09, 1D11 and 4E08 was monitored. Briefly, the solution containing CLCs was spotted in a µ-slide wells plate, before being incubated with a fixed concentration (8 mg/mL) of one of the four lead anti-galectin-10 antibodies. For each well, imaging positions were defined, and each position was imaged every 3-5 minutes. These experiments showed that several anti-galectin antibodies can solubilize recombinant CLC crystals in 1 to 2 hours, whereas irrelevant control isotype antibodies cannot (FIG. 9A). Furthermore, these high-resolution time-lapse experiments show that the CLC crystals diminish in size almost exclusively along their longest axis.

Figure 9B:
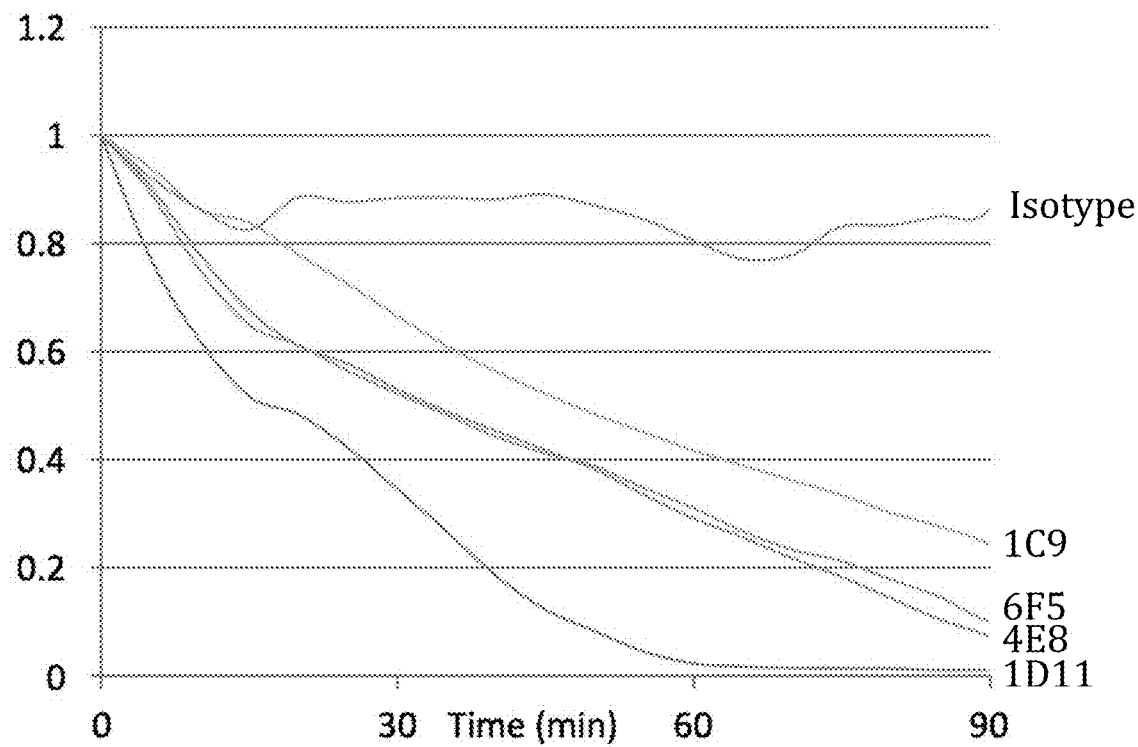

Clone 1D11 showed the best capacity to dissolve the pre-existing CLCs (FIG. 9B), where full dissolution was reached after 1 hour. The clones 6F05 and 4E08 showed similar dissolution capacity, with more than 90% CLC dissolution after 90 minutes of incubation. The mouse isotype control showed no effect on the CLCs; however, due to the displacement of the CLCs on the field, the software mis-interpreted this as a diminution of the space occupied by the CLCs.

B. Characterisation of the Binding Properties of 6F05, 1C09, 1D11 and 4E08 in Fab Format The four clones of interest were reformatted as Fab fragments. As a first step the VH and the VL of each clone were PCR amplified using specific primers, purified by electrophoresis, digested with restriction enzymes (BsmBi) and ligated in the pre-digested vectors containing the human constant domains: the human lambda constant domain for the VL (pUPEX116.9) or the CH1 constant domain for the VH (pUPEX86, including part of the hinge region). The transformation of each ligated products was done into Top10 bacteria by heat shock and transferred on agarose plate with Ampicillin (resistance gene of the vectors). After one night of incubation, ligated products showed high number of single colonies whereas no colony was observed for the negative controls (empty vectors). Per clones (VH and VL), four to eight colonies were picked and sent for sequencing. The clones that showed the proper insert were selected and amplified in order to purify the DNA sequence (MidiPrep). The production of the 4 lead clones was initiated in mammalian cells. Transfection was performed with a ratio 1 heavy chain to 1 light chain incorporated in HEK293E cells via the polyethylenimine (PEI). After 10 days of production, human Fab were purified using the Capture Select IgG-CH1 sepharose beads. Finally, SDS-PAGE analysis was carried out to assess the conformation, the purity and the integrity of the Fab molecules (55 kDa).

The binding properties of the lead antibodies in Fab format was evaluated in ELISA binding and BLI binding, using an OctetRed96 in accordance with the protocols described above. The ELISA binding data (see Table 12 below), showed that the 4 lead antibodies could be separated into 2 groups based on their binding capacity to coated galectin-10-His. The clones 1C09 and 1D11 showed the best relative binding capacity, with an EC50 value between 1.6-1.9 nM, whereas the clones 4E08 and 6F5 showed lower binding potency with an affinity between 25.6-26.7 nM.

TABLE 12

Characterization of the binding properties of the 4 lead anti-galectin-10 antibodies (Fab format) by ELISA

| Construct (Fab) | Bmax | EC50 (nM) |
| --- | --- | --- |
| 1C09 | 1.0 | 1.9 |
| 1D11 | 0.9 | 1.6 |
| 4E08 | 0.7 | 25.6 |
| 6F05 | 0.8 | 26.7 |

The binding data, obtained with the BLI technology, showed similar results, with the clones 1C09 and 1D11 having the best binding capacity (KD between 10-13 nM, kd's between $3\text{-}3.8^{E\text{-}04}$ (1/s)), and the clones 4E08 and 6F05 showing weaker binding (KD between 147-188 nM, kd's between $25\text{-}35^{E\text{-}04}$(1/s)) —see Table 13.

TABLE 13

Characterization of the binding properties of the 4 lead anti-galectin-10 antibodies (Fab format) by BLI technology

| Construct (Fab) | KD (nM) | kd 1E−04 (1/s) |
| --- | --- | --- |
| 1C09 | 13.4 | 3.83 |
| 1D11 | 10.7 | 2.99 |
| 4E08 | 147 | 24.8 |
| 6F05 | 188 | 35.6 |

Example 12. Crystal Structure of Galectin-10 Fab Fragments in Complex with Galectin-10

The crystal structure of different Fab fragments in complex with galectin-10 was obtained, revealing how galectin-10 antibodies could dissolve existing crystals. For structural studies Fab fragments of selected antibodies (1D11, 6F5, 4E8, 1C9) were produced in HEK293 cells. Recombinant His-tagged galectin-10 at 1 mg/mL was digested with TEV at room temperature overnight using a TEV:galectin-10 ratio of 1:100. Next, purified Fab was added to digested galectin-10 in 1.25 molar excess. Next, the protein mixture was injected on a HiLoad 16/600 Superdex 200 µg column running on HBS buffer to isolate the galectin-10:Fab complex. Fractions corresponding to the galectin-10:Fab complex were pooled and stored at −80° C. until further use. Galectin-10:Fab complexes were concentrated to 6-7 mg/mL before crystallization experiments. Sitting-drop nanoliter-scale vapour diffusion crystallization experiments were set up at 293 K using a Mosquito crystallization robot (TTP Labtech) and commercially available sparse-matrix screens (Molecular Dimensions, Hampton research).

Crystals of galectin-10 complexed with Fab 1D11 grew overnight in condition B7 of the ProPlex Screen (Molecular Dimensions—0.2 M ammonium acetate, 0.1 M sodium acetate pH 4.0, 15% $PEG_{4000}$). Galectin-10 complexed with Fab 6F5 crystallized within 24 hrs in condition G7 of the BCS Eco Screen (Molecular Dimensions) (0.04 M $CaCl_2$, 0.04 M Na-formate, 0.1 M PIPES pH 7.0, 8% PEG Smear High). After 2 weeks crystals appeared of galectin-10 in complex with Fab 4E8 in condition B7 of the PEG/Ion screen (Hampton Research) (0.2 M ammonium nitrate, 20% PEG3350).

Before flash-freezing into liquid nitrogen, crystals of the galectin-10:Fab complexes were cryoprotected by briefly soaking the crystals in mother liquor supplement with 25% PEG 400. Diffraction experiments at 100 K were conducted on beamlines Proxima 2A of the SOLEIL synchrotron (Gif-sur-Yvette, France) and ID23-2 of the ESRF (Grenoble, France). All data were integrated and scaled using the XDS suite (Kabsch, 2010). Molecular replacement (MR) was performed with Phaser (McCoy et al., 2007) using search models based on the structure of galectin-10 (PDB 1LCL) and a high-resolution mouse Fab structure (PDB 5X4G). Model (re)building was performed in COOT (Emsley et al., 2010) and individual coordinate and ADP refinement was performed in PHENIX (Adams et al., 2010) and autoBuster (Bricogne et al., 2017). Model and map validation tools in COOT and the PHENIX suite were used throughout the work flow to guide improvement and validate the quality of crystallographic models.

Figure 10A:
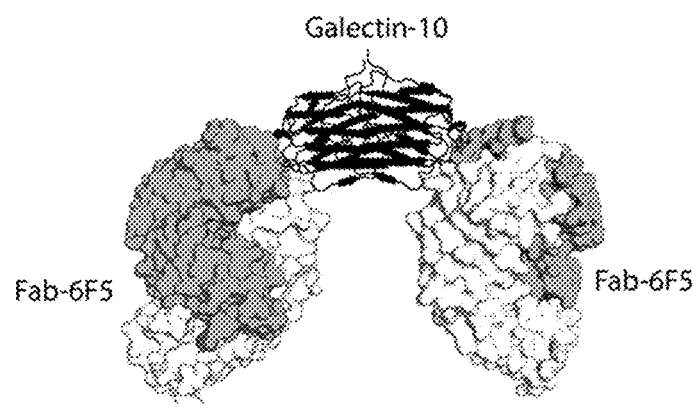
FIGS. 10A-10F: Crystal structure of Fab fragments of crystal dissolving clones in complex with Gal10
Figure 10B:
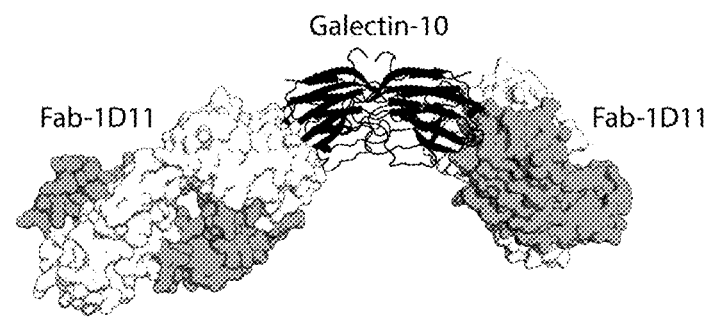
Figure 10C:
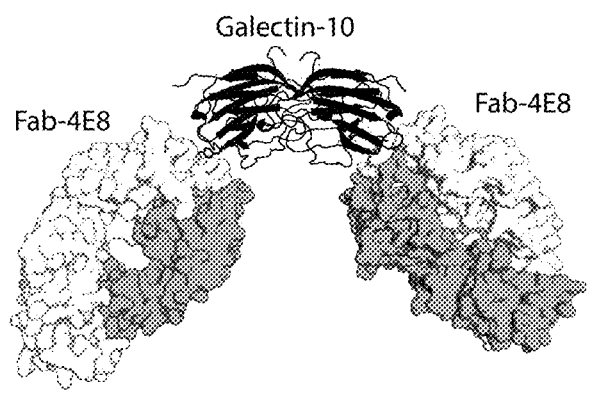
Figure 10D:
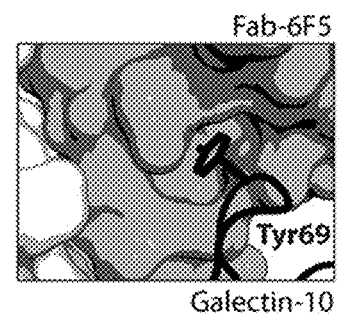
Figure 10E:
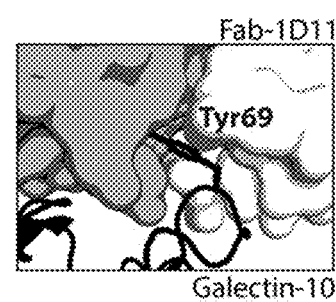
Figure 10F:
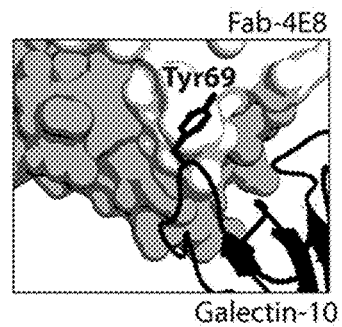

The structure of three different galectin-10:Fab complexes was determined (for antibodies 6F5, 1D11, and 4E8) (FIGS. 10A-10C, Table 17). These structures show that the different antibodies target an epitope on galectin-10 around residue Tyr69 (FIGS. 10D-10F), which was found to be key residue for the autocrystallizing behavior of galectin-10 (FIG. 3A and FIG. 3C).

Figure 11:
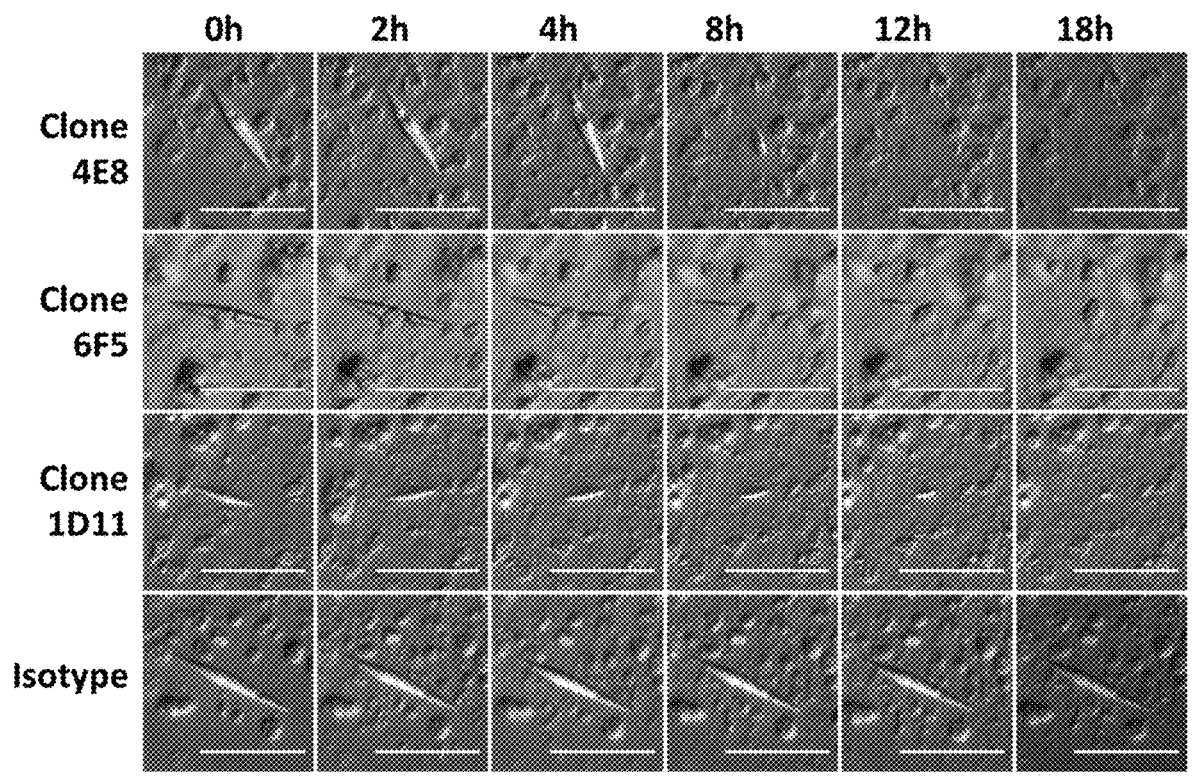
FIG. 11: Solubilization of CLC crystals in the mucus of CRSwNP patients by antibodies Fresh sticky allergic mucin of CRSwNP patients was collected during routine sinus surgery and stored for 2 days prior to addition of crystal dissolving antibodies or isotype control. Crystals could be readily identified in the fresh mucus of patients due to their highly diffractive properties in a spinning disk confocal microscope. Upon addition of crystal dissolving antibodies, the crystals dissolved overnight.

Example 13. Galectin-10 Antibodies Solubilise Patient-Grown Galectin-10 Crystals in Allergic Mucin Ex Vivo The potential of selected clones to solubilize crystals contained in allergic mucin obtained from patients with CRSwNP was studied. These crystals were therefore in a native mucus environment, and grown in vivo. Time-lapse experiments for the antibody-mediated solubilization of human CLCs in mucus were conducted as follows. 4 µL of CLC-containing mucus isolated from a patient was spotted in a well of a chamber microscope slide with glass bottom (Ibidi). Next, 4 µL of anti-galectin-10 or control antibody (at 7 mg/mL) was added to the spotted mucus. To prevent evaporation, the chamber was sealed with vacuum grease and a glass cover slide. The solubilization of human CLC was followed overtime using a spinning disk confocal microscope. Microscopic data was analyzed using Fiji. These time-lapse experiments are shown in FIG. 11. The human CLCs undergo a similar solubilization process as recombinant galectin-10 crystals, but solubilisation took longer. It was however complete by 18 h incubation of the allergic mucin with crystal dissolving antibodies.

Example 14. Galectin-10 Antibodies Inhibit the Airway Inflammation Induced by CLCs Crystal dissolving antibodies were administered to humanized NRG mice reconstituted with PBMCs of an HDM allergic asthmatic individual (Perros et al., Allergy 64(7): 995-1002 (2009)). Since mice do not produce galectin-10 crystals and the PBMC fraction does not contain human eosinophils (the source of endogenous galectin-10 in humans), galectin-10 crystals were administered to the airways of mice together with HDM challenge. It is exceedingly difficult to adoptively transfer viable human eosinophils to mice which is why the galectin-10 crystals had to be administered intratracheally at the time of the HDM allergen exposure. When CLCs were observed in the mice at day 28 of the protocol, they were always associated with Periodic Acid Schiff (PAS)-positive mucus inside the airways, just as seen in patients, adding validity to the adoptive transfer approach.

On day 0, NOD Rag$^{-/-}$ γc$^{-/-}$ (NRG) mice were reconstituted by intraperitoneal injection of 3×10$^6$ PBMCs. On days 1-4 and 7-9, all mice were injected intratracheally with 20 µg of house dust mite (HDM) extract (Greer) diluted in 50 µl of PBS. The use of humanized mice avoided any confounding effects of murine galectin-10 IgG1 antibodies that would inevitably be induced over the time frame of the 28-day protocol.

Figure 12A:
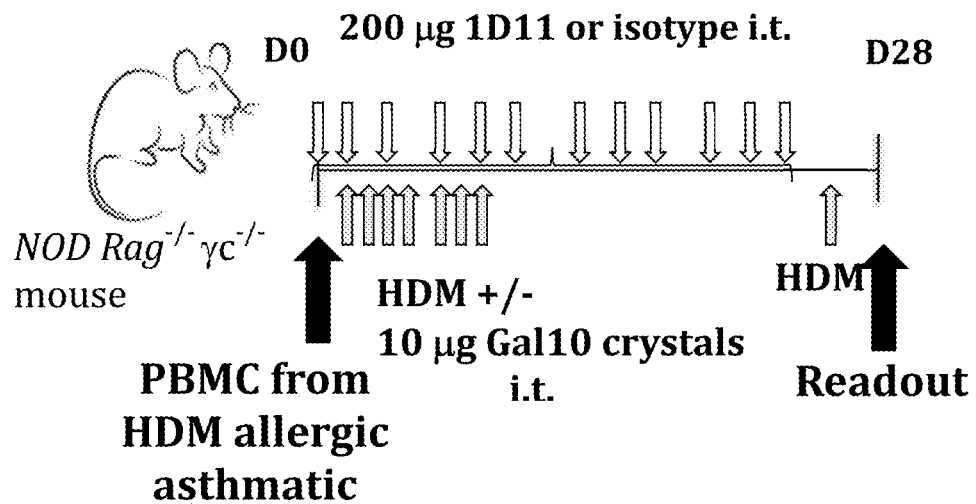
FIGS. 12A-12F: Proof of concept that solubilizing Gal10 crystals in vivo reduce key features of asthma in a humanized mouse model (FIG. 12A) Experimental setup illustrating the dosing regimen of house dust mite (HDM) extracts, galectin-10 crystals and of antibodies. Peripheral blood mononuclear cells (PBMCs) were injected intraperitoneally. House dust mite (HDM) extracts, galectin-10 crystals, 1D11 antibodies and control antibodies were all administered intratracheally.

In experiments addressing the pro-inflammatory effects of galectin-10 crystals, on days 1, 3, 7 and 9 NRG mice were treated with the following regimens: Regimen 1, 200 µg of isotype control antibodies intratracheally (diluted in 30 µl of PBS); Regimen 2, 10 µg of recombinant galectin-10 crystals (1 µl of the stock)+200 µg of isotype control antibodies intratracheally (diluted in 30 µl of PBS); Regimen 3, 10 µg of recombinant galectin-10 crystals (1 µl of the stock)+200 µg of 1D11 antibodies intratracheally (diluted in 30 µl of PBS) (FIG. 12A).

From day 11 onwards, mice received i.t. injections of 200 µg of isotype antibody or 200 µg of 1D11 antibody three times per week until the day of sectioning. On day 27, all mice were challenged one final time intratracheally with 20 µg of house dust mite extract (Greer) diluted in 80 µl of PBS. All mice were sacrificed on day 28.

Figure 12B:
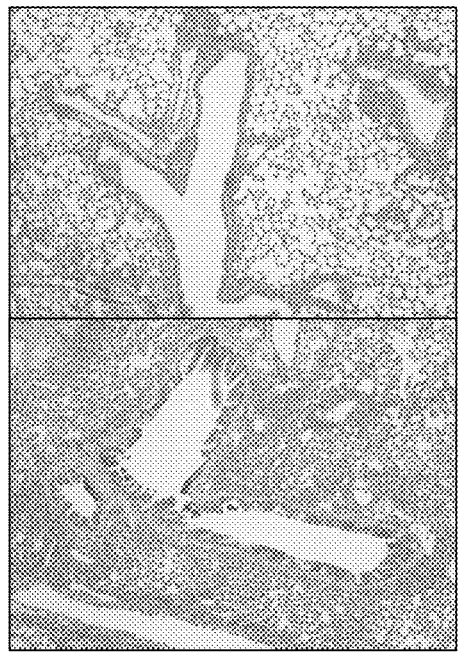
Figure 12B:
Figure 12C:
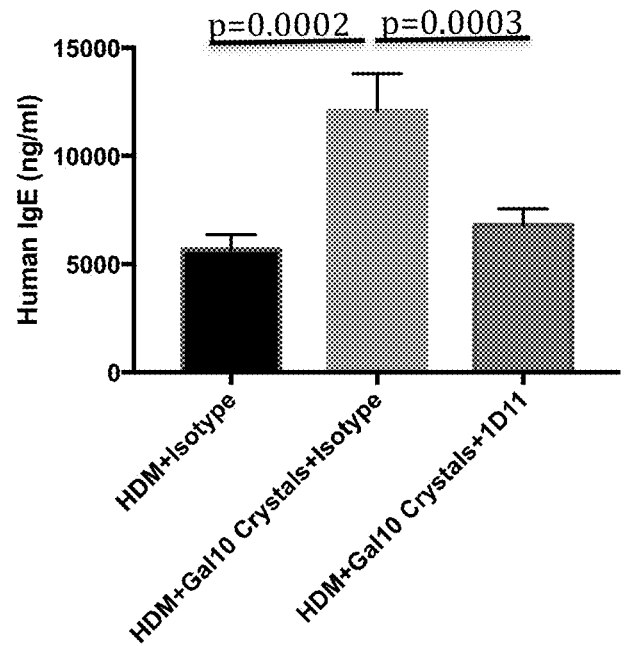
Figure 12D:
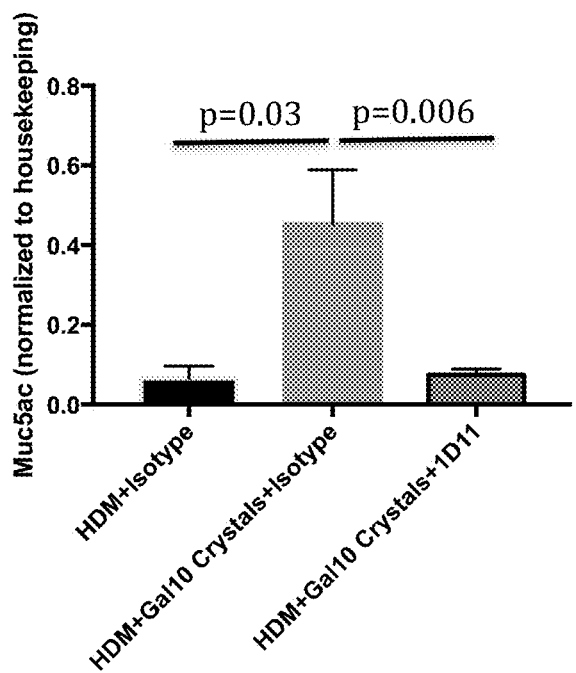
Figure 12E:
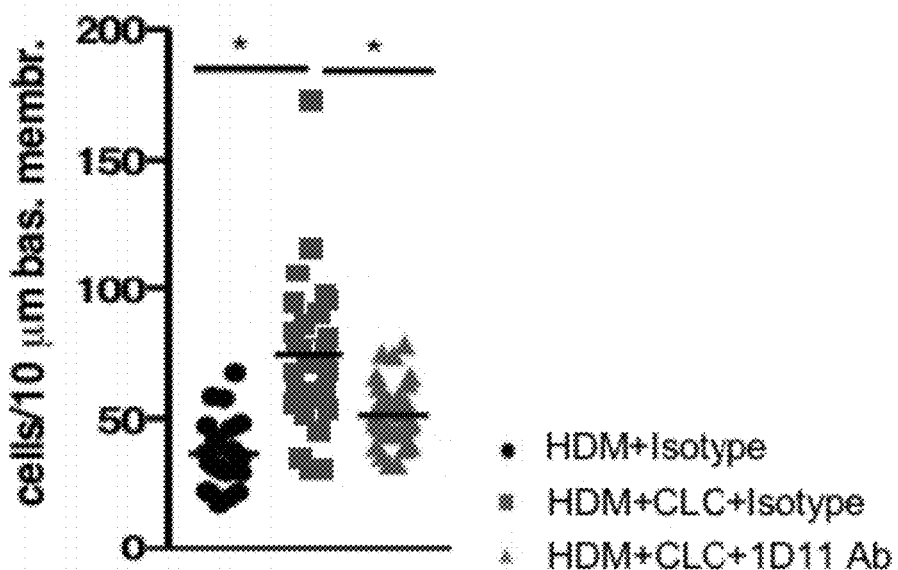

After 28 days, the degree of lung inflammation (FIG. 12B) was considerably higher in mice receiving galectin-10 crystals+isotype versus isotype alone during the HDM challenge period. Treatment with 1D11 antibody reversed the enhancing effect of galectin-10 crystals on lung inflammation. Furthermore, an investigator-blinded morphometric analysis (using QuPath image analysis software for pathology) was performed to assess the degree of cell influx in a perimeter of 500 µm from the basement membrane of the airways. This analysis revealed a markedly increased influx of inflammatory cells around the airways (FIG. 12E).

The degree of IgE synthesis (FIG. 12C) was assessed by ELISA (see example 7). After 28 days, the serum concentration of IgE (FIG. 12C) was considerably higher in mice receiving galectin-10 crystals+isotype versus isotype alone during the HDM challenge period. Treatment with 1D11 antibody reversed the enhancing effect of galectin-10 crystals on IgE concentration.

The presence of goblet cell metaplasia, measured using mucin MUC5AC mRNA levels, was also assessed. For this, frozen lung tissue was collected in an eppendorf tube and 1 ml of Tripure was added. Tissue was homogenized using a tissue homogenizer. To extract RNA, 200 µl of chloroform was added to the tubes containing the homogenized lung. After an incubation period of 5 minutes, tubes were centrifuged at 12000 g for 15 minutes. The upper transparent phase was collected in an RNase-free eppendorf, and was mixed with 500 µl of isopropanol and 1 µl of glycogen for 10 minutes. The tubes were centrifuged at 12000 g for 5 minutes. The supernatant was discarded, and the pellet containing the purified RNA was washed in 75% ethanol (centrifugation at 7500 g for 5 minutes). The pellet was air dried for 10 minutes at room temperature and was resuspended in 20 µl of RNase-free water. The tubes were placed for 10 minutes at 60° C. The concentration of RNA was determined in each sample using a Nanodrop instrument. 1

µg of RNA was used to make cDNA using the sensifast cDNA synthesis kit (Bioline). The leftover RNA was frozen at −80° C. The cDNA was diluted 10 times in water, and frozen until further use. To perform real time PCR, the following mastermix was used for each well of the PCR plate: 10 µl of Sensifast SYBR No-Rox mix, 4.75 µl water, 5 µl of cDNA. 0.125 µl of forward primer and 0.125 µl of reverse primer (taken from a 100 µM stock) were added to each PCR reaction. Primers used were the following: murine Muc5ac (Fwd: CTCCGTCTTAGTCAATAACCACC (SEQ ID NO: 156); Rev: GGAACTCGTTGGATTTTGGACTG (SEQ ID NO: 157)); Murine GAPDH as housekeeping (Fwd: ACAAAATGGTGAAGGTCGGTG (SEQ ID NO: 158); Rev: TGGCAACAATCTCCACTTTGC (SEQ ID NO: 159)).

After 28 days, the mRNA concentration of Muc5AC (FIG. 12D) was considerably higher in mice receiving galectin-10 crystals+isotype versus isotype alone during the HDM challenge period. Treatment with 1D11 antibody reversed the enhancing effect of galectin-10 crystals on MUCSAC mRNA concentration. More detailed histological analysis revealed markedly enhanced goblet cell metaplasia and mucus production, as visualized by enhanced PAS staining of lung epithelial cells that had the typical granule-rich aspect of goblet cells.

Figure 12F:
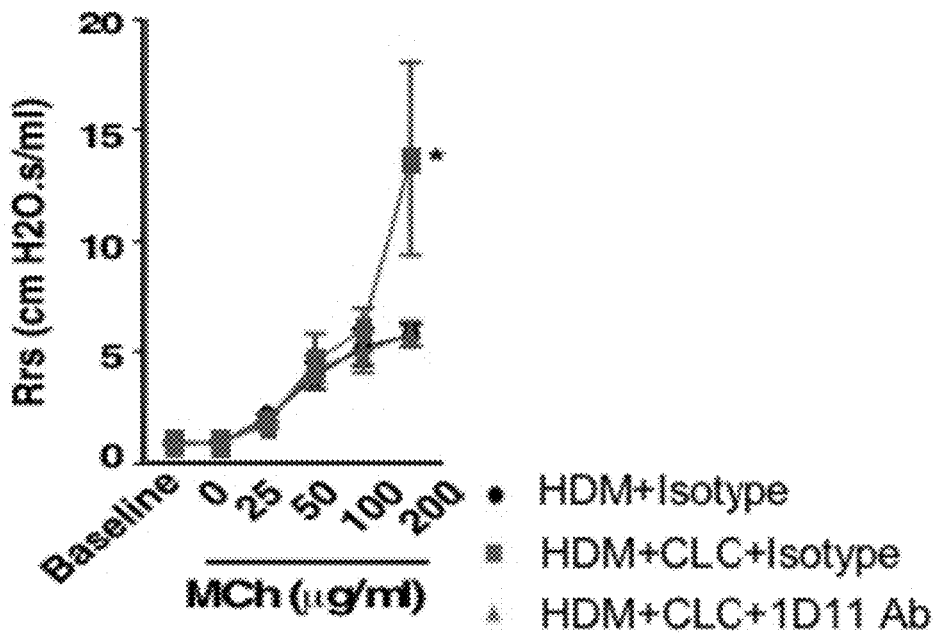

Bronchial hyperreactivity (BHR) was also assessed in the mouse model since BHR is an essential feature of asthma. The effect of CLC administration on responsiveness of mechanically ventilated mice to the inhaled bronchoconstrictor methacholine was assessed using the FlexiVent invasive measurement of dynamic resistance (Hammad et al., J. Exp. Med. 204: 357-67 (2007)). In brief, mice were anesthetized with urethane and paralyzed using D-tubocurarine, tracheotomized and intubated with an 18G catheter, followed by mechanical ventilation by a Flexivent apparatus. Increasing concentrations of methacholine (0-200 µg/ml) were aerosolized via the catheter. Dynamic resistance (rrs) was recorded after a standardized inhalation maneuver given every 10 seconds for 2 minutes after methacholine administration. Addition of CLCs to HDM boosted the degree of bronchoconstriction compared with HDM alone and treatment with 1D11 completely neutralized this effect (see FIG. 12F).

TABLE 14

Heavy chain CDR sequences of scFv antibodies binding to galectin-10

| scFv clone | CDR1 | SEQ ID NO: | CDR2 | SEQ ID NO: | CDR3 | SEQ ID NO: |
|---|---|---|---|---|---|---|
| 1D11 | DYAMS | 1 | GISWNGGSTYYAESMKG | 2 | DRNLGYRLGYPYDY | 3 |
| 6F05 | SYAMS | 4 | AINSGGGSTSYADSVKG | 5 | PGDRLWYYRYDY | 6 |
| 4E08 | TSYYAWS | 7 | VIASDGSTYYSPSLKS | 8 | YIRGSSWSGWSAYDY | 9 |
| 1C09 | TNSYYWS | 10 | AIAYSGSTYYSPSLKS | 11 | RPNWYRALDA | 12 |
| 3A03 | VYAMS | 13 | DINTSGDSTTYADSVKG | 14 | RYTQE | 15 |
| 1A12 | SYYMS | 16 | AINSGGGSTYYADSVKG | 17 | NGGIWSFGS | 18 |
| 2E11 | SYAMS | 4 | PINSGSDSASYVDSVKG | 19 | ARTSVVAGGMDY | 20 |
| 4G05 | RYWMI | 21 | SIYNDGGNTYYADSVKG | 22 | LKAAYYGMDY | 23 |
| 2C07 | SYAMS | 4 | NINSGGGSTGYADSVKG | 24 | YLRTYYPNAAFGMDY | 25 |
| 4B10 | NYWMY | 26 | AIDVGGGTTDYAGSVKG | 27 | GGSYYGGMDY | 28 |
| 6A11 | AYAMN | 29 | GVNSGGGLTSYGESVKG | 30 | SKRGAVVAGTGDDY | 31 |
| 4H10 | DYAMS | 1 | AISWNGGSTYYAESMKG | 32 | DLSASGSYYHTFGS | 33 |
| 6F11 | TGPYSWS | 34 | YIGYSGSTYYSPSLKS | 35 | SRSSPTTFGMDY | 36 |
| 2B11 | TNYYYWS | 37 | AIAYSGSTYYSPSLKS | 11 | APYGISREYDY | 38 |
| 5E12 | NYPMT | 39 | AINGGGDIPYYADSVKG | 40 | QKWGYDPRRTDFEF | 41 |
| 6A05 | SYAMS | 4 | AINSGGGWTSYVDSVKG | 42 | YSGPELNTQYGMDY | 43 |
| 6A08 | SYAMS | 4 | AINRGGGSTYYADSVKG | 44 | PGDRLWYYRYDY | 6 |
| 2F09 | TNYFYWS | 45 | AIAYSGRTYYSPSLKS | 46 | GPKGLASYYDY | 47 |
| 6F06 | RYSMS | 48 | TINSGGGSTSYVDSVKG | 49 | SQGGISFSTQYGMDY | 50 |
| 6B06 | TNYYSWS | 51 | YIAYSGSTSYSPSLKS | 52 | SRSSPTTFGMDY | 36 |
| 6E10 | SYWMY | 53 | AINTGGGSTYYADSVKG | 54 | AGSGVAGTGYDY | 55 |

TABLE 15

Light chain CDR sequences of scFv antibodies binding to galectin-10

| scFv clone | CDR1 | SEQ ID NO: | CDR2 | SEQ ID NO: | CDR3 | SEQ ID NO: |
|---|---|---|---|---|---|---|
| 1D11 | AGTSSDVGYGNYVS | 56 | EVNKRAS | 57 | ASYRSSNNAV | 58 |
| 6F05 | AGTSSDIGYGNYVS | 59 | KVSRRAS | 60 | ASYRYRNNVV | 61 |
| 4E08 | QGGNFGYYYGS | 62 | KDSERPS | 63 | QSADSSDNPV | 64 |
| 1C09 | QGANLGRYYGI | 65 | GDSNRPS | 66 | QSYESSTSPV | 67 |
| 3A03 | KPGRTLVHTDGRTYLY | 68 | QVSNRGS | 69 | AQATYYPLT | 70 |
| 1A12 | QGGNFGYYYVS | 71 | GDSNRPS | 66 | LSYESSDYPV | 72 |
| 2E11 | QGGKFGSYYVS | 73 | KDNERPS | 74 | QSGSSSDNIV | 75 |
| 4G05 | QGANLGRYYGI | 65 | GDSNRPS | 66 | QSYESSTSPV | 67 |
| 2C07 | QGGNFGRYYAS | 76 | RDSERPS | 77 | QSGRSSDNAV | 78 |
| 4B10 | QGAKLGRYYGI | 79 | GDSNRPS | 66 | QSYESSTSPV | 67 |
| 6A11 | QGGNFGRYYVS | 80 | KDSERPS | 63 | QSGSSSDNAV | 81 |
| 4H10 | AGTSSDVGYGDYVS | 82 | KVKTRAS | 83 | ASYKNGGTAV | 84 |
| 6F11 | QGGDFGRYYVA | 85 | QDSERPS | 86 | QSGISSDNIV | 87 |
| 2B11 | QGGKFGRYYAS | 88 | KDSERPS | 63 | QSGRSSDNAV | 78 |
| 5E12 | KSSQSVRIESNHKTYLN | 89 | DASSRES | 90 | QQAYAAPT | 91 |
| 6A05 | QGGNFGSYYAS | 92 | RDSGRPS | 93 | QSGSSSDNTV | 94 |
| 6A08 | GLSSGSVTSSNYPG | 95 | NTNSRYS | 96 | ALNRVRGTYRV | 97 |
| 2F09 | QGGNFGYYYVS | 71 | RDSGRPS | 93 | QSGSSSDNTV | 94 |
| 6F06 | QGGNFGRYYAN | 95 | KDSERPS | 63 | QSGSVSDNAV | 96 |
| 6B06 | QGGNFGRYYVS | 80 | QDSERPT | 97 | QSGTSSDNIV | 98 |
| 6E10 | QGGNFGYYYVS | 71 | RDSGRPS | 93 | QSGSSSDNAV | 81 |

TABLE 16

VH and VL sequences of scFv antibodies binding to galectin-10

| scFv clone | VH | SEQ ID NO: | VL | SEQ ID NO: |
|---|---|---|---|---|
| 1D11 | QVQLVESGGGLVQPGGSLRLSCAASGF TFDDYAMSWVRQAPGKGLEWVSGISWN GGSTYYAESMKGRFTISRDNAKNTLYLQ MNSLKSEDTAVYYCAKDRNLGYRLGYPY DYWGQGTQVTVSS | 99 | QSVLTQPPSVSGSPGETVTISCAGTSSDVGYGN YVSWYQQLPGMAPRLLIYEVNKRASGITDRFSG SKSGNTASLTISGLQSEDEGDYYCASYRSSNNA VFGGGTHLTVL | 100 |
| 6F05 | QLQLVESGGGLVQPGGSLRLSCAASGFT FSSYAMSWVRQAPGKGLEWVSAINSGG GSTSYADSVKGRFTISRDNAKNTLYLQM NSLKPEDTAVYYCATPGDRLWYRYDY WGQGTQVTVSS | 101 | QAGLTQPPSVSGTLGKAVTISCAGTSSDIGYGNY VSWYQQLPGTAPKLLIYKVSRRASGVPDRFSGS KSGNTASLSISGLQSEDEADYYCASYRYRNNVV FGGGTHLTVL | 102 |
| 4E08 | QVQRQESGPGLVKPSQTLSLTCTVSGGS ITTSYYAWSWIRQPPGKGLEWMGVIASD GSTYYSPSLKSRTSISRDTSKNQFSLQLS SVTPEDTAVYYCALYIRGSSWSGWSAYD YWGQGTQVTVSS | 103 | QPVLNQPSAVSVSLGQTARITCQGGNFGYYYGS WYQQKPGQAPVLVIYKDSERPSGIPERFSGSSS GGTATLTISRAQAEDEADYYCQSADSSDNPVFG GGTHLTVL | 104 |
| 1C09 | QVQLVESGPGLVKPSQTLSLTCTVSGGSI TTNSYYWSWIRQPPGKGLEWMGAIAYS GSTYYSPSLKSRTSISRDTSKNQFTLHLS SVTPEDTAVYYCARRPNWYRALDAWGQ GTLVTVSS | 105 | NFMLTQPSAVSVSLGQTARITCQGANLGRYYGI WYQQKPGQAPVQVIYGDSNRPSGIPERFSGSSS GGTATLTISGAQAEDEADYYCQSYESSTSPVFG GGTHLTVL | 106 |

TABLE 16-continued

VH and VL sequences of scFv antibodies binding to galectin-10

| scFv clone | VH | SEQ ID NO: | VL | SEQ ID NO: |
|---|---|---|---|---|
| 3A03 | QVQLVESGGGLVQPGGSLRLSCATSGFT FSVYAMSWVRQAPGKGLEWVADINTSG DSTTYADSVKGRFTISRDNAKNTLYLQM NSLKPEDTAVYYCANRYTQERGQGTQV TVSS | 107 | DVVLTQTPGSLSVVPGEAASISCKPGRTLVHTDG RTYLYWLQQKPGQRPQLLIYQVSNRGSGVPDRF TGSGSGTDFTLKISGVKAEDAGVYYCAQATYYP LTFGSGTRLEIK | 108 |
| 1A12 | QVQLVESGGGLVQPGGSLRVSCAASGF TFSSYYMSWVRQAPGKGLEWVSAINSG GGSTYYADSVKGRFTISRDNAKNTLYLQ MNSLKSEDTAVYYCVQNGGIWSFGSWG QGTQVTVSS | 109 | SSALTQPSAISVSLGQTARITCQGGNFGYYYVS WYQQKPGQAPVQVIYGDSNRPSGIPERFSGSSS GGTATLTISGAQAEDEADYYCLSYESSDYPVFG GGTHLTVL | 110 |
| 2E11 | EVQLVESGGGLVQPGGSLRLSCAASGFT FSSYAMSWVRQAPGKGLEWVSPINSGS DSASYVDSVKGRFTISRDNAKNTLYLQM NSLKPEDTAVYYCAKARTSVVAGGMDY WGKGTLVTVSS | 111 | QSALTQPSAVSVSLGQTARITCQGGKFGSYYVS WYQQKPGQAPVMVIYKDNERPSGIPERFSGSSS GSTSTLTISGAQAEDEGTYYCQSGSSSDNIVFG GGTELTVF | 112 |
| 4G05 | QLQVVESGGGLVQTGGSLTLSCTTSGFT FSRYWMIWVRQAPGKGLEWVSSIYNDG GNTYYADSVKGRFTISRDNSENTLYLQM NSLKSEDTAVYYCAKLKAAYYGMDYWG KGTLVTVSS | 113 | SSALTQPSAVSVSLGQTARITCQGANLGRYYGI WYQQKPGQAPVQVIYGDSNRPSGIPERFSGSSS GGTATLTISGAQAEDEADYYCQSYESSTSPVFG GGTHLTVL | 114 |
| 2C07 | ELQLVESGGGLVQPGGSLRLSCAASGFT FSSYAMSWVRQAPGKGLEWVSNINSGG GSTGYADSVKGRFTISRDNAKNTLYLQM NSLKPEDMAVYYCAKYLRTYYPNAAFGM DYWGKGTLVTVSS | 115 | QAVLTQPSAVSVSLGQTARITCQGGNFGRYYAS WYQQKPGQAPVLVIYRDSERPSGIPERFSGSSS GDTATLTISGAQAEDEADYYCQSGRSSDNAVFG GGTHLTGL | 116 |
| 4B10 | QLQLVESGGGLVQPGGSLRLSCAASGFT FSNYWMYWVRQAPGKGLEWVSAIDVGG GTTDYAGSVKGRFTISRDNTKSTVYLQM NTLKPEDTALYYCLRGGSYYGGMDYWG KGTLVTVSS | 117 | QSALTQPSAVSVSLGQTARITCQGAKLGRYYGI WYQQKPGQAPVQVIYGDSNRPSGIPERFSGSSS GGTATLTISGAQAEDEADYYCQSYESSTSPVFG GGTHLTVL | 118 |
| 6A11 | ELQLVESGGGLVQPGGSLRLSCSASGFT FGAYAMNWVRQAPGKGLEWVSGVNSG GGLTSYGESVKGRFTISRDNAKNTLYLQ MNRLNPDDTAVYYCAKSKRGAVVAGTG DDYWGQGTQVTVSS | 119 | SSALTQPSAVSVSLGQTARITCQGGNFGRYYVS VVYQQKPGQAPVLVIYKDSERPSGIPERFSGSSS GDTATLTISGAQAEDEADYYCQSGSSSDNAVFG GGTHLTVL | 120 |
| 4H10 | QVQLVESGGGLVQPGGSLRLSCAASGF TFDDYAMSWVRQAPGKGLEWVSAISWN GGSTYYAESMKGRFTISRDNAKNTLYLQ MNSLKSEDAAVYYCAKDLSASGSYYHTF GSWGQGTQVTVSS | 121 | QAGLTQPPSVAGTLGKTVTISCAGTSSDVGYGD YVSWYQHIPGTAPKLLIYKVKTRASGIPDRFSGS KSGNTASLTISGLQSGDESDYYCASYKNGGTAV FGGGTHLTVL | 122 |
| 6F11 | QVQRQESGPGLVKPSQTLSVTCTVSGG SITTGPYSWSWIRQPPGKGLEWIGYIGYS GSTYYSPSLKSRTSISRDTSNNQFSLQLS SVTPEDTAVYYCARSRSSPTTFGMDYW GKGTLVTVSS | 123 | SSALTQPSAVSVSLGQTARITCQGGDFGRYYVA WYTQKPGQAPVLVIYQDSERPSGIPERFSGSSS GDTATLTISGAQAEDEAEYYCQSGISSDNIVFGG GTHLTVL | 124 |
| 2B11 | QVQLQESGPGLVKPSQTLSLTCTVSGGS ITTNYYYWSWIRQPPGKGLEWMGAIAYS GSTYYSPSLKSRTSISRDTSKNQFTLQLS SVTPEDTAVYYCARAPYGISREYDYWGQ GTQVTVSS | 125 | HSAVTQPSAVSVSLGQTARITCQGGKFGRYYAS WYQQKPGQAPVLVIYKDSERPSGIPERFSGSSS GDTATLSISGAQAEDEADYFCQSGRSSDNAVFG GGTHLTVL | 126 |
| 5E12 | QLQLVESGGGLVQPGGSLRLSCVASGFT FRNYPMTWVRQAPGKGPEWVSAINGGG DIPYYADSVKGRFTISRDNAKNTVYLQMD SLKPEDTAMYYCAKQKWGYDPRRTDFE FRGQGTQVTVSS | 127 | ETVPTQSPSSVTASVGEKVTITCKSSQSVRIESN HKTYLNWYQQRPGRGPRLLIYDASSRESGIPDR FSGSGSTSDFTLTISSVQPEDAAVYYCQQAYAA PTFGQGTKLEIK | 128 |
| 6A05 | EVQLVESGGGLVQPGGSLRLSCAASGFT FSSYAMSWVRQAPGKGLEWVSAINSGG GWTSYVDSVKGRFTISRDNAKNTLYLQM DSLKPEDTAVYYCTKYSGPELNTQYGMD YWGKGTLVTVSS | 129 | NFMLTQPSAVSVSLGQTARITCQGGNFGSYYAS WYQQKPGQAPVLVIYRDSGRPSGIPERFSGSSS GDTATLTISGAQAEDEADYYCQSGSSSDNTVFG GGTHLTVL | 130 |

TABLE 16-continued

VH and VL sequences of scFv antibodies binding to galectin-10

| scFv clone | VH | SEQ ID NO: | VL | SEQ ID NO: |
|---|---|---|---|---|
| 6A08 | QVQLVESGGGLVQPGGSLRLSCAASGF TFSSYAMSWVRQAPGKGPEWVSAINRG GGSTYYADSVKGRFTISRDNAKNTLYLQ MNSLKPEDAAVYYCATPGDRLWYYRYD YWGQGAQVTVSS | 131 | QTVVTQEPSLSVSPGGTVTLTCGLSSGSVTSSN YPGWYQQTPGQAPRLLIYNTNSRYSGVPNRFS GSISGNKAALIISGAQPEDEADYHCALNRVRGTY RVFGGGTHLTVL | 132 |
| 2F09 | QVQVQESGPGLVKPSQTLSLTCTVSGGS ITTNYFYWSWIRQSPGKGLEWIGAIAYSG RTYYSPSLKSRTSISRDTSNNQFTLQLSS VTPEDTAVYYCARGPKGLASYYDYWGQ GTQVTVSS | 133 | SSALTQPSAVSVSLGQTARITCQGGNFGYYYVS WYQQKPGQAPVLVIYRDSGRPSGIPERFSGSSS GDTATLTISGAQAEDEADYYCQSGSSSDNTVFG GGTHLTVL | 134 |
| 6F06 | QVQLVESGGGLVQPGGSLRLSCAASEFT FSRYSMSWVRQAPGKGLEWVSTINSGG GSTSYVDSVKGRFTISRDNAKNTLYLQM NSLKPEDTAVYYCTKSQGGISFSTQYGM DYWGKGTLVTVSS | 135 | NFMLTQPSAVSVSLGQTARITCQGGNFGRYYAN WYQQKPGQAPVLVIYKDSERPSGIPERFSGSSS GDTATLTISGAQAEDESDYYCQSGSVSDNAVFG GGTHLAVL | 136 |
| 6B06 | QVQRQESGPGLVKPSQTLSLTCTVSGGS ITTNYYSWSWIRQPPGKGLEWIGYIAYSG STSYSPSLKSRTSISRDTSNNQFSLQLSS VTPEDTAVYYCARSRSSPTTFGMDYWG KGTLVTVSS | 137 | SSALTQPSAVSVSLGQTARITCQGGNFGRYYVS WYTQKPGQAPVLVIYQDSERPTGIPERFSGSSS GDTATLTISGAQAEDEADYYCQSGTSSDNIVFG GGTHLTVL | 138 |
| 6E10 | QLQLVESGGGLVQPGGSLRLSCAASGFT FSSYWMYWVRQAPGKGLEWVSAINTGG GSTYYADSVKGRFTISRDNAKNTLYLQM NSLKPEDTALYYCARAGSGVAGTGYDY WGQGTQVTVSS | 139 | QPVLNQPSAVSVSLGQTARITCQGGNFGYYYVS WYQQKPGQAPVLVIYRDSGRPSGIPERFSGSSS GDTATLTISGAQAEDEADYYCQSGSSSDNAVFG GGTHLTVL | 140 |

TABLE 17

X-ray data and refinement statistics

| | Recombinant Gal10 | Ex vivo CLC crystal | Recombinant Gal10-Tyr69Glu |
|---|---|---|---|
| Beam line | P14 (PetraIII) | P14 (PetraIII) | PXIII (SLS) |
| Ligands | glycerol | glycerol | PG4, PG6, PGE |
| Crystallization conditions | PBS | PBS | 0.2M ammonium sulphate pH 5.1 20% PEG$_{3350}$ |
| cryo | 35% glycerol | 35% glycerol | 25% PEG$_{400}$ |
| Data collection | | | |
| wavelength | 0.9763 | 0.9763 | 0.99998 |
| Space group | P 6522 | P 6522 | P 21 |
| Cell dimensions | | | |
| a, b, c (Å) | 48.88, 48.88, 258.64 | 48.86, 48.86, 257.88 | 72.82, 93.30, 93.07 |
| α, β, γ (°) | 90.00, 90.00, 120.00 | 90.00, 90.00, 120.00 | 90.00, 108.94, 90.00 |
| Resolution (Å) | 50.00-1.34 (1.42-1.34) | 50.00-2.22 (2.35-2.22) | 50.00-2.10 (2.23-2.10) |
| $R_{meas}$ | 7.6 (71.5) | 30.7 (194.6) | 15.4 (227.8) |
| I/σ | 25.64 (5.81) | 7.85 (1.29) | 9.33 (0.70) |
| Completeness (%) | 92.4 (68.3) | 99.9 (99.1) | 99.0 (98.6) |
| Redundancy | 17.9 (14.65) | 11.86 (12.20) | 6.90 (6.74) |
| Wilson B factor | 10.13 | 23.36 | 39.68 |
| Refinement | | | |
| Resolution (Å) | 43.10-1.38 | 43.06-2.30 | 47.30-2.10 |
| No. reflections | 37 604 | 10 056 | 68 227 |
| $R_{work}/R_{free}$ | 16.81/17.94 | 18.26/23.54 | 17.24/20.43 |
| No. atoms | | | |
| Protein | 1248 | 1122 | 6766 |
| Ligand/ion | 6 | 6 | 112 |
| Water | 209 | 129 | 648 |

TABLE 17-continued

X-ray data and refinement statistics

B-factors

| | | | |
|---|---|---|---|
| Protein | 15.04 | 28.68 | 50.77 |
| Ligand/ion | 25.31 | 53.67 | 70.35 |
| Water | 36.26 | 45.50 | 60.13 |

R.m.s. deviations

| | | | |
|---|---|---|---|
| Bond lengths (Å) | 0.005 | 0.010 | 0.010 |
| Bond angles (°) | 0.91 | 1.14 | 1.12 |

| | Recombinant Gal10:Fab-1D11 | Recombinant Gal10:Fab-6F5 | Recombinant Gal10:Fab-4E8 |
|---|---|---|---|
| Beam line | ID23-2 (ESRF) | ID23-2 (ESRF) | Proxima 2A (SOLEIL) |
| Ligands | PG4 | $Ca^{2+}$, PGE | / |
| Crystallization conditions | 0.2M ammonium acetate 0.1M sodium acetate pH 4.0 15% $PEG_{4000}$ | 0.04M CaCl2, 0.04M sodium formate, 0.1M PIPES pH 7.0 8% PEG Smear High | 0.2M ammonium nitrate 20% $PEG_{3350}$ |
| cryo | 25% $PEG_{400}$ | 25% $PEG_{400}$ | 20% $PEG_{400}$ |
| Data collection wavelength | 0.87313 | 0.87313 | 0.980058 |
| Space group | P 21 21 21 | C 2 2 21 | P 21 |
| Cell dimensions | | | |
| a, b, c (Å) | 61.63, 89.22, 249.27 | 59.01, 146.19, 185.70 | 41.33, 150.45, 94.50 |
| α, β, γ (°) | 90.00, 90.00, 90.00 | 90.00, 90.00, 90.00 | 90.00, 96.31, 90.00 |
| Resolution (Å) | 50.00-1.90 (2.02-1.90) | 50.00-1.91 (2.02-1.91) | 50.00-3.39 (3.60-3.39) |
| $R_{meas}$ | 23.4 (137.0) | 23.6 (215.1) | 21.9 (107.0) |
| I/σ | 6.72 (1.30) | 7.67 (1.00) | 5.09 (1.05) |
| Completeness (%) | 99.1 (94.6) | 99.7 (98.3) | 98.4 (98.1) |
| Redundancy | 6.40 (5.99) | 12.85 (11.44) | 3.22 (3.33) |
| Wilson B factor | 20.09 | 25.08 | 81.87 |
| Refinement | | | |
| Resolution (Å) | 46.97-1.90 | 47.24-1.91 | 46.97-3.39 |
| No. reflections | 107 597 | 63 022 | 15 645 |
| $R_{work}/R_{free}$ | 17.47/22.34 | 16.61/20.11 | 31.74/34.44 |
| No. atoms | | | |
| Protein | 8812 | 4452 | 8344 |
| Ligand/ion | 13 | 11 | / |
| Water | 1457 | 835 | / |
| β-factors | | | |
| Protein | 26.14 | 38.06 | 133.84 |
| Ligand/ion | 65.21 | 71.99 | / |
| Water | 40.34 | 52.48 | / |
| R.m.s. deviations | | | |
| Bond lengths (Å) | 0.010 | 0.010 | 0.008 |
| Bond angles (°) | 1.14 | 1.09 | 1.16 |

Example 15. Production of Additional Galectin-10 Antibodies

Additional galectin-10 antibodies were selected by bio-panning against human and cynomolgus galectin-10 and screened by ELISA and BLI for binding to galectin-10 (human and cynomolgus).

The sequences of the three cynomolgus galectin-10 isoforms (WGS, REF and YRT) are shown below together with the human sequence.

```
Human:
MSLLPVPYTEAASLSTGSTVTIKGRPLACFLNEPYLQVDFHTEMKEESDIV

FHFQVCFGRRVVMNSREYGAWKQQVESKNMPFQDGQEFELSISVLPDKYQV

MVNGQSSYTFDHRIKPEAVKMVQVWRDISLTKFNVSYLKR

WGS:
MSLLSVPHTESVSLSTGSTVTIKGRPLVCFLNEPHLQVDFHTEMKEDSDIA

FHFQVYFGNRVVMNSREFKIWKEEVESKNMPFQDGQEFELSILVLEDKYQV

MVNGQAYYNFNHRIPVSSVKMVQVWRDISLTKFNVSN---

REF:
MSLLSVPHTESVSLSTGSTVTIKGRPLVCFFNEPHLQVDFHTEMKEDSDIA

FHFQVYFGNRVVMNSREFKIWKEEVESKNMPFQDGQEFELSILVLEDKYQV

MVNGQAYYNFNHRIPVSSVKMVQVWRDISLTKFNVSN---

YRT:
MSLLSVPHTESVSLSTGSTVTIEARPLVCFFNEPHLQVDFHTEMKEDSDIA

FHFQVYFGNRVVMNSREYRTWKEEVESKNMPFQDGQEFELRILVLEDKYQV

MVNGQAYYNFNHRIPVSSVKMVQVWRDISLTKFNVSN---
```

(Human: SEQ ID NO: 141; WGS: SEQ ID NO: 267; REF: SEQ ID NO: 268; YRT: SEQ ID NO: 269)

Sequence analysis of the human and the 3 cynomolgus isoforms revealed the following:

The isoforms of cynomolgus galectin-10 show 78-81% identity to human galectin-10;

The WGS and the REF isoform differ by a single amino acid at position 31 (F/L);

The YRT isoform shows 6 different amino acids compared to the REF isoform at position 23 (K/E), 24 (G/R), 69 (F/Y), 70 (K/R), 71 (I/T) and 92 (S/R);

Only the YRT isoform has a Tyrosine residue at position 69, as in the human.

Eleven scFv clones that showed binding to galectin-10 were sequenced and reformatted as human Fc fusion molecules, as described in Example 8.

Figure 13:
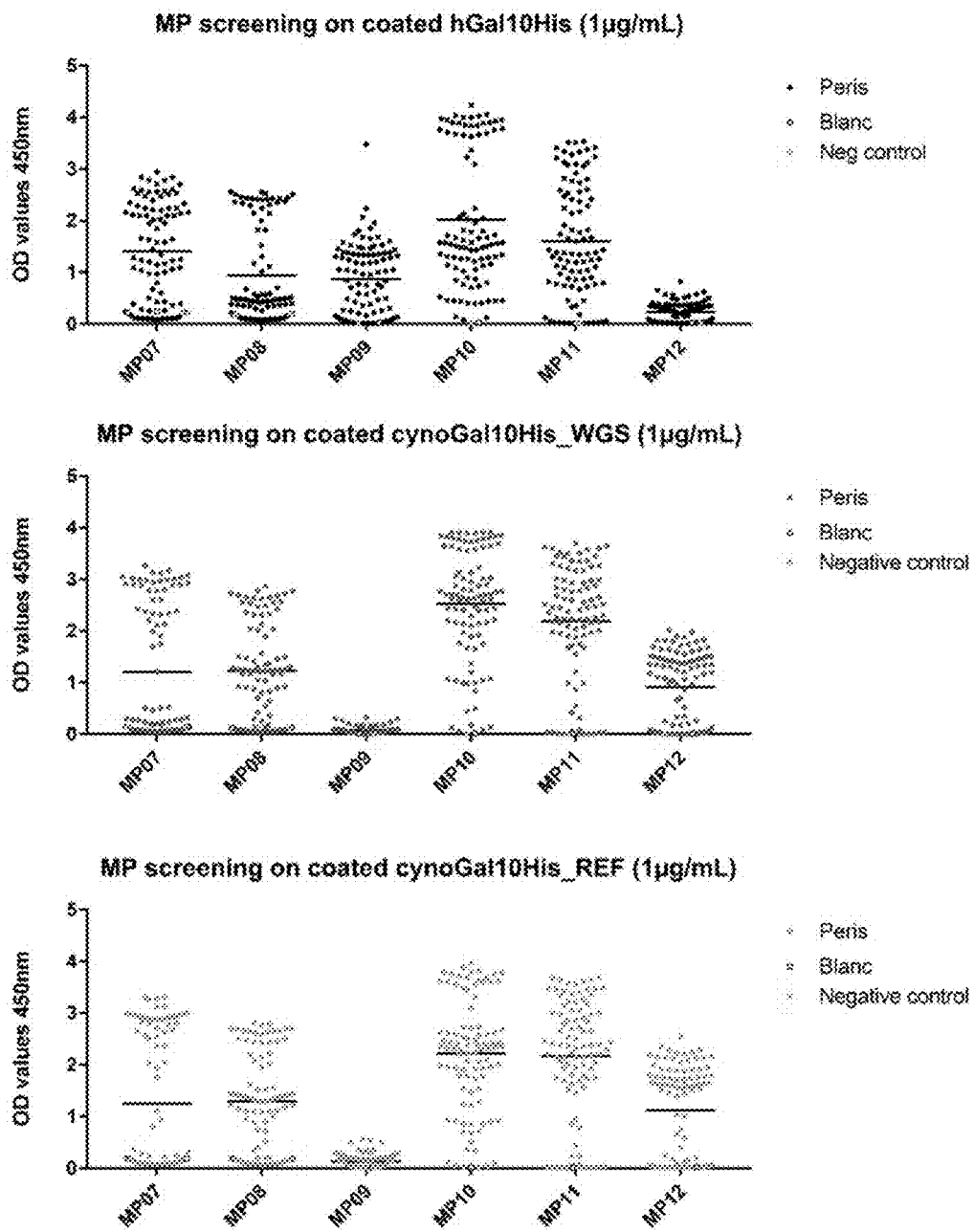
FIG. 13: Screening of scFv periplasmic extracts by ELISA

A. Screening of the scFv by ELISA and Bio-Layer Interferometry (BLI) Technology (i) ELISA Analysis The binding capacity of the scFv (periplasmic extract) to human galectin-10 and the 2 available isoforms of cynomolgus galectin-10 (WGS and REF) was analyzed on ELISA binding. Briefly, a Maxisorp plate was coated overnight with 1 μg/mL of human galectin-10-His or cynomolgus WGS or REF isoform galectin-10-His, then blocked with PBS 1% casein, before being incubated with the periplasmic extract (dilution 1/5 in PBS 0.1% Casein) containing the scFv-Myc tagged. Detection of the binder was carried out with an anti-Myc-HRP antibody (Bethyl, Catalog A190-105P). Then TMB substrate was added and the reaction was stopped with 0.5M $H_2SO_4$. Absorbance was measured at 450 nm (reference at 620 nm) with Tecan instrument. Finally, the raw data (OD values) were plotted using GraphPad Prism 7.01 and are shown in FIG. 13. The number of binders, defined by an OD value higher than 0.5, per MP plate and per library was determined. A blank control and negative control (scFv periplasmic extract binding to irrelevant target) were included and showed, as expected, no binding.

The results showed that a significant number of scFv binding to human or cynomolgus galectin-10 were isolated after the last round of selection. However, significant difference in the enrichment of human cynomolgus binders (REF and WGS isoforms) was observed between master plates, with 10.6-87% of human binders and 0-92.6% of cynomolgus WGS & REF isoforms binders. For both llamas, the Lambda library showed clearly higher percentage of scFv binding to human or cynomolgus galectin-10 than the kappa library. It was particularly the case for the library 1K that showed 0-4% of cynomolgus binders (WGS and REF isoforms). In opposition the library 1 L and 2 L showed 76-92.6% human cynomolgus binders, indicating that the lambda library may be the mean provider of human cynomolgus cross reactive binders. Master plates generated from the condition where acidic pH elution was applied (MP07 and MP08) also showed relatively high percentage of human and cynomolgus binders with 0-60.9% of binders for the Kappa libraries and 76.1-89.1% of binders for the Lambda libraries. As expected and due to their extremely close homology a general trend scFv showed similar binding to the WGS and the REF isoform of the cynomolgus galectin-10-His.

TABLE 18

ELISA binding screening of the scFv periplasmic extracts from MP generated after selection.

| MP number | Library | Galectin-10-His | Hits | % Hits |
|---|---|---|---|---|
| MP07 | 1K | human | 24 | 52.2 |
| | | cynomolgus_WGS | 1 | 2.2 |
| | | cynomolgus_REF | 0 | 0.0 |
| | 1L | human | 41 | 89.1 |
| | | cynomolgus_WGS | 41 | 89.1 |
| | | cynomolgus_REF | 41 | 89.1 |
| MP08 | 2K | human | 5 | 10.9 |
| | | cynomolgus_WGS | 28 | 60.9 |
| | | cynomolgus_REF | 28 | 60.9 |
| | 2L | human | 35 | 76.1 |
| | | cynomolgus_WGS | 36 | 78.3 |
| | | cynomolgus_REF | 38 | 82.6 |
| MP09 | 1K | human | 58 | 61.7 |
| | | cynomolgus_WGS | 0 | 0.0 |
| | | cynomolgus_REF | 4 | 4.3 |
| MP10 | 1L | human | 82 | 87.2 |
| | | cynomolgus_WGS | 87 | 92.6 |
| | | cynomolgus_REF | 87 | 92.6 |
| MP11 | 2L | human | 76 | 80.9 |
| | | cynomolgus_WGS | 80 | 85.1 |
| | | cynomolgus_REF | 79 | 84.0 |
| MP12 | 2K | human | 10 | 10.6 |
| | | cynomolgus_WGS | 59 | 62.8 |
| | | cynomolgus_REF | 59 | 62.8 |

(ii) BLI Analysis

From the six Master plates generated during selection, 321 clones that showed human and cynomolgus binding during the ELISA screening campaign were picked up and their binding capacity was tested on BLI, using the Octet RED96. Briefly, human and cynomolgus WGS or REF isoforms of galectin-10-His tagged were diluted in Kinetic buffer (PBS 0.01% BSA 0.002% Tween 20) at 200 μg/mL before being captured on Anti-Penta His 1K sensor tips (ForteBio, Cat #18-5120) until an immobilization level of 1 nm was reached. Then, diluted periplasmic extracts (1/5 in Kinetic buffer), containing the scFv clone, were applied and association/dissociation to immobilized galectin-10-His was measured using the ForteBio Data analysis 9.0 software (subtraction of the reference Tips, 1.1 binding model). During the screening, only the dissociation (off-rate) of the scFv could be determined since the effective concentration of the scFv was unknown and can vary a lot from clone to clone. The results confirmed that most of the selected scFv clones show human cynomolgus cross-reactivity (see FIG. 14).

B. Characterization of the scFv-Human Fc Panel

ELISA and SPR with a T3000 Biacore were used to assess the binding properties of the scFv-human Fc panel.

(i) ELISA Analysis

In a similar setup to that used during the initial screening, the relative binding properties of the 11 new scFv-human Fc clones were analyzed by ELISA. Briefly, a Maxisorp plate was coated overnight with human or cynomolgus WGS or YRT isoforms of galectin-10-His at 0.2 μg/mL and blocked with PBS 1% casein, before being incubated with a serial dilution of the scFv-human Fc fusion molecules (from 100 nM, dilution 1/5, 8 points of dilutions). After several washing steps, detection of the bound scFv-human Fc was carried out with an anti-human Fc-HRP antibody (Jackson ImmunoResearch, Catalog 109-035-008). Absorbance was measured at 450 nm (reference at 620 nm) with Tecan instrument. Finally, the raw data (OD values) were plotted on GraphPad Prism 7.01. The EC50 values of each clone, calculated with a non-linear regression (log(agonist) vs. response Variable slope (four parameters)) are reported in Table 19 below. As a positive control, clone 6F05 from the previous galectin-10 antibody panel was included.

TABLE 19

ELISA binding characteristics of the panel of scFv-human Fc galectin-10 antibodies

| Clone (scFv-human Fc) | humanGal10-His (0.2 µg/mL) | | cynoGal10-His_WGS (0.2 µg/mL) | | cynoGal10-His_YRT (0.2 µg/mL) | |
|---|---|---|---|---|---|---|
| | Bmax | EC50 (nM) | Bmax | EC50 (nM) | Bmax | EC50 (nM) |
| 7B07 | 0.6 | 1.11 | 0.6 | 0.82 | 0.0 | No binding |
| 7C05 | 1.0 | 0.67 | 1.5 | ambiguous | 2.1 | 2.53 |
| 7D10 | 1.5 | ambiguous | 2.3 | ambiguous | 2.3 | ambiguous |
| 7E09 | 2.0 | 1.48 | 2.9 | 1.66 | 2.3 | 1.64 |
| 8H11 | 2.3 | 0.18 | 3.1 | 0.13 | 3.1 | 0.10 |
| 10A06 | 1.2 | 0.08 | 2.5 | 0.10 | 3.0 | 0.04 |
| 10B02 | 2.2 | 0.09 | 3.3 | 0.05 | 3.2 | 0.05 |
| 10D02 | 1.9 | 0.56 | 3.1 | 1.12 | 2.0 | 1.40 |
| 10H06 | 1.9 | 0.63 | 2.9 | 0.90 | 2.4 | 0.96 |
| 11F02 | 1.5 | 0.77 | 2.5 | ambiguous | 2.5 | ambiguous |
| 11F12 | 1.8 | 0.56 | 3.1 | 0.23 | 3.0 | 0.24 |
| 6F05 | 2.4 | 0.02 | 0.3 | ambiguous | 0.3 | ambiguous |

The binding of the scFv-human Fc panel to coated human and cynomolgus galectin-10 showed a relative binding capacity ranging from 0.08-1.48 nM on human and 0.04-2.53 nM on cynomolgus WGS and YRT isoforms of galectin-10. The following observations were made:
  The positive control clone 6F05 showed the best relative binding capacity of the scFv panel against the human target (0.02 nM EC50 value and 2.4 OD value as Bmax). However, this clone showed weak binding to both cynomolgus isoforms (ambiguous fitting and Bmax equal to 0.3 OD value).
  Clones 10A06, 10B02 and 8H11 showed the best relative binding capacity, with EC50 values between 0.08-0.18 nM against human galectin-10 and 0.04-0.13 nM against both isoforms of cynomolgus galectin-10.
  With the exception of clone 7C05, the rest of the scFv-human Fc panel showed similar binding profiles on the 2 isoforms of cynomolgus galectin-10.

(ii) SPR Analysis

The binding properties of the scFv-human Fc panel to galectin-10 were analyzed on the Biacore T3000. For this purpose, a CM5 Chip was coated with polyclonal anti-human Fc at 8000 RU, then a fixed concentration of the scFv-human Fc panel (1.5 µg/mL) were captured to reach a binding signal around 150 RU. Finally, a serial dilution of human or cynomolgus WGS isoform of galectin-10-His (serial dilution, 1 over 2 from 5 µg/mL, 6 points of dilution) was injected. Raw data were analyzed via BIA evaluation software with a blank subtraction (4-3). Finally, the kd/KD and Rmax of each scFv-human Fc to galectin-10-His was determined using the Fit Kinetics simultaneous ka/kd/Binding with mass transfer/Local Rmax on BIA evaluation software. The results are shown in the table below.

TABLE 20

Characterisation of the binding properties of the panel of scFv-human Fc galectin-10 antibodies on Biacore T3000

| | Biacore binding (capture approach) of scFv-human Fc to | | | | | | | |
|---|---|---|---|---|---|---|---|---|
| | humanGal10-His | | | | cynoGal10-His_WGS | | | |
| Name | ka (1/Ms) E05 | kd (1/s) E-04 | Rmax | KD (nM) | ka (1/Ms) E05 | kd (1/s) E-04 | Rmax | KD (nM) |
| 007B07 | 15.0 | 12.4 | 90.0 | 0.8 | 500.0 | 766.0 | 37.0 | 1.5 |
| 007C05 | 9.9 | 12.4 | 31.0 | 1.3 | 3.8 | 1.4 | 10.0 | 0.4 |
| 007D10 | 7.9 | 22.2 | 28.0 | 2.8 | 1.8 | 5.8 | 35.0 | 3.2 |
| 007E09 | 5.4 | 19.0 | 19.0 | 3.5 | 4.9 | 17.4 | 14.0 | 3.6 |
| 008H11 | 4.53 | 8.2 | 55 | 1.8 | 17.5 | 16.1 | 41 | 0.9 |
| 010A06 | 9.1 | 2.5 | 42.0 | 0.3 | 6.6 | 3.5 | 27.0 | 0.5 |
| 010B02 | 5.0 | 8.1 | 39.0 | 1.6 | 7.7 | 8.0 | 52.0 | 1.0 |
| 010D02 | 3.4 | 6.6 | 39.0 | 2.0 | 4.5 | 12.2 | 24.0 | 2.7 |
| 010H06 | 3.2 | 5.6 | 40.0 | 1.8 | 3.4 | 26.2 | 15.0 | 7.8 |
| 011F02 | 3.7 | 20.3 | 22.0 | 5.4 | 2.4 | 18.5 | 21.0 | 7.9 |
| 011F12 | 3.2 | 7.2 | 40.0 | 2.3 | 75.4 | 112.0 | 35.0 | 1.5 |

In line with the ELISA binding data reported above, the panel of scFv-human Fc fusions showed diverse binding properties to both human and cynomolgus WGS isoform of galectin-10-His. The following observations were made.
  The scFv-human Fc panel showed an affinity between 0.3-5.4 nM on human galectin-10-His and 0.5-7.9 nM on cynomolgus WGS isoform of galectin-10-His.
  The clones 10A06, 7B07 and 7C05 showed the highest affinity (0.3 nM up to 1.3 nM, respectively), with off-rates of $2.5^{E-04}$ s$^{-1}$ up to $12.4^{E-04}$ s$^{-1}$ on human galectin-10-His. Clone 7B07 showed the fastest on-rate ($15^{E05}$ 1/Ms) and Rmax (90 RU) of this panel.
  The scFv-human Fc panel showed a 2-fold lower Rmax on cynomolgus galectin-10-His compared to human target.

The clones 7C05, 10A06, 8H11 showed the highest affinity (0.4 nM up to 0.9 nM, respectively), with off-rates of $1.4^{E-04}$ s$^{-1}$ up to $8^{E-04}$ s$^{-1}$ on cynomolgus WGS isoform of galectin-10-His. Clone 7B07 showed the fastest on-rate ($500^{E05}$ 1/Ms) and off-rate ($766^{E-04}$) of the panel.

C. Reformatting of Selected scFv Clones into a Mouse IQG1 Backbone

Seven selected leads, as shown in the table below, were re-cloned into a mouse IgG1 backbone for further characterization.

Example 16. Characterization of the Galectin-10 Antibodies in Mouse IgG1 Format

A. Characterization of the Binding Properties of the Galectin-10 Mouse IQG1 Panel (i) ELISA Analysis In a similar setup to that used during the characterization of the scFv-human Fc molecules, the relative binding properties of the 7 mouse IgG1 antibodies were analyzed by ELISA. A Maxisorp plate was coated overnight with 0.5 µg/mL of human or cynomolgus WGS or YRT isoform of galectin-10-His. Then a serial dilution of each clone (from

TABLE 21

Panel of scFv clones reformatted into a mouse IgG1 backbone

| Clone ScFv-hFc | VH Family | VL Family | bELISA hGal10 EC50 (nM) | bELISA cynoGal10-WGS EC50 (nM) | bELISA cynoGal10-YRT EC50 (nM) | Biacore on human Gal10 | | | Biacore on cyno Gal10 WGS | | |
|---|---|---|---|---|---|---|---|---|---|---|---|
| | | | | | | ka (1/Ms) E05 | kd (1/s) E-04 | KD (nM) | ka (1/Ms) E05 | kd (1/s) E-04 | KD (nM) |
| 007B07 | 2 | 9 | 1.11 | 0.82 | No binding | 15.0 | 12.4 | 0.8 | 500.0 | 766.0 | 1.5 |
| 008H11 | 7 | 10 | 0.18 | 0.13 | 0.10 | 4.53 | 8.2 | 1.8 | 17.5 | 16.1 | 0.9 |
| 010A06 | 12 | 34 | 0.08 | 0.10 | 0.04 | 9.1 | 2.5 | 0.3 | 6.6 | 3.5 | 0.5 |
| 010B02 | 5 | 26 | 0.09 | 0.05 | 0.05 | 5.0 | 8.1 | 1.6 | 7.7 | 8.0 | 1.0 |
| 010D02 | 6 | 17* | 0.56 | 1.12 | 1.40 | 3.4 | 6.6 | 2.0 | 4.5 | 12.2 | 2.7 |
| 011F02 | 7b | 33 | 0.77 | 10.41 | ambiguous | 3.7 | 20.3 | 5.4 | 2.4 | 18.5 | 7.9 |
| 011F12 | 7 | 16 | 0.56 | 0.23 | 0.24 | 3.2 | 7.2 | 2.3 | 75.4 | 112.0 | 1.5 |

The CDR, VH and VL sequences of these seven antibodies are shown in Tables 32, 33 and 34 below.

For the reformatting, the VH and the VL regions of each clone were PCR amplified and cloned in frame into an expression vector encoding the mouse IgG1 constant domains.

The production of the mouse IgG1 anti-galectin-10 was carried out by transfection with a ratio of 1 heavy chain for 3 light chains incorporated in HEK293E cells via the polyethylenimine (PEI). After 6 days of production, mouse monoclonal antibodies were purified from the cell supernatant using the protein-A sepharose beads. Finally, SDS-PAGE analysis was carried out to assess the purity and the integrity of the antibodies (MW equal to 150 kDa).

100 nM, dilution 1/4, 12 points of dilutions) was incubated on coated galectin-10. After several washing steps, detection of the bound mouse IgG1 was carried out with an anti-mouse Fc-HRP antibody (DAMPO, Jackson ImmunoResearch, Catalog 715-035-150). Absorbance was measured at 450 nm (reference at 620 nm) with Tecan instrument. The raw data (OD values) were plotted on GraphPad Prism 7.01. The EC50 values for each antibody, calculated with a non-linear regression (log(agonist) vs. response Variable slope (four parameters)), are shown in the table below. Antibody 1D11 from the previous panel was included for comparison.

TABLE 22

Characterization of the binding properties of the mouse IgG1 panel by ELISA

| Clones (mouse IgG1) | humanGal10-His (0.5 µg/mL) | | cynoGal10-His_WGS (0.5 µg/mL) | | cynoGal10-His_YRT (0.5 µg/mL) | |
|---|---|---|---|---|---|---|
| | OD values | EC50 (nM) | OD values | EC50 (nM) | OD values | EC50 (nM) |
| 1D11 | 2.0 | 0.10 | 0.05 | n.d | 0.03 | n.d |
| 7B07 | 0.4 | 0.57 | 3.22 | 0.06 | 0.01 | n.d |
| 8H11 | 1.5 | 1.46 | 3.61 | 0.03 | 2.97 | 0.30 |
| 10A06 | 0.3 | 0.63 | 3.69 | 0.03 | 3.38 | 0.06 |
| 10B02 | 1.4 | 2.28 | 3.70 | 0.04 | 3.36 | 0.14 |
| 10D02 | 2.7 | 3.55 | 3.51 | 0.14 | 2.63 | ambiguous |
| 11F02 | 0.9 | 3.08 | 3.29 | 0.60 | 1.70 | ambiguous |
| 11F12 | 2.7 | 4.83 | 3.69 | 0.05 | 3.35 | 0.21 |

The following observations were made.

The new panel of mouse IgG1 anti-galectin-10 antibodies showed a relative binding capacity in ELISA between 0.57 nM to 4.83 nM against human galectin-10, 0.03 nM to 0.14 nM against cynomolgus WGS isoform and 0.06 nM to 0.21 nM against cynomolgus YRT isoform, respectively.

Clone 1D11 showed the best relative binding capacity against human galectin-10 (0.10 nM EC50 value) but no binding to the cynomolgus galectin-10.

Against human galectin-10, clones 7B07, 10A06 and 8H111 showed the best relative binding capacity with an EC50 value between 0.57 nM and 1.46 nM. Against the WGS isoform of galectin-10, clones 8H111, 10A06 and 10B02 were found to be the best binders, with EC50 values between 0.03 nM and 0.04 nM, 18-53-fold more potent compared to the human target.

Finally, clones 10A06, 10B02 and 11F12 showed the best relative binding capacity against the YRT isoform of the cynomolgus galectin-10-His, with EC50 values between 0.06 nM and 0.21 nM.

(ii) SPR Analysis

The binding capacity of the mouse IgG1 antibody panel to galectin-10 was analysed on Biacore T3000. For this purpose, a capture approach was used, where a fixed concentration (1.5 µg/mL) of the mouse IgG1 clone was captured by polyclonal anti-mouse Fc antibodies immobilized on CM5 Chip to reach a binding signal around 150 RU. Then a serial dilution of human and cynomolgus WGS isoform of galectin-10-His (serial dilution, 1 over 2 from 5 µg/mL) diluted in HBS-EP pH7.4 was injected. Raw data were analysed via BIA evaluation software with a blank subtraction. The kd/KD and Rmax of each mAbs to galectin-10-His was determined using the Fit Kinetics simultaneous ka/kd/Binding with mass transfer/Local Rmax on BIA evaluation software.

TABLE 23

Characterization of the binding properties
of the mouse IgG1 panel by Biacore T3000

Biacore binding (capture approach) of mouse IgG1 to:

| Clone (mouse IgG1) | humanGal10-His | | | | cynoGal10-His_WGS | | | |
|---|---|---|---|---|---|---|---|---|
| | ka (1/Ms) E05 | kd (1/s) E-04 | Rmax | KD (nM) | ka (1/Ms) E05 | kd (1/s) E-04 | Rmax | KD (nM) |
| 1D11 | 127 | 93.1 | 68 | 0.7 | n.d | n.d | 7 | n.d |
| 7B07 | 27.8 | 39 | 65 | 1.4 | 454 | 660 | 24 | 1.5 |
| 8H11 | 23.1 | 19.7 | 50 | 0.9 | 1.7 | 7.54 | 30 | 4.4 |
| 10A06 | 117 | 101 | 39 | 0.9 | 129 | 147 | 21 | 1.1 |
| 10B02 | 14.2 | 20.5 | 37 | 1.5 | 4.94 | 4.2 | 40 | 0.9 |
| 10D02 | 5.47 | 8.65 | 37 | 1.6 | 4.77 | 9.12 | 21 | 1.9 |
| 11F02 | 22.7 | 48.9 | 24 | 2.2 | 3.94 | 19.8 | 17 | 5.0 |
| 11F12 | 30.4 | 22.4 | 37 | 0.7 | 4.94 | 5.94 | 30 | 1.2 |

The following observations were made.

In this setup, the 7 human cynomolgus cross reactive clones showed an affinity in a nanomolar up to sub-nanomolar range against human and cynomolgus galectin-10 (WGS isoform), with an off rate ranging between $4.2 \times 10^{-4}$ $s^{-1}$ and $660 \times 10^{-4}$ $s^{-1}$.

For both human and cynomolgus galectin-10-His, clones 8H11, 10A06 and 11F12 showed the best binding capacity with an affinity between 0.7 nM and 0.9 nM for the human target and between 0.9 nM and 1.2 nM for the cynomolgus antigen (WGS isoform).

Clone 1D11 was found to be one of the best binders to human galectin-10 (affinity equal to 0.7 nM) but showed no/low binding to the cynomolgus antigen (Rmax equal to 7 RU).

B. Dissolution of Recombinant Human CLC Crystals In Vitro

The dissolution of CLCs induced by the anti-galectin-10 mouse IgG1 clones was monitored using a spinning disk confocal microscope. Briefly, the solution containing human CLCs was spotted in a µ-slide wells plate before being incubated with a fixed concentration (50 µM) of the mouse IgG1 anti-galectin-10 antibodies. Finally, for each well, imaging positions were defined, and each position was imaged every 3-5 minutes for a total of 120 minutes. Finally, based on software, the surface occupied by the CLC was determined, and the initial area covered by the CLC at the beginning of the experiment was defined as 1. As a negative control, a mouse IgG1 isotype control was included. The overall size of the CLC were measured overtime and plotted on GraphPad Prism 7.01 (see FIG. 15). The EC50 and EC90 values of each mouse IgG1 clone were calculated with a non-linear regression (log(agonist) vs. response Variable slope (four parameters)) and are reported in the table below.

TABLE 24

Dissolution of galectin-10 crystals in vitro

| Concentration (µM) | Clones | Format | 50% dissolution (min) | 90% dissolution (min) |
|---|---|---|---|---|
| 50 | 1D11 | mIgG1 | 30.1 | 56.7 |
| | 7B07 | | 13.2 | 44.4 |

TABLE 24-continued

Dissolution of galectin-10 crystals in vitro

| Concentration (µM) | Clones | Format | 50% dissolution (min) | 90% dissolution (min) |
|---|---|---|---|---|
| | 8H11 | | 22.4 | 43.5 |
| | 10A06 | | 44.5 | 86.6 |

TABLE 24-continued

Dissolution of galectin-10 crystals in vitro

| Concentration (μM) | Clones | Format | 50% dissolution (min) | 90% dissolution (min) |
|---|---|---|---|---|
| | 10B02 | | 25.1 | 47.4 |
| | 10D02 | | 26.5 | 58.6 |
| | 11F02 | | 25.5 | 57.5 |
| | 11F12 | | 21.3 | 42.6 |

Example 17. Characterization of the Galectin-10 Antibodies in Fab Format

A. Generation of the Fab Clones and bELISA Data

In order to determine the exact epitope of the seven galectin-10 mouse IgG1 antibodies on galectin-10, a crystallography study was initiated. For this purpose, the seven anti-galectin-10 antibodies characterised in Example 16 above were produced as Fabs.

For this, the VH and the VL of each clone were PCR amplified using specific primers, purified by electrophoresis, digested with restriction enzymes (BsmBi) and ligated in the pre-digested vectors containing the human constant domains: the human lambda constant domain for the VL (pUPEX116.9) or the CH1 constant domain for the VH (pUPEX86, including part of the hinge region). The transformation of each of the ligated products was carried out into Top10 bacteria by heat shock and the cells were transferred onto agarose plates with Ampicillin (resistance gene of the vectors). After one night of incubation, ligated products showed high numbers of single colonies whereas no colonies were observed for the negative controls (empty vectors). Per clones (VH and VL), four to eight colonies were picked and sent for sequencing. The clones that showed the correct insert were selected and amplified in order to purify the DNA sequence (MidiPrep).

The production of the seven Fab lead clones was initiated in mammalian cells. Transfection was performed with a ratio of 1 heavy chain for 3 light chains incorporated in HEK293E cells via the polyethylenimine (PEI). After 10 days of production, human Fab were purified from the cell supernatant using the Capture Select IgG-CH1 sepharose beads. Finally, SDS-PAGE analysis was carried out to assess the purity and integrity of the Fab molecules (MW ~55 kDa).

The binding capacity of the lead anti-galectin-10 Fabs was tested by binding ELISA. Briefly, a Maxisorp plate was coated overnight with 1 μg/mL of human galectin-10-His. Then a serial dilution of each clone (from 4 μM, dilution 1/4, 12 points of dilutions) was incubated on coated galectin-10. After several washing steps, detection of the bound Fab was carried out with an anti-human IgG Fab specific-peroxidase. Absorbance was measured at 450 nm (reference at 620 nm) with Tecan instrument. The results are shown in Table 25 below.

The ELISA binding data showed that the Fabs could be separated into 3 groups based on their binding capacity to coated human galectin-10-His:

Group 1: Clones 8H111, 10D02 and 11F12 were found as the best binders with the highest relative binding capacity (16-24 nM) and Bmax (0.74-1.3 OD values).

Group 2: Clone 7B07 showed a relatively good binding capacity with an EC50 value equal to 24 nM and max binding capacity equal to 0.65 OD values, but showed a slow hill slope, suggesting another binding interaction with galectin-10.

Group 3: The less potent binders with the lowest relative binding capacity (61-90 nM) and Bmax (0.36-0.74 OD values), included clones 10B02, 10A06 and 11F02.

With a relative binding capacity equal to 1.4 nM, the clone 1D11 showed the best binding capacity to human galectin-10, consistent with the full mAb data.

TABLE 25

Characterization of the binding properties of the galectin-10 Fabs

| | bELISA on galectin-10-His coated at 1 μg/mL | |
|---|---|---|
| | Bmax | EC50 (nM) |
| 1D11 | 1.59 | 1.4 |
| 7B07 | 0.65 | 24.4 |
| 8H11 | 0.95 | 24.3 |
| 10A06 | 0.36 | 89.5 |
| 10B02 | 0.74 | 61.2 |
| 10D02 | 1.03 | 16.1 |
| 11F02 | 0.46 | 81.4 |
| 11F12 | 1.375 | 22.4 |

B. Crystal Structure of Galectin-10 Fab Fragments in Complex with Galectin-10

The crystal structure of different Fab fragments in complex with galectin-10 was obtained as described in Example 12. The results are shown in FIG. 16. These structures show that clones 8H11, 1D11, 4E8, 6F5, 10D2 and 11F12 bind to tyrosine 69 (Y69), or an epitope in close proximity of Y69, whereas 7B7 binds to the opposite side of the galectin-10 dimer.

The residues of galectin-10 involved in the binding of the galectin-10 Fabs to the galectin-10 dimer are shown in Table 26 below.

TABLE 26

Residues of galectin-10 that make a direct interaction with the CDRs of the galectin-10 Fabs

| | Galectin-10 residues interacting with | |
|---|---|---|
| clone | VH | VL |
| 1D11 | 42, 49, 68, 69, 73, 115-117, 119-120 | 69, 70, 71 and 73 |
| 6F5 | 43, 49, 68, 69, 114-117, 119-120 | 73, 98, 113-115 and 117 |
| 4E8 | 74, 113-115 | 49, 68, 69, 73, 98, 115-117 |
| 8H11 | 33, 59, 60, 78-82 and 109 | 60, 74, 75, 77 and 79 |
| 11F12 | 33, 59, 60, 72, 79-82, 84 and 109 | 74, 75, 76, 77 and 79 |
| 10B02 | 33, 59, 60, 77-84 | 74, 75, 76, 77 and 79 |
| 10D02 | 31, 33, 59, 60, 78-82 and 84 | 79 |
| 7B7 | 2-5, 7-11, 25, 44, 88, 123, 125, 133 and 135 | 2, 23, 25, 86-90, 105 and 134 |

The galectin-10 Fab CDR residues involved in binding to the galectin-10 dimer are shown in Table 27 below.

TABLE 27

CDR residues of the Fabs that make contact with residues of the galectin-10 dimer in the crystal structure

| Clone | | CDR residues Fab1 | Galectin-10 residues (Monomer A) | CDR residues Fab2 | Galectin-10 residues (Monomer B) |
|---|---|---|---|---|---|
| 1D11 | VH | CDR1 - 31<br>CDR2 - 53<br>CDR3 - 102-107 | 42, 49, 68, 69, 73, 115-117, 119-120 | CDR1 - 31<br>CDR2 - 53<br>CDR3 - 102-107 | 42, 49, 68, 69, 73, 115-117, 119-120 |
| | VL | CDR1 - 31 and 34<br>CDR3 - 93 and 97 | 69, 70, 71, 73 | CDR1 - 31 and 34<br>CDR3 - 93, 96 and 97 | 69, 70, 71, 73 |
| 6F5 | VH | CDR1 - 2, 27, 31 and 32<br>CDR3 - 98, 99, 102-105, 107, 110 | 43, 49, 68, 69, 114-117, 119-120 | CDR1 - 2, 27, 31 and 32<br>CDR3 - 98, 99, 102-105, 107, 110 | 43, 49, 68, 69, 114-117, 119-120 |
| | VL | CDR1 - 33 and 34<br>CDR2 - 51, 52, 55 and 58 | 73, 98, 113-115 and 117 | CDR1 - 33 and 34<br>CDR2 - 51, 52, 55 and 58 | 73, 98, 113-115 and 117 |
| 4E8 | VH | CDR2 - 60<br>CDR3 - 105, 107 and 109 | 74, 113-115 | CDR2 - 60<br>CDR3 - 104, 105, 107 and 109 | 74, 113-115 |
| | VL | CDR1 - 26, 28-31<br>CDR2 - 49<br>CDR3 - 91-94 | 49, 68, 69, 73, 98, 115-117 | CDR1 - 26, 28-31<br>CDR3 - 91-94 | 49, 68, 69, 73, 98, 115-117 |
| 7B07 | VH | CDR1 - 30 and 31<br>CDR2 - 53-57<br>CDR3 - 100, 102-105 | 2, 3, 25, 88 and 133 | CDR1 - 30 and 31<br>CDR2 - 53-57<br>CDR3 - 100, 102-104 | 4, 5, 7-11, 44, 123, 125, 135 |
| | VL | CDR1 - 26, 28-31<br>CDR2 - 48, 50, 51<br>CDR3 - 65, 91-93 | 2, 23, 25, 86-90, 105 and 134 | CDR1 - 26, 28-31<br>CDR2 - 48, 50, 51<br>CDR3 - 65, 91-93 | 2, 23, 25, 86-90, 105, 134 |
| 8H11 | VH | CDR1 - 31-33<br>CDR2 - 52-54, 56, 57 and 59<br>CDR3 - 99-101 | 33, 59, 60, 78-82 and 109 | CDR1 - 30-33<br>CDR2 - 52-54, 56, 57 and 59<br>CDR3 - 100 and 101 | 33, 59, 60, 78-82 and 109 |
| | VL | CDR1 - 31, 32 and 34<br>CDR3 - 93 and 97 | 60, 74, 75, 77 and 79 | CDR1 - 31, 32 and 34<br>CDR3 - 93 and 97 | 60, 74, 75, 77 and 79 |
| 11F12 | VH | CDR1 - 30-33<br>CDR2 - 52-54, 56 and 57<br>CDR3 - 99-101 | 33, 59, 60, 72, 79-82, 84 and 109 | CDR1 - 30-33<br>CDR2 - 52-54, 57<br>CDR3 - 99-101 | 33, 59, 60, 78-82 and 109 |
| | VL | CDR1 32 and 34<br>CDR3 97 | 74, 75, 76, 77 and 79 | CDR1 - 32 and 34<br>CDR3 - 97 | 74, 75, 77 and 79, |
| 10B02 | VH | CDR1 - 31-33<br>CDR2 - 52-54, 56, 57 and 59<br>CDR3 - 99-102 | 33, 59, 60, 70, 72, 77-82, 84 | CDR1 - 31 and 33<br>CDR2 - 53-54, 56, 57 and 59<br>CDR3 - 99-102 | 33, 59, 60, 70, 72, 77-82, 84 |
| | VL | CDR1 - 31, 32 and 34<br>CDR3 - 93 and 97 | 74, 75, 76, 77 and 79 | CDR1 - 30, 31, 32 and 34<br>CDR3 - 93 and 97 | 74, 75, 76, 77 and 79 |
| 10D02 | VH | CDR1 - 28, 30-33<br>CDR2 - 53-57<br>CDR3 - 99-101 | 31, 33, 59, 60, 70, 72, 78-82, 84, | CDR1 - 28, 30-33<br>CDR2 - 52-54, 56 and 57<br>CDR3 - 99-103 | 31, 33, 59, 60, 70, 72, 78-82, 84, |
| | VL | CDR3 - 97 | 79 | CDR3 - 97 | 2, 79 |

Example 18. Comparison of CLC Dissolution by Galectin-10 mAbs and Fab Fragments The ability of the galectin-10 Fabs to solubilize pre-existing recombinant human galectin-10 crystals in vitro was compared with the galectin-10 mAbs. The protocol was as described in Example 16 above.

The results are shown in FIG. 17 and also in the table below. In some cases, the Fab fragments were more effective at dissolving the CLCs than the corresponding mAbs.

TABLE 28

CLC dissolution mediated by galectin-10 mAbs and Fabs

| Concentration (µM) | Clone | Format | 50% crystal dissolution (min) | 90% crystal dissolution (min) |
|---|---|---|---|---|
| 50 | 7B07 | mIgG1 | 31.76 | 93.02 |
|  | 8H11 |  | 68.29 | >120 |
|  | 10A06 |  | >120 | >120 |
|  | 10B02 |  | 73.66 | >120 |
|  | 11F12 |  | 65.43 | >120 |
|  | 1D11 |  | 100 | >120 |
| 50 | 7B07 | hFab | 15.09 | 54.14 |
|  | 8H11 |  | 48.53 | >120 |
|  | 10A06 |  | 49.15 | >120 |
|  | 10B02 |  | 102.2 | >120 |
|  | 10D02 |  | 59.67 | >120 |
|  | 11F02 |  | 77.86 | >120 |
|  | 11F12 |  | 61.96 | >120 |
|  | 1D11 |  | 33.42 | 97.85 |

Example 19. Production of VHH Antibodies that Bind to Galectin-10

Two llamas were immunized with recombinant human galectin-10. Messenger RNA (mRNA) was purified from the PBMCs isolated from the blood of the immunized llamas. The mRNA was reverse transcribed with random hexamer primers to obtain cDNA. Tagged primers were used directly on the cDNA to PCR amplify the VHH region. The PCR product was then purified, digested and cloned in the phagemid vector (VHH-Myc-His tagged) to create a VHH library.

To select VHH clones with the appropriate binding capacity to both human and cynomolgus galectin-10, a bio-panning approach was used. For this purpose, the first round of selection was carried out against human galectin-10-His, followed by a second round of enrichment against human or cynomolgus WGS or YRT isoforms (His tag). Briefly, human or cynomolgus (WGS or YRT isoform) galectin-10-His was immobilized on Maxisorp ELISA plate, then the VHH phage library (Input) was added. Unbound phages were removed via multiple washing steps. Finally, E. coli infection was carried out in order to amplify the selected phages. This process resulted in the enrichment of the phage population expressing VHH with high affinity against human and cynomolgus galectin-10.

From the eluted phages of round 2, versus 0.5 and 0.05 µg/mL of human, cynomolgus WGS isoform and cynomolgus YRT isoform of galectin-10, single clones were generated. Periplasmic extracts containing the VHH clone anti-human and cynomolgus galectin-10 were screened for binding capacity on ELISA and BioLayer Interferometry (BLI).

The binding capacity of the VHH (periplasmic extract) to human and cynomolgus (WGS and YRT isoforms) galectin-10 was analysed by ELISA. Briefly, a Maxisorp plate was coated overnight with 1 µg/mL of human galectin-10-His or cynomolgus WGS or YRT isoform galectin-10-His, then blocked with PBS 1% casein, before being incubated with the periplasmic extract (dilution 1/5 in PBS 0.1% casein) containing the VHH-Myc tagged. Detection of the binders was carried out with an anti-Myc-HRP antibody (Bethyl, Catalog A190-105P). TMB substrate was then added and the reaction was stopped with 0.5 M $H_2SO_4$. Absorbance was measured at 450 nm (reference at 620 nm) with Tecan instrument. Finally, the raw data (OD values) were plotted using GraphPad Prism 7.01 and are shown in FIG. 18. The number of binders, defined by an OD value higher than 0.5, per MP plate was determined. A blank control and negative control (VHH periplasmic extract binding to irrelevant target) were included and showed, as expected, no binding.

TABLE 29

Characterization of the VHH periplasmic extracts by ELISA screening

| MP number | Antigen | Hits | % Hits |
|---|---|---|---|
| MP13 | human Gal10HIS | 51 | 53.1 |
|  | cyno Gal10HIS_WGS | 57 | 59.4 |
|  | cyno Gal10HIS_YRT | 67 | 69.8 |
| MP14 | human Gal10HIS | 14 | 14.6 |
|  | cyno Gal10HIS_WGS | 13 | 13.5 |
|  | cyno Gal10HIS_YRT | 34 | 35.4 |

In addition to the binding ELISA, BLI was used to screen for galectin-10-binding clones.

From the two Master plates generated during selection, 130 clones that showed human and cynomolgus binding during the ELISA screening campaign were picked and their binding capacity was tested on BLI, using the Octet RED96. Briefly, human and cynomolgus WGS or YRT isoforms of galectin-10-His tagged were diluted in Kinetic buffer (PBS 0.01% BSA 0.002% Tween 20) at 200 µg/mL before being captured on Anti-Penta His 1K sensor tips (ForteBio, Cat #18-5120) until an immobilization level of 1 nm was reached. Then, diluted periplasmic extracts (1/5 in Kinetic buffer) containing the VHH clones were applied and association/dissociation to immobilized galectin-10-His was measured using the ForteBio Data analysis 9.0 software (subtraction of the reference Tips (loaded up to 1 nm with irrelevant His tagged protein, 1.1 binding model)). During the screening, only the dissociation (off-rate) of the VHH could be determined since the effective concentration of the VHH was unknown and can vary a lot from clone to clone. The results are shown in FIG. 19 and confirm that most of the selected VHH clones showed human cynomolgus cross reactivity.

Selected VHH clones that showed binding to galectin-10 were sent for sequencing. Based on their CDR1-2-3 VHH sequences, each clone was classified into a family. This process resulted in the determination of 44 families. Based on their screening binding data (ELISA and BLI) and their sequences, 15 VHH clones were selected for further characterization. Production of purified VHH was initiated in E. coli. For this purpose, selected VHH were first grown in 2TY medium with low amount of glucose and production of the VHH was induced by an overnight incubation with IPTG (1 mM). The next day, the bacteria pellets were lysed by two cycles of freeze/thaw (−80° C. and −20° C.). After centrifugation, VHH-His tagged were purified from the cell supernatant using the Talon Metal affinity Resin (BD Catalog 635504). Finally, SDS-PAGE analysis was done to assess the purity and the integrity of the VHH molecules (MW~15 kDa).

The CDR and VHH domain sequences of the 15 clones selected for further characterization are shown in Tables 35 and 36 below.

Example 20. Characterization of VHH Antibodies that Bind to Galectin-10

A. Binding of VHH Clones to Galectin-10 as Measured by ELISA

The binding capacity of the 15 VHH clones was analysed by ELISA. Briefly, a Maxisorp plate was coated overnight with human or cynomolgus WGS or YRT isoforms galectin-10-His at 1 μg/mL and blocked with PBS 1% casein, before being incubated with a serial dilution of the VHH (from 4 μM, dilution 1/3, 12 points of dilutions). After several washing steps, detection of the bound VHH was carried out with an anti-Myc-HRP antibody (Bethyl, Catalog A190-105P). Absorbance was measured at 450 nm (reference at 620 nm) with Tecan instrument. Finally, the raw data (OD values) were plotted on GraphPad Prism 7.01. The EC50 values of each compound, calculated with a non-linear regression (log(agonist) vs. response Variable slope (four parameters)) was reported in Table 27 below. As a positive control, clone 1D06 from the previous human specific panel was included. The results are shown in Table 30.

binding capacity to the cynomolgus galectin-10, with EC50 values between 7.1-480 nM on WGS isoform and 1.3-33 nM on YRT isoform.

Clone 13C03 showed a strong binding to the human galectin-10, with a relative binding capacity equal to 30 nM but a weak binding to the cynomolgus isoforms (Bmax 0.1 OD value).

Clone 1D06, isolated from the previous scFv library selected exclusively against human galectin-10, showed an EC50 value equal to 90 nM but no cynomolgus cross reactivity.

B. VHH Clones Dissolve Human Recombinant CLCs In Vitro

The CLC dissolution induced by the VHH clone 1D06 was monitored using a spinning disk confocal microscope. Briefly, the solution containing human CLCs was spotted in a μ-slide wells plate, before being incubated with a fixed concentration (50 μM or 100 μM) of the VHH antibody 1D06. Finally, for each well, imaging positions were defined, and each position was imaged every 3-5 minutes for a total of 120 minutes. Finally, based on software, the surface occupied by the CLC was determined, and the initial area covered by the CLC at the beginning of the experiment was defined as 1. As a negative control a VHH isotype control was included. The overall size of the CLC were measured overtime and plotted on GraphPad Prism 7.01 (see FIG. 20). The EC50 and EC90 values of the VHH clone were calculated with a non-linear regression (log(agonist) vs. response Variable slope (four parameters)) and reported in the table below.

TABLE 30

Characterization of the galectin-10 VHH clones by ELISA bELISA of VHH on coated Gal10-HIS at 1 μg/mL

| Clone (VHH) | Human Bmax (OD values) | Human EC50 (nM) | Cyno_WGS Bmax (OD values) | Cyno_WGS EC50 (nM) | Cyno_YRT Bmax (OD values) | Cyno_YRT EC50 (nM) |
|---|---|---|---|---|---|---|
| 13A05 | 1.8 | 69.7 | 2.7 | 77.8 | 2.9 | 66.3 |
| 13B06 | 1.0 | ambiguous | 1.4 | Ambiguous | 2.0 | ambiguous |
| 13C03 | 2.0 | 30.6 | 0.1 | / | 0.1 | / |
| 13C04 | 1.1 | ambiguous | 2.7 | 369.1 | 2.5 | ambiguous |
| 13C06 | 2.8 | 27.5 | 2.9 | 10.3 | 2.9 | 16.2 |
| 13C07 | 1.3 | 106.7 | 2.9 | 7.1 | 2.8 | 33.2 |
| 13C10 | 1.0 | ambiguous | 2.3 | Ambiguous | 2.7 | 185.8 |
| 13D12 | 0.8 | ambiguous | 1.3 | Ambiguous | 2.4 | 118.9 |
| 13E07 | 1.1 | ambiguous | 2.3 | 371.0 | 2.4 | ambiguous |
| 13E09 | 1.8 | 105.7 | 2.3 | 438.4 | 3.0 | 66.9 |
| 13G12 | 1.6 | 141.0 | 2.9 | 11.8 | 3.1 | 3.1 |
| 13H07 | 1.5 | 179.9 | 2.7 | 15.6 | 3.1 | 1.3 |
| 14E02 | 0.7 | ambiguous | 1.8 | Ambiguous | 2.1 | ambiguous |
| 14E10 | 0.5 | ambiguous | 1.4 | Ambiguous | 2.7 | 15.8 |
| 14F10 | 0.5 | ambiguous | 2.6 | 60.4 | 3.0 | 3.0 |
| 1D06 | 1.2 | 90.7 | 0.0 | / | 0.0 | / |

The following observations were made:
Clones 13C06 and 13A05 were the best human cynomolgus cross reactive binders, with a relative binding capacity equal to 27-30.6 nM EC50 values on human galectin-10 and 10.3-77.8 nM EC50 values on WGS isoform and 16.2-66.3 nM EC50 values on YRT isoform of cynomolgus galectin-10.
Clones 13C07, 13E09, 13G12 and 13H07 showed a moderate binding capacity to human galectin-10, with an EC50 values between 105-180 nM, but a strong

TABLE 31

Dissolution of CLCs by the VHH clone 1D06

| Concentration (μM) | Clones | Format | 50% dissolution (min) | 90% dissolution (min) |
|---|---|---|---|---|
| 50 | 1D06 | VHH | 20.1 | 13.6 |
| 100 | | | 7.2 | 43.96 |

TABLE 32

Heavy chain CDR sequences of scFv antibodies binding to galectin-10

| scFv clone | CDR1 | SEQ ID NO: | CDR2 | SEQ ID NO: | CDR3 | SEQ ID NO: |
|---|---|---|---|---|---|---|
| 71307 | SYDMS | 160 | AIKNGGGITYYADSVKG | 161 | THGIGTLGFGS | 162 |
| 8H11 | TNYMN | 163 | GITSGGGRTYYADSVKG | 164 | TDHAWLDA | 165 |
| 10A06 | NYDMS | 166 | DINSGGGSTYYADSVKG | 167 | GYTGYYY | 168 |
| 10B02 | YHYMN | 169 | GISAGGGRTYYADSVKG | 170 | VHGITNDY | 171 |
| 10D02 | SYYMS | 172 | GIVTGGGRTHYTDSVKG | 173 | VNGVVTNYDY | 174 |
| 11F02 | TNYMN | 163 | GITSHGARTYYADSVKG | 175 | TDHASLDA | 176 |
| 11F12 | TNYMN | 163 | GITSGGGRTYYADSVKG | 164 | TDHAWLDA | 165 |

TABLE 33

Light chain CDR sequences of scFv antibodies binding to galectin-10

| scFv clone | CDR1 | SEQ ID NO: | CDR2 | SEQ ID NO: | CDR3 | SEQ ID NO: |
|---|---|---|---|---|---|---|
| 7B07 | DGNNIGSKSAQ | 177 | ADEYRPE | 178 | QVWDGSAAV | 179 |
| 8H11 | AGTSSDVGYGNYVS | 180 | AVSTRAS | 181 | ASYRSSNNYV | 182 |
| 10A06 | GLSSGSVTSSNYPA | 183 | SINSRHS | 184 | TLYMGTGSNNVV | 185 |
| 10B02 | AGTSSDVGYGNYVS | 180 | EVNKRAS | 186 | ASYRNSNNWV | 187 |
| 10D02 | AGTSSDVGYGNYVS | 180 | DVNKRAS | 188 | ASYRSPNNVV | 189 |
| 11F02 | GLSSGSVTSSNYPG | 190 | NTNSRYS | 191 | ALYMGSSSYNTV | 192 |
| 11F12 | AGTSSDVGYGNYVS | 180 | AVSTRAS | 181 | ASYSVRNNVV | 193 |

TABLE 34

VH and VL sequences of scFv antibodies binding to galectin-10

| scFv clone | VH | SEQ ID NO: | VL | SEQ ID NO: |
|---|---|---|---|---|
| 7B07 | QVQLVESGGGLVQPGGSLRLSCAASGFTFRSYDMSWVRQAPGKGPEWVSAIKNGGGITYYADSVKGRFTISRDNAKNTLYLQMNSLKPEDTAVYYCATTHGIGTLGFGSWGQGTQVTVSS | 194 | SYELTQSASVSVALTQTAKITCDGNNIGSKSAQWYQQKPGQAPALVIYADEYRPEGIPERFSGSNSGNTATLIISGAQAEDEADYYCQVWDGSAAVFGRGTHLTVL | 195 |
| 8H11 | ELQLVESGGGLVQPGGSLRLSCAASGFTFSTNYMNWVRQAPGKGLEWVSGITSGGGRTYYADSVKGRFTISRDNAKNTLYLQMNSLKPEDTALYYCARTDHAWLDAWGQGTLVTVSS | 196 | QAGLTQPPSVSGTLGKTVTISCAGTSSDVGYGNYVSWYQQLPGTAPKLLIYAVSTRASGIPDRFSGSKSGNTASLTISGLLSEDEADYYCASYRSSNNYVFGGGTKLTVL | 197 |
| 10A06 | QVQLVESGGGLVQPGGSLRLSCAASGFTFGNYDMSWVRQAPGKGPEWVSDINSGGGSTYYADSVKGRFTISRDNAKNSLLLQMNSLKPEDTAVYYYCATGYTGYYYWGQGTQVTVSS | 198 | QTVVTQEPSLSVSPGGTVTLTCGLSSGSVTSSNYPAWYQQTPGQAPRALIYSINSRHSGVPDRFSGSISGNKAALTITGAQAEDEADYYCTLYMGTGSNNVVFGGGTHLTVL | 199 |
| 10B02 | QVQLVESGGGLVQPGGSLRVSCAASGFTFSYHYMNWVRQAPGKGLEWVSGISAGGGRTYYADSVKGRFTISRDNAKNTLYLQMNSLNAEDTALYYCARVHGITNDYWGQGTQVTVSS | 200 | QSALTQPPSVSGSPGKTVTISCAGTSSDVGYGNYVSWYQQLPGMAPKLLIYEVNKRASGITDRFSGSKSGNTAFLTISGLQSEDEADYYCASYRNSNNWVFGGGTHLTVL | 201 |
| 10D02 | EVQLVESGGGLVQPGGSLRVSCAASGFTFSSYYMSWVRQAPGKGLEWVSGIVTGGGRTHYTDSVKGRFTITRDNAKNTLYLQMNSLRPEDTALYYCARVNGVVTNYDYWGQGTQVTVSS | 202 | QAVLTQPPSVSGSPGKTVTISCAGTSSDVGYGNYVSWYQQLPGMAPKLLIYDVNKRASGITDRFSGSKSGNTASLTISGLQSEDEADYFCASYRSPNNVVFGQGTHLTVL | 203 |

TABLE 34-continued

VH and VL sequences of scFv antibodies binding to galectin-10

| scFv clone | VH | SEQ ID NO: | VL | SEQ ID NO: |
|---|---|---|---|---|
| 11F02 | ELQVVESGGGLVQPGGSLRLSCAASGFTFST NYMNWVRQAPGKGLEWVSGITSHGARTYYA DSVKGRFTISRDNSKNTLYLQMNSLKPEDTAL YYCARTDHASLDAWGQGTLVTVSS | 204 | QTVVTQEPSLSVSPGGTVTLTCGLSSGSVTSSNYP GWYQQKPGQAPRTLIYNTNSRYSGVPNRFSGSISG NKAALTITGAQPEDEADYYCALYMGSSSYNTVFGG GTHLTVL | 205 |
| 11F12 | QVQLQESGGGLVQPGGSLRLSCAASGFTFST NYMNWVRQAPGKGLEWVSGITSGGGRTYYA DSVKGRFTISRDNAKNTLYLQMNSLKPEDTAL YYCARTDHAWLDAWGQGTLVTVSS | 206 | HSAVTQPPSVSGTLGKTVTISCAGTSSDVGYGNYV SWYQHLPGTAPKLLIYAVSTRASGVPDRFSGSKSG NTASLTISGLQSEDEGDYYCASYSVRNNVVFGGGT RLTVL | 207 |

TABLE 35

CDR sequences of VHH antibodies binding to galectin-10

| VHH clone | CDR1 | SEQ ID NO: | CDR2 | SEQ ID NO: | CDR3 | SEQ ID NO: |
|---|---|---|---|---|---|---|
| 13G12 | AYSMG | 208 | VISWSGGSHYDDSVKG | 209 | GTLYSFRYRDYDY | 210 |
| 13H07 | TYAMD | 211 | AISWHSAIYYADAVKG | 212 | ALRYRFNPSAMEY | 213 |
| 14F10 | GYAVG | 214 | IISWNGGTHYADSVKG | 215 | SPKYYFSPETYNY | 216 |
| 13C06 | SYSMG | 217 | TISWSGGFYYDDSVKG | 218 | GTRFSFSYREYHY | 219 |
| 13C07 | AYSMA | 220 | AITWSGGSHHDDSVKG | 221 | GTLYSFSYRDYDY | 222 |
| 14E10 | PYAMG | 223 | VISLSGAYTYNVNAVKG | 224 | SRTYYRTDESTYEY | 225 |
| 13D12 | SYHMM | 226 | ALAWRGGTYCANSVKG | 227 | SRRYVFDPSAMDY | 228 |
| 13A05 | SYSMS | 229 | IISWSGGTYYDDSVKG | 230 | GTQFSFSYREYDY | 231 |
| 13C04 | TYSMA | 232 | AITRSGGNTYADSVKG | 233 | GGTYSFVPRSYNY | 234 |
| 13E09 | SYHMM | 226 | AIAWRGGTYCANSVKG | 235 | SLRYVFDPSAMDY | 236 |
| 14E02 | TYSMA | 232 | AITWAGGYTYGADSEKG | 237 | GRLFTSQSSAYQY | 238 |
| 13C10 | PYTMG | 239 | VVSSGGGTYYANSVKG | 240 | GSIFRWSPMSYDY | 241 |
| 13E07 | SYHMM | 226 | AIAWRGGTYCANSVKG | 235 | SLRYVFDPSAMDY | 236 |
| 13C03 | ISRMG | 242 | IIFSDASTDYADSVKG | 243 | VLRAAGYGYFNQY | 244 |
| 13B06 | TYSMA | 232 | AITRSGGNTYADSVKG | 233 | GGTYSFVPRSYNY | 234 |
| 1D6 | TYAMG | 245 | AITRAGGNTYNADSVKG | 246 | GPRYSTISTMFPY | 247 |
| 15A2 | SYSMG | 217 | TISWSGGNYVDNSVKG | 248 | GTQFSFSYRQYDY | 249 |

TABLE 36

VHH domain sequences of VHH antibodies binding to galectin-10

| Clone | VHH sequence | SEQ ID NO: |
|---|---|---|
| 13G12 | QLQVVESGGGLVQAGGSLRLSCAASSSAYSMGWFRQAPGKEREFVAVISWSGGSHYDDSVKGRF TISRDGAKNTVYLQMNSLKPEDTAVYYCAVGTLYSFRYRDYDYWGQGTQVTVSS | 250 |
| 13H07 | QLQLVESGGGLVQAGGSLRLSCVASGRTFSTYAMDWFRQAPGKEREFVAAISWHSAIYYADAVKG RFTISRDNGKNTMYLQMNNLKPEDTAVYFCAAALRYRFNPSAMEYWGKGTLVTVSS | 251 |
| 14F10 | EVQLVESGGGLVQAGDSLRLSCAASGRTFSGYAVGWFRQAPGKEREFVTIISWNGGTHYADSVKG RFAISRDNAKNTVYLQMNNLKPEDTAVYYCAVSPKYYFSPETYNYWGQGTQVTVSS | 252 |
| 13C06 | QLQLVESGGGLVQAGGSLRLSCAASSSSYSMGWFRQAPGKEREFVATISWSGGFYYDDSVKGRFT VSRDNAKNTVYLQMNSLKPEDTAVYYCAAGTRFSFSYREYHYWGQGTQVTVSS | 253 |

TABLE 36-continued

VHH domain sequences of VHH antibodies binding to galectin-10

| Clone | VHH sequence | SEQ ID NO: |
|---|---|---|
| 13C07 | QLQVVESGGGLVQAGGSLRLSCAASSSAYSMAWFRQAPGKEREFVAAITWSGGSHHDDSVKGRF TISRDGAKNTVYLQMNSLKPEDTAVYYCAVGTLYSFSYRDYDYWGQGTQVTVSS | 254 |
| 14E10 | ELQLVESGGGLVQAGGSLRLSCAASEGTFRPYAMGWFRQAPRKEREFVAVISLSGAYTYNVNAVK GRFTISRDNAKNTVYLQMNSLTPEDTAIYYCGASRTYYRTDESTYEYWGQGTQVTVSS | 255 |
| 13D12 | QLQLVESGGGLVQAGDSLRLSCAASGRTFSSYHMMWFRQAPGKEREFVAALAWRGGTYCANSVK GRCTISRDNAQDTVYLQMNSLKPEDTAVYFCAASRRYVFDPSAMDYWAKGTLVTVSS | 256 |
| 13A05 | QVQLVESGGGLVQAGGSLRLSCAASSSSYSMSWFRQAPGKEREFVAIISWSGGTYYDDSVKGRFT VSRDNAKNTVYLQMNSLKPEDTAVYYCAAGTQFSFSYREYDYWGQGTQVTVSS | 257 |
| 13C04 | ELQVVESGGGLVQAGGSLRLSCAASGRTFSTYSMAWFRQAPGKEREFVAAITRSGGNTYADSVKG RFTISRDNAKNTVTLQMNSLKPEDTAAYHCAAGGTYSFVPRSYNYWGQGTQVTVSS | 258 |
| 13E09 | QVQVQESGGGLVQAGNSLRLSCAASGRTFSSYHMMWFRQAPGKEREFVAAIAWRGGTYCANSVK GRCTISRDNAKDTVYLQMNSLKPEDTAVYFCAASLRYVFDPSAMDYWGKGTLVTVSS | 259 |
| 14E02 | QVQLVESGGGLAQAGGSLRLSCVASGRAAGTYSMAWFRQAPGKEREFVAAITWAGGYTYGADSE KGRFTISRDNAKNTVYLQMNSLKPEDTAVYSCAGGRLFTSQSSAYQYWGQGTQVTVSS | 260 |
| 13C10 | QLQLVESGGGLVQAGGSLKLSCAASGRTFNPYTMGWFRQAPGKEREFVAVVSSGGGTYYANSVK GRFTISRDNAKATVYLQMNSLKPEDTAVYYCAAGSIFRWSPMSYDYWGQGTQVTVSS | 261 |
| 13E07 | ELQVVESGGGLVQAGDSLRLSCAVSGRTFSSYHMMWFRQAPGKEREFVAAIAWRGGTYCANSVK GRCTISRDNAKDTVYLQMNSLKPEDTAVYFCAASLRYVFDPSAMDYWGKGTLVTVSS | 262 |
| 13C03 | QVQLVESGGGLVQPGGSLRLSCAASGSIFSISRMGWYRQAPGKQRELVAIIFSDASTDYADSVKGRF TISRSNAKNTVYLQMNSLKPEDTAVYYCKSVLRAAGYGYFNQYWGQGTQVTVSS | 263 |
| 13B06 | QVQLVESGGGLVQAGGSLRLSCAASGRTFSTYSMAWFRQAPGKEREFVAAITRSGGNTYADSVKG RFTISRDNAKNTVTLQMNSLKPEDTAAYHCAAGGTYSFVPRSYNYWGQGTQVTVSS | 264 |
| 1D6 | QLQLVESGGGLVQPGGSLRLSCAASENSVSTYAMGWFRQAPGKEREFVAAITRAGGNTYNADSVK GRFTISRDNAENTIYLQMNSLKPEDTAVYSCAAGPRYSTISTMFPYWGQGTQVTVSS | 265 |
| 15A2 | QVQLVESGGGLVQAGGSLRLSCAASGSSYSMGWFRQAPGKEREFVATISWSGGNYVDNSVKGRF TVSRDNAKNTVYLQMNSLKPEDTAVYYCAAGTQFSFSYRQYDYWGQGTQVTVSS | 266 |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

INCORPORATION BY REFERENCE

Various publications are cited in the foregoing description and throughout the following examples, each of which is incorporated by reference herein in its entirety.

The invention claimed is:

1. A method of inhibiting galectin-10 crystal formation in a subject in need thereof, the method comprising administering to the subject a therapeutically effective amount of an antibody or antigen binding fragment thereof which specifically binds to human galectin-10, wherein the subject has a disease or condition selected from the group consisting of asthma; chronic rhinosinusitis; celiac disease; helminth infection; gastrointestinal eosinophilic inflammation; cystic fibrosis (CF); allergic bronchopulmonary aspergillosis (ABPA); Churg-Strauss vasculitis; chronic eosinophilic pneumonia; and acute myeloid leukemia, and wherein the antibody or antigen binding fragment thereof cross competes for binding to human galectin-10 with an antibody or antigen binding fragment thereof comprising a variable heavy chain domain (VH) and a variable light chain domain (VL) wherein the VH and VL domains comprise the CDR sequences selected from the group consisting of:
   (i) HCDR3 comprising SEQ ID NO: 3, HCDR2 comprising SEQ ID NO: 2, HCDR1 comprising SEQ ID NO: 1, LCDR3 comprising SEQ ID NO: 58, LCDR2 comprising SEQ ID NO: 57, and LCDR1 comprising SEQ ID NO: 56;
   (ii) HCDR3 comprising SEQ ID NO: 9, HCDR2 comprising SEQ ID NO: 8, HCDR1 comprising SEQ ID NO: 7, LCDR3 comprising SEQ ID NO: 64, LCDR2 comprising SEQ ID NO: 63, and LCDR1 comprising SEQ ID NO: 62;
   (iii) HCDR3 comprising SEQ ID NO: 12, HCDR2 comprising SEQ ID NO: 11, HCDR1 comprising SEQ ID NO: 10, LCDR3 comprising SEQ ID NO: 67, LCDR2 comprising SEQ ID NO: 66, and LCDR1 comprising SEQ ID NO: 65;
   (iv) HCDR3 comprising SEQ ID NO: 25, HCDR2 comprising SEQ ID NO: 24, HCDR1 comprising SEQ ID NO: 4, LCDR3 comprising SEQ ID NO: 78, LCDR2 comprising SEQ ID NO: 77, and LCDR1 comprising SEQ ID NO: 76;
   (v) HCDR3 comprising SEQ ID NO: 47, HCDR2 comprising SEQ ID NO: 46, HCDR1 comprising SEQ ID NO: 45, LCDR3 comprising SEQ ID NO: 94, LCDR2 comprising SEQ ID NO: 93, and LCDR1 comprising SEQ ID NO: 71;
   (vi) HCDR3 comprising SEQ ID NO: 43, HCDR2 comprising SEQ ID NO: 42, HCDR1 comprising SEQ ID NO: 4, LCDR3 comprising SEQ ID NO: 94, LCDR2 comprising SEQ ID NO: 93, and LCDR1 comprising SEQ ID NO: 92;
   (vii) HCDR3 comprising SEQ ID NO: 6, HCDR2 comprising SEQ ID NO: 44, HCDR1 comprising SEQ ID NO: 4, LCDR3 comprising SEQ ID NO: 97, LCDR2 comprising SEQ ID NO: 96, and LCDR1 comprising SEQ ID NO: 95;
   (viii) HCDR3 comprising SEQ ID NO: 36, HCDR2 comprising SEQ ID NO: 52, HCDR1 comprising SEQ ID NO: 51, LCDR3 comprising SEQ ID NO: 98, LCDR2 comprising SEQ ID NO: 97, and LCDR1 comprising SEQ ID NO: 80;
   (ix) HCDR3 comprising SEQ ID NO: 55, HCDR2 comprising SEQ ID NO: 54, HCDR1 comprising SEQ ID NO: 53, LCDR3 comprising SEQ ID NO: 81, LCDR2 comprising SEQ ID NO: 93, and LCDR1 comprising SEQ ID NO: 71;
   (x) HCDR3 comprising SEQ ID NO: 50, HCDR2 comprising SEQ ID NO: 49, HCDR1 comprising SEQ ID NO: 48, LCDR3 comprising SEQ ID NO: 96, LCDR2 comprising SEQ ID NO: 63, and LCDR1 comprising SEQ ID NO: 95;
   (xi) HCDR3 comprising SEQ ID NO: 6, HCDR2 comprising SEQ ID NO: 5, HCDR1 comprising SEQ ID NO: 4, LCDR3 comprising SEQ ID NO: 61, LCDR2 comprising SEQ ID NO: 60, and LCDR1 comprising SEQ ID NO: 59;
   (xii) HCDR3 comprising SEQ ID NO: 165, HCDR2 comprising SEQ ID NO: 164, HCDR1 comprising SEQ ID NO: 163, LCDR3 comprising SEQ ID NO: 182, LCDR2 comprising SEQ ID NO: 181, and LCDR1 comprising SEQ ID NO: 180;
   (xiii) HCDR3 comprising SEQ ID NO: 174, HCDR2 comprising SEQ ID NO: 173, HCDR1 comprising SEQ ID NO: 172, LCDR3 comprising SEQ ID NO: 189, LCDR2 comprising SEQ ID NO: 188, and LCDR1 comprising SEQ ID NO: 180; and
   (xiv) HCDR3 comprising SEQ ID NO: 165, HCDR2 comprising SEQ ID NO: 164, HCDR1 comprising SEQ ID NO: 163, LCDR3 comprising SEQ ID NO: 193, LCDR2 comprising SEQ ID NO: 181, and LCDR1 comprising SEQ ID NO: 180.

2. A method of inhibiting galectin-10 crystal formation in a subject in need thereof, the method comprising administering to the subject a therapeutically effective amount of an antibody or antigen binding fragment thereof which specifically binds to human galectin-10, wherein:
   (a) the antibody or antigen binding fragment thereof comprises a VH and a VL wherein the VH and VL domains comprise the CDR sequences selected from the group consisting of:
      (i) HCDR3 comprising SEQ ID NO: 3, HCDR2 comprising SEQ ID NO: 2, HCDR1 comprising SEQ ID NO: 1, LCDR3 comprising SEQ ID NO: 58, LCDR2 comprising SEQ ID NO: 57, and LCDR1 comprising SEQ ID NO: 56;
      (ii) HCDR3 comprising SEQ ID NO: 6, HCDR2 comprising SEQ ID NO: 5, HCDR1 comprising SEQ ID NO: 4, LCDR3 comprising SEQ ID NO: 61, LCDR2 comprising SEQ ID NO: 60, and LCDR1 comprising SEQ ID NO: 59;
      (iii) HCDR3 comprising SEQ ID NO: 9, HCDR2 comprising SEQ ID NO: 8, HCDR1 comprising SEQ ID NO: 7, LCDR3 comprising SEQ ID NO: 64, LCDR2 comprising SEQ ID NO: 63, and LCDR1 comprising SEQ ID NO: 62;
      (iv) HCDR3 comprising SEQ ID NO: 12, HCDR2 comprising SEQ ID NO: 11, HCDR1 comprising SEQ ID NO: 10, LCDR3 comprising SEQ ID NO: 67, LCDR2 comprising SEQ ID NO: 66, and LCDR1 comprising SEQ ID NO: 65;
      (v) HCDR3 comprising SEQ ID NO: 15, HCDR2 comprising SEQ ID NO: 14, HCDR1 comprising SEQ ID NO: 13, LCDR3 comprising SEQ ID NO: 70, LCDR2 comprising SEQ ID NO: 69, and LCDR1 comprising SEQ ID NO: 68;
      (vi) HCDR3 comprising SEQ ID NO: 18, HCDR2 comprising SEQ ID NO: 17, HCDR1 comprising SEQ ID NO: 16, LCDR3 comprising SEQ ID NO: 72, LCDR2 comprising SEQ ID NO: 66, and LCDR1 comprising SEQ ID NO: 71;
      (vii) HCDR3 comprising SEQ ID NO: 20, HCDR2 comprising SEQ ID NO: 19, HCDR1 comprising SEQ ID NO: 4, LCDR3 comprising SEQ ID NO: 75, LCDR2 comprising SEQ ID NO: 74, and LCDR1 comprising SEQ ID NO: 73;

(viii) HCDR3 comprising SEQ ID NO: 23, HCDR2 comprising SEQ ID NO: 22, HCDR1 comprising SEQ ID NO: 21, LCDR3 comprising SEQ ID NO: 67, LCDR2 comprising SEQ ID NO: 66, and LCDR1 comprising SEQ ID NO: 65;

(ix) HCDR3 comprising SEQ ID NO: 25, HCDR2 comprising SEQ ID NO: 24, HCDR1 comprising SEQ ID NO: 4, LCDR3 comprising SEQ ID NO: 78, LCDR2 comprising SEQ ID NO: 77, and LCDR1 comprising SEQ ID NO: 76;

(x) HCDR3 comprising SEQ ID NO: 28, HCDR2 comprising SEQ ID NO: 27, HCDR1 comprising SEQ ID NO: 26, LCDR3 comprising SEQ ID NO: 67, LCDR2 comprising SEQ ID NO: 66, and LCDR1 comprising SEQ ID NO: 79;

(xi) HCDR3 comprising SEQ ID NO: 31, HCDR2 comprising SEQ ID NO: 30, HCDR1 comprising SEQ ID NO: 29, LCDR3 comprising SEQ ID NO: 81, LCDR2 comprising SEQ ID NO: 63, and LCDR1 comprising SEQ ID NO: 80;

(xii) HCDR3 comprising SEQ ID NO: 33, HCDR2 comprising SEQ ID NO: 32, HCDR1 comprising SEQ ID NO: 1, LCDR3 comprising SEQ ID NO: 84, LCDR2 comprising SEQ ID NO: 83, and LCDR1 comprising SEQ ID NO: 82;

(xiii) HCDR3 comprising SEQ ID NO: 36, HCDR2 comprising SEQ ID NO: 35, HCDR1 comprising SEQ ID NO: 34, LCDR3 comprising SEQ ID NO: 87, LCDR2 comprising SEQ ID NO: 86, and LCDR1 comprising SEQ ID NO: 85;

(xiv) HCDR3 comprising SEQ ID NO: 38, HCDR2 comprising SEQ ID NO: 11, HCDR1 comprising SEQ ID NO: 37, LCDR3 comprising SEQ ID NO: 78, LCDR2 comprising SEQ ID NO: 63, and LCDR1 comprising SEQ ID NO: 88;

(xv) HCDR3 comprising SEQ ID NO: 41, HCDR2 comprising SEQ ID NO: 40, HCDR1 comprising SEQ ID NO: 39, LCDR3 comprising SEQ ID NO: 91, LCDR2 comprising SEQ ID NO: 90, and LCDR1 comprising SEQ ID NO: 89;

(xvi) HCDR3 comprising SEQ ID NO: 43, HCDR2 comprising SEQ ID NO: 42, HCDR1 comprising SEQ ID NO: 4, LCDR3 comprising SEQ ID NO: 94, LCDR2 comprising SEQ ID NO: 93, and LCDR1 comprising SEQ ID NO: 92;

(xvii) HCDR3 comprising SEQ ID NO: 6, HCDR2 comprising SEQ ID NO: 44, HCDR1 comprising SEQ ID NO: 4, LCDR3 comprising SEQ ID NO: 97, LCDR2 comprising SEQ ID NO: 96, and LCDR1 comprising SEQ ID NO: 95;

(xviii) HCDR3 comprising SEQ ID NO: 47, HCDR2 comprising SEQ ID NO: 46, HCDR1 comprising SEQ ID NO: 45, LCDR3 comprising SEQ ID NO: 94, LCDR2 comprising SEQ ID NO: 93, and LCDR1 comprising SEQ ID NO: 71;

(xix) HCDR3 comprising SEQ ID NO: 50, HCDR2 comprising SEQ ID NO: 49, HCDR1 comprising SEQ ID NO: 48, LCDR3 comprising SEQ ID NO: 96, LCDR2 comprising SEQ ID NO: 63, and LCDR1 comprising SEQ ID NO: 95;

(xx) HCDR3 comprising SEQ ID NO: 36, HCDR2 comprising SEQ ID NO: 52, HCDR1 comprising SEQ ID NO: 51, LCDR3 comprising SEQ ID NO: 98, LCDR2 comprising SEQ ID NO: 97, and LCDR1 comprising SEQ ID NO: 80; and (xxi) HCDR3 comprising SEQ ID NO: 55, HCDR2 comprising SEQ ID NO: 54, HCDR1 comprising SEQ ID NO: 53, LCDR3 comprising SEQ ID NO: 81, LCDR2 comprising SEQ ID NO: 93, and LCDR1 comprising SEQ ID NO: 71;

(xxii) HCDR3 comprising SEQ ID NO: 162, HCDR2 comprising SEQ ID NO: 161, HCDR1 comprising SEQ ID NO: 160, LCDR3 comprising SEQ ID NO: 179, LCDR2 comprising SEQ ID NO: 178, and LCDR1 comprising SEQ ID NO: 177;

(xxiii) HCDR3 comprising SEQ ID NO: 165, HCDR2 comprising SEQ ID NO: 164, HCDR1 comprising SEQ ID NO: 163, LCDR3 comprising SEQ ID NO: 182, LCDR2 comprising SEQ ID NO: 181, and LCDR1 comprising SEQ ID NO: 180;

(xxiv) HCDR3 comprising SEQ ID NO: 168, HCDR2 comprising SEQ ID NO: 167, HCDR1 comprising SEQ ID NO: 166, LCDR3 comprising SEQ ID NO: 185, LCDR2 comprising SEQ ID NO: 184, and LCDR1 comprising SEQ ID NO: 183;

(xxv) HCDR3 comprising SEQ ID NO: 171, HCDR2 comprising SEQ ID NO: 170, HCDR1 comprising SEQ ID NO: 169, LCDR3 comprising SEQ ID NO: 187, LCDR2 comprising SEQ ID NO: 186, and LCDR1 comprising SEQ ID NO: 180;

(xxvi) HCDR3 comprising SEQ ID NO: 174, HCDR2 comprising SEQ ID NO: 173, HCDR1 comprising SEQ ID NO: 172, LCDR3 comprising SEQ ID NO: 189, LCDR2 comprising SEQ ID NO: 188, and LCDR1 comprising SEQ ID NO: 180;

(xxvii) HCDR3 comprising SEQ ID NO: 176, HCDR2 comprising SEQ ID NO: 175, HCDR1 comprising SEQ ID NO: 163, LCDR3 comprising SEQ ID NO: 192, LCDR2 comprising SEQ ID NO: 191, and LCDR1 comprising SEQ ID NO: 190; and (xxviii) HCDR3 comprising SEQ ID NO: 165, HCDR2 comprising SEQ ID NO: 164, HCDR1 comprising SEQ ID NO: 163, LCDR3 comprising SEQ ID NO: 193, LCDR2 comprising SEQ ID NO: 181, and LCDR1 comprising SEQ ID NO: 180; or (b) the antibody comprises a VHH domain comprising the CDR sequences selected from the group consisting of:

(i) CDR3 comprising SEQ ID NO: 210, CDR2 comprising SEQ ID NO: 209, and CDR1 comprising SEQ ID NO: 208;

(ii) CDR3 comprising SEQ ID NO: 213, CDR2 comprising SEQ ID NO: 212, and CDR1 comprising SEQ ID NO: 211;

(iii) CDR3 comprising SEQ ID NO: 216, CDR2 comprising SEQ ID NO: 215, and CDR1 comprising SEQ ID NO: 214;

(iv) CDR3 comprising SEQ ID NO: 219, CDR2 comprising SEQ ID NO: 218, and CDR1 comprising SEQ ID NO: 217;

(v) CDR3 comprising SEQ ID NO: 222, CDR2 comprising SEQ ID NO: 221, and CDR1 comprising SEQ ID NO: 220;

(vi) CDR3 comprising SEQ ID NO: 225, CDR2 comprising SEQ ID NO: 224, and CDR1 comprising SEQ ID NO: 223;

(vii) CDR3 comprising SEQ ID NO: 228, CDR2 comprising SEQ ID NO: 227, and CDR1 comprising SEQ ID NO: 226;

(viii) CDR3 comprising SEQ ID NO: 231, CDR2 comprising SEQ ID NO: 230, and CDR1 comprising SEQ ID NO: 229;

(ix) CDR3 comprising SEQ ID NO: 234, CDR2 comprising SEQ ID NO: 233, and CDR1 comprising SEQ ID NO: 232;

(x) CDR3 comprising SEQ ID NO: 236, CDR2 comprising SEQ ID NO: 235, and CDR1 comprising SEQ ID NO: 226;
(xi) CDR3 comprising SEQ ID NO: 238, CDR2 comprising SEQ ID NO: 237, and CDR1 comprising SEQ ID NO: 232;
(xii) CDR3 comprising SEQ ID NO: 241, CDR2 comprising SEQ ID NO: 240, and CDR1 comprising SEQ ID NO: 239;
(xiii) CDR3 comprising SEQ ID NO: 236, CDR2 comprising SEQ ID NO: 235, and CDR1 comprising SEQ ID NO: 226;
(xiv) CDR3 comprising SEQ ID NO: 244, CDR2 comprising SEQ ID NO: 243, and CDR1 comprising SEQ ID NO: 242;
(xv) CDR3 comprising SEQ ID NO: 234, CDR2 comprising SEQ ID NO: 233, and CDR1 comprising SEQ ID NO: 232;
(xvi) CDR3 comprising SEQ ID NO: 247, CDR2 comprising SEQ ID NO: 246, and CDR1 comprising SEQ ID NO: 245; and
(xvii) CDR3 comprising SEQ ID NO: 249, CDR2 comprising SEQ ID NO: 248, and CDR1 comprising SEQ ID NO: 217.

3. The method of claim 2, wherein the antibody or antigen binding fragment thereof comprises a combination of a VH and a VL selected from the following:
(i) a VH comprising the amino acid sequence of SEQ ID NO: 99 or an amino acid sequence at least 90% identical thereto and a VL comprising the amino acid sequence of SEQ ID NO: 100 or an amino acid sequence at least 90% identical thereto;
(ii) a VH comprising the amino acid sequence of SEQ ID NO: 101 or an amino acid sequence at least 90% identical thereto and a VL comprising the amino acid sequence of SEQ ID NO: 102 or an amino acid sequence at least 90% identical thereto;
(iii) a VH comprising the amino acid sequence of SEQ ID NO: 103 or an amino acid sequence at least 90% identical thereto and a VL comprising the amino acid sequence of SEQ ID NO: 104 or an amino acid sequence at least 90% identical thereto;
(iv) a VH comprising the amino acid sequence of SEQ ID NO: 105 or an amino acid sequence at least 90% identical thereto and a VL comprising the amino acid sequence of SEQ ID NO: 106 or an amino acid sequence at least 90% identical thereto;
(v) a VH comprising the amino acid sequence of SEQ ID NO: 107 or an amino acid sequence at least 90% identical thereto and a VL comprising the amino acid sequence of SEQ ID NO: 108 or an amino acid sequence at least 90% identical thereto;
(vi) a VH comprising the amino acid sequence of SEQ ID NO: 109 or an amino acid sequence at least 90% identical thereto and a VL comprising the amino acid sequence of SEQ ID NO: 110 or an amino acid sequence at least 90% identical thereto;
(vii) a VH comprising the amino acid sequence of SEQ ID NO: 111 or an amino acid sequence at least 90% identical thereto and a VL comprising the amino acid sequence of SEQ ID NO: 112 or an amino acid sequence at least 90% identical thereto;
(viii) a VH comprising the amino acid sequence of SEQ ID NO: 113 or an amino acid sequence at least 90% identical thereto and a VL comprising the amino acid sequence of SEQ ID NO: 114 or an amino acid sequence at least 90% identical thereto;
(ix) a VH comprising the amino acid sequence of SEQ ID NO: 115 or an amino acid sequence at least 90% identical thereto and a VL comprising the amino acid sequence of SEQ ID NO: 116 or an amino acid sequence at least 90% identical thereto;
(x) a VH comprising the amino acid sequence of SEQ ID NO: 117 or an amino acid sequence at least 90% identical thereto and a VL comprising the amino acid sequence of SEQ ID NO: 118 or an amino acid sequence at least 90% identical thereto;
(xi) a VH comprising the amino acid sequence of SEQ ID NO: 119 or an amino acid sequence at least 90% identical thereto and a VL comprising the amino acid sequence of SEQ ID NO: 120 or an amino acid sequence at least 90% identical thereto;
(xii) a VH comprising the amino acid sequence of SEQ ID NO: 121 or an amino acid sequence at least 90% identical thereto and a VL comprising the amino acid sequence of SEQ ID NO: 122 or an amino acid sequence at least 90% identical thereto;
(xiii) a VH comprising the amino acid sequence of SEQ ID NO: 123 or an amino acid sequence at least 90% identical thereto and a VL comprising the amino acid sequence of SEQ ID NO: 124 or an amino acid sequence at least 90% identical thereto;
(xiv) a VH comprising the amino acid sequence of SEQ ID NO: 125 or an amino acid sequence at least 90% identical thereto and a VL comprising the amino acid sequence of SEQ ID NO: 126 or an amino acid sequence at least 90% identical thereto;
(xv) a VH comprising the amino acid sequence of SEQ ID NO: 127 or an amino acid sequence at least 90% identical thereto and a VL comprising the amino acid sequence of SEQ ID NO: 128 or an amino acid sequence at least 90% identical thereto;
(xvi) a VH comprising the amino acid sequence of SEQ ID NO: 129 or an amino acid sequence at least 90% identical thereto and a VL comprising the amino acid sequence of SEQ ID NO: 130 or an amino acid sequence at least 90% identical thereto;
(xvii) a VH comprising the amino acid sequence of SEQ ID NO: 131 or an amino acid sequence at least 90% identical thereto and a VL comprising the amino acid sequence of SEQ ID NO: 132 or an amino acid sequence at least 90% identical thereto;
(xviii) a VH comprising the amino acid sequence of SEQ ID NO: 133 or an amino acid sequence at least 90% identical thereto and a VL comprising the amino acid sequence of SEQ ID NO: 134 or an amino acid sequence at least 90% identical thereto;
(xix) a VH comprising the amino acid sequence of SEQ ID NO: 135 or an amino acid sequence at least 90% identical thereto and a VL comprising the amino acid sequence of SEQ ID NO: 136 or an amino acid sequence at least 90% identical thereto;
(xx) a VH comprising the amino acid sequence of SEQ ID NO: 137 or an amino acid sequence at least 90% identical thereto and a VL comprising the amino acid sequence of SEQ ID NO: 138 or an amino acid sequence at least 90% identical thereto;
(xxi) a VH comprising the amino acid sequence of SEQ ID NO: 139 or an amino acid sequence at least 90% identical thereto and a VL comprising the amino acid sequence of SEQ ID NO: 140 or an amino acid sequence at least 90% identical thereto;
(xxii) a VH comprising the amino acid sequence of SEQ ID NO: 194 or an amino acid sequence at least 90% identical thereto and a VL comprising the amino acid sequence of SEQ ID NO: 195 or an amino acid sequence at least 90% identical thereto;

(xxiii) a VH comprising the amino acid sequence of SEQ ID NO: 196 or an amino acid sequence at least 90% identical thereto and a VL comprising the amino acid sequence of SEQ ID NO: 197 or an amino acid sequence at least 90% identical thereto;

(xxiv) a VH comprising the amino acid sequence of SEQ ID NO: 198 or an amino acid sequence at least 90% identical thereto and a VL comprising the amino acid sequence of SEQ ID NO: 199 or an amino acid sequence at least 90% identical thereto;

(xxv) a VH comprising the amino acid sequence of SEQ ID NO: 200 or an amino acid sequence at least 90% identical thereto and a VL comprising the amino acid sequence of SEQ ID NO: 201 or an amino acid sequence at least 90% identical thereto;

(xxvi) a VH comprising the amino acid sequence of SEQ ID NO: 202 or an amino acid sequence at least 90% identical thereto and a VL comprising the amino acid sequence of SEQ ID NO: 203 or an amino acid sequence at least 90% identical thereto;

(xxvii) a VH comprising the amino acid sequence of SEQ ID NO: 204 or an amino acid sequence at least 90% identical thereto and a VL comprising the amino acid sequence of SEQ ID NO: 205 or an amino acid sequence at least 90% identical thereto; and (xxviii) a VH comprising the amino acid sequence of SEQ ID NO: 206 or an amino acid sequence at least 90% identical thereto and a VL comprising the amino acid sequence of SEQ ID NO: 207 or an amino acid sequence at least 90% identical thereto.

4. The method of claim 2, wherein the antibody comprises a VHH domain and wherein the VHH domain comprises or consists of the amino acid sequence represented by any one of SEQ ID NOs: 250, 251, 252, 253, 254, 255, 256, 257, 258, 259, 260, 261, 262, 263, 264, 265 or 266, or an amino acid sequence at least 90% identical thereto.

5. A method of reducing the amount of galectin-10 crystals in a subject in need thereof, the method comprising administering to the subject a therapeutically effective amount of an antibody or antigen binding fragment thereof which specifically binds to human galectin-10, wherein the antibody or antigen binding fragment thereof cross competes for binding to human galectin-10 with an antibody or antigen binding fragment thereof comprising a variable heavy chain domain (VH) and a variable light chain domain (VL) wherein the VH and VL domains comprise the CDR sequences selected from the group consisting of:

(i) HCDR3 comprising SEQ ID NO: 3, HCDR2 comprising SEQ ID NO: 2, HCDR1 comprising SEQ ID NO: 1, LCDR3 comprising SEQ ID NO: 58, LCDR2 comprising SEQ ID NO: 57, and LCDR1 comprising SEQ ID NO: 56;

(ii) HCDR3 comprising SEQ ID NO: 9, HCDR2 comprising SEQ ID NO: 8, HCDR1 comprising SEQ ID NO: 7, LCDR3 comprising SEQ ID NO: 64, LCDR2 comprising SEQ ID NO: 63, and LCDR1 comprising SEQ ID NO: 62;

(iii) HCDR3 comprising SEQ ID NO: 12, HCDR2 comprising SEQ ID NO: 11, HCDR1 comprising SEQ ID NO: 10, LCDR3 comprising SEQ ID NO: 67, LCDR2 comprising SEQ ID NO: 66, and LCDR1 comprising SEQ ID NO: 65;

(iv) HCDR3 comprising SEQ ID NO: 25, HCDR2 comprising SEQ ID NO: 24, HCDR1 comprising SEQ ID NO: 4, LCDR3 comprising SEQ ID NO: 78, LCDR2 comprising SEQ ID NO: 77, and LCDR1 comprising SEQ ID NO: 76;

(v) HCDR3 comprising SEQ ID NO: 47, HCDR2 comprising SEQ ID NO: 46, HCDR1 comprising SEQ ID NO: 45, LCDR3 comprising SEQ ID NO: 94, LCDR2 comprising SEQ ID NO: 93, and LCDR1 comprising SEQ ID NO: 71;

(vi) HCDR3 comprising SEQ ID NO: 43, HCDR2 comprising SEQ ID NO: 42, HCDR1 comprising SEQ ID NO: 4, LCDR3 comprising SEQ ID NO: 94, LCDR2 comprising SEQ ID NO: 93, and LCDR1 comprising SEQ ID NO: 92;

(vii) HCDR3 comprising SEQ ID NO: 6, HCDR2 comprising SEQ ID NO: 44, HCDR1 comprising SEQ ID NO: 4, LCDR3 comprising SEQ ID NO: 97, LCDR2 comprising SEQ ID NO: 96, and LCDR1 comprising SEQ ID NO: 95;

(viii) HCDR3 comprising SEQ ID NO: 36, HCDR2 comprising SEQ ID NO: 52, HCDR1 comprising SEQ ID NO: 51, LCDR3 comprising SEQ ID NO: 98, LCDR2 comprising SEQ ID NO: 97, and LCDR1 comprising SEQ ID NO: 80;

(ix) HCDR3 comprising SEQ ID NO: 55, HCDR2 comprising SEQ ID NO: 54, HCDR1 comprising SEQ ID NO: 53, LCDR3 comprising SEQ ID NO: 81, LCDR2 comprising SEQ ID NO: 93, and LCDR1 comprising SEQ ID NO: 71;

(x) HCDR3 comprising SEQ ID NO: 50, HCDR2 comprising SEQ ID NO: 49, HCDR1 comprising SEQ ID NO: 48, LCDR3 comprising SEQ ID NO: 96, LCDR2 comprising SEQ ID NO: 63, and LCDR1 comprising SEQ ID NO: 95;

(xi) HCDR3 comprising SEQ ID NO: 6, HCDR2 comprising SEQ ID NO: 5, HCDR1 comprising SEQ ID NO: 4, LCDR3 comprising SEQ ID NO: 61, LCDR2 comprising SEQ ID NO: 60, and LCDR1 comprising SEQ ID NO: 59;

(xii) HCDR3 comprising SEQ ID NO: 165, HCDR2 comprising SEQ ID NO: 164, HCDR1 comprising SEQ ID NO: 163, LCDR3 comprising SEQ ID NO: 182, LCDR2 comprising SEQ ID NO: 181, and LCDR1 comprising SEQ ID NO: 180;

(xiii) HCDR3 comprising SEQ ID NO: 174, HCDR2 comprising SEQ ID NO: 173, HCDR1 comprising SEQ ID NO: 172, LCDR3 comprising SEQ ID NO: 189, LCDR2 comprising SEQ ID NO: 188, and LCDR1 comprising SEQ ID NO: 180; and (xiv) HCDR3 comprising SEQ ID NO: 165, HCDR2 comprising SEQ ID NO: 164, HCDR1 comprising SEQ ID NO: 163, LCDR3 comprising SEQ ID NO: 193, LCDR2 comprising SEQ ID NO: 181, and LCDR1 comprising SEQ ID NO: 180.

6. The method of claim 5, wherein the subject has a disease or condition selected from the group consisting of asthma; chronic rhinosinusitis; celiac disease; helminth infection; gastrointestinal eosinophilic inflammation; cystic fibrosis (CF); allergic bronchopulmonary aspergillosis (ABPA); Churg-Strauss vasculitis; chronic eosinophilic pneumonia; and acute myeloid leukemia.

7. A method of reducing the amount of galectin-10 crystals in a subject in need thereof, the method comprising administering to the subject a therapeutically effective amount of an antibody or antigen binding fragment thereof which specifically binds to human galectin-10, wherein:

(a) the antibody or antigen binding fragment thereof comprises a VH and a VL wherein the VH and VL domains comprise the CDR sequences selected from the group consisting of:
  (i) HCDR3 comprising SEQ ID NO: 3, HCDR2 comprising SEQ ID NO: 2, HCDR1 comprising SEQ ID NO: 1, LCDR3 comprising SEQ ID NO: 58, LCDR2 comprising SEQ ID NO: 57, and LCDR1 comprising SEQ ID NO: 56;
  (ii) HCDR3 comprising SEQ ID NO: 6, HCDR2 comprising SEQ ID NO: 5, HCDR1 comprising SEQ ID NO: 4, LCDR3 comprising SEQ ID NO: 61, LCDR2 comprising SEQ ID NO: 60, and LCDR1 comprising SEQ ID NO: 59;
  (iii) HCDR3 comprising SEQ ID NO: 9, HCDR2 comprising SEQ ID NO: 8, HCDR1 comprising SEQ ID NO: 7, LCDR3 comprising SEQ ID NO: 64, LCDR2 comprising SEQ ID NO: 63, and LCDR1 comprising SEQ ID NO: 62;
  (iv) HCDR3 comprising SEQ ID NO: 12, HCDR2 comprising SEQ ID NO: 11, HCDR1 comprising SEQ ID NO: 10, LCDR3 comprising SEQ ID NO: 67, LCDR2 comprising SEQ ID NO: 66, and LCDR1 comprising SEQ ID NO: 65;
  (v) HCDR3 comprising SEQ ID NO: 15, HCDR2 comprising SEQ ID NO: 14, HCDR1 comprising SEQ ID NO: 13, LCDR3 comprising SEQ ID NO: 70, LCDR2 comprising SEQ ID NO: 69, and LCDR1 comprising SEQ ID NO: 68;
  (vi) HCDR3 comprising SEQ ID NO: 18, HCDR2 comprising SEQ ID NO: 17, HCDR1 comprising SEQ ID NO: 16, LCDR3 comprising SEQ ID NO: 72, LCDR2 comprising SEQ ID NO: 66, and LCDR1 comprising SEQ ID NO: 71;
  (vii) HCDR3 comprising SEQ ID NO: 20, HCDR2 comprising SEQ ID NO: 19, HCDR1 comprising SEQ ID NO: 4, LCDR3 comprising SEQ ID NO: 75, LCDR2 comprising SEQ ID NO: 74, and LCDR1 comprising SEQ ID NO: 73;
  (viii) HCDR3 comprising SEQ ID NO: 23, HCDR2 comprising SEQ ID NO: 22, HCDR1 comprising SEQ ID NO: 21, LCDR3 comprising SEQ ID NO: 67, LCDR2 comprising SEQ ID NO: 66, and LCDR1 comprising SEQ ID NO: 65;
  (ix) HCDR3 comprising SEQ ID NO: 25, HCDR2 comprising SEQ ID NO: 24, HCDR1 comprising SEQ ID NO: 4, LCDR3 comprising SEQ ID NO: 78, LCDR2 comprising SEQ ID NO: 77, and LCDR1 comprising SEQ ID NO: 76;
  (x) HCDR3 comprising SEQ ID NO: 28, HCDR2 comprising SEQ ID NO: 27, HCDR1 comprising SEQ ID NO: 26, LCDR3 comprising SEQ ID NO: 67, LCDR2 comprising SEQ ID NO: 66, and LCDR1 comprising SEQ ID NO: 79;
  (xi) HCDR3 comprising SEQ ID NO: 31, HCDR2 comprising SEQ ID NO: 30, HCDR1 comprising SEQ ID NO: 29, LCDR3 comprising SEQ ID NO: 81, LCDR2 comprising SEQ ID NO: 63, and LCDR1 comprising SEQ ID NO: 80;
  (xii) HCDR3 comprising SEQ ID NO: 33, HCDR2 comprising SEQ ID NO: 32, HCDR1 comprising SEQ ID NO: 1, LCDR3 comprising SEQ ID NO: 84, LCDR2 comprising SEQ ID NO: 83, and LCDR1 comprising SEQ ID NO: 82;
  (xiii) HCDR3 comprising SEQ ID NO: 36, HCDR2 comprising SEQ ID NO: 35, HCDR1 comprising SEQ ID NO: 34, LCDR3 comprising SEQ ID NO: 87, LCDR2 comprising SEQ ID NO: 86, and LCDR1 comprising SEQ ID NO: 85;
  (xiv) HCDR3 comprising SEQ ID NO: 38, HCDR2 comprising SEQ ID NO: 11, HCDR1 comprising SEQ ID NO: 37, LCDR3 comprising SEQ ID NO: 78, LCDR2 comprising SEQ ID NO: 63, and LCDR1 comprising SEQ ID NO: 88;
  (xv) HCDR3 comprising SEQ ID NO: 41, HCDR2 comprising SEQ ID NO: 40, HCDR1 comprising SEQ ID NO: 39, LCDR3 comprising SEQ ID NO: 91, LCDR2 comprising SEQ ID NO: 90, and LCDR1 comprising SEQ ID NO: 89;
  (xvi) HCDR3 comprising SEQ ID NO: 43, HCDR2 comprising SEQ ID NO: 42, HCDR1 comprising SEQ ID NO: 4, LCDR3 comprising SEQ ID NO: 94, LCDR2 comprising SEQ ID NO: 93, and LCDR1 comprising SEQ ID NO: 92;
  (xvii) HCDR3 comprising SEQ ID NO: 6, HCDR2 comprising SEQ ID NO: 44, HCDR1 comprising SEQ ID NO: 4, LCDR3 comprising SEQ ID NO: 97, LCDR2 comprising SEQ ID NO: 96, and LCDR1 comprising SEQ ID NO: 95;
  (xviii) HCDR3 comprising SEQ ID NO: 47, HCDR2 comprising SEQ ID NO: 46, HCDR1 comprising SEQ ID NO: 45, LCDR3 comprising SEQ ID NO: 94, LCDR2 comprising SEQ ID NO: 93, and LCDR1 comprising SEQ ID NO: 71;
  (xix) HCDR3 comprising SEQ ID NO: 50, HCDR2 comprising SEQ ID NO: 49, HCDR1 comprising SEQ ID NO: 48, LCDR3 comprising SEQ ID NO: 96, LCDR2 comprising SEQ ID NO: 63, and LCDR1 comprising SEQ ID NO: 95;
  (xx) HCDR3 comprising SEQ ID NO: 36, HCDR2 comprising SEQ ID NO: 52, HCDR1 comprising SEQ ID NO: 51, LCDR3 comprising SEQ ID NO: 98, LCDR2 comprising SEQ ID NO: 97, and LCDR1 comprising SEQ ID NO: 80, and
  (xxi) HCDR3 comprising SEQ ID NO: 55, HCDR2 comprising SEQ ID NO: 54, HCDR1 comprising SEQ ID NO: 53, LCDR3 comprising SEQ ID NO: 81, LCDR2 comprising SEQ ID NO: 93, and LCDR1 comprising SEQ ID NO: 71;
  (xxii) HCDR3 comprising SEQ ID NO: 162, HCDR2 comprising SEQ ID NO: 161, HCDR1 comprising SEQ ID NO: 160, LCDR3 comprising SEQ ID NO: 179, LCDR2 comprising SEQ ID NO: 178, and LCDR1 comprising SEQ ID NO: 177;
  (xxiii) HCDR3 comprising SEQ ID NO: 165, HCDR2 comprising SEQ ID NO: 164, HCDR1 comprising SEQ ID NO: 163, LCDR3 comprising SEQ ID NO: 182, LCDR2 comprising SEQ ID NO: 181, and LCDR1 comprising SEQ ID NO: 180;
  (xxiv) HCDR3 comprising SEQ ID NO: 168, HCDR2 comprising SEQ ID NO: 167, HCDR1 comprising SEQ ID NO: 166, LCDR3 comprising SEQ ID NO: 185, LCDR2 comprising SEQ ID NO: 184, and LCDR1 comprising SEQ ID NO: 183;
  (xxv) HCDR3 comprising SEQ ID NO: 171, HCDR2 comprising SEQ ID NO: 170, HCDR1 comprising SEQ ID NO: 169, LCDR3 comprising SEQ ID NO: 187, LCDR2 comprising SEQ ID NO: 186, and LCDR1 comprising SEQ ID NO: 180;
  (xxvi) HCDR3 comprising SEQ ID NO: 174, HCDR2 comprising SEQ ID NO: 173, HCDR1 comprising SEQ ID NO: 172, LCDR3 comprising SEQ ID NO: 189, LCDR2 comprising SEQ ID NO: 188, and LCDR1 comprising SEQ ID NO: 180;

(xxvii) HCDR3 comprising SEQ ID NO: 176, HCDR2 comprising SEQ ID NO: 175, HCDR1 comprising SEQ ID NO: 163, LCDR3 comprising SEQ ID NO: 192, LCDR2 comprising SEQ ID NO: 191, and LCDR1 comprising SEQ ID NO: 190; and (xxviii) HCDR3 comprising SEQ ID NO: 165, HCDR2 comprising SEQ ID NO: 164, HCDR1 comprising SEQ ID NO: 163, LCDR3 comprising SEQ ID NO: 193, LCDR2 comprising SEQ ID NO: 181, and LCDR1 comprising SEQ ID NO: 180; or (b) the antibody comprises a VHH domain comprising the CDR sequences selected from the group consisting of:

(i) CDR3 comprising SEQ ID NO: 210, CDR2 comprising SEQ ID NO: 209, and CDR1 comprising SEQ ID NO: 208;

(ii) CDR3 comprising SEQ ID NO: 213, CDR2 comprising SEQ ID NO: 212, and CDR1 comprising SEQ ID NO: 211;

(iii) CDR3 comprising SEQ ID NO: 216, CDR2 comprising SEQ ID NO: 215, and CDR1 comprising SEQ ID NO: 214;

(iv) CDR3 comprising SEQ ID NO: 219, CDR2 comprising SEQ ID NO: 218, and CDR1 comprising SEQ ID NO: 217;

(v) CDR3 comprising SEQ ID NO: 222, CDR2 comprising SEQ ID NO: 221, and CDR1 comprising SEQ ID NO: 220;

(vi) CDR3 comprising SEQ ID NO: 225, CDR2 comprising SEQ ID NO: 224, and CDR1 comprising SEQ ID NO: 223;

(vii) CDR3 comprising SEQ ID NO: 228, CDR2 comprising SEQ ID NO: 227, and CDR1 comprising SEQ ID NO: 226;

(viii) CDR3 comprising SEQ ID NO: 231, CDR2 comprising SEQ ID NO: 230, and CDR1 comprising SEQ ID NO: 229;

(ix) CDR3 comprising SEQ ID NO: 234, CDR2 comprising SEQ ID NO: 233, and CDR1 comprising SEQ ID NO: 232;

(x) CDR3 comprising SEQ ID NO: 236, CDR2 comprising SEQ ID NO: 235, and CDR1 comprising SEQ ID NO: 226;

(xi) CDR3 comprising SEQ ID NO: 238, CDR2 comprising SEQ ID NO: 237, and CDR1 comprising SEQ ID NO: 232;

(xii) CDR3 comprising SEQ ID NO: 241, CDR2 comprising SEQ ID NO: 240, and CDR1 comprising SEQ ID NO: 239;

(xiii) CDR3 comprising SEQ ID NO: 236, CDR2 comprising SEQ ID NO: 235, and CDR1 comprising SEQ ID NO: 226;

(xiv) CDR3 comprising SEQ ID NO: 244, CDR2 comprising SEQ ID NO: 243, and CDR1 comprising SEQ ID NO: 242;

(xv) CDR3 comprising SEQ ID NO: 234, CDR2 comprising SEQ ID NO: 233, and CDR1 comprising SEQ ID NO: 232;

(xvi) CDR3 comprising SEQ ID NO: 247, CDR2 comprising SEQ ID NO: 246, and CDR1 comprising SEQ ID NO: 245; and (xvii) CDR3 comprising SEQ ID NO: 249, CDR2 comprising SEQ ID NO: 248, and CDR1 comprising SEQ ID NO: 217.

8. The method of claim 7, wherein the antibody or antigen binding fragment thereof comprises a combination of a VH and a VL selected from the following:

(i) a VH comprising the amino acid sequence of SEQ ID NO: 99 or an amino acid sequence at least 90% identical thereto and a VL comprising the amino acid sequence of SEQ ID NO: 100 or an amino acid sequence at least 90% identical thereto;

(ii) a VH comprising the amino acid sequence of SEQ ID NO: 101 or an amino acid sequence at least 90% identical thereto and a VL comprising the amino acid sequence of SEQ ID NO: 102 or an amino acid sequence at least 90% identical thereto;

(iii) a VH comprising the amino acid sequence of SEQ ID NO: 103 or an amino acid sequence at least 90% identical thereto and a VL comprising the amino acid sequence of SEQ ID NO: 104 or an amino acid sequence at least 90% identical thereto;

(iv) a VH comprising the amino acid sequence of SEQ ID NO: 105 or an amino acid sequence at least 90% identical thereto and a VL comprising the amino acid sequence of SEQ ID NO: 106 or an amino acid sequence at least 90% identical thereto;

(v) a VH comprising the amino acid sequence of SEQ ID NO: 107 or an amino acid sequence at least 90% identical thereto and a VL comprising the amino acid sequence of SEQ ID NO: 108 or an amino acid sequence at least 90% identical thereto;

(vi) a VH comprising the amino acid sequence of SEQ ID NO: 109 or an amino acid sequence at least 90% identical thereto and a VL comprising the amino acid sequence of SEQ ID NO: 110 or an amino acid sequence at least 90% identical thereto;

(vii) a VH comprising the amino acid sequence of SEQ ID NO: 111 or an amino acid sequence at least 90% identical thereto and a VL comprising the amino acid sequence of SEQ ID NO: 112 or an amino acid sequence at least 90% identical thereto;

(viii) a VH comprising the amino acid sequence of SEQ ID NO: 113 or an amino acid sequence at least 90% identical thereto and a VL comprising the amino acid sequence of SEQ ID NO: 114 or an amino acid sequence at least 90% identical thereto;

(ix) a VH comprising the amino acid sequence of SEQ ID NO: 115 or an amino acid sequence at least 90% identical thereto and a VL comprising the amino acid sequence of SEQ ID NO: 116 or an amino acid sequence at least 90% identical thereto;

(x) a VH comprising the amino acid sequence of SEQ ID NO: 117 or an amino acid sequence at least 90% identical thereto and a VL comprising the amino acid sequence of SEQ ID NO: 118 or an amino acid sequence at least 90% identical thereto;

(xi) a VH comprising the amino acid sequence of SEQ ID NO: 119 or an amino acid sequence at least 90% identical thereto and a VL comprising the amino acid sequence of SEQ ID NO: 120 or an amino acid sequence at least 90% identical thereto;

(xii) a VH comprising the amino acid sequence of SEQ ID NO: 121 or an amino acid sequence at least 90% identical thereto and a VL comprising the amino acid sequence of SEQ ID NO: 122 or an amino acid sequence at least 90% identical thereto;

(xiii) a VH comprising the amino acid sequence of SEQ ID NO: 123 or an amino acid sequence at least 90% identical thereto and a VL comprising the amino acid sequence of SEQ ID NO: 124 or an amino acid sequence at least 90% identical thereto;

(xiv) a VH comprising the amino acid sequence of SEQ ID NO: 125 or an amino acid sequence at least 90% identical thereto and a VL comprising the amino acid sequence of SEQ ID NO: 126 or an amino acid sequence at least 90% identical thereto;

(xv) a VH comprising the amino acid sequence of SEQ ID NO: 127 or an amino acid sequence at least 90% identical thereto and a VL comprising the amino acid sequence of SEQ ID NO: 128 or an amino acid sequence at least 90% identical thereto;

(xvi) a VH comprising the amino acid sequence of SEQ ID NO: 129 or an amino acid sequence at least 90% identical thereto and a VL comprising the amino acid sequence of SEQ ID NO: 130 or an amino acid sequence at least 90% identical thereto;

(xvii) a VH comprising the amino acid sequence of SEQ ID NO: 131 or an amino acid sequence at least 90% identical thereto and a VL comprising the amino acid sequence of SEQ ID NO: 132 or an amino acid sequence at least 90% identical thereto;

(xviii) a VH comprising the amino acid sequence of SEQ ID NO: 133 or an amino acid sequence at least 90% identical thereto and a VL comprising the amino acid sequence of SEQ ID NO: 134 or an amino acid sequence at least 90% identical thereto;

(xix) a VH comprising the amino acid sequence of SEQ ID NO: 135 or an amino acid sequence at least 90% identical thereto and a VL comprising the amino acid sequence of SEQ ID NO: 136 or an amino acid sequence at least 90% identical thereto;

(xx) a VH comprising the amino acid sequence of SEQ ID NO: 137 or an amino acid sequence at least 90% identical thereto and a VL comprising the amino acid sequence of SEQ ID NO: 138 or an amino acid sequence at least 90% identical thereto;

(xxi) a VH comprising the amino acid sequence of SEQ ID NO: 139 or an amino acid sequence at least 90% identical thereto and a VL comprising the amino acid sequence of SEQ ID NO: 140 or an amino acid sequence at least 90% identical thereto;

(xxii) a VH comprising the amino acid sequence of SEQ ID NO: 194 or an amino acid sequence at least 90% identical thereto and a VL comprising the amino acid sequence of SEQ ID NO: 195 or an amino acid sequence at least 90% identical thereto;

(xxiii) a VH comprising the amino acid sequence of SEQ ID NO: 196 or an amino acid sequence at least 90% identical thereto and a VL comprising the amino acid sequence of SEQ ID NO: 197 or an amino acid sequence at least 90% identical thereto;

(xxiv) a VH comprising the amino acid sequence of SEQ ID NO: 198 or an amino acid sequence at least 90% identical thereto and a VL comprising the amino acid sequence of SEQ ID NO: 199 or an amino acid sequence at least 90% identical thereto;

(xxv) a VH comprising the amino acid sequence of SEQ ID NO: 200 or an amino acid sequence at least 90% identical thereto and a VL comprising the amino acid sequence of SEQ ID NO: 201 or an amino acid sequence at least 90% identical thereto;

(xxvi) a VH comprising the amino acid sequence of SEQ ID NO: 202 or an amino acid sequence at least 90% identical thereto and a VL comprising the amino acid sequence of SEQ ID NO: 203 or an amino acid sequence at least 90% identical thereto;

(xxvii) a VH comprising the amino acid sequence of SEQ ID NO: 204 or an amino acid sequence at least 90% identical thereto and a VL comprising the amino acid sequence of SEQ ID NO: 205 or an amino acid sequence at least 90% identical thereto; and (xxviii) a VH comprising the amino acid sequence of SEQ ID NO: 206 or an amino acid sequence at least 90% identical thereto and a VL comprising the amino acid sequence of SEQ ID NO: 207 or an amino acid sequence at least 90% identical thereto.

9. The method of claim 7, wherein the antibody comprises a VHH domain and wherein the VHH domain comprises or consists of the amino acid sequence represented by any one of SEQ ID NOs: 250, 251, 252, 253, 254, 255, 256, 257, 258, 259, 260, 261, 262, 263, 264, 265 or 266, or an amino acid sequence at least 90% identical thereto.

10. The method of claim 1, wherein the subject has asthma.

11. The method of claim 2, wherein the subject has a disease or condition selected from the group consisting of asthma; chronic rhinosinusitis; celiac disease; helminth infection; gastrointestinal eosinophilic inflammation; cystic fibrosis (CF); allergic bronchopulmonary aspergillosis (ABPA); Churg-Strauss vasculitis; chronic eosinophilic pneumonia; and acute myeloid leukemia.

12. The method of claim 2, wherein the subject has asthma.

13. The method of claim 5, wherein the subject has asthma.

14. The method of claim 7, wherein the subject has a disease or condition selected from the group consisting of asthma; chronic rhinosinusitis; celiac disease; helminth infection; gastrointestinal eosinophilic inflammation; cystic fibrosis (CF); allergic bronchopulmonary aspergillosis (ABPA); Churg-Strauss vasculitis; chronic eosinophilic pneumonia; and acute myeloid leukemia.

15. The method of claim 7, wherein the subject has asthma.

\* \* \* \* \*

UNITED STATES PATENT AND TRADEMARK OFFICE
CERTIFICATE OF CORRECTION

PATENT NO. : 11,713,354 B2
APPLICATION NO. : 17/194950
DATED : August 1, 2023
INVENTOR(S) : Percier et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 125 days.

Signed and Sealed this
Twelfth Day of November, 2024

Katherine Kelly Vidal
*Director of the United States Patent and Trademark Office*